US006309822B1

(12) United States Patent
Fodor et al.

(10) Patent No.: US 6,309,822 B1
(45) Date of Patent: *Oct. 30, 2001

(54) METHOD FOR COMPARING COPY NUMBER OF NUCLEIC ACID SEQUENCES

(75) Inventors: Stephen P. A. Fodor, Palo Alto; Dennis W. Solas, San Francisco; William J. Dower, Menlo Park, all of CA (US)

(73) Assignee: Affymetrix, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/772,376

(22) Filed: Dec. 23, 1996

Related U.S. Application Data

(63) Continuation-in-part of application No. 08/670,118, filed on Jun. 25, 1990, now Pat. No. 5,800,992, and a continuation-in-part of application No. 08/529,115, filed on Sep. 15, 1999, now Pat. No. 6,040,138, which is a division of application No. 08/168,904, filed on Dec. 15, 1993, now abandoned, which is a continuation of application No. 07/624,114, filed on Dec. 6, 1990, now abandoned, which is a continuation-in-part of application No. 07/362,901, filed on Jun. 7, 1989, now abandoned.

(30) Foreign Application Priority Data

Sep. 13, 1996 (WO) .................................. PCT/US96/14839

(51) Int. Cl.[7] .............................. C12Q 1/68; C12M 1/34; C07H 21/04; C07H 21/02
(52) U.S. Cl. ...................... 435/6; 435/287.2; 435/288.3; 435/288.7; 536/23.1; 536/24.3; 536/24.31
(58) Field of Search ...................... 435/6, 287.2, 288.3, 435/288.7; 536/24.3, 24.31, 23.1

(56) References Cited

U.S. PATENT DOCUMENTS

| | | |
|---|---|---|
| 3,849,137 | 11/1974 | Barzynski et al. . |
| 3,862,056 | 1/1975 | Hartman . |
| 3,939,350 | 2/1976 | Kronick et al. . |
| 4,072,576 | 2/1978 | Arwin et al. . |
| 4,180,739 | 12/1979 | Abu-Shumays . |
| 4,238,757 | 12/1980 | Schenck . |
| 4,269,933 | 5/1981 | Pazos . |
| 4,314,821 | 2/1982 | Rice . |
| 4,327,073 | 4/1982 | Huang . |
| 4,339,528 | 7/1982 | Goldman . |
| 4,342,905 | 8/1982 | Fujii et al. . |
| 4,373,071 | 2/1983 | Itakura . |
| 4,405,771 | 9/1983 | Jagur . |

(List continued on next page.)

FOREIGN PATENT DOCUMENTS

| | | |
|---|---|---|
| 2242394 | 3/1974 | (DE) . |
| 3440141 | 5/1986 | (DE) . |
| 3505287 | 3/1988 | (DE) . |
| 046 083 | 2/1982 | (EP) . |
| 088 636 | 9/1983 | (EP) . |
| 103 197 | 3/1984 | (EP) . |
| 127 438 | 12/1984 | (EP) . |
| 063 810 | 3/1986 | (EP) . |
| 194 132 | 9/1986 | (EP) . |
| 228 075 | 7/1987 | (EP) . |
| 245 662 | 11/1987 | (EP) . |
| 268 237 | 5/1988 | (EP) . |
| 281 927 | 9/1988 | (EP) . |

(List continued on next page.)

OTHER PUBLICATIONS

Perkin Elmer Cetus, Gene Amp DNA Amplication Reagent Kit, insert, Oct. 1988.
Church et al, Proc. Natl. Acad. Sci., 81:1991–1995 (Apr., 1984).
Chetverin et al, Bio/Tech., 12:1093–1099 (Nov. 1994).
Coulson et al, Proc. Natl. Acad. Sci. USA, 83:7821–7825 (Oct. 1986).
Dower et al, Ann. Rep. Med. Chem., 26:271–280 (1991).
Dramanac et al, J. Biomol. Struc. Dyn., 8(5):1085–1102 (1991).
Hodgson et al, Nucl. Acids. Res., 15(15):6295 (1987).
Khrapko et al, DNA Seq. Map, 1:375–388 (1991).
Lander et al, Genomics, 2:231–239 (1988).
Little, Nature, 346:611–612 (1990).
Lysov et al, Dokl. Akad. Nauk. SSSR, 303:1508–1511 (1988).
Olson et al, Proc. Natl. Acad. Sci. USA, 83:7826–7830 (Oct. 1986).
Pevzner, Algorithmica, 13(1–2):77–105 (1995).
Pevzner et al, Algorithmica, 13(1–2):135–154 (1995).
Pfeifer et al, Science, 246:810–813 (Nov. 10, 19889).
Seed, Nucl. Acids. Res., 10(5):1799–1810 (1982).
Wood et al, Proc. Natl. Acad. Sci. USA, 82:1585–1588 (1985).
Feinberg et al, Annal. Biochem., 137:266–267 (1984).
Pevzner et al, Adv. Applied Math, 14:139–171 (1993).
Schena et al, Proc. Natl. Acad. Sci. USA, 93:10614–10619 (Oct. 1996).
Sequencing by Hybridization Workshop, listing of participants and workshop presentation summaries (1991).
"A Sequencing Reality Check," *Science* 242:1245 (1988).
"Affymax raises $25 million to develop high–speed drug discovery system," *Biotechnology News*, 10(3):7–8 (1990).

(List continued on next page.)

*Primary Examiner*—Stephanie Zitomer
(74) *Attorney, Agent, or Firm*—Pillsbury Winthrop LLP

(57) ABSTRACT

The present invention provides methods for comparing and identifying differences in nucleic acid sequences using a plurality of sequence specific recognition reagents (i.e., probes comprising a nucleic acid complementary to a nucleic acid sequence in collections to be compared) bound to a solid surface.

17 Claims, 12 Drawing Sheets

U.S. PATENT DOCUMENTS

| | | |
|---|---|---|
| 4,444,878 | 4/1984 | Paulus . |
| 4,444,892 | 4/1984 | Malmros . |
| 4,448,534 | 5/1984 | Wertz et al. . |
| 4,458,066 | 7/1984 | Caruthers et al. . |
| 4,483,920 | 11/1984 | Gillespie et al. . |
| 4,500,707 | 2/1985 | Caruthers et al. . |
| 4,516,833 | 5/1985 | Fusek . |
| 4,517,338 | 5/1985 | Urdea et al. . |
| 4,537,861 | 8/1985 | Elings et al. . |
| 4,542,102 | 9/1985 | Dattagupta et al. . |
| 4,555,490 | 11/1985 | Merril . |
| 4,562,157 | 12/1985 | Lowe et al. . |
| 4,569,967 | 2/1986 | Kornreich et al. . |
| 4,580,895 | 4/1986 | Patel . |
| 4,584,277 | 4/1986 | Ullman . |
| 4,613,566 | 9/1986 | Potter . |
| 4,624,915 | 11/1986 | Schindler et al. . |
| 4,626,684 | 12/1986 | Landa . |
| 4,631,211 | 12/1986 | Houghten . |
| 4,637,861 | 1/1987 | Krull et al. . |
| 4,677,054 | 6/1987 | White et al. . |
| 4,681,859 | 7/1987 | Kramer . |
| 4,683,202 | 7/1987 | Mullis . |
| 4,689,405 | 8/1987 | Frank et al. . |
| 4,704,353 | 11/1987 | Humphries et al. . |
| 4,711,955 | 12/1987 | Ward et al. . |
| 4,713,326 | 12/1987 | Dattagupta et al. . |
| 4,713,347 | 12/1987 | Mitchell et al. . |
| 4,719,615 | 1/1988 | Feyrer et al. . |
| 4,722,906 | 2/1988 | Guire . |
| 4,728,502 | 3/1988 | Hamill . |
| 4,728,591 | 3/1988 | Clark et al. . |
| 4,731,325 | 3/1988 | Palva et al. . |
| 4,755,458 | 7/1988 | Rabbani et al. . |
| 4,762,881 | 8/1988 | Kauer . |
| 4,777,019 | 10/1988 | Dandekar . |
| 4,780,504 | 10/1988 | Buendia et al. . |
| 4,786,170 | 11/1988 | Groebler . |
| 4,786,684 | 11/1988 | Glass . |
| 4,794,150 | 12/1988 | Steel . |
| 4,808,508 | 2/1989 | Platzer . |
| 4,810,869 | 3/1989 | Yabe et al. . |
| 4,811,062 | 3/1989 | Tabata et al. . |
| 4,812,512 | 3/1989 | Buendia et al. . |
| 4,820,630 | 4/1989 | Taub . |
| 4,822,566 | 4/1989 | Newman . |
| 4,833,092 | 5/1989 | Geysen . |
| 4,844,617 | 7/1989 | Kelderman . |
| 4,846,552 | 7/1989 | Veldkamp et al. . |
| 4,849,513 | 7/1989 | Smith et al. . |
| 4,855,225 * | 8/1989 | Fung et al. ............................... 435/6 |
| 4,865,990 | 9/1989 | Stead et al. . |
| 4,868,103 | 9/1989 | Stavrianopoulos et al. . |
| 4,874,500 | 10/1989 | Madou et al. . |
| 4,886,741 | 12/1989 | Schwartz . |
| 4,888,278 | 12/1989 | Singer et al. . |
| 4,923,901 | 5/1990 | Koester et al. . |
| 4,925,785 | 5/1990 | Wang et al. . |
| 4,946,942 | 8/1990 | Fuller et al. . |
| 4,965,188 | 10/1990 | Mullis et al. ............................ 435/6 |
| 4,973,493 | 11/1990 | Guire . |
| 4,979,959 | 12/1990 | Guire . |
| 4,981,783 | 1/1991 | Augenlicht ............................... 435/6 |
| 4,981,985 | 1/1991 | Kaplan et al. . |
| 4,984,100 | 1/1991 | Takayama et al. . |
| 4,987,065 | 1/1991 | Stavrianopoulos et al. . |
| 4,988,617 | 1/1991 | Landegren et al. . |
| 4,992,383 | 2/1991 | Farnsworth . |
| 4,994,373 | 2/1991 | Stavrianopoulos et al. . |
| 5,002,867 | 3/1991 | Macevicz . |
| 5,021,550 | 6/1991 | Zeiger . |
| 5,026,773 | 6/1991 | Steel . |
| 5,026,840 | 6/1991 | Dattagupta et al. . |
| 5,028,525 | 7/1991 | Gray et al. . |
| 5,043,265 | 8/1991 | Tanke et al. . |
| 5,047,524 | 9/1991 | Andrus et al. . |
| 5,079,600 | 1/1992 | Schnur et al. . |
| 5,081,584 | 1/1992 | Omichinski et al. . |
| 5,082,830 | 1/1992 | Brakel et al. . |
| 5,091,652 | 2/1992 | Mathies et al. . |
| 5,112,962 | 5/1992 | Letsinger et al. . |
| 5,141,813 | 8/1992 | Nelson . |
| 5,143,854 | 9/1992 | Pirrung et al. . |
| 5,153,319 | 10/1992 | Caruthers et al. . |
| 5,192,980 | 3/1993 | Dixon et al. . |
| 5,200,051 | 4/1993 | Cozzette et al. . |
| 5,202,231 | 4/1993 | Drmanac et al. . |
| 5,206,137 | 4/1993 | Ip et al. . |
| 5,215,882 * | 6/1993 | Bahl et al. ............................... 435/6 |
| 5,215,889 | 6/1993 | Schultz . |
| 5,232,829 | 8/1993 | Longiaru et al. . |
| 5,235,028 | 8/1993 | Barany et al. . |
| 5,242,974 | 9/1993 | Holmes . |
| 5,252,743 | 10/1993 | Barrett et al. . |
| 5,256,549 | 10/1993 | Urdea et al. . |
| 5,258,506 | 11/1993 | Urdea et al. . |
| 5,306,641 | 4/1994 | Saccocio . |
| 5,310,893 | 5/1994 | Erlich et al. . |
| 5,324,633 | 6/1994 | Fodor et al. . |
| 5,348,855 | 9/1994 | Dattagupta et al. . |
| 5,384,261 | 1/1995 | Winkler et al. . |
| 5,405,783 | 4/1995 | Pirrung et al. . |
| 5,424,186 | 6/1995 | Fodor et al. . |
| 5,436,327 | 7/1995 | Southern et al. . |
| 5,445,934 | 8/1995 | Fodor et al. . |
| 5,447,841 | 9/1995 | Gray et al. . |
| 5,474,796 * | 12/1995 | Brennan ............................... 427/2.13 |
| 5,486,452 | 1/1996 | Gordon et al. . |
| 5,489,507 | 2/1996 | Chehab . |
| 5,489,678 | 2/1996 | Fodor et al. . |
| 5,492,806 | 2/1996 | Drmanac et al. . |
| 5,510,270 | 4/1996 | Fodor et al. . |
| 5,525,464 | 6/1996 | Drmanac et al. . |
| 5,527,681 | 6/1996 | Holmes . |
| 5,552,270 | 9/1996 | Khrapko et al. . |
| 5,556,961 | 9/1996 | Foote et al. . |
| 5,561,071 | 10/1996 | Hollenberg et al. . |
| 5,571,639 | 11/1996 | Hubbell et al. . |
| 5,593,839 | 1/1997 | Hubbell et al. . |
| 5,653,939 | 8/1997 | Hollis et al. . |
| 5,667,667 | 9/1997 | Southern . |
| 5,667,972 | 9/1997 | Drmanac et al. . |
| 5,695,940 | 12/1997 | Drmanac et al. . |
| 5,698,393 | 12/1997 | Macioszek et al. . |
| 5,700,637 | 12/1997 | Southern ............................... 435/6 |
| 5,707,806 | 1/1998 | Shuber . |
| 5,744,305 | 4/1998 | Fodor et al. . |
| 5,777,888 | 7/1998 | Rine et al. . |
| 5,800,992 | 9/1998 | Fodor et al. . |
| 5,807,522 * | 9/1998 | Brown et al. ........................... 422/50 |
| 5,830,645 * | 11/1998 | Pinkel et al. ............................ 435/6 |
| 5,843,767 | 12/1998 | Beattie . |
| 5,846,708 | 12/1998 | Hollis et al. . |
| 5,871,697 | 2/1999 | Rothberg et al. . |

FOREIGN PATENT DOCUMENTS

| | | |
|---|---|---|
| 228 310 | 10/1988 | (EP) . |
| 288 310 | 10/1988 | (EP) . |
| 304 202 | 2/1989 | (EP) . |
| 307 476 | 3/1989 | (EP) . |
| 319 012 | 6/1989 | (EP) . |
| 328 256 | 8/1989 | (EP) . |
| 333 561 | 9/1989 | (EP) . |
| 337 498 | 10/1989 | (EP) . |
| 386 229 | 4/1990 | (EP) . |
| 373 203 | 6/1990 | (EP) . |
| 392 546 | 10/1990 | (EP) . |
| 173 339 | 1/1992 | (EP) . |
| 171 150 | 3/1992 | (EP) . |

| | | |
|---|---|---|
| 237 362 | 3/1992 | (EP). |
| 185 547 | 6/1992 | (EP). |
| 260 634 | 6/1992 | (EP). |
| 232 967 | 4/1993 | (EP). |
| 235 726 | 5/1993 | (EP). |
| 476 014 | 8/1994 | (EP). |
| 225 807 | 10/1994 | (EP). |
| 717 113 | 6/1996 | (EP). |
| 0 721 016 A3 | 7/1996 | (EP). |
| 848 067 | 6/1998 | (EP). |
| 619 321 | 1/1999 | (EP). |
| 2156074 | 3/1988 | (GB). |
| 2559783 | 3/1988 | (FR). |
| 2196476 | 4/1988 | (GB). |
| 8810400.5 | 5/1988 | (GB). |
| 2233654 | 1/1991 | (GB). |
| 2248840 | 9/1992 | (GB). |
| 49-110601 | 10/1974 | (JP). |
| 60-248669 | 12/1985 | (JP). |
| 63-084499 | 4/1988 | (JP). |
| 63-223557 | 9/1988 | (JP). |
| 1-233447 | 9/1989 | (JP). |
| P 913186 | 8/1991 | (NO). |
| WO 84/03151 | 8/1984 | (WO). |
| WO 84/03564 | 9/1984 | (WO). |
| WO 85/01051 | 3/1985 | (WO). |
| WO 86/00991 | 2/1986 | (WO). |
| WO 86/06487 | 11/1986 | (WO). |
| WO 88/04777 | 6/1988 | (WO). |
| WO 89/05616 | 6/1989 | (WO). |
| WO 89/08834 | 9/1989 | (WO). |
| WO 89/10977 | 11/1989 | (WO). |
| WO 89/11548 | 11/1989 | (WO). |
| WO 89/12819 | 12/1989 | (WO). |
| WO 90/00626 | 1/1990 | (WO). |
| WO 90/00887 | 2/1990 | (WO). |
| WO 90/15070 | 2/1990 | (WO). |
| WO 90/03382 | 4/1990 | (WO). |
| WO 90/04652 | 5/1990 | (WO). |
| WO 91/04266 | 4/1991 | (WO). |
| WO 91/07087 | 5/1991 | (WO). |
| WO 92/16655 | 1/1992 | (WO). |
| WO 92/10092 | 6/1992 | (WO). |
| WO 92/10588 | 6/1992 | (WO). |
| WO 93/02992 | 2/1993 | (WO). |
| WO 93/09668 | 5/1993 | (WO). |
| WO 88/01302 | 6/1993 | (WO). |
| WO 93/11262 | 6/1993 | (WO). |
| WO 93/17126 | 9/1993 | (WO). |
| WO 93/22456 | 11/1993 | (WO). |
| WO 93/22480 | 11/1993 | (WO). |
| WO 95/00530 | 1/1995 | (WO). |
| WO 95/11995 | 5/1995 | (WO). |
| WO 95/33846 | 12/1995 | (WO). |
| WO 96/23078 | 8/1996 | (WO). |
| WO 97/10365 | 3/1997 | (WO). |
| WO 97/17317 | 5/1997 | (WO). |
| WO 97/19410 | 5/1997 | (WO). |
| WO 97/27317 | 7/1997 | (WO). |
| WO 97/29212 | 8/1997 | (WO). |
| WO 98/31836 | 7/1998 | (WO). |

OTHER PUBLICATIONS

"Preparation of fluorescent–labeled DNA and its use as a probe in molecular hybridization," *Bioorg Khim.* 12(11):1508–1513 (1986).

Abbott et al., "Manipulation of the Wettability of Surfces on the 0.1– to 1–Micrometer Scale Through Micromachining and Molecular Self–Assembly," *Science,* 257:1380–1382 (1992).

Adams et al., "Complementary DNA Sequencing: Expressed Sequence Tags and Human Genome Project," *Science,* 252(5013):1651–1656 (1991).

Adams et al., "Photolabile Chelators That "Cage" Calcium with Improved Speed of Release and Pre–Photolysis Affinity," *J. Gen. Physiol.,* p. 9a (Dec. 1986).

Adams et al., "Biologically Useful Chelators That Take Up Ca2+ upon Illumination," *J. Am. Chem. Soc.,* 111:7957–7968 (1989).

Amit et al., "Photosensitive Protecting Groups of Amino Sugars and Their Use in Glycoside Synthesis. 2–Nitrobenzyloxycarbonylamino and 6–Nitroveratryloxycarbonylamino Derivatives," *J.Org.Chem,* 39(2):192–196 (1974).

Amit et al., "Photosensitive Protecting Groups—A Review," *Israel J. Chem.,* 12(1–2):103–113 (1974).

Applied Biosystems, Model 431A Peptide Synthesizer User's manual, Sections 2 and 6, (Aug. 15, 1989).

Ajayaghosh et al., "Solid–Phase Synthesis of N–Methyl– and N–Ethylamides of Peptides Using Photolytically Detachable ((3–Nitro–4((alkylamino)methyl)benzamido) methyl)polystyrene Resin," *J.Org.Chem.,* 55(9):2826–2829 (1990).

Ajayaghosh et al., "Solid–phase synthesis of C–terminal peptide amides using a photoremovable α–methylphenacylamido anchoring linkage," *Proc. Ind. Natl. Sci. (Chem.Sci.),* 100(5):389–396 (1988).

Ajayaghosh et al., "Polymer–supported Solid–phase Synthesis of C–Terminal Peptide N–Methylamides Using a Modified Photoremovable 3–Nitro–4–N–methylaminomethylpolystyrene Support," *Ind.J.Chem.,* 27B:1004–1008 (1988).

Ajayaghosh et al., "Polymer–Supported Synthesis of Protected Peptide Segments on a Photosensitive o–Nitro(α–Methyl)Bromobenzyl Resin," *Tetrahedron,* 44(21):6661–6666 (1988).

Arnold et al., "A Novel Universal Support for DNA & RNA Synthesis," abstract from Federation Proceedings, 43(7):abstract No. 3669 (1984).

Atherton et al., Solid Phase Peptide Synthesis: A Practical Approach, IRL Press, (1989), tbl. of cont., pp. vii–ix.

Augenlicht et al., "Cloning and Screening of Sequences Expressed in a Mouse Colon Tumor," *Cancer Research,* 42:1088–1093 (1982).

Augenlicht et al., "Expression of Cloned Sequences in Biopsies of Human Colonic Tissue and in Colonic Carcinoma Cells Induced to Differentiate in Vitro," *Cancer Res.,* 47:6017–6021 (1987).

Bains, W., "Hybridization Methods for DNA Sequencing," *Genomics,* 11(2):294–301 (1991).

Bains et al., "A Novel Method for Nucleic Acid Sequence Determination," *J.Theor.Biol.,* 135:303–307 (1988).

Bains, W., "Alternative Routes Through Genome," *Biotechnology,* 8:1251–1256 (1988).

Balachander et al., "Functionalized Siloxy–Anchored Monolayers with Exposed Amino, Azido, Bromo, or Cyano Groups," *Tetrahed. Ltrs.,* 29(44):5593–5594 (1988).

Baldwin et al, "New Photolabile Phosphate Protecting Groups," *Tetrahed.,* 46(19):6879–6884 (1990).

Barltrop et al., "Photosensitive Protective Groups," *Chemical Communications,* pp. 822–823 (1966).

Baringa, M., "Will 'DNA Chip' Speed Genome Initiative," *Science,* 253:1489 (1985).

Bart et al., "Microfabricated Electrohydrodynamic Pumps," *Sensors and Actuators,* A21–A23:193–197 (1990).

Bartsh et al., "Cloning of mRNA sequences from the human colon: Preliminary characterisation of defined mRNAs in normal and neoplastic tissues," *Br.J.Can.,* 54:791–798 (1986).

Baum, R., "Fledging firm targets drug discovery process," *Chem. Eng. News,* pp. 10–11 (1990).

Beltz et al., "Isolation of Multigene Families and Determination of Homologies by Filter Hybridization Methods," *Methods in Enzymology*, 100:266–285 (1983).

Benschop, Chem. Abstracts 114(26):256643 (1991).

Bhatia et al., "New Approach To Producing Patterned Biomolecular Assemblies," *J. American Chemical Society*, 114:4432–4433 (1992).

Biorad Chromatography Electrophoresis Immunochemistry Molecular Biology HPLC catalog M 1987 p. 182.

Blawas et al., "Step–and–Repeat Photopatterning of Protein Features Using Caged–Biotin–BSA: Characterization and Resolution," *Langmuir*, 14(15):4243–4250 (1998).

Blawas, A.S., "Photopatterning of Protein Features using Caged–biotin–Bovine Serum Albumin," dissertation for Ph.D at Duke University in 1998.

Bos et al., "Amino–acid substirutions at codon 13 of the N–ras oncogene in human acute myeloid leukaemia," *Nature*, 315:726–730 (1985).

Boyle et al., "Differential distribution of long and short interspersed element sequences in the mouse genome: Chromosome karyotyping by fluorescence in situ hybridization," *PNAS*, 87:7757–7761 (1990).

Brock et al., "Rapid fluorescence detection of in situ hybridization with biotinylated bovine herpesvirus–1 DNA Probes," *J.Veterinary Diagnostic Invest.*, 1:34–38 (1989).

Burgi et al., "Optimization in Sample Stacking for High–Performance Capillary Electrophoresis," *Anal. Chem.*, 63:2042–2047 (1991).

Cameron et al., "Photogeneration of Organic Bases from o–Nitrobenzyl–Derived Carbamates," *J. Am. Chem. Soc.*, 113:4303–4313 (1991).

Carrano et al., "A High–Resolution, Fluorescence–Based, Semiautomated Method for DNA Fingerprinting," *Genomics*, 4:129–136 (1989).

Caruthers, M.H., "Gene Synthesis Machines: DNA Chemistry and Its Uses," *Science*, 230:281–285 (1985).

Chatterjee et al., "Inducible Alkylation of DNA Using an Oligonucleotide–Quinone Conjugate," *Am. J. Chem. Soc.*, 112:6397–6399 (1990).

Chee et al., "Accessing Genetic Information with High–Density DNA Arrays," *Science*, 274:610–614 (1996).

Chehab et al., "Detection of sicle cell anaemia mutation by colour DNA amplification," *Lancet*, 335:15–17 (1990).

Chehab et al., "Detection of specific DNA sequences by fluorescence amplification: A color complementation assay," *PNAS*, 86:9178–9182 (1989).

Clevite Corp., Piezoelectric Technology, Data for Engineers.

Corbett et al., "Reaction of Nitroso Aromatics with Glyoxylic Acid. A New Path to Hydroxamic Acids," *J. Org. Chem.*, 45:2834–2839 (1980).

Craig et al., "Ordering of cosmid clones covering the Herpes simplex virus type 1 (HSV–1) genome: a test case for fingerprinting by hybridization," *Nuc. Acid. Res.*, 18(9):2653–2660 (1990).

Cummings et al., "Photoactivable Fluorophores. 1. Synthesis and Photoactivation of o–Nitrobenzyl–Quenched Fluorescent Carbamates," *Tetrahedron Letters*, 29(1):65–68 (1988).

Diggelmann, "Investigating the VLSIPS synthesis process," Sep. 9, 1994.

Di Mauro et al., "DNA Technology in Chip Construction," *Adv. Mater.*, 5(5):384–386 (1993).

Drmanac et al., "Partial Sequencing by Oligo–Hybridization Concept and Applications in Genome Analysis," 1st Int. Conf. Electrophor., Supercomp., Hum. Genome pp. 60–74 (1990).

Drmanac et al., "Sequencing by Oligonucleotide Hybridization: A Promising Framework in Decoding of the Genome Program?," 1st Int. Conf. Electrophor., Supercomp., Hum. Genome pp. 47–59 (1990).

Drmanac et al., "Laboratory Methods, Reliable Hybridization of Oligonucleotides as Short as Six Nucleotides," *DNA and Cell Biol.*, 9(7):527–534 (1990).

Drmanac et al., "Sequencing of Megabase Plus DNA by Hybridization: theory of the Method," *Genomics*, 4:114–128 (1989).

Dramanac et al., "Sequencing of Megabase Plus DNA by Hybridization: Theory of the Method," abstract of presentation given at Cold Spring Harbor Symposium on Genome Mapping and Sequencing, Apr. 27, 1988 thru May 1, 1988.

Dulcey et al., "Deep UV Photochemistry of Chemisorbed Monolayers: Patterned Coplanar Molecular Assemblies," *Science*, 252:551–554 (1991).

Duncan et al., "Affinity Chromatography of a Sequence–Specific DNA Binding Protein Using Teflon–Linked Oligonucleotides," *Analytical Biochemistry*, 169:104–108 (1988).

Effenhauser et al., "Glass Chips for High–speed Capillary Electrophoresis Separations with Submicrometer Plate Heights," Anal. Chem., 65:2637–2642 (1993).

Effenhauser et al., "High–Speed Separation of Antisense Oligonucleotides on a Micromachined Capillary Electrophoresis Device," *Anal. Chem.*, 66:2949–2953 (1994).

Ekins et al., "High Specific Activity Chemiluminescent and Fluorescent Markers: their Potential Application to High Sensitivity and 'Multi–analyte' Immunoassays," *J. Bioluminescence Chemiluminescence*, 4:59–78 (1989).

Ekins et al., "Development of Microspot Multi–Analyte Ratiometric Immunoassay Using dual Fluorescent–Labelled Antibodies," *Anal. Chemica Acta*, 227:73–96 (1989).

Ekins et al., "Multianalyte Microspot Immunoassay–Microanalytical 'Compact Disk' of the Future," *Clin. Chem.*, 37(11):1955–1967 (1991).

Ekins, R.P., "Multi–Analyte immunoassay*," *J. Pharmaceut. Biomedical Analysis*, 7(2):155–168 (1989).

Ekins et al., "Fluorescence Spectroscopy and its Application to a New Generation of High Sensitivity, Multi–Microspot, Multianalyte, Immunoassay," *Clin. Chim. Acta*, 194:91–114 (1990).

Evans et al., "Microfabrication for Automation of Molecular processes in Human Genome Analysis," *Clin. Chem.*, 41(11):1681 (1995).

Evans et al., "Physical mapping of complex genomes by cosmid multiplex analysis," *PNAS*, 86:5030–5034 (1989).

Ezaki et al., "Small–Scale DNA Preparation for Rapid Genetic Identification of campylobacter species without Radioisotope," *Microbiol. Immunology*, 32(2):141–150 (1988).

Fan et al., "Mapping small DNA sequences by fluorescence in situ hybridization directly on banded metaphase chromosomes," *PNAS*, 87(16):6223–6227 (1990).

Fan et al., "Micromachining of Capillary Electrophoresis Injectors and Separators on Glass Chips and Evaluation of Flow at Capillary Intersections," Anal. Chem., 66:177–184 (1994).

Fettinger et al., "Stacked modules for micro flow systems in chemical analysis: concept and studies using an enlarged model," *Sensors and Actuators*, B17:19–25 (1993).

Flanders et al., "A new interferometric alignment technique," *App. Phys. Ltrs.*, 31(7):426–429 (1977).

Fodor et al., "Multiplexed biochemical assays with biological chips," *Nature*, 364:555–556 (1993).

Fodor et al., "Light–directed, Spatially Addressable Parallel Chemical Synthesis," *Science*, 251:767–773 (1991).

Forman et al., "Thermodynamics of Duplex Formation and Mismatch Discrimination on Photolithographically Synthesized Oligonucleotide Arrays," chapter 13 pp. 206–228 from *Molecular Modeling of Nucleic Acids*, ACS Symposium Series 682, Apr. 13–17, 1997, Leontis et al., eds.

Frank et al., "Simultaneous Multiple Peptide Synthesis Under Continuous flow Conditions on Cellulose Paper Discs as Segmental Solid Supports," *Tetrahedron*, 44(19):6031–6040 (1988).

Frank et al., "Automation of DNA Sequencing Reactions and Related Techniques: A Workstation for Micromanipulation of Liquids," *Bio/Technology*, 6:1211–1212 (1988).

Frank et al., "Simultaneous Synthesis and Biological Applications of DNA Fragments: An Efficient and Complete Methodology," *Methods in Enzymology*, 154:221–250 (1987).

Fuhr et al., "Travelling wave–driven microfabricated electrohydrodynamic pumps for liquids," *J. Micromech. Microeng.*, 4:217–226 (1994).

Fuller et al., "Urethane–Protected Amino Acid N–Carboxy Anhydrides and Their Use in Peptide Synthesis," *J. Amer. Chem. Soc.*, 112(20):7414–7416 (1990).

Furka et al., "General method for rapid synthesis of multicomponent peptide mixtures," *Int. J. Peptide Protein Res.*, 37:487–493 (1991).

Furka et al., "Cornucopia of Peptides by Synthesis," 14th Int. Congress of Biochem. abst.# FR:013, Jul. 10–15, 1988 Prague, Czechoslavakia.

Furka et al., "More Peptides by Less Labour," abst. 288, Int. Symp. Med. Chem., Budapest Hungary Aug. 15–19, 1988.

Gait, eds., pp. 1–115 from *Oligonucleotide Synthesis: A Practical Approach*, IRL Press, (1984).

Gazard et al., "Lithographic Technique Using Radiation–Induced Grafting of Acrylic Acid into Poly(Methyl Methacrylate) Films," *Polymer Engineering and Science*, 20(16):1069–1072 (1980).

Gergen et al., "Filter replicas and permanent collections of recombinant DNA plasmids," *Nuc. Acids Res.*, 7(8):2115–2137 (1979).

Getzoff et al., "Mechanisms of Antibody Binding to a Protein," *Science*, 235:1191–1196 (1987).

Geysen et al., "Strategies for epitope analysis using peptide synthesis," *J. Immunol. Meth.*, 102:259–274 (1987).

Geysen et al., "Use of peptide synthesis to probe viral antigens for epitopes to a resolution of a single amino acid," *PNAS*, 81:3998–4002 (1984).

Geysen et al., "A synthetic strategy for epitope mapping," from Peptides:Chem. & Biol., Proc. of 10th Am. Peptide Symp., May 23–28, 1987, pp. 519–523, (1987).

Geysen, "Antigen–antibody interactions at the molecular level: adventures in peptide synthesis," *Immunol. Today*, 6(12):364–369 (1985).

Geysen et al., "Cognitive Features of Continuous Antigenic Determinants," from Synthetic Peptides: Approaches to Biological Probes, pp. 19–30, (1989).

Geysen et al., "Chemistry of Antibody Binding to a Protein," *Science*, 235:1184–1190 (1987).

Geysen et al., "The delineation of peptides able to mimic assembled epitopes," 1986 CIBA Symp., pp. 130–149.

Geysen et al., "Cognitive Features of Continuous Antigenic Determinants," *Mol. Recognit.*, 1(1):1–10 (1988).

Geysen et al., "A Prio Ri Delineation of a Peptide Which Mimics A Discontinuous Antigenic Determinant," *Mol. Immunol.*, 23(7):709–715 (1986).

Gilon et al., "Backbone Cyclization: A New Method for Conferring Conformational Constraint on Peptides," *Biopolymers*, 31(6):745–750 (1991).

Gingeras et al., "Hybridization properties of immobilized nucleic acids," *Nuc. Acids Res.*, 15(13):5373–5390 (87).

Gummerlock et al., "RAS Enzyme–Linked Immunoblot Assay Discriminates p21 Species: A Technique to Dissect Gene Family Expression," *Anal. Biochem.*, 180:158–168 (1989).

Gurney et al., "Activation of a potassium current by rapid photochemically generated step increases of intracellular calcium in rat sympathetic neurons," *PNAS*, 84:3496–3500 (1987).

Haase et al., "Detection of Two Viral Genomes in Single Cells by Double–Label Hybridization in Situ and Color Microradioautography," *Science*, 227:189–192 (1985).

Hacia, et al., "Two color hybridization analysis using high density oligonucleotide arrays and energy transfer dyes," *Nuc. Acids Res.*, 26(16):3865–3866 (1998).

Hack, M.L., "Conics Formed to Make Fluid & Industrial Gas Micromachines," *Genetic Engineering News*, 15(18):1, 29 (1995).

Hagedorn et al., "Pumping of Water Solutions in Microfabricated Electrohydrodynamic Systems," from Micro Electro Mechanical Systems conference in Travemunde Germany (1992).

Hames et al., *Nuclear acid hybridization, a practical approach*, cover page and table of contents (1985).

Hanahan et al., "Plasmid Screening at High Colony Density," *Meth. Enzymology*, 100:333–342 (1983).

Hanahan et al., "Plasmid screening at high colony density," *Gene*, 10:63–67 (1980).

Haridasan et al., "Peptide Synthesis using Photolytically Cleavable 2–Nitrobenzyloxycarbonyl Protecting Group," *Proc. Indian Natn. Sci. Acad.*, 53A(6):717–728 (1987).

Harrison et al., "Capillary Electrophoresis and Sample Injection Systems Integrated on a Planar Glass Chip," *Anal. Chem.*, 64:1926–1932 (1992).

Harrison et al., "Micromachining a Minaturized Capillary Electrophoresis–Based Chemical Analysis System on a Chip," Science, 261:895–897 (1993).

Harrison et al., "Towards minaturized electrophoresis and chemical analysis systems on silicon: an alternative to chemical sensors*," *Sensors and Actuators*, B10:107–116 (1993).

Harrison et al., "Rapid separation of fluorescein derivatives using a micromachined capillary electrophoresis system," *Analytica Chemica Acta*, 283:361–366 (1993).

Hellberg et al., "Minimum analogue peptide sets (MAPS) for quantitative structure–activity relationships," *Int. J. Peptide Protein Res.*, 37:414–424 (1991).

Hilser et al., "Protein and peptide mobility in capillary zone electrophoresis, A comparison of existing models and further analysis," *J. Chromatography*, 630:329–336 (1993).

Ho et al., "Highly Stable Biosensor Using an Artificial Enzyme," *Anal. Chem.*, 59:536–537 (1987).

Hochgeschwender et al., "Preferential expression of a defined T–cell receptor β–chain gene in hapten–specific cytotoxic T–cell clones," *Nature*, 322:376–378 (1986).

Hodgson, J., "Assays A La Photolithography," *Biotech.*, 9:419 (1991).

Hopman et al., "Bi–color detection of two target DNAs by non–radioactive in situ hybridization*," *Histochem.*, 85:1–4 (1986).

Iwamara et al., "1–Pyrenylmethyl Esters, Photolabile Protecting Groups for Carboxlic Acids," *Tetrahedron Ltrs.*, 28(6):679–682 (1987).

Iwamura et al., "1–(α–Diazobenzyl)pyrene: A Reagent for Photolabile and Fluorescent Protection of Carboxyl Groups of Amino Acids and Peptides," *Synlett*, pp. 35–36 (1991).

Jacobson et al., "Effects of Injection Schemes and Column Geometry on the Performance of Microchip Electrophoresis Devices," Anal. Chem., 66:1107–1113 (1994).

Jacobsen et al., "Open Channel Electrochromatrography on a Microchip," Anal. chem., 66:2369–2373 (1994).

Jacobson et al., "Microchip Capillary Electrophoresis with an Integrated Postcolumn Reactor" Anal. Chem., 66:3472–3476 (1994).

Jacobson et al., "Precolumn Reactions with Electrophoretic Analysis Integrated on a Microchip," *Anal. Chem.*, 66:4127–4132 (1994).

Jacobson et al., "Microfabricated chemical measurement systems," *Nature Medicine*, 1(10:1093–1096 (1995).

Jacobsen et al., "Fused Quartz Substrates for Microchip Electrophoresis," *Anal. chem.*, 67:2059–2063 (1995).

Jacobson et al., "High–Speed Separtions on a Micrchip," Anal. Chem., 66:1114–1118 (1994).

Jacobson et al., "Microchip electrophoresis with sample stacking," *Electrophoresis*, 16:481–486 (1995).

Jayakumari, "Peptide synthesis in a triphasic medium catalysed by papain immobilized on a crosslinked polystyrene support,"0 *Indian J. Chemistry*, 29B:514–517 (1990).

Kaiser et al., "Peptide and Protein Synthesis by Segment Synthesis–Condensation," *Science*, 243:187–192 (1989).

Kaplan et al., "Photolabile chelators for the rapid photorelease of divalent cations," *PNAS*, 85:6571–6575 (1988).

Karube, "Micro–biosensors based on silicon fabrication technology," chapter 25 from Biosensors:Fundamentals and Applications, Turner ed al., eds., Oxford Publ., 1987, pp. 471–480 (1987).

Kates et al., "A Novel. Convenient, Three–dimensional Orthogaonal Strategy for Solid–Phase Synthesis of Cyclic Peptides 1–3," *Tetrahed. Letters*, 34(10):1549–1552 (1993).

Kerkof et al., "A Procedure for Making Simultaneous Determinations of the Relative Levels of Gene Transcripts in Tissues or Cells," *Anal. Biochem.*, 188:349–355 (1990).

Khrapko et al., "An Oligonucleotide hybridization approach to DNA sequencing," *FEBS Lett.*, 256(1,2):118–122 (1989).

Kievits et al., "Rapid subchromosomal localization of cosmids by nonradioactive in situ hybridization," *Cytogenetics Cell Genetics*, 53(2–3):134–136 (1990).

Kimura et al., "An Immobilized Enzyme Membrane Fabrication Method using an Ink Jet Nozzle," *Biosensors*, 4:41–52 (1988).

Kimura et al., "An Integrated SOS/FET Multi–Biosensor," *Sensors & Actuators*, 9:373–387 (1986).

Kitazawa et al., "In situ DNA–RNA hybridization using in vivo bromodeoxyuridine–labeled DNA probe," *Histochemistry*, 92:195–199 (1989).

Kleinfeld et al., "Controlled Outgrowth of Dissociated Neurons on Patterned Substrates," *J. Neurosci.*, 8(11):4098–4120 (1988).

Knight, P., "Materials and Methods/Microsequencers for Proteins and Oligosaccharides," *Bio/Tech.*, 7:1075–76 (1989).

Kohara et al., "The Physical Map of the Whole E. coli Chromosome: Application of a New Strategy for Rapid Analysis and Sorting of a Large Genomic Library," *Cell*, 50:495–508 (1987).

Krile et al., "Multiplex holography with chirp–modulated binary phase–coded reference–beam masks," *Applied Opt.*, 18(1):52–56 (1979).

Labat, I., "Subfragments as an informative characteristic of the DNA molecule—computer simulation," research report submitted to the University of Belgrade College of Natural Sciences and Mathematics, (1988).

Lainer et al., "Human Lymphocyte Subpopulations Identified by Using Three–Color Immunofluorescence and Flow Cytometry Analysis: Correlation of Leu–2, Leu–3, Leu–7, Leu–8, and Leu–11 Clee Surface Antigen Expression," *Journal of Immunology*, 132(1):151–156 (1984).

Lam et al., "A new type of synthetic peptide library for identifying ligand–binding activity," *Nature*, 354:82–84 (1991).

Laskey et al., "Messenger RNA prevalence in sea urchin embryos measured with cloned cDNAs," *PNAS*, 77(9):5317–5321 (1980).

Lee et al., "synthesis of a Polymer Surface Containing Covalently Attached Triethoxysilane Functionality: Adhesion to Glass," *Macromolecules*, 21:3353–3356 (1988).

Lehrach et al., "Labelling oligonucleotides to high specific activity (I)," *Nuc. Acids Res.*, 17(12):4605–4610 (89).

Lehrach et al., "Phage Vectors—EMBL Series," *Meth. Enzymology*, 153:103–115 (1987).

Levy, M.F., "Preparing Additive Printed Circuits," *IBM Tech. Discl. Bull.*, 9(11):1473 (1967).

Lichter et al., "High–Resolution Mapping of Human Chromosome 11 by in Situ hybridization with Cosmid Clones," *Science*, 247:64–69 (1990).

Lichter et al., "Fluorescence in situ hybridization with Alu and L1 polymerase chain reaction probes for rapid characterization of human chromosomes in hybrid cell lines," *PNAS*, 87:6634–6638 (1990).

Lichter et al., "Rapid detection of human chromosome 21 aberrations by in situ hybridization," *PNAS*, 85:9664–9668 (1988).

Lichter et al., "Is non–isotopic in situ hybridization finally coming of age," *Nature*, 345:93–94 (1990).

Lieberman et al., "A Light source Smaller Than the Optical Wavelength," *Science*, 247:59–61 (1990).

Lipshutz et al., "Using Oligonucleotide Probe Arrays To Access Genetic Diversity," *BioTech.*, 19(3):442–7 (1995).

Liu et al., "Sequential Injection Analysis in Capillary Format with an Electroosmotic Pump," *Talanta*, 41(11):1903–1910 (1994).

Lockhart et al., "Expression monitoring by hybridization to high–density oligonucleotide arrays," *Nat. Biotech.*, 14:1675–1680 (1996).

Logue et al., "General Approaches to Mask Design for Binary Optics," SPIE, 1052:19–24 (1989).

Loken et al., "three–color Immunofluorescence Analysis of Leu Antigens on Human Peripharal Blood Using Two Lasers on a Fluorescence–Activated Cell Sorter," *Cymoetry*, 5:151–158 (1984).

Love et al., "Screening of λ Library for Differentially Expressed Genes Using in Vitro Transcripts," *Anal. Biochem.*, 150:429–441 (1985).

Lowe, C.R., "Biosensors," *Trends in Biotech.*, 2:59–65 (1984).

Lowe, C.R., "An Introduction to the Concepts and Technology of Biosensors," *Biosensors*, 1:3–16 (1985).

Lowe, C.R., Biotechnology and Crop Improvement and Protection, BCPC Publications, pp. 131–138 (1986).

Lowe et al., "Solid–Phase Optoelectronic Biosensors," *Methods in Enzymology*, 137:338–347 (1988).

Lowe, C.R., "Biosensors," *Phil. Tran. R. Soc. Lond.*, 324:487–496 (1989).

Lu et al., "Differential screening of murine ascites cDNA libraries by means of in vitro transcripts of cell–cycle–phase–specific cDNA and digital image processing," *Gene*, 86:185–192 (1990).

Lysov et al., "A new method for determining the DNA nucleotide sequence by hybridization with oligonucleotides," *Doklady Biochem.*, 303(1–6):436–438 (1989).

Lysov et al., "DNA Sequencing by Oligonucleotide Hybridization," First International Conference on Electrophoresis, Supercomputing and the Human Genome, Apr. 10–13, 1990 p. 157.

MacDonald et al., "A Rapid ELISA for Measuring Insulin in a Large No. of Research Samples," *Metabolism*, 38(5):450–452 (1989).

Mairanovsky, V.G., "Electro–Deprotection–Electrochemical Removal of Protecting Groups**," *Agnew. Chem. Int. Ed. Engl.*, 15(5):281–292 (1976).

Manz et al., "Miniaturized Total Chemical Analysis Systems: a Novel Concept for Chemical Sensing," *Sensors and Actuators*, B1:244–248 (1990).

Manz et al., "Micromachining of monocrystalline silicon and glass for chemical analysis systems, A look into next century's technology or just a fashionable craze?," *Trends in Analytical Chem.*, 10(5):144–149 (1991).

Manz et al., "Planar chips technology for minaturization and integration of separation techniques into monitoring systems, Capillary electrophoresis on a chip," J. Chromatography, 593:253–258 (1992).

Manz et al., "Planar Chips Technology for Miniaturization of Separation Systems: A Developing Perspective in Chemical Monitoring," chapter 1, 1–64 (1993).

Manz et al., "Electroosmotic pumping and electrophoretic separations for miniaturized chemical analysis systems," *J. Micromech. Microeng.*, 4:257–265 (1994).

Masiakowski et al., "Cloning of cDNA sequences of hormone–regulated genes from the MCF–7 human breast cancer cell line," *Nuc. Acids Res.*, 10(24):7895–7903 (1982).

Matsumoto et al., "Preliminary Investigation of Micropumping Based on Electrical Control of Interfacial Tension," *IEEE*, pp. 105–110 (1990).

Matsuzawa et al., "Containment and growth of neuroblastoma cells on chemically patterned substrates," *J. Neurosci. Meth.*, 50:253–260 (1993).

McCray et al., "Properties and Uses of Photoreactive Caged Compounds," *Ann. Rev. Biophys. Biophys. Chem.*, 18:239–270 (1989).

McGall et al., "The Efficiency of Light–Directed Synthesis of DNA Arrays on Glass Substrates," *J. American Chem. Soc.*, 119(22):5081–5090 (1997).

McGillis, VLSI Technology, Sze, eds., Chapter 7, "Lithography," pp. 267–301 (1983).

McMurray, J.S., "Solid Phase Synthesis of a Cyclic Peptide Using Fmoc Chemistry," *Tetrahedron Letters*, 32(52):7679–7682 (1991).

Meinkoth et al., "Review: Hybridization of Nucleic Acids Immobilized on solid Supports," *Analytical Biochem.*, 138:267–284 (1984).

Melcher et al., "Traveling–Wave Bulk Electroconvection Induced across a Temperature Gradient," *Physics of Fluids*, 10(6):1178–1185 (1967).

Merrifield, R.B., "Solid Phase peptide Synthesis. I. The Synthesis of a Tetrapeptide," *J.Am.Chem.Soc.*, 85:2149–2154 (1963).

Michiels et al., "Molecular approaches to genome analysis: a strategy for the construction of ordered overlapping clone libraries," *CABIOS*, 3(3):203–10 (1987).

Mirzabekov, A.D., "DNA sequencing by hybridization—a megasequencing method and a diagnostic tool?," *TEBTECH*, 12:27–32 (1994).

Monaco et al., "Human Genome Linking with Cosmids and Yeast Artificial Chromosomes", abstract from CSHS, p. 50, (1989).

Morita et al., "Direct pattern fabrication on silicone resin by vapor phase electron beam polymerization," *J.Vac.Sci.Technol.*, B1(4):1171–1173 (1983).

Morrison et al., "Solution–Phase Detection of Polynucleotides Using Interacting Fluorescent Labels and Competitive Hybridization," *Anal. Biochem.*, 183:231–244 (1989).

Munegumi et al., "thermal Synthesis of Polypeptides from N–Boc–Amino Acid (Aspartic Acid, β–Aminoglutaric Acid) Anhydrides," *Chem. Letters*, pp. 1643–1646 (1988).

Mutter et al., "Impact of Conformation on the Synthetic Strategies for Peptide Sequences," pp. 217–228 from Chemistry of Peptides and Proteins, vol. 1, Proceedings of the Third USSR–FRG Symp., in USSR (1982).

Nakamori et al., "A Simple and Useful Method for Simultaneous Screening of Elevated Levels of Expression of a Variety of Oncogenes in Malignant Cells," *Jpn. J. Cancer Res.*, 79:1311–1317 (1988).

Nederlof et al., "Multiple Fluorescence In Situ Hybridization," *Cytometry*, 11:126–131 (1990).

Nyborg, W., "Acoustic Streaming," chapter 11 pp. 265–329 from Physical Acoustics, Principles and Methods, Mason, eds., vol. II, part B, Academic Press, New York and London (1965).

Ocvirk et al., "High Performance Liquid Chromatography Partially Integrated onto a Silicon Chip," *Analyt. Meth. Instrumentation*, 2(2):74–82 (1995).

Ohtsuka et al., "Studies on transfer ribonucleic acids and related compounds. IX Ribonucleic oligonucleotide synthesis using a photosensitive 0–nitrobenzyl protection at the 2'–hydroxl group," *Nuc.Acids.Res.*, 1(10):1351–1357 (1974).

Olefirowicz et al., "Capillary Electrophoresis for Sampling Single Nerve Cells," *Chimia*, 45(4):106–108 (1991).

Patchornik et al., "Photosensitive Protecting Groups," *J.Am. Chem.Soc.*, 92(21):6333–6335 (1970).

Patent Abstracts of Japan from EPO, Abst. 13:557, JP 1–233 447 (1989).

Pease et al., "Light–generated oligonucleotide arrays for rapid DNA sequence analysis," *PNAS*, 901:5022–26 (1994).

Pevzner, P.A., "1–Tuple DNA Sequencing: Computer Analysis," *J. Biomol. Struct. Dynam.*, 7(1):63–69 (1989).

Pfahler et al., "Liquid Transport in Micron and Submicron Channels," *Sensors and Actuators*, A21–A23:431–4 (90).

Pidgeon et al., "Immobilized Artificial Membrane Chromatography: Supports Composed of Membrane Lipids," *Anal. Biochem.*, 176:36–47 (89).

Pillai, V.N., "Photoremovable Protecting Groups in Organic Synthesis," *Synthesis*, pp. 1–26 (1980).

Pillai et al., "3–Nitro–4 Aminomethylbenzoylderivate von Polyethylenglykolen: Eine neue Klasse von Photosensitiven loslichen Polymeren Tragern zur Synthese von C–terminalen Peptiamiden," *Tetrah. ltr.*, # 36 pp. 3409–3412 (1979).

Pillai et al., "Synthetic Hydrophilic Polymers, Biomedical and Chemical Applications," *Naturwissenschaften*, 68:558–566 (1981).

Pirrung et al., "Proofing of Photolithographic DNA Synthesis with 3',5'–Dimethoxybenzoinyloxycarbonyl–Protected Deoxynucleoside Phosphoramidites," *J. Org. Chem.*, 63(2):241–246 (1998).

Pirrung et al., "Comparison of Methods for Photochemical Phosphoramidite–Based DNA Synthesis," *J. Org. Chem.*, 60:6270–6276 (1995).

Ploax et al., "Cyclization of peptides on a solid support," *Int. J. Peptide Protein Research*, 29:162–169 (1987).

Polsky–Cynkin et al., "Use of DNA Immobilized on Plastic and Agarose Supports to Detect DNA by Sandwich Hybridization," *Clin. Chem.*, 31(9):1428–1443 (1985).

Poustka et al., "Molecular Approaches to Mammalian Genetics," Cold Spring Harbor Symposia on Quantitive Biology, 51:131–139 (1986).

Purushothaman et al., "Synthesis of 4,5–diarylimidazoline–2–thiones and their photoconversion to bis(4,5–diarylimidazol–2–yl) sulphides," *Ind. J. Chem.*, 29B:18–21 (1990).

Quesada et al., "High–Sensitivity DNA Detection with a Laser–Exited Confocal Fluorescence Gel Scanner," *Biotechniques*, 10:616 (1991).

Reichmanis et al., *J. Polymer Sci. Polymer Chem. Edition*, 23:1–8 (1985).

Richter et al., "An Electrohydrodynamic Micropump," *IEEE*, pp. 99–104 (1990).

Richter et al., "Electrohydrodynamic Pumping and Flow Measurement," *IEEE*, pp. 271–276 (1991).

Richter et al., "A Micromachined electrohydrodynamic (EHD) pump," *Sensors and Actuators*, A29:159–168 (91).

Robertson et al., "A General and Efficient Route for Chemical Aminoacylation of Transfer RNAs," *J. Am. Chem. Soc.*, 113:2722–2729 (1991).

Rodda et al., "The Antibody Response to Myoglobin–1. Systematic Synthesis of Myglobin Peptides Reveals Location and Substructure of Species–Dependent Continuous Antigenic Determinants," *Mol. Immunol.*, 23(6):603–610 (1986).

Rodgers, R.P., "Data Processing of Immunoassay Results," Manual of Clin. Lab. Immunol., 3rd ed., ch. 15, pp. 82–87 (1986).

Rose, D.J., "Free–solution reactor for post–column fluorescence detection in capillary zone electrophoresis," *J. Chromatography*, 540:343–353 (1991).

Rovero et al., "Synthesis of Cylic Peptides on solid Support," *Tetrahed. Letters*, 32(23):2639–2642 (1991).

Sambrook, Molecular Cloning—A Laboratory Manual, publ. in 1989 (not included).

Saiki et al., "Genetic analysis of amplified DNA with immobilized sequence–specific oligonucleotide probes," *PNAS*, 86:6230–6234 (1989).

Saiki et al., "Analysis of enzymatically amplified β–globin and HLA–DQα DNA with Allele–specific oligonucleotide probes," *Nature*, 324:163–166 (1986).

Scharf et al., "HLA class II allelic variation and susceptibility to pemphigus vulgaris," *PNAS*, 85(10):3504–3508 (1988).

Schuup et al., "Mechanistic Studies of the Photorearrangement of o–Nitrobenzyl Esters," *J. Photochem.*, 36:85–97 (1987).

Seiler et al., "Planar Glass Chips for Capillary Electrophoresis: Repetitive Sample Injection. Quantitation, and Separation Efficiency," *Anal. Chem.*, 65:1481–1488 (1993).

Seller et al., "Electroosmotic Pumping and Valveless Control of Fluid Flow within a Manifold of Capillaries on a Glass Chip," Anal. Chem., 66:3485–3491 (1994).

Semmelhack et al., "Selective Removal of Protecting Groups Using Controlled Potential Electrolysis," *J. Am. Chem. Society*, 94(14):5139–5140 (1972).

Sheldon et al., "Matrix DNA Hybridization," *Clinical Chemistry*, 39(4):718–719 (1993).

Shin et al., "Dehydrooligonpeptides. XI. Facile Synthesis of Various Kinds of Dehydrodi– and tripeptides, and Dehydroenkephalins Containing Tyr Residue by Using N–Carboxydehydrotyrosine Anyhydride," *Bull. Chem. Soc. Jpn.*, 62:1127–1135 (1989).

Sim et al., "Use of a cDNA Library for Studies on Evolution and Developmental Expression of the Chorion Multigene Families," *Cell*, 18:1303–1316 (1979).

Smith et al., "A Novel Method for Delineating Antigenic Determinants: Peptide Synthesis and Radioimmunoassay Using the Same Solid Support," *Immunochemistry*, 14:565–568 (1977).

Southern et al., "Report on the Sequencing by Hybridization Workshop," *Genomics*, 13:1378–1383 (1992).

Southern et al., "Oligonucleotide hybridisations on glass supports: a novel linker for oligonucleotide synthesis and hybridization properties of oligonucleotides synthesized in situ," *Nuc. Acids Res.*, 20(7):1679–1684 (1992).

Southern et al., "Analyzing and Comparing Nucleic Acid Sequences by Hybridization to Arrays of Oligonucleotides: Evaluation Using Experimental Models," Genomics, 13:1008–10017 (1992).

Stemme et al., "A valveless diffuser/nozzle–based fluid pump," *Sensors and Actuators*, A39:159–167 (1993).

Stryer, L., "DNA Probes and Genes Can by Synthesized by Automated Solid–Phase Methods," from *Biochemistry*, Third Edition, published by W.H. Freeman & Co., (1988).

Stuber et al., "Synthesis and photolytic cleavage of bovine insulin B22–30 on a nitrobenzoylglycl–poly (ethylene glycol) support," *Int. J. Peptide Protein Res.*, 22(3):277–283 (1984).

Sundberg et al., "Spatially–Addressable Immobilization of Macromolecules on Solid Supports," *J. Am. Chem. Soc.*, 117(49):12050–12057 (1995).

Swedberg, S.A., "Use of non–ionic and zwitterionic surfactants to enhance selectivity in high–performance capillary electrophoresis, An apparant micellar electrokinetic capillary chromatography mechanism," *J. Chromatography*, 503:449–452 (1990).

Titus et al., "Texas Red, a Hydrophilic, red–emitting fluorophore for use with fluorescein in dual parameter plow microfluorometric and fluorescence microscopic studies," *J. Immunol. Meth.*, 50:193–204 (1982).

Tkachuk et al., "Detection of bcr–abl Fusion in chronic Myelogeneous Leukemia by in situ Hybridization," *Science*, 250:559–562 (90).

Trzeciak et al., "Synthesis of 'Head–to–Tail' Cyclized Peptides on Solid Support by FMOC Chemistry," *Tetrahed. Letters*, 33(32):4557–4560 (1992).

Tsien et al., "Control of Cytoplasmic Calcium with Photolabile Tetracarboxylate 2–Nitrobenzhydrol Chelators," *Biophys. J.*, 50:843–853 (1986).

Tsutsumi et al., "Expression of L– and M– Type Pyruvate Kinase in Human Tissues," *Genomics*, 2:86–89 (1988).

Turchinskii et al., "Multiple Hybridization in Genome Analysis, Reaction of Diamines and Bisulfate with Cytosine for Introduction of Nonradioactive labels Into DNA," *Molecular Biology*, 22:1229–1235 (1988).

Turner et al., "Photochemical Activation of Acylated α–Thrombin," *J. Am. Chem. Soc.*, 109:1274–1275 (1987).

Urdea et al., "A novel method for the rapid detection of specific nucleotide sequences in crude biological samples without blotting or radioactivity; application to the anaylsis of hepatitis B virus in human serum," Gene, 61:253–264 (1987).

Urdea et al., "A comparison of non–radioisotopic hybridization assay methods using fluorescent, chemiluminescent and enzyme labeled synthetic oligodeoxyribonucleotide probes," *Nuc. Acids Res.*, 16(11):4937–4956 (1988).

Van der Voort et al., "Design and Use of a Computer Controlled Confocal Microscope for Biological Applications," *Scanning*, 7(2):66–78 (1985).

Van Hijfte et al., "Intramolecular 1,3–Diyl Trapping Reactions. A Formal Total Synthesis of –Coriolin," J. Organic Chemistry, 50:3942–3944 (1985).

Veldkamp, W.B., "Binary optics: the optics technology of the 1990s," CLEO 90, vol. 7, paper # CMG6 (1990).

Verlaan–de Vries et al., "A dot–blot screening procedure for mutated ras oncogenes using synthetic oligodeoxynucleotides," *Gene*, 50:313–320 (1986).

Verpoorte et al., "Three–dimensional micro flow manifolds for miniaturized chemical analysis systems," *J. Micromech. Microeng.*, 4:246–256 (1994).

Volkmuth et al., "DNA electrophoresis in microlithographic arrays," *Nature*, 358:600–602 (1992).

Voss et al., "The immobilization of oligonucleotides and their hybridization properties," *Biochem. Soc. Transact.*, 16:216–217 (1988).

Walker et al., "Photolabile Protecting Groups for an Acetylcholine Receptor Ligand. Synthesis and Photochemistry of a New Class of o–Nitrobenzyl Derivatives and their Effects on Receptor Function," *Biochemistry*, 25:1799–1805 (1986).

Wallace et al., "Hybridization of synthetic oligodeoxyribonucleotides to $\Phi\chi$ 174 DNA: the effect of single base pair mismatch," *Nuc. Acids. Res.*, 11(6):343–3557 (1979).

Washizu et al., "Handling Biological Cells Using a Fluid Integrated Circuit," *IEEE Transactions Industry Applications*, 26(2):352–358 (1990).

Werner et al., "Size–Dependent Separation of Proteins Denatured in SDS by Capillary Electrophoresis Using a Replaceable Sieving Matrix," *Anal. Biochem.*, 212:253–258 (1993).

White et al., "An Evaluation of Confocal Versus Conventional Imaging of Biological Structures by Fluorescence Light Microscopy," *J. Cell Biol.*, 105(1):41–48 (1987).

Widacki et al., "Biochemical Differences in Qa–2 Antigens Expressed by Qa–2+,6+ and Qa–2a+,6– Strains. Evidence for Differential Expression of the Q7 and Q9 Genes," *Mol. Immunology*, 27(6):559–570 (1990).

Wilcox et al., "Synthesis of Photolabile 'Precursors' of Amino Acid Neurotransmitters," *J. Org. Chem.*, 55:1585–1589 (1990).

Wilding et al., "PCR in a Silicon Microstructure," *Clin. Chem.*, 40(9):1815–1818 (1994).

Wilding et al., "Manipulation and Flow of Biological Fluids in Straight Channels Micromachined in Silicon," *Clin. Chem.*, 40(1):43–47 (1994).

Wittman–Liebold, eds., Methods in Protein Sequence Analysis, from Proceedings of 7th Int'l Conf., Berlin, Germany, Jul. 3–8, 1988, table of contents, pp. xi–xx* (1989).

Woolley et al., "Ultra–high–speed DNA fragment separations using microfabricated capillary array electrophoresis chips," *PNAS*, 91:11348–11352 (1994).

Wu et al., "Synthesis and Properties of Adenosine–5'–triphosphor–$\gamma$–5–(5–sulfonic acid)naphthyl Ethylamidate: A Fluorescent Nucleotide Substrate for DNA–Dependent RNA Polymerase from *Escherichia coli*," *Arch. Biochem. Biophys.*, 246(2):564–571 (1986).

Wu et al., "Laboratory Methods, Direct Analysis of Single Nucleotide Variation in Human DNA and RNA Using In Situ Dot Hybridization," *DNA*, 8(2):135–142 (1989).

Yamamoto et al., "Features and applications of the laser scanning microscope," *J. Mod. Optics*, 37(11):1691–1701 (1990).

Yarbrough et al., "Synthesis and Properties of Fluorescent Nucleotide Substrates for DNA–dependent RNA Polymerases," *J. Biol. Chem.*, 254(23):12069–12073 (1979).

Yosomiya et al., "Performance, Glass fiber Having Isocyanate Group on the Surface. Preparation and Reaction with Amino Acid," *Polymer Bulletin*, 12:41–48 (1984).

Young, W.S., "Simultaneous Use of Digoxigenin– and Radiolabeled Oligodeoxyribonucleotide Probes for Hybridization Histochemistry," *Neuropeptides*, 13:271–275 (1989).

Yue et al., "Miniature Field–Flow Fractionation System for Analysis of Blood Cells," *Clin. Chem.*, 40(9):1810–1814 (1994).

Zehavi et al., "Light–Sensitive Glycosides. I 6–Nitroveratryl $\beta$–D–Glucopyranoside and 2–Nitrobenzyl $\beta$–D–Glucopyranoside," *J. Org. Chem*, 37(14):2281–2285 (1972).

Zengerle et al., "Transient measurements on miniaturized diaphragm pumps in microfluid systems," *Sensors and Actuators*, A46–47:557–561 (1995).

* cited by examiner

METHOD FOR COMPARING COPY NUMBER OF NUCLEIC ACID SEQUENCES

CROSS-REFERENCE TO RELATED APPLICATIONS

This is a continuation-in-part of U.S. Ser. No. 08/529,115 filed on Sep. 15, 1995, now U.S. Pat. No. 5,040,138, which is herein incorporated by reference for all purposes. This application is also a continuation-in-part of U.S. Ser. No. 08/670,118 filed on Jun. 25, 1996, now U.S. Pat. No. 5,800,992, which is a division of U.S. Ser. No. 08/168,904 filed Dec. 15, 1993, now abandoned, which is a continuation of U.S. Ser. No. 07/624,114 filed Dec. 6, 1990, now abandoned. U.S. Ser. No. 07/624,114 is a CIP of U.S. Ser. No. 07/362,901 filed Jun. 7, 1989, now abandoned. All of the above applications are incorporated herein by reference.

BACKGROUND OF THE INVENTION

A portion of the disclosure of this patent document contains material which subject to copyright protection. The copyright owner has no objection to the xerographic reproduction by anyone of the patent document or the patent disclosure in exactly the form it appears in the Patent and Trademark Office patent file or records, but otherwise reserves all copyright rights whatsoever.

Many disease states are characterized by differences in the expression levels of various genes either through changes in the copy number of the genetic DNA or through changes in levels of transcription (e.g. through control of initiation, provision of RNA precursors, RNA processing, etc.) of particular genes. For example, losses and gains of genetic material play an important role in malignant transformation and progression. These gains and losses are thought to be "driven" by at least two kinds of genes. Oncogenes are positive regulators of tumorgenesis, while tumor suppressor genes are negative regulators of tumorgenesis (Marshall, Cell, 64: 313–326 (1991); Weinberg, Science, 254: 1138–1146 (1991)) incorporated herein by reference for all purposes. Therefore, one mechanism of activating unregulated growth is to increase the number of genes coding for oncogene proteins or to increase the level of expression of these oncogenes (e.g. in response to cellular or environmental changes), and another is to lose genetic material or to decrease the level of expression of genes that code for tumor suppressors. This model is supported by the losses and gains of genetic material associated with glioma progression (Mikkelson et al. J. Cellular Biochm. 46: 3–8 (1991)). Thus, changes in the expression (transcription) levels of particular genes (e.g. oncogenes or tumor suppressors), serve as signposts for the presence and progression of various cancers.

Similarly, control of the cell cycle and cell development, as well as diseases, are characterized by the variations in the transcription levels of particular genes. Thus, for example, a viral infection is often characterized by the elevated expression of genes of the particular virus. For example, outbreaks of Herpes simplex, Epstein-Barr virus infections (e.g. infectious mononucleosis), cytomegalovirus, Varicella-zoster virus infections, parvovirus infections, human papillomavirus infections, etc. are all characterized by elevated expression of various genes present in the respective virus. Detection of elevated expression levels of characteristic viral genes provides an effective diagnostic of the disease state. In particular, viruses such as herpes simplex, enter quiescent states for periods of time only to erupt in brief periods of rapid replication. Detection of expression levels of characteristic viral genes allows detection of such active proliferative (and presumably infective) states.

Oligonucleotide probes have long been used to detect complementary nucleic acid sequences in a nucleic acid of interest (the "target" nucleic acid) and have been used to detect expression of particular genes (e.g., a Northern Blot). In some assay formats, the oligonucleotide probe is tethered, i.e., by covalent attachment, to a solid support, and arrays of oligonucleotide probes immobilized on solid supports have been used to detect specific nucleic acid sequences in a target nucleic acid.

The use of "traditional" hybridization protocols for monitoring or quantifying gene expression is problematic. For example two or more gene products of approximately the same molecular weight will prove difficult or impossible to distinguish in a Northern blot because they are not readily separated by electrophoretic methods. Similarly, as hybridization efficiency and cross-reactivity varies with the particular subsequence (region) of a gene being probed it is difficult to obtain an accurate and reliable measure of gene expression with one, or even a few, probes to the target gene.

The development of VLSIPS™ technology provided methods for synthesizing arrays of many different oligonucleotide probes that occupy a very small surface area. See U.S. Pat. No. 5,143,854 and PCT patent publication No. WO 90/15070. U.S. patent application Ser. No. 082,937, filed Jun. 25, 1993, describes methods for making arrays of oligonucleotide probes that can be used to provide the complete sequence of a target nucleic acid and to detect the presence of a nucleic acid containing a specific nucleotide sequence.

SUMMARY OF THE INVENTION

The present invention is premised, in part, on the discovery that microfabricated arrays of large numbers of different oligonucleotide probes (DNA chips) may effectively be used to not only detect the presence or absence of target nucleic acid sequences, but to quantify the relative abundance of the target sequences in a complex nucleic acid pool. In addition, it was also a surprising discovery that relatively short oligonucleotide probes (e.g., 20 mer) are sufficiently specific to allow quantitation of gene expression in complex mixtures of nucleic acids particularly when provided as in high density oligonucleotide probe arrays.

Prior to this invention it was unknown that hybridization to high density probe arrays would permit small variations in expression levels of a particular gene to be identified and quantified in a complex population of nucleic acids that out number the target nucleic acids by 1,000 fold to 1,000,000 fold or more. It was also unknown that the transcription levels of specific genes can be quantitated in a complex nucleic acid mixture with only a few (e.g., less than 20 or even less than 10) relatively short oligonucleotide probes.

Thus, this invention provides for a method of simultaneously monitoring the expression (e.g. detecting and or quantifying the expression) of a multiplicity of genes. The levels of transcription, RNA processing and degradation for virtually any number of genes may be determined simultaneously. Typically, at least about 10 genes, preferably at least about 100, more preferably at least about 1000 and most preferably at least about 10,000 different genes are assayed at one time.

The method involves providing a pool of target nucleic acids comprising RNA transcripts of one or more of said genes, or nucleic acids derived from the RNA transcripts; hybridizing the pool of nucleic acids to an array of oligonucleotide probes immobilized on a surface, where the array comprises more than 100 different oligonucleotides, each different oligonucleotide is localized in a predetermined region of said surface, each different oligonucleotide is attached to the surface through a single covalent bond, the density of the different oligonucleotides is greater than about 60 different oligonucleotides (where different oligonucleotides refers to oligonucleotides having different sequences) per 1 $cm^2$, and the oligonucleotide probes are complementary to the RNA transcripts or nucleic acids derived from the RNA transcripts; and quantifying the hybridized nucleic acids in the array. The method can additionally include a step of quantifying the hybridization of the target nucleic acids to the array. The quantification preferably provides a measure of the levels of transcription of the genes. In a preferred embodiment, the pool of target nucleic acids is one in which the concentration of the target nucleic acids (pre-mRNA transcripts, mRNA transcripts or nucleic acids derived from the RNA transcripts) is proportional to the expression levels of genes encoding those target nucleic acids.

In a preferred embodiment, the array of oligonucleotide probes is a high density array comprising greater than about 100, preferably greater than about 1,000 more preferably greater than about 16,000 and most preferably greater than about 65,000 or 250,000 or even 1,000,000 different oligonucleotide probes. Such high density arrays comprise a probe density of generally greater than about 60, more generally greater than about 100, most generally greater than about 600, often greater than about 1000, more often greater than about 5,000, most often greater than about 10,000, preferably greater than about 40,000 more preferably greater than about 100,000, and most preferably greater than about 400,000 different oligonucleotide probes per $cm^2$ (where different oligonucleotides refers to oligonucleotides having different sequences). The oligonucleotide probes range from about 5 to about 500, preferably 5 to 50, nucleotides, preferably from about 5 to about 45 nucleotides, still more preferably from about 10 to about 40 nucleotides and most preferably from about 15 to about 40 nucleotides in length. Particularly preferred arrays contain probes ranging from about 20 to about 25 oligonucleotides in length. The array may comprise more than 10, preferably more than 50, more preferably more than 100, and most preferably more than 1000 oligonucleotide probes specific for each target gene. In a preferred embodiment, the array comprises at least 10 different oligonucleotide probes for each gene. In another preferred embodiment, the array has 20 or fewer oligonucleotides complementary each gene. Although a planar array surface is preferred, the array may be fabricated on a surface of virtually any shape or even a multiplicity of surfaces.

The array may further comprise mismatch control probes. Where such mismatch controls are present, the quantifying step may comprise calculating the difference in hybridization signal intensity between each of the oligonucleotide probes and its corresponding mismatch control probe. The quantifying may further comprise calculating the average difference in hybridization signal intensity between each of the oligonucleotide probes and its corresponding mismatch control probe for each gene.

The probes present in the high density array can be oligonucleotide probes selected according to selection and optimization methods described below. Alternatively, non-optimal probes may be included in the array, but the probes used for quantification (analysis) can be selected according to the optimization methods described below.

Oligonucleotide arrays for the practice of some embodiments of this invention are, in preferred embodiments, chemically synthesized by parallel immobilized polymer synthesis methods, more preferably by light directed polymer synthesis methods. Chemically synthesized arrays are advantageous in that probe preparation does not require cloning, a nucleic acid amplification step, or enzymatic synthesis. Indeed, the preparation of the probes does not require handling of any biological materials.

The array includes test probes which are oligonucleotide probes each of which has a sequence that is complementary to a subsequence of one of the genes (or the mRNA or the corresponding antisense cRNA) whose expression is to be detected. In addition, the array can contain normalization controls, mismatch controls and expression level controls as described herein.

In a particularly preferred embodiment, the variation between different copies (within and/or between batches) of each array is less than 20%, more preferably less than about 10%, and most preferably less than about 5% where the variation is measured as the coefficient of variation in hybridization intensity averaged over at least 5 oligonucleotide probes for each gene whose expression the array is to detect.

The pool of nucleic acids may be labeled before, during, or after hybridization, although in a preferred embodiment, the nucleic acids are labeled before hybridization. Fluorescence labels are particularly preferred, more preferably labeling with a single fluorophore, and, where fluorescence labeling is used, quantification of the hybridized nucleic acids is by quantification of fluorescence from the hybridized fluorescently labeled nucleic acid. Such quantification is facilitated by the use of a fluorescence microscope which can be equipped with an automated stage to permit automatic scanning of the array, and which can be equipped with a data acquisition system for the automated measurement recording and subsequent processing of the fluorescence intensity information. Preferred devices for reading such arrays are the GeneChip™ reader, available from Affymetrix, Inc. of Santa Clara, Calif.

In a preferred embodiment, hybridization is at low stringency (e.g. about 20° C. to about 50° C., more preferably about 30° C. to about 40° C., and most preferably about 37° C. and 6×SSPE-T or lower) with at least one wash at higher stringency. Hybridization may include subsequent washes at progressively increasing stringency until a desired level of hybridization specificity is reached.

Quantification of the hybridization signal can be by any means known to one of skill in the art. However, in a particularly preferred embodiment, quantification is achieved by use of a confocal fluorescence microscope. Data is preferably evaluated by calculating the difference in hybridization signal intensity between each oligonucleotide probe and its corresponding mismatch control probe. It is particularly preferred that this difference be calculated and evaluated for each gene. Particularly preferred analytical methods are provided herein.

The pool of target nucleic acids can be the total $polyA^+$ mRNA isolated from a biological sample, or cDNA made by reverse transcription of the RNA or second strand cDNA or RNA transcribed from the double stranded cDNA intermediate. Alternatively, the pool of target nucleic acids can be treated to reduce the complexity of the sample and thereby reduce the background signal obtained in hybridization. In one approach, a pool of mRNAs, derived from a biological sample, is hybridized with a pool of oligonucleotides comprising the oligonucleotide probes present in the high density array. The pool of hybridized nucleic acids is then treated with RNase A which digests the single stranded regions. The remaining double stranded hybridization complexes are then denatured and the oligonucleotide probes are removed, leaving a pool of mRNAs enhanced for those mRNAs complementary to the oligonucleotide probes in the high density array.

In another approach to background reduction, a pool of mRNAs derived from a biological sample is hybridized with paired target specific oligonucleotides where the paired target specific oligonucleotides are complementary to regions flanking subsequences of the mRNAs complementary to the oligonucleotide probes in the high density array. The pool of hybridized nucleic acids is treated with RNase H which digests the hybridized (double stranded) nucleic acid sequences. The remaining single stranded nucleic acid sequences which have a length about equivalent to the region flanked by the paired target specific oligonucleotides are then isolated (e.g. by electrophoresis) and used as the pool of nucleic acids for monitoring gene expression.

Finally, a third approach to background reduction involves eliminating or reducing the representation in the pool of particular preselected target mRNA messages (e.g., messages that are characteristically overexpressed in the sample). This method involves hybridizing an oligonucleotide probe that is complementary to the preselected target mRNA message to the pool of polyA$^+$ mRNAs derived from a biological sample. The oligonucleotide probe hybridizes with the particular preselected polyA$^+$ mRNA (message) to which it is complementary. The pool of hybridized nucleic acids is treated with RNase H which digests the double stranded (hybridized) region thereby separating the message from its polyA$^+$ tail. Isolating or amplifying (e.g., using an oligo dT column) the polyA$^+$ mRNA in the pool then provides a pool having a reduced or no representation of the preselected target mRNA message.

It will be appreciated that the methods of this invention can be used to monitor (detect and/or quantify) the expression of any desired gene of known sequence or subsequence. Moreover, these methods permit monitoring expression of a large number of genes simultaneously and effect significant advantages in reduced labor, cost and time. The simultaneous monitoring of the expression levels of a multiplicity of genes permits effective comparison of relative expression levels and identification of biological conditions characterized by alterations of relative expression levels of various genes. Genes of particular interest for expression monitoring include genes involved in the pathways associated with various pathological conditions (e.g., cancer) and whose expression is thus indicative of the pathological condition. Such genes include, but are not limited to the HER2 (c-erbB-2/neu) proto-oncogene in the case of breast cancer, receptor tyrosine kinases (RTKs) associated with the etiology of a number of tumors including carcinomas of the breast, liver, bladder, pancreas, as well as glioblastomas, sarcomas and squamous carcinomas, and tumor suppressor genes such as the P53 gene and other "marker" genes such as RAS, MSH2, MLH1 and BRCA1. Other genes of particular interest for expression monitoring are genes involved in the immune response (e.g., interleukin genes), as well as genes involved in cell adhesion (e.g., the integrins or selectins), apoptosis and signal transduction (e.g., tyrosine kinases), etc. Of course, the invention is not limited to the monitoring of expression in human samples, but may also be used in the evaluation of bacterial or viral genes.

In another embodiment, this invention provides a method of identifying genes the expression of which is affected by one or more drugs, or conversely, screening a number of drugs to identify those that have an effect on particular gene(s). This involves providing a pool of target nucleic acids from one or more cells contacted with the drug or drugs and hybridizing that pool to any of the high density oligonucleotide arrays described herein. The expression levels of the genes targeted by the probes in the array are determined and compared to expression levels of genes from "control" cells not exposed to the drug or drugs. The genes that are overexpressed or underexpressed in response to the drug or drugs are identified or conversely the drug or drugs that alter expression of one or more genes are identified.

In still yet another embodiment, this invention provide for a composition comprising any of the high density oligonucleotide arrays disclosed herein where the oligonucleotide probes are specifically hybridized to one or more fluorescently labeled nucleic acids (which are the transcription products of genes or derived from those transcription products) thereby forming a fluorescent array in which the fluorescence of the array is indicative of the transcription levels of the multiplicity of genes. One of skill will appreciate that such a hybridized array may be used as a reference, control, or standard (e.g., provided in a kit) or may itself be a diagnostic array indicating the expression levels of a multiplicity of genes in a sample.

This invention also provides kits for simultaneously monitoring expression levels of a multiplicity of genes. The kits include an array of immobilized oligonucleotide probes complementary to subsequences of the multiplicity of target genes, as described herein. The kit may also include instructions describing the use of the array for detection and/or quantification of expression levels of the multiplicity of genes. The kit may additionally include one or more of the following: buffers, hybridization mix, wash and read solutions, labels, labeling reagents (enzymes etc.), "control" nucleic acids, software for probe selection, array reading or data analysis and any of the other materials or reagents described herein for the practice of the claimed methods.

In another embodiment, this invention provides for a method of selecting a set of oligonucleotide probes that specifically bind to a target nucleic acid (e.g., a gene or genes whose expression is to be monitored or nucleic acids derived from the gene or its transcribed mRNA). The method involves providing a high density array of oligonucleotide probes where the array comprises a multiplicity of probes wherein each probe is complementary to a subsequence of the target nucleic acid. The target nucleic acid is then hybridized to the array of oligonucleotide probes to identify and select those probes where the difference in hybridization signal intensity between each probe and its mismatch control is detectable (preferably greater than about 10% of the background signal intensity, more preferably greater than about 20% of the background signal intensity and most preferably greater than about 50% of the background signal intensity). The method can further comprise hybridizing the array to a second pool of nucleic acids comprising nucleic acids other than the target nucleic acids; and identifying and selecting probes having the lowest hybridization signal and where both the probe and its mismatch control have a hybridization intensity equal to or less than about 5 times the background signal intensity, preferably equal to or less than about 2 times the background signal intensity, more preferably equal to or less than about 1 times the background signal intensity, and most preferably equal or less than about half the background signal intensity.

In a preferred embodiment, the multiplicity of probes can include every different probe of length n that is complementary to a subsequence of the target nucleic acid. The probes can, in one embodiment, range from about 10 to about 500 nucleotide bases in length. The array is preferably a high density array as described above. Similarly, the hybridization methods, conditions, times, fluid volumes, detection methods are as herein.

In another embodiment, the invention provides a computer-implemented method of monitoring expression of genes comprising the steps of: receiving input of hybridization intensities for a plurality of nucleic acid probes including pairs of perfect match probes and mismatch probes, the hybridization intensities indicating hybridization affinity between the plurality of nucleic acid probes and nucleic acids corresponding to a gene, and each pair including a perfect match probe that is perfectly complementary to a portion of the nucleic acids and a mismatch probe that differs from the perfect match probe by at least one nucleotide; comparing the hybridization intensities of the perfect match and mismatch probes of each pair; and indicating expression of the gene according to results of the comparing step. Preferably, the differences between the hybridization intensities of the perfect match and mismatch probes of each pair are calculated.

Additionally, the invention provides a computer-implemented method for monitoring expression of genes comprising the steps of: receiving input of a nucleic acid sequence constituting a gene; generating a set of probes that are perfectly complementary to the gene; and identifying a subset of probes, including less than all of the probes in the set, for monitoring the expression of the gene. Each probe of the set may be analyzed by criteria that specify characteristics indicative of low hybridization or high cross hybridization. The criteria may include if occurrences of a specific nucleotide in a probe crosses a threshold value, if the number of a specific nucleotide that repeats sequentially in a probe crosses a threshold value, if the length of a palindrome in a probe crosses a threshold value, and the like.

Definitions

The phrase "massively parallel screening" refers to the simultaneous screening of at least about 100, preferably about 1000, more preferably about 10,000 and most preferably about 1,000,000 different nucleic acid hybridizations.

The terms "nucleic acid" or "nucleic acid molecule" refer to a deoxyribonucleotide or ribonucleotide polymer in either single-or double-stranded form, and unless otherwise limited, would encompass analogs of natural nucleotide that can function in a similar manner as naturally occurring nucleotide.

An oligonucleotide is a single-stranded nucleic acid ranging in length from 2 to about 500 bases.

As used herein a "probe" is defined as an oligonucleotide (or a nucleic acid) capable of binding to a target nucleic acid of complementary sequence through one or more types of chemical bonds, usually through complementary base pairing, usually through hydrogen bond formation. As used herein, a probe may include natural (i.e. A, G, U, C, or T) or modified bases (7-deazaguanosine, inosine, etc.). In addition, the bases in probes may be joined by a linkage other than a phosphodiester bond, so long as it does not interfere with hybridization. Thus, probes may be peptide nucleic acids in which the constituent bases are joined by peptide bonds rather than phosphodiester linkages.

The term "target nucleic acid" refers to a nucleic acid (often derived from a biological sample), to which the probe is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding probe directed to the target. The term target nucleic acid may refer to the specific subsequence of a larger nucleic acid to which the probe is directed or to the overall sequence (e.g., gene or mRNA) whose expression level it is desired to detect. The difference in usage will be apparent from context.

The term "mRNA" refers to transcripts of a gene. Transcripts are RNA including, for example, mature messenger RNA ready for translation, products of various stages of transcript processing. Transcript processng may include splicing and degradation.

"Subsequence" refers to a sequence of nucleic acids that comprise a part of a longer sequence of nucleic acids.

The term "complexity" is used here according to standard meaning of this term as established by Britten et al. *Methods of Enzymol.* 29:363 (1974). See, also *Cantor and Schimmel Biophysical Chemistry: Part III* at 1228–1230 for further explanation of nucleic acid complexity.

"Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

The phrase "hybridizing specifically to", refers to the binding, duplexing, or hybridizing of a molecule substantially to or only to a particular nucleotide sequence or sequences under stringent conditions when that sequence is present in a complex mixture (e.g., total cellular) DNA or RNA. The term "stringent conditions" refers to conditions under which a probe will hybridize to its target subsequence, but with only insubstantial hybridization to other sequences or to other sequences such that the difference may be identified. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is at least about 0.01 to 1.0 M Na ion concentration (or other salts) at pH 7.0 to 8.3 and the temperature is at least about 30° C. for short probes (e.g., 10 to 50 nucleotide). Stringent conditions may also be achieved with the addition of destabilizing agents such as formamide.

The term "perfect match probe" refers to a probe that has a sequence that is perfectly complementary to a particular target sequence. The test probe is typically perfectly complementary to a portion (subsequence) of the target sequence. The perfect match (PM) probe can be a "test probe", a "normalization control" probe, an expression level control probe and the like. A perfect match control or perfect match probe is, however, distinguished from a "mismatch control" or "mismatch probe."

The term "mismatch control" or "mismatch probe" refer to probes whose sequence is deliberately selected not to be perfectly complementary to a particular target sequence. For each mismatch (MM) control in a high-density array there typically exists a corresponding perfect match (PM) probe that is perfectly complementary to the same particular target sequence. The mismatch may comprise one or more bases. While the mismatch(s) may be locates anywhere in the mismatch probe, terminal mismatches are less desirable as a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions.

The terms "background" or "background signal intensity" refer to hybridization signals resulting from non-specific binding, or other interactions, between the labeled target nucleic acids and components of the oligonucleotide array (e.g., the oligonucleotide probes, control probes, the array substrate, etc.). Background signals may also be produced by intrinsic fluorescence of the array components themselves. A single background signal can be calculated for the entire array, or a different background signal may be calculated for each target nucleic acid. In a preferred embodiment, background is calculated as the average hybridization signal intensity for the lowest 5% to 10% of the probes in the array, or, where a different background signal is calculated for each target gene, for the lowest 5% to 10% of the probes for each gene. Of course, one of skill in the art will appreciate that where the probes to a particular gene hybridize well and thus appear to be specifically binding to a target sequence, they should not be used in a background signal calculation. Alternatively, background may be calculated as the average hybridization signal intensity produced by hybridization to probes that are not complementary to any sequence found in the sample (e.g probes directed to nucleic acids of the opposite sense or to genes not found in the sample such as bacterial genes where the sample is mammalian nucleic acids). Background can also be calculated as the average signal intensity produced by regions of the array that lack any probes at all.

The term "quantifying" when used in the context of quantifying transcription levels of a gene can refer to absolute or to relative quantification. Absolute quantification may be accomplished by inclusion of known concentration(s) of one or more target nucleic acids (e.g. control nucleic acids such as Bio B or with known amounts the target nucleic acids themselves) and referencing the hybridization intensity of unknowns with the known target nucleic acids (e.g. through generation of a standard curve). Alternatively, relative quantification can be accomplished by comparison of hybridization signals between two or more genes, or between two or more treatments to quantify the changes in hybridization intensity and, by implication, transcription level.

The "percentage of sequence identity" or "sequence identity" is determined by comparing two optimally aligned sequences or subsequences over a comparison window or span, wherein the portion of the polynucleotide sequence in the comparison window may optionally comprise additions or deletions (i.e., gaps) as compared to the reference sequence (which does not comprise additions or deletions) for optimal alignment of the two sequences. The percentage is calculated by determining the number of positions at which the identical subunit (e.g. nucleic acid base or amino acid residue) occurs in both sequences to yield the number of matched positions, dividing the number of matched positions by the total number of positions in the window of comparison and multiplying the result by 100 to yield the percentage of sequence identity. Percentage sequence identity when calculated using the programs GAP or BESTFIT (see below) is calculated using default gap weights.

Methods of alignment of sequences for comparison are well known in the art. Optimal alignment of sequences for comparison may be conducted by the local homology algorithm of Smith and Waterman, *Adv. Appl. Math.* 2: 482 (1981), by the homology alignment algorithm of Needleman and Wunsch *J. Mol. Biol.* 48: 443 (1970), by the search for similarity method of Pearson and Lipman, *Proc. Natl. Acad. Sci. USA* 85: 2444 (1988), by computerized implementations of these algorithms (including, but not limited to CLUSTAL in the PC/Gene program by Intelligenetics, Moutain View, Calif., GAP, BESTFIT, FASTA, and TFASTA in the Wisconsin Genetics Software Package, Genetics Computer Group (GCG), 575 Science Dr., Madison, Wis., USA), or by inspection. In particular, methods for aligning sequences using the CLUSTAL program are well described by Higgins and Sharp in *Gene,* 73: 237–244 (1988) and in *CABIOS* 5: 151–153 (1989)).

DETAILED DESCRIPTION OF THE PREFERRED EMBODIMENTS

Figure 1:
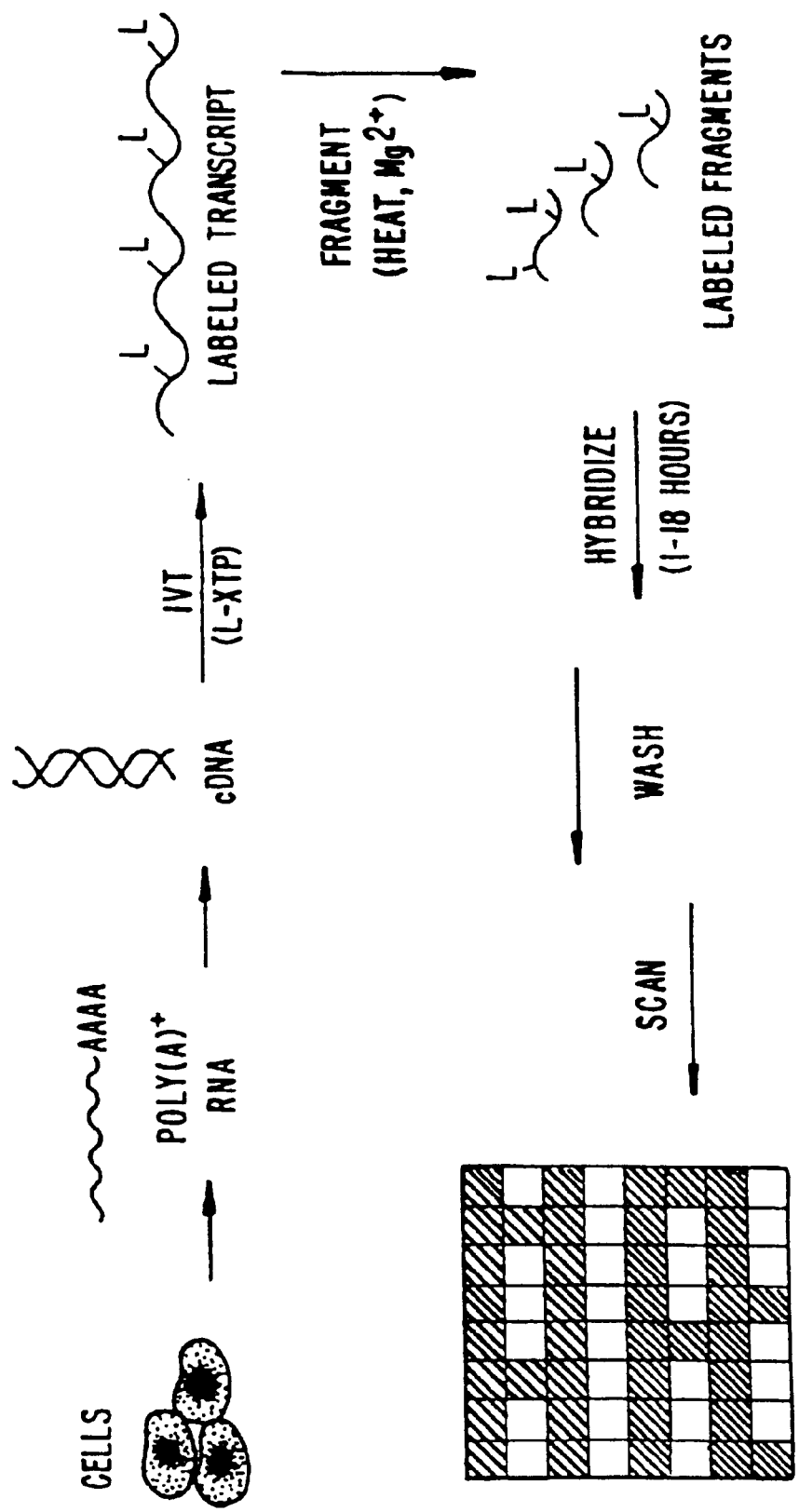
FIG. 1 shows a schematic of expression monitoring using oligonucleotide arrays. Extracted poly $(A)^+$ RNA is converted to cDNA, which is then transcribed in the presence of labeled ribonucleotide triphosphates. L is either biotin or a dye such as fluorescein. RNA is fragmented with heat in the presence of magnesium ions. Hybridizations are carried out in a flow cell that contains the two-dimensional DNA probe arrays. Following a brief washing step to remove unhybridized RNA, the arrays are scanned using a scanning confocal microscope. Alternatives in which cellular mRNA is directly labeled without a cDNA intermediate are described in the Examples. Image analysis software converts the scanned array images into text files in which the observed intensities at specific physical locations are associated with particular probe sequences.

I. High Density Arrays for Monitoring Gene Expression

This invention provides methods of monitoring (detecting and/or quantifying) the expression levels of one or more genes. The methods involve hybridization of a nucleic acid target sample to a high density array of nucleic acid probes and then quantifying the amount of target nucleic acids hybridized to each probe in the array.

While nucleic acid hybridization has been used for some time to determine the expression levels of various genes (e.g., Northern Blot), it was a surprising discovery of this invention that high density arrays are suitable for the quantification of the small variations in expression (transcription) levels of a gene in the presence of a large population of heterogenous nucleic acids. The signal may be present at a concentration of less than about 1 in 1,000, and is often present at a concentration less than 1 in 10,000 more preferably less than about 1 in 50,000 and most preferably less than about 1 in 100,000, 1 in 300,000, or even 1 in 1,000,000.

Prior to this invention, it was expected that hybridization of such a complex mixture to a high density array might overwhelm the available probes and make it impossible to detect the presence of low-level target nucleic acids. It was thus unclear that a low level signal could be isolated and detected in the presence of misleading signals due to cross-hybridization and non-specific binding both to substrate and probe. It was therefore a surprising discovery that, to the contrary, high density arrays are particularly well suited for monitoring expression of a multiplicity of genes and provide a level of sensitivity and discrimination hitherto unexpected.

It was also a surprising discovery of this invention that when used in a high-density array, even relatively short oligonucleotides can be used to accurately detect and quantify expression (transcription) levels of genes. Thus oligonucleotide arrays having oligonucleotides as short as 10 nucleotide, more preferably 15 oligonucleotides and most preferably 20 or 25 oligonucleotides are used to specifically detect and quantify gene expression levels. Of course arrays containing longer oligonucleotides, as described herein, are also suitable.

A. Advantages of Oligonucleotide Arrays

In one preferred embodiment, the high density arrays used in the methods of this invention comprise chemically synthesized oligonucleotides. The use of chemically synthesized oligonucleotide arrays, as opposed to, for example, blotted arrays of genomic clones, restriction fragments, oligonucleotides, and the like, offers numerous advantages. These advantages generally fall into four categories:

1) Efficiency of production;
2) Reduced intra- and inter-array variability;
3) Increased information content; and
4) Higher signal to noise ratio (improved sensitivity).

1. Efficiency of Production

In a preferred embodiment, the arrays are synthesized using methods of spatially addressed parallel synthesis (see, e.g., Section V, below). The oligonucleotides are synthesized chemically in a highly parallel fashion covalently attached to the array surface. This allows extremely efficient array production. For example, arrays containing tens (or even hundreds) of thousands of specifically selected 20 mer oligonucleotides are synthesized in fewer than 80 synthesis cycles. The arrays are designed and synthesized based on sequence information alone. Thus, unlike blotting methods, the array preparation requires no handling of biological materials. There is no need for cloning steps, nucleic acid amplifications, cataloging of clones or amplification products, and the like. The preferred chemical synthesis of expression monitoring arrays in this invention is thus more efficient blotting methods and permits the production of highly reproducible high-density arrays with relatively little labor and expense.

2. Reduced Intra- and Inter-array Variability

The use of chemically synthesized high-density oligonucleotide arrays in the methods of this invention improves intra- and inter-array variability. The oligonucleotide arrays preferred for this invention are made in large batches (presently 49 arrays per wafer with multiple wafers synthesized in parallel) in a highly controlled reproducible manner. This makes them suitable as general diagnostic and research tools permitting direct comparisons of assays performed anywhere in the world.

Because of the precise control obtainable during the chemical synthesis the arrays of this invention show less than about 25%, preferably less than about 20%, more preferably less than about 15%, still more preferably less than about 10%, even more preferably less than about 5%. and most preferably less than about 2% variation between high density arrays (within or between production batches) having the same probe composition. Array variation is assayed as the variation in hybridization intensity (against a labeled control target nucleic acid mixture) in one or more oligonucleotide probes between two or more arrays. More preferably, array variation is assayed as the variation in hybridization intensity (against a labeled control target nucleic acid mixture) measured for one or more target genes between two or more arrays.

In addition to reducing inter- and intra-array variability, chemically synthesized arrays also reduce variations in relative probe frequency inherent in spotting methods, particularly spotting methods that use cell-derived nucleic acids (e.g., cDNAs). Many genes are expressed at the level of thousands of copies per cell, while others are expressed at only a single copy per cell. A cDNA library will reflect this very large bias as will a cDNA library made from this material. While normalization (adjustment of the amount of each different probe e.g., by comparison to a reference cDNA) of the library will reduce the representation of over-expressed sequences, normalization has been shown to lessen the odds of selecting highly expressed cDNAs by only about a factor of 2 or 3. In contrast, chemical synthesis methods can insure that all oligonucleotide probes are represented in approximately equal concentrations. This decreases the inter-gene (intra-array) variability and permits direct comparison between characteristically overexpressed and underexpressed nucleic acids.

3. Increased Information Content

As indicated above, it was a discovery of this invention that the use of high density oligonucleotide arrays for expression monitoring provides a number of advantages not found with other methods. For example, the use of large numbers of different probes that specifically bind to the transcription product of a particular target gene provides a high degree of redundancy and internal control that permits optimization of probe sets for effective detection of particular target genes and minimizes the possibility of errors due to cross-reactivity with other nucleic acid species.

Apparently suitable probes often prove ineffective for expression monitoring by hybridization. For example, certain subsequences of a particular target gene may be found in other regions of the genome and probes directed to these subsequences will cross-hybridize with the other regions and not provide a signal that is a meaningful measure of the expression level of the target gene. Even probes that show little cross reactivity may be unsuitable because they generally show poor hybridization due to the formation of structures that prevent effective hybridization. Finally, in sets with large numbers of probes, it is difficult to identify hybridization conditions that are optimal for all the probes in a set. Because of the high degree of redundancy provided by the large number of probes for each target gene, it is possible to eliminate those probes that function poorly under a given set of hybridization conditions and still retain enough probes to a particular target gene to provide an extremely sensitive and reliable measure of the expression level (transcription level) of that gene.

In addition, the use of large numbers of different probes to each target gene makes it possible to monitor expression of families of closely-related nucleic acids. The probes may be selected to hybridize both with subsequences that are conserved across the family and with subsequences that differ in the different nucleic acids in the family. Thus, hybridization with such arrays permits simultaneous monitoring of the various members of a gene family even where the various genes are approximately the same size and have high levels of homology. Such measurements are difficult or impossible with traditional hybridization methods.

Because the high density arrays contain such a large number of probes it is possible to provide numerous controls including, for example, controls for variations or mutations in a particular gene, controls for overall hybridization conditions, controls for sample preparation conditions, controls for metabolic activity of the cell from which the nucleic acids are derived and mismatch controls for non-specific binding or cross hybridization.

Moreover, as explained above, it was a surprising discovery of this invention that effective detection and quantitation of gene transcription in complex mammalian or other cell message populations can be determined with relatively short oligonucleotides and with relative few (e.g., fewer than 40, preferably fewer than 30, more preferably fewer than 25, and most preferably fewer than 20, 15, or even 10) oligonucleotide probes per gene. In general, it was a discovery of this invention that there are a large number of probes which hybridize both strongly and specifically for each gene. This does not mean that a large number of probes is required for detection, but rather that there are many from which to choose and that choices can be based on other considerations such as sequence uniqueness (gene families), checking for splice variants, or genotyping hot spots (things not easily done with cDNA spotting methods).

Based on these discoveries, sets of four arrays are made that contain approximately 400,000 probes each can readily be fabricated at reasonable cost. Sets of about 40 probes (20 probe pairs) are chosen that are complementary to each of about 40,000 genes for which there are ESTs in the public database. This set of ESTs covers roughly one-third to one-half of all human genes and these arrays will allow the levels of all of them to be monitored in a parallel set of overnight hybridizations.

4. Improved Signal to Noise Ratio

Blotted nucleic acids typically rely on ionic, electrostatic, and hydrophobic interactions to attach the blotted nucleic acids to the substrate. Bonds are formed at multiple points along the nucleic acid restricting degrees of freedom and interfering with the ability of the nucleic acid to hybridize to its complementary target. In contrast, the preferred arrays of this invention are chemically synthesized. The oligonucleotide probes are attached to the substrate by a single terminal covalent bond. The probes have more degrees of freedom and are capable of participating in complex interactions with their complementary targets. Consequently, the probe arrays of this invention show significantly higher hybridization efficiencies (10 times, 100 times, and even 1000 times more efficient) than blotted arrays. Less target oligonucleotide is used to produce a given signal thereby dramatically improving the signal to noise ratio. Consequently the methods of this invention permit detection of only a few copies of a nucleic acid in extremely complex nucleic acid mixtures.

B. Preferred High Density Arrays

Preferred high density arrays of this invention comprise greater than about 100, preferably greater than about 1000, more preferably greater than about 16,000 and most preferably greater than about 65,000 or 250,000 or even greater than about 1,000,000 different oligonucleotide probes, preferably in less than 1 cm2 of surface area. The oligonucleotide probes range from about 5 to about 50 or about 5 to about 45 nucleotide, more preferably from about 10 to about 40 nucleotide and most preferably from about 15 to about 40 nucleotide in length. In particular preferred embodiments, the oligonucleotide probes are 20 or 25 nucleotide in length. It was a discovery of this invention that relatively short oligonucleotide probes sufficient to specifically hybridize to and distinguish target sequences. Thus in one preferred embodiment, the oligonucleotide probes are less than 50 nucleotide in length, generally less than 46 nucleotide, more generally less than 41 nucleotide, most generally less than 36 nucleotide, preferably less than 31 nucleotide, more preferably less than 26 nucleotide, and most preferably less than 21 nucleotide in length. The probes can also be less than 16 nucleotide or less than even 11 nucleotide in length.

The location and sequence of each different oligonucleotide probe sequence in the array is known. Moreover, the large number of different probes occupies a relatively small area providing a high density array having a probe density of generally greater than about 60, more generally greater than about 100, most generally greater than about 600, often greater than about 1000, more often greater than about 5,000, most often greater than about 10,000, preferably greater than about 40,000 more preferably greater than about 100,000, and most preferably greater than about 400,000 different oligonucleotide probes per cm. The small surface area of the array (often less than about 10 cm$^2$, preferably less than about 5 cm$^2$ more preferably less than about 2 cm$^2$, and most preferably less than about 1.6 cm$^2$) permits extremely uniform hybridization conditions (temperature regulation, salt content, etc.) while the extremely large number of probes allows massively parallel processing of hybridizations.

Finally, because of the small area occupied by the high density arrays, hybridization may be carried out in extremely small fluid volumes (e.g., 250 µl or less, more preferably 100 µl or less, and most preferably 10 µl or less). In small volumes, hybridization may proceed very rapidly. In addition, hybridization conditions are extremely uniform throughout the sample, and the hybridization format is amenable to automated processing.

II. Uses of Expression Monitoring

This invention demonstrates that hybridization with high density oligonucleotide probe arrays provides an effective means of monitoring expression of a multiplicity of genes. In addition this invention provides for methods of sample treatment and array designs and methods of probe selection that optimize signal detection at extremely low concentrations in complex nucleic acid mixtures.

The expression monitoring methods of this invention may be used in a wide variety of circumstances including detection of disease, identification of differential gene expression between two samples (e.g., a pathological as compared to a healthy sample), screening for compositions that upregulate or downregulate the expression of particular genes, and so forth.

In one preferred embodiment, the methods of this invention are used to monitor the expression (transcription) levels of nucleic acids whose expression is altered in a disease state. For example, a cancer may be characterized by the overexpression of a particular marker such as the HER2 (c-erbB-2/neu) proto-oncogene in the case of breast cancer. Similarly, overexpression of receptor tyrosine kinases (RTKs) is associated with the etiology of a number of tumors including carcinomas of the breast, liver, bladder, pancreas, as well as glioblastomas, sarcomas and squamous carcinomas (see Carpenter, *Ann. Rev. Biochem.*, 56: 881–914 (1987)). Conversely, a cancer (e.g., colerectal, lung and breast) may be characterized by the mutation of or underexpress ion of a tumor suppressor gene such as P53 (see, e.g., Tominaga et al. *Critical Rev. in Oncogenesis*, 3: 257–282 (1992)).

In another preferred embodiment, the methods of this invention are used to monitor expression of various genes in response to defined stimuli, such as a drug. The methods are particularly advantageous because they permit simultaneous monitoring of the expression of thousands of genes. This is especially useful in drug research if the end point description is a complex one, not simply asking if one particular gene is overexpressed or underexpressed. Thus, where a disease state or the mode of action of a drug is not well characterized, the methods of this invention allow rapid determination of the particularly relevant genes.

As indicated above, the materials and methods of this invention are typically used to monitor the expression of a multiplicity of different genes simultaneously. Thus, in one embodiment, the invention provide for simultaneous monitoring of at least about 10, preferably at least about 100, more preferably at least about 1000, still more preferably at least about 10,000, and most preferably at least about 100,000 different genes.

The expression monitoring methods of this invention can also be used for gene discovery. Many genes that have been discovered to date have been classified into families based on commonality of the sequences. Because of the extremely large number of probes it is possible to place in the high density array, it is possible to include oligonucleotide probes representing known or parts of known members from every gene class. In utilizing such a "chip" (high density array) genes that are already known would give a positive signal at loci containing both variable and common regions. For unknown genes, only the common regions of the gene family would give a positive signal. The result would indicate the possibility of a newly discovered gene.

The expression monitoring methods of this invention can also be used for monitoring the processing and eventual degradation of transcripts. RNA processing is monitored by quantifying nascent transcripts, processing intermediates, mature mRNA, and degradation products. The use of oligonucleotide arrays provides a means for simultaneous quantification of processing intermediates and alternatively spliced mRNA of many or all expressed genes.

The expression monitoring method is also used for sequencing or mutation detection in conjunction with the monitoring of expression. Transcripts are not only detected and quantified, but also can be partially or completely sequenced. Thus, using a sample from a patient, this method can not only detect whether certain genes are up or down regulated, but also detect whether those genes are mutated, and identify the exact mutations. Specific methods for mutation detection (or "resequencing") are disclosed in, for example, Kozal et al., *Nature Medicine,* Vol. 2, No. 7, July 1996, pp. 753–757, and Chee et al., *Science,* Vol. 274, Oct. 25, 1996, pp. 610–614, both incorporated herein by reference.

The expression monitoring methods of this invention also allow the development of "dynamic" gene databases. The Human Genome Project and commercial sequencing projects have generated large static databases which list thousands of sequences without regard to function or genetic interaction. Expression analysis using the methods of this invention produces "dynamic" databases that define a gene's function and its interactions with other genes. Without the ability to monitor the expression of large numbers of genes simultaneously ,however, the work of creating such a database is enormous. The tedious nature of using DNA sequence analysis for determining an expression pattern involves preparing a cDNA library from the RNA isolated from the cells of interest and then sequencing the library. As the DNA is sequenced, the operator lists the sequences that are obtained and counts them. Thousands of sequences would have to be determined and then the frequency of those gene sequences would define the expression pattern of genes for the cells being studied.

By contrast, using an expression monitoring array to obtain the data according to the methods of this invention is relatively fast and easy. The process involves stimulating the cells to induce expression, obtaining the RNA from the cells and then either labeling the RNA directly or creating a cDNA copy of the RNA. If cDNA is to be hybridized to the chip, fluorescent molecules are incorporated during the DNA polymerization. Either the labeled RNA or the labeled cDNA is then hybridized to a high density array in one overnight experiment. The hybridization provides a quantitative assessment of the levels of every single one of the genes with no additional sequencing. In addition the methods of this invention are much more sensitive allowing a few copies of expressed genes per cell to be detected. This procedure is demonstrated in the examples provided herein.

III. Methods of Monitoring Gene Expression

Generally the methods of monitoring gene expression of this invention involve (1) providing a pool of target nucleic acids comprising RNA transcript(s) of one or more target gene(s), or nucleic acids derived from the RNA transcript(s); (2) hybridizing the nucleic acid sample to a high density array of probes (including control probes); and (3) detecting the hybridized nucleic acids and calculating a relative expression (transcription) level.

A. Providing a Nucleic Acid Sample

One of skill in the art will appreciate that in order to measure the transcription level (and thereby the expression level) of a gene or genes, it is desirable to provide a nucleic acid sample comprising mRNA transcript(s) of the gene or genes, or nucleic acids derived from the mRNA transcript(s). As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, suitable samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

In a particularly preferred embodiment, where it is desired to quantify the transcription level (and thereby expression) of a one or more genes in a sample, the nucleic acid sample is one in which the concentration of the mRNA transcript(s) of the gene or genes, or the concentration of the nucleic acids derived from the mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity is sufficient for most purposes. Where more precise quantification is required appropriate controls can be run to correct for variations introduced in sample preparation and hybridization as described herein. In addition, serial dilutions of "standard" target mRNAs can be used to prepare calibration curves according to methods well known to those of skill in the art. Of course, where simple detection of the presence or absence of a transcript is desired, no elaborate control or calibration is required.

In the simplest embodiment, such a nucleic acid sample is the total mRNA isolated from a biological sample. The term "biological sample", as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

The nucleic acid (either genomic DNA or mRNA) may be isolated from the sample according to any of a number of methods well known to those of skill in the art. One of skill will appreciate that where alterations in the copy number of a gene are to be detected genomic DNA is preferably isolated. Conversely, where expression levels of a gene or genes are to be detected, preferably RNA (mRNA) is isolated.

Methods of isolating total mRNA are well known to those of skill in the art. For example, methods of isolation and purification of nucleic acids are described in detail in Chapter 3 of *Laboratory Techniques in Biochemistry and Molecular Biology: Hybridization With Nucleic Acid Probes, Part I. Theory and Nucleic Acid Preparation,* P. Tijssen, ed. Elsevier, N.Y. (1993) and Chapter 3 of *Laboratory Techniques in Biochemistry and Molecular Biology: Hybridization With Nucleic Acid Probes, Part I. Theory and Nucleic Acid Preparation,* P. Tijssen, ed. Elsevier, N.Y. (1993)).

In a preferred embodiment, the total RNA is isolated from a given sample using, for example, an acid guanidiniumphenol-chloroform extraction method and polyA+ mRNA is isolated by oligo dT column chromatography or by using (dT)n magnetic beads (see, e.g., Sambrook et al., *Molecular Cloning: A Laboratory Manual* (2nd ed.), Vols. 1–3, Cold Spring Harbor Laboratory, (1989), or *Current Protocols in Molecular Biology*, F. Ausubel et al., ed. Greene Publishing and Wiley-Interscience, New York (1987)).

Frequently, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids to achieve quantitative amplification.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid.

One preferred internal standard is a synthetic AW106 cRNA. The AW106 cRNA is combined with RNA isolated from the sample according to standard techniques known to those of skill in the art. The RNA is then reverse transcribed using a reverse transcriptase to provide copy DNA. The cDNA sequences are then amplified (e.g., by PCR) using labeled primers. The amplification products are separated, typically by electrophoresis, and the amount of radioactivity (proportional to the amount of amplified product) is determined. The amount of mRNA in the sample is then calculated by comparison with the signal produced by the known AW106 RNA standard. Detailed protocols for quantitative PCR are provided in *PCR Protocols, A Guide to Methods and Applications*, Innis et al., Academic Press, Inc. N.Y., (1990).

Other suitable amplification methods include, but are not limited to polymerase chain reaction (PCR) (Innis, et al., *PCR Protocols. A guide to Methods and Application*. Academic Press, Inc. San Diego, (1990)), ligase chain reaction (LCR) (see Wu and Wallace, *Genomics*, 4: 560 (1989), Landegren, et al., *Science*, 241: 1077 (1988) and Barringer, et al., *Gene*, 89: 117 (1990), transcription amplification (Kwoh, et al., *Proc. Natl. Acad. Sci. USA*, 86: 1173 (1989)), and self-sustained sequence replication (Guatelli, et al., *Proc. Nat. Acad. Sci. USA*, 87: 1874 (1990)).

In a particularly preferred embodiment, the sample mRNA is reverse transcribed with a reverse transcriptase and a primer consisting of oligo dT and a sequence encoding the phage T7 promoter to provide single stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA. Methods of in vitro polymerization are well known to those of skill in the art (see, e.g., Sambrook, supra.) and this particular method is described in detail by Van Gelder, et al., *Proc. Natl. Acad. Sci. USA*, 87: 1663–1667 (1990) who demonstrate that in vitro amplification according to this method preserves the relative frequencies of the various RNA transcripts. Moreover, Eberwine et al. *Proc. Natl. Acad. Sci. USA*, 89: 3010–3014 provide a protocol that uses two rounds of amplification via in vitro transcription to achieve greater than $10^6$ fold amplification of the original starting material thereby permitting expression monitoring even where biological samples are limited.

It will be appreciated by one of skill in the art that the direct transcription method described above provides an antisense (aRNA) pool. Where antisense RNA is used as the target nucleic acid, the oligonucleotide probes provided in the array are chosen to be complementary to subsequences of the antisense nucleic acids. Conversely, where the target nucleic acid pool is a pool of sense nucleic acids, the oligonucleotide probes are selected to be complementary to subsequences of the sense nucleic acids. Finally, where the nucleic acid pool is double stranded, the probes may be of either sense as the target nucleic acids include both sense and antisense strands.

The protocols cited above include methods of generating pools of either sense or antisense nucleic acids. Indeed, one approach can be used to generate either sense or antisense nucleic acids as desired. For example, the cDNA can be directionally cloned into a vector (e.g., Stratagene's p Bluscript II KS (+) phagemid) such that it is flanked by the T3 and T7 promoters. In vitro transcription with the T3 polymerase will produce RNA of one sense (the sense depending on the orientation of the insert), while in vitro transcription with the T7 polymerase will produce RNA having the opposite sense. Other suitable cloning systems include phage lambda vectors designed for Cre-loxP plasmid subcloning (see e.g., Palazzolo et al., *Gene*, 88: 25–36 (1990)).

In a particularly preferred embodiment, a high activity RNA polymerase (e.g. about 2500 units/$\mu$L for T7, available from Epicentre Technologies) is used.

B. Labeling Nucleic Acids

In a preferred embodiment, the hybridized nucleic acids are detected by detecting one or more labels attached to the sample nucleic acids. The labels may be incorporated by any of a number of means well known to those of skill in the art. However, in a preferred embodiment, the label is simultaneously incorporated during the amplification step in the preparation of the sample nucleic acids. Thus, for example, polymerase chain reaction (PCR) with labeled primers or labeled nucleotides will provide a labeled amplification product. In a preferred embodiment, transcription amplification, as described above, using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodarnine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label. Colloidal gold label can be detected by measuring scattered light.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an aviden-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology, Vol. 24: Hybridization With Nucleic Acid Probes,* P. Tijssen, ed. Elsevier, N.Y., (1993)).

Fluorescent labels are preferred and easily added during an in vitro transcription reaction. In a preferred embodiment, fluorescein labeled UTP and CTP are incorporated into the RNA produced in an in vitro transcription reaction as described above.

C. Modifying Sample to Improve Signal/Noise Ratio

The nucleic acid sample may be modified prior to hybridization to the high density probe array in order to reduce sample complexity thereby decreasing background signal and improving sensitivity of the measurement. In one embodiment, complexity reduction is achieved by selective degradation of background mRNA. This is accomplished by hybridizing the sample mRNA (e.g., polyA$^+$ RNA) with a pool of DNA oligonucleotides that hybridize specifically with the regions to which the probes in the array specifically hybridize. In a preferred embodiment, the pool of oligonucleotides consists of the same probe oligonucleotides as found on the high density array.

The pool of oligonucleotides hybridizes to the sample mRNA forming a number of double stranded (hybrid duplex) nucleic acids. The hybridized sample is then treated with RNase A, a nuclease that specifically digests single stranded RNA. The RNase A is then inhibited, using a protease and/or commercially available RNase inhibitors, and the double stranded nucleic acids are then separated from the digested single stranded RNA. This separation may be accomplished in a number of ways well known to those of skill in the art including, but not limited to, electrophoresis, and gradient centrifugation. However, in a preferred embodiment, the pool of DNA oligonucleotides is provided attached to beads forming thereby a nucleic acid affinity column. After digestion with the RNase A, the hybridized DNA is removed simply by denaturing (e.g., by adding heat or increasing salt) the hybrid duplexes and washing the previously hybridized mRNA off in an elution buffer.

The undigested mRNA fragments which will be hybridized to the probes in the high density array are then preferably end-labeled with a fluorophore attached to an RNA linker using an RNA ligase. This procedure produces a labeled sample RNA pool in which the nucleic acids that do not correspond to probes in the array are eliminated and thus unavailable to contribute to a background signal.

Another method of reducing sample complexity involves hybridizing the mRNA with deoxyoligonucleotides that hybridize to regions that border on either size the regions to which the high density array probes are directed. Treatment with RNAse H selectively digests the double stranded (hybrid duplexes) leaving a pool of single-stranded mRNA corresponding to the short regions (e.g., 20 mer) that were formerly bounded by the deoxyoligonucleotide probes and which correspond to the targets of the high density array probes and longer mRNA sequences that correspond to regions between the targets of the probes of the high density array. The short RNA fragments are then separated from the long fragments (e.g., by electrophoresis), labeled if necessary as described above, and then are ready for hybridization with the high density probe array.

In a third approach, sample complexity reduction involves the selective removal of particular (preselected) mRNA messages. In particular, highly expressed mRNA messages that are not specifically probed by the probes in the high density array are preferably removed. This approach involves hybridizing the polyA$^+$ mRNA with an oligonucleotide probe that specifically hybridizes to the preselected message close to the 3' (poly A) end. The probe may be selected to provide high specificity and low cross reactivity. Treatment of the hybridized message/probe complex with RNase H digests the double stranded region effectively removing the polyA$^+$ tail from the rest of the message. The sample is then treated with methods that specifically retain or amplify polyA$^+$ RNA (e.g., an oligo dT column or (dT)n magnetic beads). Such methods will not retain or amplify the selected message(s) as they are no longer associated with a polyA$^+$ tail. These highly expressed messages are effectively removed from the sample providing a sample that has reduced background mRNA.

IV. Hybridization Array Design

A. Probe Composition

One of skill in the art will appreciate that an enormous number of array designs are suitable for the practice of this invention. The high density array will typically include a number of probes that specifically hybridize to the nucleic acid(s) expression of which is to be detected. In addition, in a preferred embodiment, the array will include one or more control probes.

1. Test Probes

In its simplest embodiment, the high density array includes "test probes" . These are oligonucleotides that range from about 5 to about 45 or 5 to about 50 nucleotides, more preferably from about 10 to about 40 nucleotides and most preferably from about 15 to about 40 nucleotides in length. In other particularly preferred embodiments the probes are 20 or 25 nucleotides in length. These oligonucleotide probes have sequences complementary to particular subsequences of the genes whose expression they are designed to detect. Thus, the test probes are capable of specifically hybridizing to the target nucleic acid they are to detect.

In addition to test probes that bind the target nucleic acid(s) of interest, the high density array can contain a number of control probes. The control probes fall into three categories referred to herein as 1) Normalization controls; 2) Expression level controls; and 3) Mismatch controls.

2. Normalization Controls

Normalization controls are oligonucleotide probes that are perfectly complementary to labeled reference oligonucleotides that are added to the nucleic acid sample. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g., fluorescence intensity) read from all other probes in the array are divided by the signal (e.g., fluorescence intensity) from the control probes thereby normalizing the measurements.

Virtually any probe may serve as a normalization control. However, it is recognized that hybridization efficiency varies with base composition and probe length. Preferred normalization probes are selected to reflect the average length of the other probes present in the array, however, they can be selected to cover a range of lengths. The normalization control(s) can also be selected to reflect the (average) base composition of the other probes in the array, however in a preferred embodiment, only one or a few normalization probes are used and they are selected such that they hybridize well (i.e. no secondary structure) and do not match any target-specific probes.

Normalization probes can be localized at any position in the array or at multiple positions throughout the array to control for spatial variation in hybridization efficiently. In a preferred embodiment, the normalization controls are located at the corners or edges of the array as well as in the middle.

3. Expression Level Controls

Expression level controls are probes that hybridize specifically with constitutively expressed genes in the biological sample. Expression level controls are designed to control for the overall health and metabolic activity of a cell. Examination of the covariance of an expression level control with the expression level of the target nucleic acid indicates whether measured changes or variations in expression level of a gene is due to changes in transcription rate of that gene or to general variations in health of the cell. Thus, for example, when a cell is in poor health or lacking a critical metabolite the expression levels of both an active target gene and a constitutively expressed gene are expected to decrease. The converse is also true. Thus where the expression levels of both an expression level control and the target gene appear to both decrease or to both increase, the change may be attributed to changes in the metabolic activity of the cell as a whole, not to differential expression of the target gene in question. Conversely, where the expression levels of the target gene and the expression level control do not covary, the variation in the expression level of the target gene is attributed to differences in regulation of that gene and not to overall variations in the metabolic activity of the cell.

Virtually any constitutively expressed gene provides a suitable target for expression level controls. Typically expression level control probes have sequences complementary to subsequences of constitutively expressed "housekeeping genes" including, but not limited to the β-actin gene, the transferrin receptor gene, the GAPDH gene, and the like.

4. Mismatch Controls

Mismatch controls may also be provided for the probes to the target genes, for expression level controls or for normalization controls. Mismatch controls are oligonucleotide probes identical to their corresponding test or control probes except for the presence of one or more mismatched bases. A mismatched base is a base selected so that it is not complementary to the corresponding base in the target sequence to which the probe would otherwise specifically hybridize. One or more mismatches are selected such that under appropriate hybridization conditions (e.g. stringent conditions) the test or control probe would be expected to hybridize with its target sequence, but the mismatch probe would not hybridize (or would hybridize to a significantly lesser extent). Preferred mismatch probes contain a central mismatch. Thus, for example, where a probe is a 20 mer, a corresponding mismatch probe will have the identical sequence except for a single base mismatch (e.g., substituting a G, a C or a T for an A) at any of positions 6 through 14 (the central mismatch).

Mismatch probes thus provide a control for non-specific binding or cross-hybridization to a nucleic acid in the sample other than the target to which the probe is directed. Mismatch probes thus indicate whether a hybridization is specific or not. For example, if the target is present the perfect match probes should be consistently brighter than the mismatch probes. In addition, if all central mismatches are present, the mismatch probes can be used to detect a mutation. Finally, it was also a discovery of the present invention that the difference in intensity between the perfect match and the mismatch probe (I(PM)-I(MM)) provides a good measure of the concentration of the hybridized material.

5. Sample Preparation/Amplification Controls

The high density array may also include sample preparation/amplification control probes. These are probes that are complementary to subsequences of control genes selected because they do not normally occur in the nucleic acids of the particular biological sample being assayed. Suitable sample preparation/amplification control probes include, for example, probes to bacterial genes (e.g., Bio B) where the sample in question is a biological from a eukaryote.

The RNA sample is then spiked with a known amount of the nucleic acid to which the sample preparation/ amplification control probe is directed before processing. Quantification of the hybridization of the sample preparation/amplification control probe then provides a measure of alteration in the abundance of the nucleic acids caused by processing steps (e.g. PCR, reverse transcription, in vitro transcription, etc.).

B. Probe Selection and Optimization

In a preferred embodiment, oligonucleotide probes in the high density array are selected to bind specifically to the nucleic acid target to which they are directed with minimal non-specific binding or cross-hybridization under the particular hybridization conditions utilized. Because the high density arrays of this invention can contain in excess of 1,000,000 different probes, it is possible to provide every probe of a characteristic length that binds to a particular nucleic acid sequence. Thus, for example, the high density array can contain every possible 20 mer sequence complementary to an IL-2 mRNA.

There, however, may exist 20 mer subsequences that are not unique to the IL-2 mRNA. Probes directed to these subsequences are expected to cross hybridize with occurrences of their complementary sequence in other regions of the sample genome. Similarly, other probes simply may not hybridize effectively under the hybridization conditions (e.g., due to secondary structure, or interactions with the substrate or other probes). Thus, in a preferred embodiment, the probes that show such poor specificity or hybridization efficiency are identified and may not be included either in the high density array itself (e.g., during fabrication of the array) or in the post-hybridization data analysis.

In addition, in a preferred embodiment, expression monitoring arrays are used to identify the presence and expression (transcription) level of genes which are several hundred base pairs long. For most applications it would be useful to identify the presence, absence, or expression level of several thousand to one hundred thousand genes. Because the number of oligonucleotides per array is limited in a preferred embodiment, it is desired to include only a limited set of probes specific to each gene whose expression is to be detected.

It is a discovery of this invention that probes as short as 15, 20, or 25 nucleotide are sufficient to hybridize to a subsequence of a gene and that, for most genes, there is a set of probes that performs well across a wide range of target nucleic acid concentrations. In a preferred embodiment, it is desirable to choose a preferred or "optimum" subset of probes for each gene before synthesizing the high density array.

1. Hybridization and Cross-Hybridization Data

Thus, in one embodiment, this invention provides for a method of optimizing a probe set for detection of a particular gene. Generally, this method involves providing a high density array containing a multiplicity of probes of one or more particular length(s) that are complementary to subsequences of the mRNA transcribed by the target gene. In one embodiment the high density array may contain every probe of a particular length that is complementary to a particular mRNA. The probes of the high density array are then hybridized with their target nucleic acid alone and then hybridized with a high complexity, high concentration nucleic acid sample that does not contain the targets complementary to the probes. Thus, for example, where the target nucleic acid is an RNA, the probes are first hybridized with their target nucleic acid alone and then hybridized with RNA made from a cDNA library (e.g., reverse transcribed polyA$^+$ mRNA) where the sense of the hybridized RNA is opposite that of the target nucleic acid (to insure that the high complexity sample does not contain targets for the probes). Those probes that show a strong hybridization signal with their target and little or no cross-hybridization with the high complexity sample are preferred probes for use in the high density arrays of this invention.

The high density array may additionally contain mismatch controls for each of the probes to be tested. In a preferred embodiment, the mismatch controls contain a central mismatch. Where both the mismatch control and the target probe show high levels of hybridization (e.g., the hybridization to the mismatch is nearly equal to or greater than the hybridization to the corresponding test probe), the test probe is preferably not used in the high density array.

In a particularly preferred embodiment, optimal probes are selected according to the following method: First, as indicated above, an array is provided containing a multiplicity of oligonucleotide probes complementary to subsequences of the target nucleic acid. The oligonucleotide probes may be of a single length or may span a variety of lengths ranging from 5 to 50 nucleotide. The high density array may contain every probe of a particular length that is complementary to a particular mRNA or may contain probes selected from various regions of particular mRNAs. For each target-specific probe the array also contains a mismatch control probe; preferably a central mismatch control probe.

The oligonucleotide array is hybridized to a sample containing target nucleic acids having subsequences complementary to the oligonucleotide probes and the difference in hybridization intensity between each probe and its mismatch control is determined. Only those probes where the difference between the probe and its mismatch control exceeds a threshold hybridization intensity (e.g. preferably greater than 10% of the background signal intensity, more preferably greater than 20% of the background signal intensity and most preferably greater than 50% of the background signal intensity) are selected. Thus, only probes that show a strong signal compared to their mismatch control are selected.

The probe optimization procedure can optionally include a second round of selection. In this selection, the oligonucleotide probe array is hybridized with a nucleic acid sample that is not expected to contain sequences complementary to the probes. Thus, for example, where the probes are complementary to the RNA sense strand a sample of antisense RNA is provided. Of course, other samples could be provided such as samples from organisms or cell lines known to be lacking a particular gene, or known for not expressing a particular gene.

Only those probes where both the probe and its mismatch control show hybridization intensities below a threshold value (e.g. less than about 5 times the background signal intensity, preferably equal to or less than about 2 times the background signal intensity, more preferably equal to or less than about 1 times the background signal intensity, and most preferably equal or less than about half background signal intensity) are selected. In this way probes that show minimal non-specific binding are selected. Finally, in a preferred embodiment, the n probes (where n is the number of probes desired for each target gene) that pass both selection criteria and have the highest hybridization intensity for each target gene are selected for incorporation into the array, or where already present in the array, for subsequent data analysis. Of course, one of skill in the art, will appreciate that either selection criterion could be used alone for selection of probes.

2. Heuristic Rules

Using the hybridization and cross-hybridization data obtained as described above, graphs can be made of hybridization and cross-hybridization intensities versus various probe properties e.g., number of As, number of Cs in a window of 8 bases, palindomic strength, etc. The graphs can then be examined for correlations between those properties and the hybridization or cross-hybridization intensities. Thresholds can be set beyond which it looks like hybridization is always poor or cross hybridization is always very strong. If any probe fails one of the criteria, it is rejected from the set of probes and therefore, not placed on the chip. This will be called the heuristic rules method.

One set of rules developed for 20 mer probes in this manner is the following:

Hybridization rules:
1) Number of As is less than 9.
2) Number of Ts is less than 10 and greater than 0.
3) Maximum run of As, Gs, or Ts is less than 4 bases in a row.
4) Maximum run of any 2 bases is less than 11 bases.
5) Palindrome score is less than 6.
6) Clumping score is less than 6.
7) Number of As +Number of Ts is less than 14
8) Number of As +number of Gs is less than 15

With respect to rule number 4, requiring the maximum run of any two bases to be less than 11 bases guarantees that at least three different bases occur within any 12 consecutive nucleotide. A palindrome score is the maximum number of complementary bases if the oligonucleotide is folded over at a point that maximizes self complementarity. Thus, for example a 20 mer that is perfectly self-complementary would have a palindrome score of 10. A clumping score is the maximum number of three-mers of identical bases in a given sequence. Thus, for example, a run of 5 identical bases will produce a clumping score of 3 (bases 1–3, bases 2–4, and bases 3–5).

If any probe failed one of these criteria (1–8), the probe was not a member of the subset of probes placed on the chip. For example, if a hypothetical probe was 5'-AGCTTTTTTCATGCATCTAT-3' the probe would not be synthesized on the chip because it has a run of four or more bases (i.e., run of six).

The cross hybridization rules developed for 20 mers were as follows:
1) Number of Cs is less than 8;
2) Number of Cs in any window of 8 bases is less than 4.

Thus, if any probe failed any of either the hybridization ruses (1–8) or the cross-hybridization rules (1–2), the probe was not a member of the subset of probes placed on the chip. These rules eliminated many of the probes that cross hybridized strongly or exhibited low hybridization, and performed moderate job of eliminating weakly hybridizing probes.

These heuristic rules may be implemented by hand calculations, or alternatively, they may be implemented in software as is discussed below in Section IV.B.7.

3. Neural Net

In another embodiment, a neural net can be trained to predict the hybridization and cross-hybridization intensities based on the sequence of the probe or on other probe properties. The neural net can then be used to pick an arbitrary number of the "best" probes. One such neural net was developed for selecting 20-mer probes. This neural net was produced a moderate (0.7) correlation between predicted intensity and measured intensity, with a better model for cross hybridization than hybridization. Details of this neural net are provided in Example 6.

4. ANOVA Model

An analysis of variance (ANOVA) model may be built to model the intensities based on positions of consecutive base pairs. This is based on the theory that the melting energy is based on stacking energies of consecutive bases. The annova model was used to find correlation between the a probe sequence and the hybridization and cross-hybridization intensities. The inputs were probe sequences broken down into consecutive base pairs. One model was made to predict hybridization, another was made to predict cross hybridization. The output was the hybridization or cross-hybridization intensity.

There were 304 (19*16) possible inputs, consisting of the 14 possible two base combinations, and the 19 positions that those combinations could be found in. For example, the sequence aggctga . . . has "ag" in the first position, "gg" in the second position, "gc" in the third, "ct" in the fourth and so on.

The resulting model assigned a component of the output intensity to each of the possible inputs, so to estimate the intensity for a given sequence one simply adds the intensities for each of it's 19 components.

5. Pruning (Removal) of Similar Probes

One of the causes of poor signals in expression chips is that genes other than the ones being monitored have sequences which are very similar to parts of the sequences which are being monitored. The easiest way to solve this is to remove probes which are similar to more than one gene. Thus, in a preferred embodiment, it is desirable to remove (prune) probes that hybridize to transcription products of more than one gene.

The simplest pruning method is to line up a proposed probe with all known genes for the organism being monitored, then count the number of matching bases. For example, given a probe to gene 1 of an organism and gene 2 of an organism as follows:

```
probe from gene 1: aagcgcgatcgattatgctc
                   |      |||||||
gene 2:                   atctcggatcgatcggataagcgcgatcgattatgctcggcga
``` has 8 matching bases in this alignment, but 20 matching bases in the following alignment:

```
probe from gene 1:                     aagcgcgatcgattatgctc
                                       ||||||||||||||||||||
gene 2:                   atctcggatcgatcggataagcgcgatcgattatgctcggcga
```

More complicated algorithms also exist, which allow the detection of insertion or deletion mismatches. Such sequence alignment algorithms are well known to those of skill in the art and include, but are not limited to BLAST, or FASTA, or other gene matching programs such as those described above in the definitions section.

In another variant, where an organism has many different genes which are very similar, it is difficult to make a probe set that measures the concentration only one of those very similar genes. One can then prune out any probes which are dissimilar, and make the probe set a probe set for that family of genes.

6. Synthesis Cycle Pruning

The cost of producing masks for a chip is approximately linearly related to the number of synthesis cycles. In a normal set of genes the distribution of the number of cycles any probe takes to build approximates a Gaussian distribution. Because of this the mask cost can normally be reduced by 15% by throwing out about 3 percent of the probes. In a preferred embodiment, synthesis cycle pruning simply involves eliminating (not including) those probes those probes that require a greater number of synthesis cycles than the maximum number of synthesis cycles selected for preparation of the particular subject high density oligonucleotide array. Since the typical synthesis of probes follows a regular pattern of bases put down (acgtacgtacgt) counting the number of synthesis steps needed to build a probe is easy. The listing shown in Table 1 provides typical code for counting the number of synthesis cycles a probe will need.

TABLE 1

Typical code for counting synthesis cycles required for the chemical synthesis of a probe.
```
static char base[] = "acgt";
//                    a b c d e f g h i j k l m n o p q r s t u v w x y z
static short index[] = { 0, 0, 1, 0, 0, 0, 2, 0, 0, 0, 0, 0, 0, 0, 0, 0, 0, 0, 0, 3, 0, 0, 0, 0, 0,
0};
short lookupIndex( char aBase ){
```

TABLE 1-continued

```
        if( isupper( aBase) ||!isalpha( aBase) ){
            errorHwnd("illegal base");
            return -1;
        }
        if( strchr( base, aBase) == NULL ){
            errorHwnd( "non-dna base");
            return 0;
        }
    return index[aBase - 'a'];
}
static short calculateMinNumberOfSynthesisStepsForComplement( char local * buffer ){
        short i, last, current, cycles = 1;
        char buffer1[40];
        for( i =3D 0; buffer[i] != 0; i++){
            switch( tolower(buffer[i]) ){
                case 'a': buffer1 [i] = 't';break;
                case 'c': buffer1 [i] = 'g';break;
                case 'g': buffer1 [i] = 'c';break;
                case 't': buffer1 [i] = 'a';break;
            }
        }
        buffer1[i] = 0;
        if( buffer1[0] = 0) return 0;
        last = lookupIndex( buffer1[0]);
        for(i = 1; buffer1[i] != 0;i++){
            current = lookupIndex( buffer1 [i]);
            if( current <= last ) cycles++;
            last = current;
        }
        return (short)((cycles -1) * 4 + current +1);
}
```

7. Combination of Selection Methods

The heuristic rules, neural net and annova model provide ways of pruning or reducing the number of probes for monitoring the expression of genes. As these methods do not necessarily produce the same results, or produce entirely independent results, it may be advantageous to combine the methods. For example, probes may be pruned or reduced if more than one method (e.g., two out of three) indicate the probe will not likely produce good results. Then, synthesis cycle pruning may be performed to reduce costs.

Figure 11:
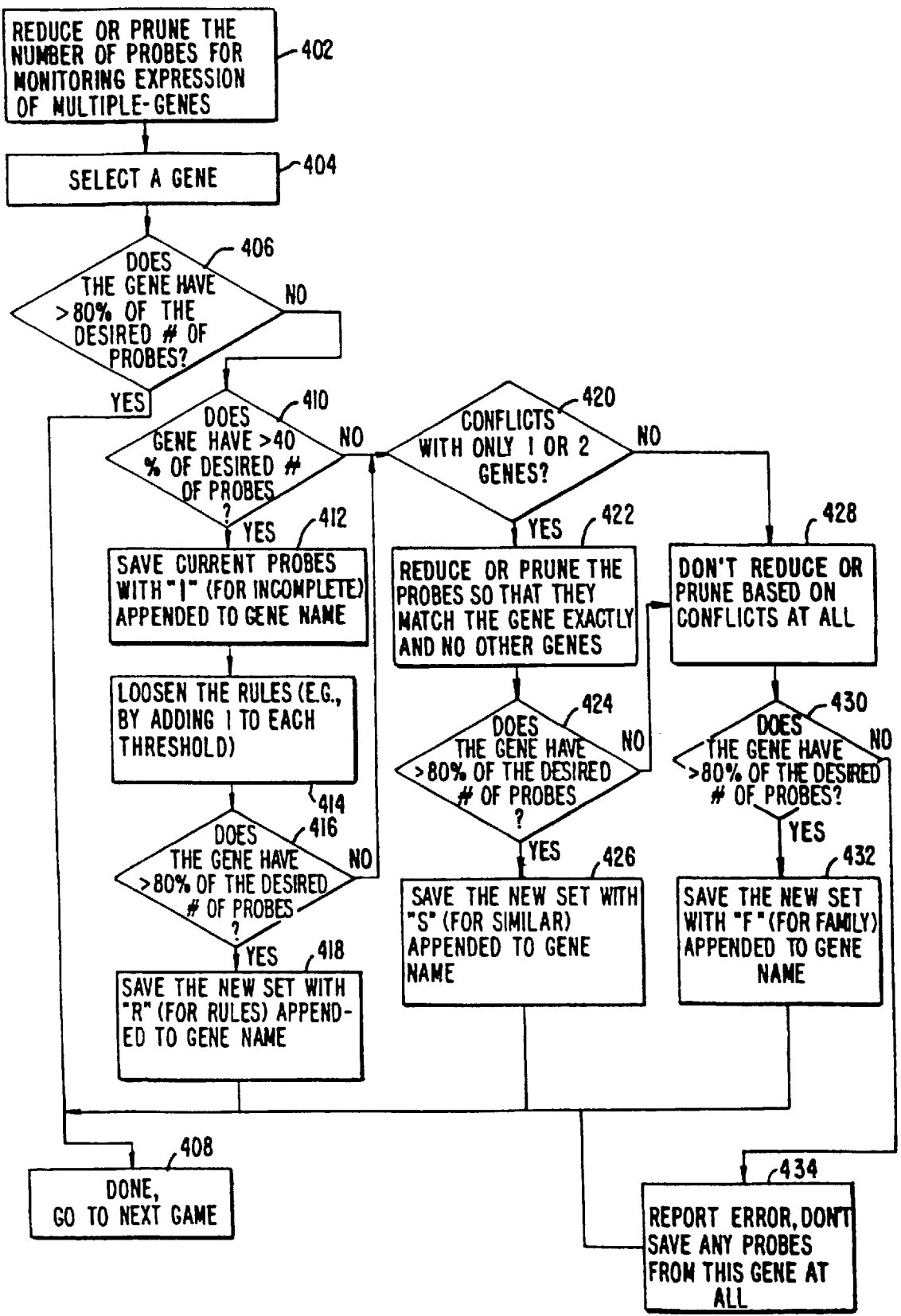
FIG. 11 shows the flow of a process of increasing the number of probes for monitoring the expression of genes after the number of probes has been reduced or pruned.

FIG. 11 shows the flow of a process of increasing the number of probes for monitoring the expression of genes after the number of probes has been reduced or pruned. In one embodiment, a user is able to specify the number of nucleic acid probes that should be placed on the chip to monitor the expression of each gene. As discussed above, it is advantageous to reduce probes that will not likely produce good results; however, the number of probes may be reduced to substantially less than the desired number of probes.

At step 402, the number of probes for monitoring multiple genes is reduced by the heuristic rules method, neural net, annova model, synthesis cycle pruning, or any other method, or combination of methods. A gene is selected at step 404.

A determination is made whether the remaining probes for monitoring the selected gene number greater than 80% (which may be varied or user defined) of the desired number of probes. If yes, the computer system proceeds to the next gene at step 408 which will generally return to step 404.

If the remaining probes for monitoring the selected gene do not number greater than 80% of the desired number of probes, a determination is made whether the remaining probes for monitoring the selected gene number greater than 40% (which may be varied or user defined) of the desired number of probes. If yes, an "i" is appended to the end of the gene name to indicate that after pruning, the probes were incomplete at step 412.

At step 414, the number of probes is increased by loosening the constraints that rejected probes. For example, the thresholds in the heuristic rules may be increased by 1. Therefore, if previously probes were rejected if they had four As in a row, the rule may be loosened to five As in a row.

A determination is then made whether the remaining probes for monitoring the selected gene number greater than 80% of the desired number of probes at step 416. If yes, an "r" is appended to the end of the gene name at step 412 to indicate that the rules were loosened to generate the number of synthesized probes for that gene.

At step 420, a check is made to see if the probes for monitoring the selected gene only conflict with one or two other genes. If yes, the full set of probes complementary to the gene (or target sequence) are taken and pruned so that the probes remaining are exactly complementary to the selected gene exclusively at step 422.

A determination is then made whether the remaining probes for monitoring the selected gene number greater than 80% of the desired number of probes at step 424. If yes, an "s" is appended to the end of the gene name at step 426 to indicate that the only a few genes were similar to the selected gene.

At step 428, the probes for monitoring the selected gene are not reduced by conflicts at all. A determination is then made whether the remaining probes for monitoring the selected gene number greater than 80% of the desired number of probes at step 430. If yes, an "f" is appended to the end of the gene name at step 432 to indicate that the probes include the whole family of probes perfectly complementary to the gene.

If there are still not 80% of the desired number of probes, an error is reported at step 434. Any number of error handling procedures may be undertaken. For example, an error message may be generated for the user and the probes for the gene may not be stored. Alternatively, the user may be prompted to enter a new desired number of probes.

V. Synthesis of High Density Arrays

Methods of forming high density arrays of oligonucleotides, peptides and other polymer sequences with a minimal number of synthetic steps are known. The oligonucleotide analogue array can be synthesized on a solid substrate by a variety of methods, including, but not limited to, light-directed chemical coupling, and mechanically directed coupling. See Pirrung et al., U.S. Pat. No. 5,143,854 (see also PCT application No. WO 90/15070) and Fodor et al., PCT Publication Nos. WO 92/10092 and WO 93/09668 and U.S. Ser. No. 07/980,523 which disclose methods of forming vast arrays of peptides, oligonucleotides and other molecules using, for example, light-directed synthesis techniques. See also, Fodor et al., Science, 251, 767–77 (1991). These procedures for synthesis of polymer arrays are now referred to as VLSIPS™ procedures. Using the VLSIPS™ approach, one heterogenous array of polymers is converted, through simultaneous coupling at a number of reaction sites, into a different heterogenous array. See, U.S. application Ser. Nos. 07/796,243 and 07/980,523.

The development of VLSIPS™ technology as described in the above-noted U.S. Pat. No. 5,143,854 and PCT patent publication Nos. WO 90/15070 and 92/10092, is considered pioneering technology in the fields of combinatorial synthesis and screening of combinatorial libraries. More recently, patent application Ser. No. 08/082,937, filed Jun. 25, 1993 describes methods for making arrays of oligonucleotide probes that can be used to check or determine a partial or complete sequence of a target nucleic acid and to detect the presence of a nucleic acid containing a specific oligonucleotide sequence.

In brief, the light-directed combinatorial synthesis of oligonucleotide arrays on a glass surface proceeds using automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithogaphic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents.

In the event that an oligonucleotide analogue with a polyamide backbone is used in the VLSIPS™ procedure, it is generally inappropriate to use phosphoramidite chemistry to perform the synthetic steps, since the monomers do not attach to one another via a phosphate linkage. Instead, peptide synthetic methods are substituted. See, e.g., Pirrung et al. U.S. Pat. No. 5,143,854.

Peptide nucleic acids are commercially available from, e.g., Biosearch, Inc. (Bedford, Mass.) which comprise a polyamide backbone and the bases found in naturally occurring nucleosides. Peptide nucleic acids are capable of binding to nucleic acids with high specificity, and are considered "oligonucleotide analogues" for purposes of this disclosure.

In addition to the foregoing, additional methods which can be used to generate an array of oligonucleotides on a single substrate are described in co-pending applications Ser. No. 07/980,523, filed Nov. 20, 1992, and 07/796,243, filed Nov. 22, 1991 and in PCT Publication No. WO 93/09668. In the methods disclosed in these applications, reagents are delivered to the substrate by either (1) flowing within a channel defined on predefined regions or (2) "spotting" on predefined regions or (3) through through the use of photoresist. However, other approaches, as well as combinations of spotting and flowing, may be employed. In each instance, certain activated regions of the substrate are mechanically separated from other regions when the monomer solutions are delivered to the various reaction sites.

A typical "flow channel" method applied to the compounds and libraries of the present invention can generally be described as follows. Diverse polymer sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

The "spotting" methods of preparing compounds and libraries of the present invention can be implemented in much the same manner as the flow channel methods. For example, a monomer A can be delivered to and coupled with a first group of reaction regions which have been appropriately activated. Thereafter, a monomer B can be delivered to and reacted with a second group of activated reaction regions. Unlike the flow channel embodiments described above, reactants are delivered by directly depositing (rather than flowing) relatively small quantities of them in selected regions. In some steps, of course, the entire substrate surface can be sprayed or otherwise coated with a solution. In preferred embodiments, a dispenser moves from region to region, depositing only as much monomer as necessary at each stop. Typical dispensers include a micropipette to deliver the monomer solution to the substrate and a robotic system to control the position of the micropipette with respect to the substrate. In other embodiments, the dispenser includes a series of tubes, a manifold, an array of pipettes, or the like so that various reagents can be delivered to the reaction regions simultaneously.

VI. Hybridization

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency in this case in 6×SSPE-T at 37° C. (0.005% Triton X-100) to ensure hybridization and then subsequent washes are performed at higher stringency (e.g., 1×SSPE-T at 37° C.) to eliminate mismatched hybrid duplexes. Successive washes may be performed at increasingly higher stringency (e.g., down to as low as 0.25× SSPE-T at 37° C. to 50° C.) until a desired level of hybridization specificity is obtained. Stringency can also be increased by addition of agents such as formamide. Hybridization specificity may be evaluated by comparison of hybridization to the test probes with hybridization to the various controls that can be present (e.g., expression level control, normalization control, mismatch controls, etc.).

In general, there is a trade off between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

In a preferred embodiment, background signal is reduced by the use of a detergent (e.g., C-TAB) or a blocking reagent (e.g., sperm DNA, cot-1 DNA, etc.) during the hybridization to reduce non-specific binding. In a particularly preferred embodiment, the hybridization is performed in the presence of about 0.5 mg/ml DNA (e.g., herring sperm DNA). The use of blocking agents in hybridization is well known to those of skill in the art (see, e.g., Chapter 8 in P. Tijssen, supra.)

The stability of duplexes formed between RNAs or DNAs are generally in the order of RNA:RNA>RNA:DNA>DNA:DNA, in solution. Long probes have better duplex stability with a target, but poorer mismatch discrimination than shorter probes (mismatch discrimination refers to the measured hybridization signal ratio between a perfect match probe and a single base mismatch probe). Shorter probes (e.g., 8-mers) discriminate mismatches very well, but the overall duplex stability is low.

Altering the thermal stability ($T_m$) of the duplex formed between the target and the probe using, e.g., known oligonucleotide analogues allows for optimization of duplex stability and mismatch discrimination. One useful aspect of altering the $T_m$ arises from the fact that adenine-thymine (A-T) duplexes have a lower $T_m$ than guanine-cytosine (G-C) duplexes, due in part to the fact that the A-T duplexes have 2 hydrogen bonds per base-pair, while the G-C duplexes have 3 hydrogen bonds per base pair. In heterogeneous oligonucleotide arrays in which there is a non-uniform distribution of bases, it is not generally possible to optimize hybridization for each oligonucleotide probe simultaneously. Thus, in some embodiments, it is desirable to selectively destabilize G-C duplexes and/or to increase the stability of A-T duplexes. This can be accomplished, e.g., by substituting guanine residues in the probes of an array which form G-C duplexes with hypoxanthine, or by substituting adenine residues in probes which form A-T duplexes with 2,6 diaminopurine or by using the salt tetramethyl ammonium chloride (TMACl) in place of NaCl.

Altered duplex stability conferred by using oligonucleotide analogue probes can be ascertained by following, e.g., fluorescence signal intensity of oligonucleotide analogue arrays hybridized with a target oligonucleotide over time. The data allow optimization of specific hybridization conditions at, e.g., room temperature (for simplified diagnostic applications in the future).

Another way of verifying altered duplex stability is by following the signal intensity generated upon hybridization with time. Previous experiments using DNA targets and DNA chips have shown that signal intensity increases with time, and that the more stable duplexes generate higher signal intensities faster than less stable duplexes. The signals reach a plateau or "saturate" after a certain amount of time due to all of the binding sites becoming occupied. These data allow for optimization of hybridization, and determination of the best conditions at a specified temperature.

Methods of optimizing hybridization conditions are well known to those of skill in the art (see, e.g., *Laboratory Techniques in Biochemistry and Molecular Biology, Vol. 24. Hybridization With Nucleic Acid Probes*, P. Tijssen, ed. Elsevier, N.Y., (1993)).

VII. Signal Detection

Means of detecting labeled target (sample) nucleic acids hybridized to the probes of the high density array are known to those of skill in the art. Thus, for example, where a colorimetric label is used, simple visualization of the label is sufficient. Where a radioactive labeled probe is used, detection of the radiation (e.g with photographic film or a solid state detector) is sufficient.

In a preferred embodiment, however, the target nucleic acids are labeled with a fluorescent label and the localization of the label on the probe array is accomplished with fluorescent microscopy. The hybridized array is excited with a light source at the excitation wavelength of the particular fluorescent label and the resulting fluorescence at the emission wavelength is detected. In a particularly preferred embodiment, the excitation light source is a laser appropriate for the excitation of the fluorescent label.

The confocal microscope may be automated with a computer-controlled stage to automatically scan the entire high density array. Similarly, the microscope may be equipped with a phototransducer (e.g., a photomultiplier, a solid state array, a ccd camera, etc.) attached to an automated data acquisition system to automatically record the fluorescence signal produced by hybridization to each oligonucleotide probe on the array. Such automated systems are described at length in U.S. Pat. No: 5,143,854, PCT application 20 92/10092, and copending U.S. Ser. No. 08/195,889 filed on Feb. 10, 1994. Use of laser illumination in conjunction with automated confocal microscopy for signal detection permits detection at a resolution of better than about 100 μm, more preferably better than about 50 μm, and most preferably better than about 25 μm.

VIII. Signal Evaluation

One of skill in the art will appreciate that methods for evaluating the hybridization results vary with the nature of the specific probe nucleic acids used as well as the controls provided. In the simplest embodiment, simple quantification of the fluorescence intensity for each probe is determined. This is accomplished simply by measuring probe signal strength at each location (representing a different probe) on the high density array (e.g., where the label is a fluorescent label, detection of the amount of florescence (intensity) produced by a fixed excitation illumination at each location on the array). Comparison of the absolute intensities of an array hybridized to nucleic acids from a "test" sample with intensities produced by a "control" sample provides a measure of the relative expression of the nucleic acids that hybridize to each of the probes.

One of skill in the art, however, will appreciate that hybridization signals will vary in strength with efficiency of hybridization, the amount of label on the sample nucleic acid and the amount of the particular nucleic acid in the sample. Typically nucleic acids present at very low levels (e.g., <1 pM) will show a very weak signal. At some low level of concentration, the signal becomes virtually indistinguishable from background. In evaluating the hybridization data, a threshold intensity value may be selected below which a signal is not counted as being essentially indistinguishable from background.

Where it is desirable to detect nucleic acids expressed at lower levels, a lower threshold is chosen. Conversely, where only high expression levels are to be evaluated a higher threshold level is selected. In a preferred embodiment, a suitable threshold is about 10% above that of the average background signal.

In addition, the provision of appropriate controls permits a more detailed analysis that controls for variations in hybridization conditions, cell health, non-specific binding and the like. Thus, for example, in a preferred embodiment, the hybridization array is provided with normalization controls as described above in Section IV.A.2. These normalization controls are probes complementary to control sequences added in a known concentration to the sample. Where the overall hybridization conditions are poor, the normalization controls will show a smaller signal reflecting reduced hybridization. Conversely, where hybridization conditions are good, the normalization controls will provide a higher signal reflecting the improved hybridization. Normalization of the signal derived from other probes in the array to the normalization controls thus provides a control for variations in hybridization conditions. Typically, normalization is accomplished by dividing the measured signal from the other probes in the array by the average signal produced by the normalization controls. Normalization may also include correction for variations due to sample preparation and amplification. Such normalization may be accomplished by dividing the measured signal by the average signal from the sample preparation/amplfication control probes (e.g., the Bio B probes). The resulting values may be multiplied by a constant value to scale the results.

As indicated above, the high density array can include mismatch controls. In a preferred embodiment, there is a mismatch control having a central mismatch for every probe (except the normalization controls) in the array. It is expected that after washing in stringent conditions, where a perfect match would be expected to hybridize to the probe, but not to the mismatch, the signal from the mismatch controls should only reflect non-specific binding or the presence in the sample of a nucleic acid that hybridizes with the mismatch. Where both the probe in question and its corresponding mismatch control both show high signals, or the mismatch shows a higher signal than its corresponding test probe, there is a problem with the hybridization and the signal from those probes is ignored. The difference in hybridization signal intensity between the target specific probe and its corresponding mismatch control is a measure of the discrimination of the target-specific probe. Thus, in a preferred embodiment, the signal of the mismatch probe is subtracted from the signal from its corresponding test probe to provide a measure of the signal due to specific binding of the test probe.

The concentration of a particular sequence can then be determined by measuring the signal intensity of each of the probes that bind specifically to that gene and normalizing to the normalization controls. Where the signal from the probes is greater than the mismatch, the mismatch is subtracted. Where the mismatch intensity is equal to or greater than its corresponding test probe, the signal is ignored. The expression level of a particular gene can then be scored by the number of positive signals (either absolute or above a threshold value), the intensity of the positive signals (either absolute or above a selected threshold value), or a combination of both metrics (e.g., a weighted average).

It is a surprising discovery of this invention, that normalization controls are often unnecessary for useful quantification of a hybridization signal. Thus, where optimal probes have been identified in the two step selection process as described above, in Section II.B., the average hybridization signal produced by the selected optimal probes provides a good quantified measure of the concentration of hybridized nucleic acid.

IX. Computer-implemented Expression Monitoring

The methods of monitoring gene expression of this invention may be performed utilizing a computer. The computer typically runs a software program that includes computer code incorporating the invention for analyzing hybridization intensities measured from a substrate or chip and thus, monitoring the expression of one or more genes. Although the following will describe specific embodiments of the invention, the invention is not limited to any one embodiment so the following is for purposes of illustration and not limitation.

Figure 6:
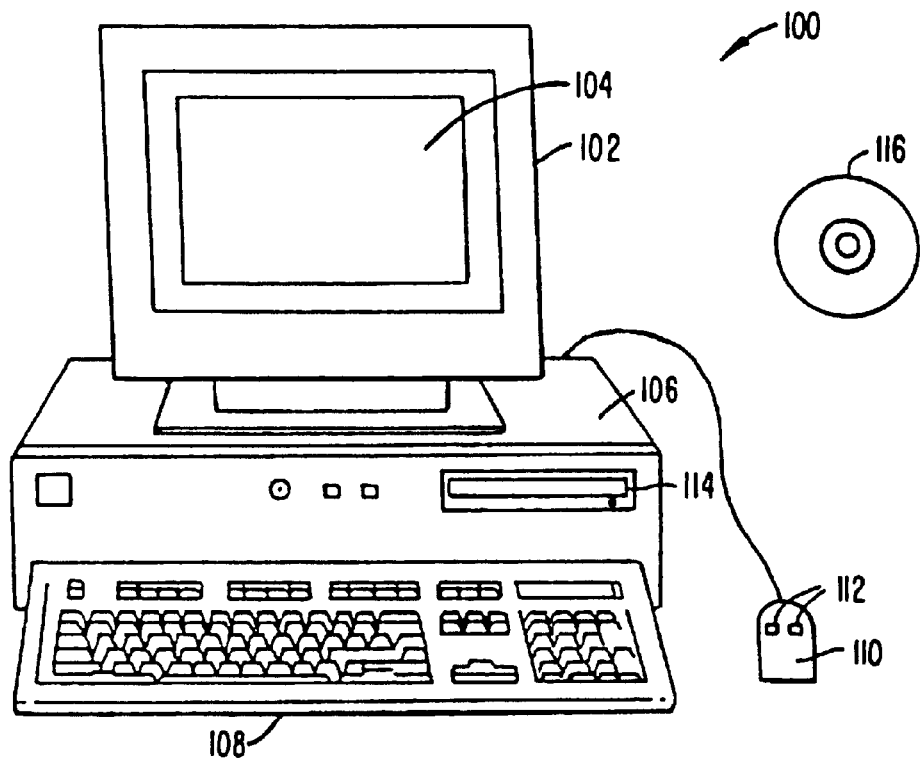
FIG. 6 shows an example of a computer system used to execute the software of an embodiment of the present invention.

FIG. 6 illustrates an example of a computer system used to execute the software of an embodiment of the present invention. As shown, shows a computer system 100 includes a monitor 102, screen 104, cabinet 106, keyboard 108, and mouse 110. Mouse 110 may have one or more buttons such as mouse buttons 112. Cabinet 106 houses a CD-ROM drive 114, a system memory and a hard drive (both shown in FIG. 7) which may be utilized to store and retrieve software programs incorporating computer code that implements the invention, data for use with the invention, and the like. Although a CD-ROM 116 is shown as an exemplary computer readable storage medium, other computer readable storage media including floppy disks, tape, flash memory, system memory, and hard drives may be utilized. Cabinet 106 also houses familiar computer components (not shown) such as a central processor, system memory, hard disk, and the like.

Figure 7:
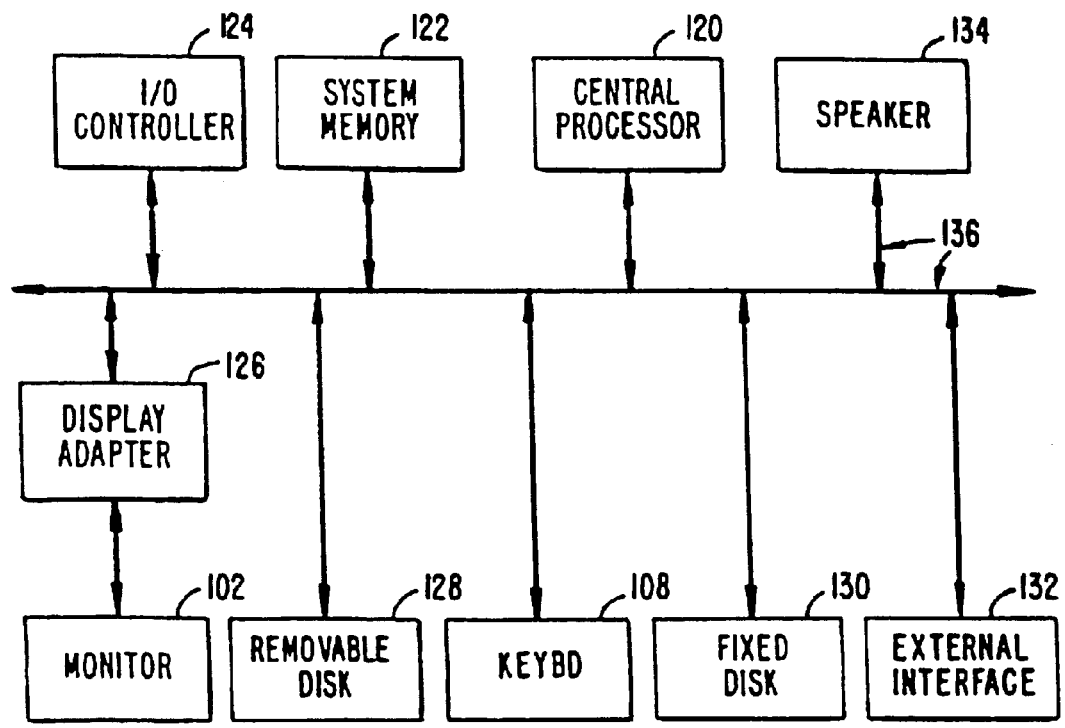
FIG. 7 shows a system block diagram of a typical computer system used to execute the software of an embodiment of the present invention.

FIG. 7 shows a system block diagram of computer system 100 used to execute the software of an embodiment of the present invention. As in FIG. 6, computer system 100 includes monitor 102 and keyboard 108. Computer system 100 further includes subsystems such as a central processor 120, system memory 122, I/O controller 124, display adapter 126, removable disk 128 (e.g., CD-ROM drive), fixed disk 130 (e.g., hard drive), network interface 132, and speaker 134. Other computer systems suitable for use with the present invention may include additional or fewer subsystems. For example, another computer system could include more than one processor 120 (i.e., a multi-processor system) or a cache memory.

Arrows such as 136 represent the system bus architecture of computer system 100. However, these arrows are illustrative of any interconnection scheme serving to link the subsystems. For example, a local bus could be utilized to connect the central processor to the system memory and display adapter. Computer system 100 shown in FIG. 7 is but an example of a computer system suitable for use with the present invention. Other configurations of subsystems suitable for use with the present invention will be readily apparent to one of ordinary skill in the art.

Figure 8:
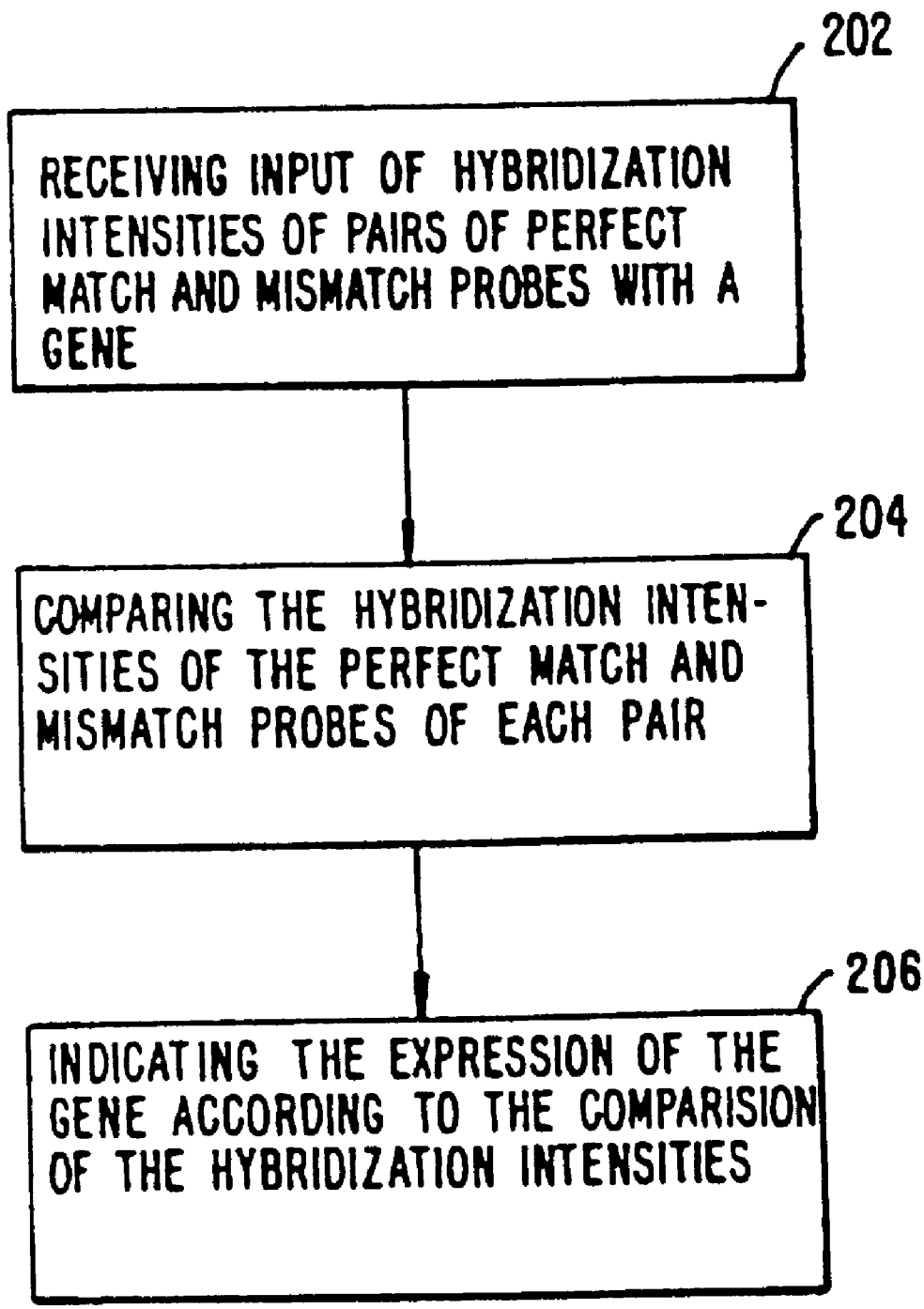
FIG. 8 shows the high level flow of a process of monitoring the expression of a gene by comparing hybridization intensities of pairs of perfect match and mismatch probes.

FIG. 8 shows a flowchart of a process of monitoring the expression of a gene. The process compares hybridization intensities of pairs of perfect match and mismatch probes that are preferably covalently attached to the surface of a substrate or chip. Most preferably, the nucleic acid probes have a density greater than about 60 different nucleic acid probes per 1 cm$^2$ of the substrate. Although the flowcharts show a sequence of steps for clarity, this is not an indication that the steps must be performed in this specific order. One of ordinary skill in the art would readily recognize that many of the steps may be reordered, combined, and deleted without departing from the invention.

Initially, nucleic acid probes are selected that are complementary to the target sequence (or gene). These probes are the perfect match probes. Another set of probes is specified that are intended to be not perfectly complementary to the target sequence. These probes are the mismatch probes and each mismatch probe includes at least one nucleotide mismatch from a perfect match probe. Accordingly, a mismatch probe and the perfect match probe from which it was derived make up a pair of probes. As mentioned earlier, the nucleotide mismatch is preferably near the center of the mismatch probe.

The probe lengths of the perfect match probes are typically chosen to exhibit high hybridization affinity with the target sequence. For example, the nucleic acid probes may be all 20-mers. However, probes of varying lengths may also be synthesized on the substrate for any number of reasons including resolving ambiguities.

The target sequence is typically fragmented, labeled and exposed to a substrate including the nucleic acid probes as described earlier. The hybridization intensities of the nucleic acid probes is then measured and input into a computer system. The computer system may be the same system that directs the substrate hybridization or it may be a different system altogether. Of course, any computer system for use with the invention should have available other details of the experiment including possibly the gene name, gene sequence, probe sequences, probe locations on the substrate, and the like.

Referring to FIG. 8, after hybridization, the computer system receives input of hybridization intensities of the multiple pairs of perfect match and mismatch probes at step 202. The hybridization intensities indicate hybridization affinity between the nucleic acid probes and the target nucleic acid (which corresponds to a gene). Each pair includes a perfect match probe that is perfectly complementary to a portion of the target nucleic acid and a mismatch probe that differs from the perfect match probe by at least one nucleotide.

At step 204, the computer system compares the hybridization intensities of the perfect match and mismatch probes of each pair. If the gene is expressed, the hybridization intensity (or affinity) of a perfect match probe of a pair should be recognizably higher than the corresponding mismatch probe. Generally, if the hybridizations intensities of a pair of probes are substantially the same, it may indicate the gene is not expressed. However, the determination is not based on a single pair of probes, the determination of whether a gene is expressed is based on an analysis of many pairs of probes. An exemplary process of comparing the hybridization intensities of the pairs of probes will be described in more detail in reference to FIG. 9.

After the system compares the hybridization intensity of the perfect match and mismatch probes, the system indicates expression of the gene at step 206. As an example, the system may indicate to a user that the gene is either present (expressed), marginal or absent (unexpressed).

Figure 9:
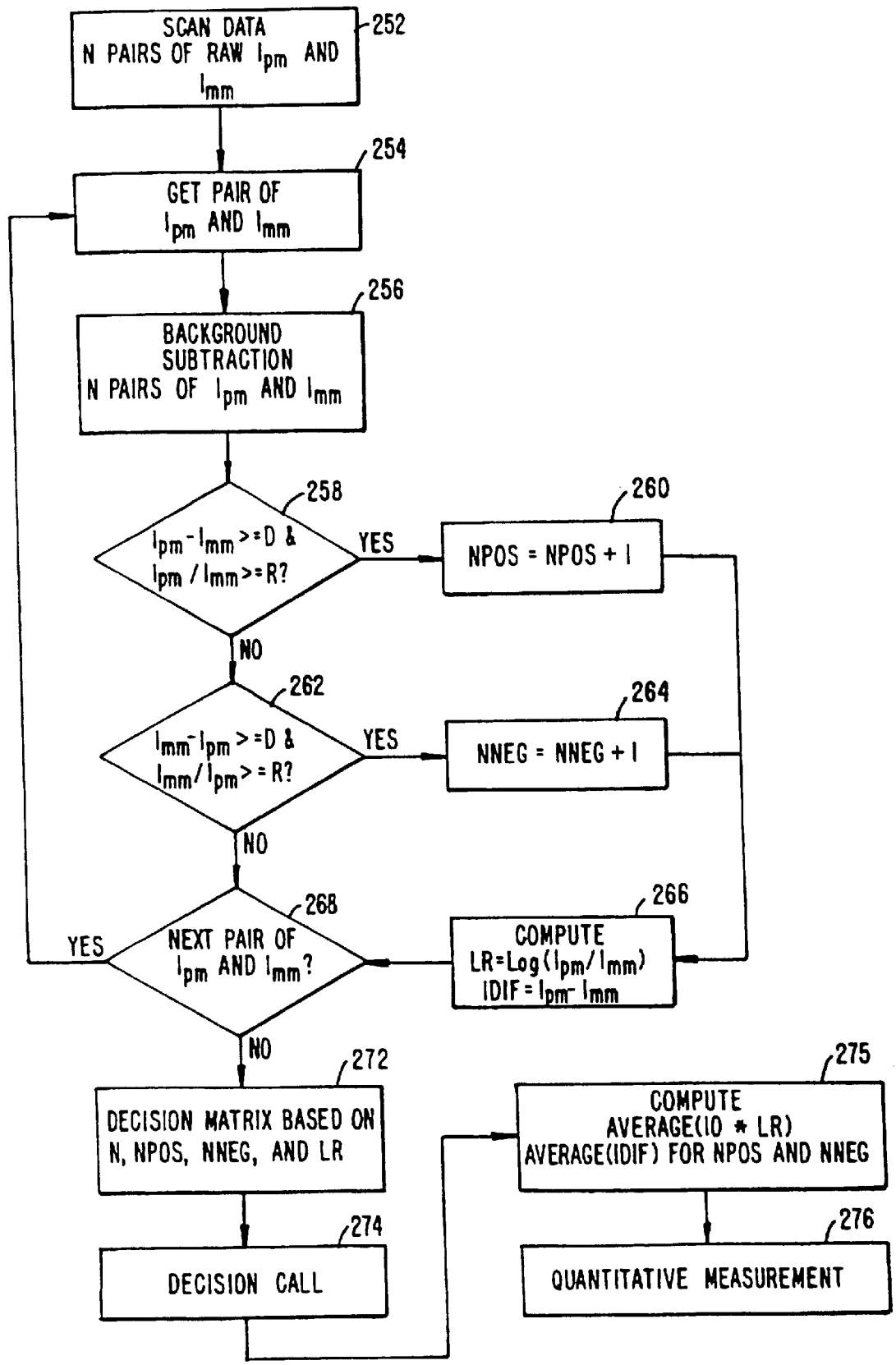
FIG. 9 shows the flow of a process of determining if a gene is expressed utilizing a decision matrix.

FIG. 9 shows a flowchart of a process of determining if a gene is expressed utilizing a decision matrix. At step 252, the computer system receives raw scan data of N pairs of perfect match and mismatch probes. In a preferred embodiment, the hybridization intensities are photon counts from a fluorescein labeled target that has hybridized to the probes on the substrate. For simplicity, the hybridization intensity of a perfect match probe will be designed "$I_{pm}$" and the hybridization intensity of a mismatch probe will be designed "$I_{mm}$."

Hybridization intensities for a pair of probes is retrieved at step 254. The background signal intensity is subtracted from each of the hybridization intensities of the pair at step 256. Background subtraction may also be performed on all the raw scan data at the same time.

At step 258, the hybridization intensities of the pair of probes are compared to a difference threshold (D) and a ratio threshold (R). It is determined if the difference between the hybridization intensities of the pair ($I_{pm}-I_{mm}$) is greater than or equal to the difference threshold AND the quotient of the hybridization intensities of the pair ($I_{pm}/I_{mm}$) is greater than or equal to the ratio threshold. The difference thresholds are typically user defined values that have been determined to produce accurate expression monitoring of a gene or genes. In one embodiment, the difference threshold is 20 and the ratio threshold is 1.2.

If $I_{pm}-I_{mm}>=D$ and $I_{pm}/I_{mm}>=R$, the value NPOS is incremented at step 260. In general, NPOS is a value that indicates the number of pairs of probes which have hybridization intensities indicating that the gene is likely expressed. NPOS is utilized in a determination of the expression of the gene.

At step 262, it is determined if $I_{mm}-I_{pm}>=D$ and $I_{mm}/I_{pm}>=R$. If this expression is true, the value NNEG is incremented at step 264. In general, NNEG is a value that indicates the number of pairs of probes which have hybridization intensities indicating that the gene is likely not expressed. NNEG, like NPOS, is utilized in a determination of the expression of the gene.

For each pair that exhibits hybridization intensities either indicating the gene is expressed or not expressed, a log ratio value (LR) and intensity difference value (IDIF) are calculated at step 266. LR is calculated by the log of the quotient of the hybridization intensities of the pair ($I_{pm}/I_{mm}$). The IDIF is calculated by the difference between the hybridization intensities of the pair ($I_{pm}-I_{mm}$). If there is a next pair of hybridization intensities at step 268, they are retrieved at step 254.

At step 272, a decision matrix is utilized to indicate if the gene is expressed. The decision matrix utilizes the values N, NPOS, NNEG, and LR (multiple LRs). The following four assignments are performed:

P1=NPOS/NNEG
P2=NPOS/N
P3=(10*SUM(LR))/(NPOS+NNEG)

These P values are then utilized to determine if the gene is expressed.

For purposes of illustration, the P values are broken down into ranges. If P1 is greater than or equal to 2.1, then A is true. If P1 is less than 2.1 and greater than or equal to 1.8, then B is true. Otherwise, C is true. Thus, P1 is broken down into three ranges A, B and C. This is done to aid the readers understanding of the invention.

Thus, all of the P values are broken down into ranges according to the following:

A=(P1>=2.1)
B=(2.1>P1>=1.8)
C=(P1<1.8)
X=(P2>=0.35)
Y=(0.35>P2>=0.20)
Z=(P2<0.20)
Q=(P3>=1.5)
R=(1.5>P3>=1.1)
S=(P3<1.1)

Once the P values are broken down into ranges according to the above boolean values, the gene expression is determined.

The gene expression is indicated as present (expressed), marginal or absent (not expressed). The gene is indicated as expressed if the following expression is true: A and (X or Y) and (Q or R). In other words, the gene is indicated as expressed if P1>=2.1, P2>=0.20 and P3>=1.1. Additionally, the gene is indicated as expressed if the following expression is true: B and X and Q.

With the forgoing explanation, the following is a summary of the gene expression indications:

| | |
|---|---|
| Present | A and (X or Y) and ( Q or R) |
| | B and X and I |
| Marginal | A and X and S |
| | B and X and R |
| | B and Y and ( Q or R) |
| Absent | All other cases (e.g, any C combination) |

In the output to the user, present may be indicated as "P," marginal as "M" and absent as "A" at step 274.

Once all the pairs of probes have been processed and the expression of the gene indicated, an average of ten times the LRs is computed at step 275. Additionally, an average of the IDIF values for the probes that incremented NPOS and NNEG is calculated. These values may be utilized for quantitative comparisons of this experiments with other experiments.

Quantitative measurements may be performed at step 276. For example, the current experiment may be compared to a previous experiment (e.g., utilizing values calculated at step 270). Additionally, the experiment may be compared to hybridization intensities of RNA (such as from bacteria) present in the biological sample in a known quantity. In this manner, one may verify the correctness of the gene expression indication or call, modify threshold values, or perform any number of modifications of the preceding.

For simplicity, FIG. 9 was described in reference to a single gene. However, the process may be utilized on multiple genes in a biological sample. Therefore, any discussion of the analysis of a single gene is not an indication that the process may not be extended to processing multiple genes.

Figure 10A:
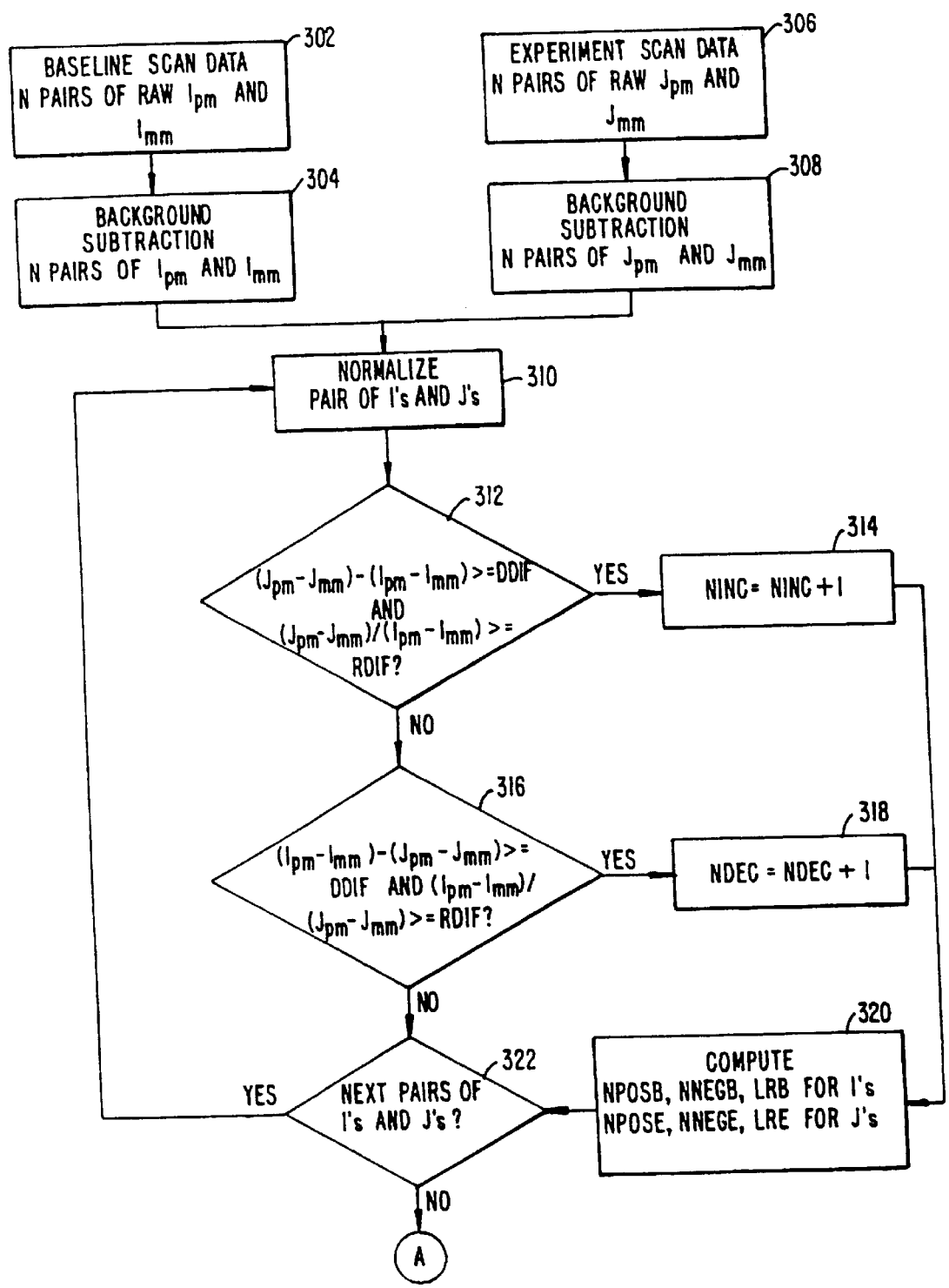
FIGS. 10A and 10B show the flow of a process of determining the expression of a gene by comparing baseline scan data and experimental scan data.
Figure 10B:
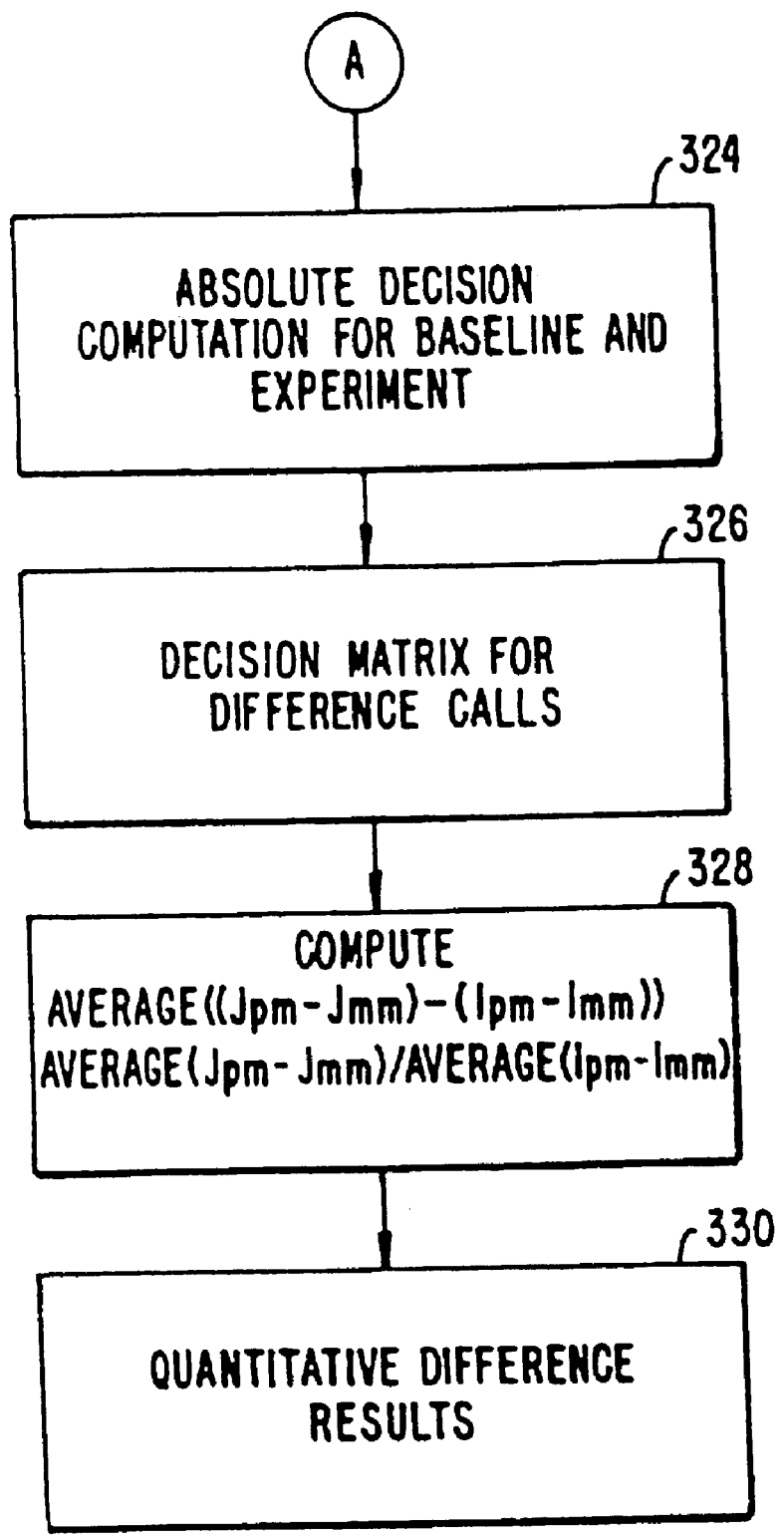

FIGS. 10A and 10B show the flow of a process of determining the expression of a gene by comparing baseline scan data and experimental scan data. For example, the baseline scan data may be from a biological sample where it is known the gene is expressed. Thus, this scan data may be compared to a different biological sample to determine if the gene is expressed. Additionally, it may be determined how the expression of a gene or genes changes over time in a biological organism.

At step 302, the computer system receives raw scan data of N pairs of perfect match and mismatch probes from the baseline. The hybridization intensity of a perfect match probe from the baseline will be designed "$I_{pm}$" and the hybridization intensity of a mismatch probe from the baseline will be designed "$I_{mm}$." The background signal intensity is subtracted from each of the hybridization intensities of the pairs of baseline scan data at step 304.

At step 306, the computer system receives raw scan data of N pairs of perfect match and mismatch probes from the experimental biological sample. The hybridization intensity of a perfect match probes from the experiment will be designed "$J_{pm}$" and the hybridization intensity of a mismatch probe from the experiment will be designed "$J_{mm}$." The background signal intensity is subtracted from each of the hybridization intensities of the pairs of experimental scan data at step 308.

The hybridization intensities of an I and J pair may be normalized at step 310. For example, the hybridization intensities of the I and J pairs may be divided by the hybridization intensity of control probes as discussed in Section II.A.2.

At step 312, the hybridization intensities of the I and J pair of probes are compared to a difference threshold (DDIF) and a ratio threshold (RDIF). It is determined if the difference between the hybridization intensities of the one pair ($J_{pm}-J_{mm}$) and the other pair ($I_{pm}-I_{mm}$) are greater than or equal to the difference threshold AND the quotient of the hybridization intensities of one pair ($J_{pm}-J_{mm}$) and the other pair ($I_{pm}-I_{mm}$) are greater than or equal to the ratio threshold. The difference thresholds are typically user defined values that have been determined to produce accurate expression monitoring of a gene or genes.

If ($J_{pm}-J_{mm}$)−($I_{pm}-I_{mm}$)>=DDIF and ($J_{pm}-J_{mm}$)/($I_{pm}-I_{mm}$)>=RDIF, the value NINC is incremented at step 314. In general, NINC is a value that indicates the experimental pair of probes indicates that the gene expression is likely greater (or increased) than the baseline sample. NINC is utilized in a determination of whether the expression of the gene is greater (or increased), less (or decreased) or did not change in the experimental sample compared to the baseline sample.

At step 316, it is determined if ($J_{pm}-J_{mm}$)−($I_{pm}-I_{mm}$)>=DDIF and ($J_{pm}-J_{mm}$)/($I_{pm}-I_{mm}$)>=RDIF. If this expression is true, NDEC is incremented. In general, NDEC is a value that indicates the experimental pair of probes indicates that the gene expression is likely less (or decreased) than the baseline sample. NDEC is utilized in a determination of whether the expression of the gene is greater (or increased), less (or decreased) or did not change in the experimental sample compared to the baseline sample.

For each of the pairs that exhibits hybridization intensities either indicating the gene is expressed more or less in the experimental sample, the values NPOS, NNEG and LR are calculated for each pair of probes. These values are calculated as discussed above in reference to FIG. 9. A suffix of either "B" or "E" has been added to each value in order to indicate if the value denotes the baseline sample or the experimental sample, respectively. If there are next pairs of hybridization intensities at step 322, they are processed in a similar manner as shown.

Referring now to FIG. 10B, an absolute decision computation is performed for both the baseline and experimental samples at step 324. The absolute decision computation is an indication of whether the gene is expressed, marginal or absent in each of the baseline and experimental samples. Accordingly, in a preferred embodiment, this step entails performing steps 272 and 274 from FIG. 9 for each of the samples. This being done, there is an indication of gene expression for each of the samples taken alone.

At step 326, a decision matrix is utilized to determine the difference in gene expression between the two samples. This decision matrix utilizes the values, N, NPOSB, NPOSE, NNEGB, NNEGE, NINC, NDEC, LRB, and LRE as they were calculated above. The decision matrix performs different calculations depending on whether NINC is greater than or equal to NDEC. The calculations are as follows.

If NINC>=NDEC, the following four P values are determined:
P1=NINC/NDEC
P2=NINC/N
P3=((NPOSE−NPOSB)−(NNEGE−NNEGB))/N
P4=10*SUM(LRE−LRB)/N These P values are then utilized to determine the difference in gene expression between the two samples.

For purposes of illustration, the P values are broken down into ranges as was done previously. Thus, all of the P values are broken down into ranges according to the following:
A=(P1>=2.7)
B=(2.7>P1>=1.8)
C=(P1<1.8)
X=(P2>=0.24)
Y=(0.24>P2>=0.16)
Z=(P2<0.160)
M=(P3>=0.17)
N=(0.17>P3>=0.10)
O=(P3<0.10)
Q=(P4>=1.3)
R=(1.3>P4>=0.9)
S=(P4<0.9)

Once the P values are broken down into ranges according to the above boolean values, the difference in gene expression between the two samples is determined.

In this case where NINC>=NDEC, the gene expression change is indicated as increased, marginal increase or no change. The following is a summary of the gene expression indications:

| | |
|---|---|
| Increased | A and (X or Y) and (Q or R) and (M or N or O) |
| | A and (X or Y) and (Q or R or S) and (M or N) |
| | B and (X or Y) and (Q or R) and (M or N) |
| | A and X and (Q or R or S) and (M or N or O) |
| Marginal Increase | A or Y or S or O |
| | B and (X or Y) and (Q or R) and O |
| | B and (X or Y) and S and (M or N) |
| | C and (X or Y) and (Q or R) and (M or N) |
| No Change | All others cases (e.g, any Z combination) |

In the output to the user, increased may be indicated as "I," marginal increase as "MI" and no change as "NC."

If NINC<NDEC, the following four P values are determined:
P1=NDEC/NINC
P2=NDEC/N
P3=((NNEGE−NNEGB)−(NPOSE−NPOSB))/N
P4=10*SUM(LRE−LRB)/N These P values are then utilized to determine the difference in gene expression between the two samples.

The P values are broken down into the same ranges as for the other case where NINC>=NDEC. Thus, P values in this case indicate the same ranges and will not be repeated for the sake of brevity. However, the ranges generally indicate different changes in the gene expression between the two samples as shown below.

In this case where NINC<NDEC, the gene expression change is indicated as decreased, marginal decrease or no change. The following is a summary of the gene expression indications:

| | |
|---|---|
| Decreased | A and (X or Y) and (Q or R) and (M or N or O) |
| | A and (X or Y) and (Q or R or S) and (M or N) |
| | B and (X or Y) and (Q or R) and (M or N) |
| | A and X and (Q or R or S) and (M or N or O) |
| Marginal Increase | A or Y or S or O |
| | B and (X or Y) and (Q or R) and O |
| | B and (X or Y) and S and (M or N) |
| | C and (X or Y) and (Q or R) and (M or N) |
| No Change | All others cases (e.g, any Z combination) |

In the output to the user, decreased may be indicated as "D," marginal decrease as "MD" and no change as "NC."

The above has shown that the relative difference between the gene expression between a baseline sample and an experimental sample may be determined. An additional test may be performed that would change an I, MI, D, or MD (i.e., not NC) call to NC if the gene is indicated as expressed in both samples (e.g., from step 324) and the following expressions are all true:
Average(IDIFB)>=200
Average(IDIFE)>=200
1.4>=Average(IDIFE)/Average(IDIFB)>=0.7

Thus, when a gene is expressed in both samples, a call of increased or decreased (whether marginal or not) will be changed to a no change call if the average intensity difference for each sample is relatively large or substantially the same for both samples. The IDIFB and IDIFE are calculated as the sum of all the IDIFs for each sample divided by N.

At step 328, values for quantitative difference evaluation are calculated. An average of $((J_{pm}-J_{mm})-(I_{pm}-I_{mm}))$ for each of the pairs is calculated. Additionally, a quotient of the average of $J_{pm}-J_{mm}$ and the average of $I_{pm}-I_{mm}$ is calculated. These values may be utilized to compare the results with other experiments in step 330.

X. Monitoring Expression Levels

As indicated above, the methods of this invention may be used to monitor expression levels of a gene in a wide variety of contexts. For example, where the effects of a drug on gene expression is to be determined the drug will be administered to an organism, a tissue sample, or a cell. Nucleic acids from the tissue sample, cell, or a biological sample from the organism and from an untreated organism tissue sample or cell are isolated as described above, hybridized to a high density probe array containing probes directed to the gene of interest and the expression levels of that gene are determined as described above.

Similarly, where the expression levels of a disease marker (e.g., P53, RTK, or HER2) are to be detected (e.g, for the diagnosis of a pathological condition in a patient), comparison of the expression levels of the disease marker in the sample to disease markers from a healthy organism will reveal any deviations in the expression levels of the marker in the test sample as compared to the healthy sample. Correlation of such deviations with a pathological condition provides a diagnostic assay for that condition.

XI. Other Embodiments i. Overall Description
   A. general
   B. VLSIPS substrates
   C. binary masking
   D. applications
   E. detection methods and apparatus
   F. data analysis
ii. Theoretical Analysis
   A. simple n-mer structure; theory
   B. complications
   C. non-polynucleotide embodiments
iii. Polynucleotide Sequencing
   A. preparation of substrate matrix
   B. labeling target polynucleotide
   C. hybridization conditions
   D. detection; VLSIPS scanning
   E. analysis
   F. substrate reuse
   G. non-polynucleotide aspects
iv. Fingerprinting
   A. general
   B. preparation of substrate matrix
   C. labeling target nucleotides
   D. hybridization conditions
   E. detection; VLSIPS scanning
   F. analysis
   G. substrate reuse
   H. non-polynucleotide aspects
v. Mapping
   A. general
   B. preparation of substrate matrix
   C. labeling
   D. hybridization/specific interaction
   E. detection
   F. analysis
   G. substrate reuse
   H. non-polynucleotide aspects
vi. Additional Screening
   A. specific interactions
   B. sequence comparisons
   C. categorizations
   D. statistical correlations
vii. Formation of Substrate
   A. instrumentation
   B. binary masking
   C. synthetic methods
   D. surface immobilization
viii. Hybridization/Specific Interaction
   A. general
   B. important parameters
ix. Detection Methods
   A. labeling techniques
   B. scanning system
x. Data Analysis
   A. general
   B. hardware
   C. software
xi. Substrate Reuse
   A. removal of label
   B. storage and preservation
   C. processes to avoid degradation of oligomers
xii. Integrated Sequencing Strategy
   A. initial mapping strategy
   B. selection of smaller clones
   C. actual sequencing procedures
xiii. Commercial Applications
   A. sequencing
   B. fingerprinting
   C. mapping i. OVERALL DESCRIPTION

A. General

The present invention relies in part on the ability to synthesize or attach specific recognition reagents at known locations on a substrate, typically a single substrate. In particular, the present invention provides the ability to prepare a substrate having a very high density matrix pattern of positionally defined specific recognition reagents. The reagents are capable of interacting with their specific targets while attached to the substrate, e.g., solid phase interactions, and by appropriate labeling of these targets, the sites of the interactions between the target and the specific reagents may be derived. Because the reagents are positionally defined, the sites of the interactions will define the specificity of each interaction. As a result, a map of the patterns of interactions with specific reagents on the substrate is convertible into information on the specific interactions taking place, e.g., the recognized features. Where the specific reagents recognize a large number of possible features, this system allows the determination of the combination of specific interactions which exist on the target molecule. Where the number of features is sufficiently large, the identical same combination, or pattern, of features is sufficiently unlikely that a particular target molecule may often be uniquely defined by its features. In the extreme, the features may actually be the subunit sequence of the target molecule, and a given target sequence may be uniquely defined by its combination of features.

In particular, the methodology is applicable to sequencing polynucleotides. The specific sequence recognition reagents will typically be oligonucleotide probes which hybridize with specificity to subsequences found on the target sequence. A sufficiently large number of those probes allows the fingerprinting of a target polynucleotide or the relative mapping of a collection of target polynucleotides, as described in greater detail below.

In the high resolution fingerprinting provided by a saturating collection of probes which include all possible subsequences of a given size. Although a polynucleotide sequence analysis is a preferred embodiment, for which the specific reagents are most easily accessible, the invention is also applicable to analysis of other polymers, including polypeptides, carbohydrates, and synthetic polymers, including α-, β-, and ω-amino acids, polyurethanes, polyesters, polycarbonates, polyureas, polyamides, polyethyleneimines, polyarylene sulfides, polysiloxanes, polyimides, polyacetates, and mixed polymers. Various optical isomers, e.g., various D- and L- forms of the monomers, may be used.

Sequence analysis will take the form of complete sequence determrnination, to the level of the sequence of individual subunits along the entire length of the target sequence. Sequence analysis also takes the form of sequence homology, e.g., less than absolute subunit resolution, where "similarity" in the sequence will be detectable, or the form of selective sequences of homology interspersed at specific or irregular locations.

In either case, the sequence is determinable at selective resolution or at particular locations. Thus, the hybridization method will be useful as a means for identification, e.g., a "fingerprint", much like a Southern hybridization method is used. It is also useful to map particular target sequences.

B. VLSIPS™ Substrates

The invention is enabled by the development of technology to prepare substrates on which specific reagents may be either positionally attached or synthesized. In particular, the very large scale immobilized polymer synthesis (VLSIPS™) technology allows for the very high density production of an enormous diversity of reagents mapped out in a known matrix pattern on a substrate. These reagents specifically recognize subsequences in a target polymer and bind thereto, producing a map of positionally defined regions of interaction. These map positions are convertible into actual features recognized, and thus would be present in the target molecule of interest.

As indicated, the sequence specific recognition reagents will often be oligonucleotides which hybridize with fidelity and discrimination to the target sequence. For use with other polymers, monoclonal or polyclonal antibodies having high sequence specificity will often be used.

In the generic sense, the VLSIPS technology allows the production of a substrate with a high density matrix of positionally mapped regions with specific recognition reagents attached at each distinct region. By use of protective groups which can be positionally removed, or added, the regions can be activated or deactivated for addition of particular reagents or compounds. Details of the protection are described below and in related U.S. application Ser. No. 07/492,462 (U.S. Pat. No. 5,143,854) filed Mar. 7, 1990. In a preferred embodiment, photosensitive protecting agents will be used and the regions of activation or deactivation may be controlled by electro-optical and optical methods, similar to many of the processes used in semiconductor wafer and chip fabrication.

In the nucleic acid nucleotide sequencing application, a VLSIPS substrate is synthesized having positionally defined oligonucleotide probes. See U.S. Ser. No. 07/492,462 (U.S. Pat. No. 5,143,854); and U.S. Ser. No. 07/624,120 (U.S. Pat. No. 5,498,678). By use of masking technology and photosensitive synthetic subunits, the VLSIPS apparatus allows for the stepwise synthesis of polymers according to a positionally defined matrix pattern. Each oligonucleotide probe will be synthesized at known and defined positional locations on the substrate. This forms a matrix pattern of known relationship between position and specificity of interaction. The VLSIPS technology allows the production of a very large number of different oligonucleotide probes to be simultaneously and automatically synthesized including numbers in excess of about $10^2$, $10^3$, $10^4$, $10^5$, $10^6$, or even more, and at densities of at least about $10^2$, $10^3/cm^2$, $10^4/cm^2$, $10^5/cm^2$ and up to $10^6/cm^2$ or more. This application discloses methods for synthesizing polymers on a silicon or other suitably derivatized substrate, methods and chemistry for synthesizing specific types of biological polymers on those substrates, apparatus for scanning and detecting whether interaction has occurred at specific locations on the substrate, and various other technologies related to the use of a high density very large scale immobilized polymer substrate. In particular, sequencing, fingerprinting, and mapping applications are discussed herein in detail, though related technologies are described in simultaneously filed U.S. applications Ser. No. 07/624,120 (U.S. Pat. No. 5,498,678), and Serial No. 07/517,659 each of which is hereby incorporated herein by reference.

In other embodiments, antibody probes will be generated which specifically recognize particular subsequences found on a polymer. Antibodies would be generated which are specific for recognizing a three contiguous amino acid sequence, and monoclonal antibodies may be preferred. Optimally, these antibodies would not recognize any sequences other than the specific three amino acid stretch desired and the binding affinity should be insensitive to flanking or remote sequences found on a target molecule. Likewise, antibodies specific for particular carbohydrate linkages or sequences will be generated. A similar approach could be used for preparing specific reagents which recognize other polymer subunit sequences. These reagents would typically be site specifically localized to a substrate matrix pattern where the regions are closely packed.

These reagents could be individually attached at specific sites on the substrate in a matrix by an automated procedure where the regions are positionally targeted by some other specific mechanism, e.g., one which would allow the entire collection of reagents to be attached to the substrate in a single reaction. Each reagent could be separately attached to a specific oligonucleotide sequence by an automated procedure. This would produce a collection of reagents where, e.g., each monoclonal antibody would have a unique oligonucleotide sequence attached to it. By virtue of a VLSIPS substrate which has different complementary oligonucleotides synthesized on it, each monoclonal antibody would specifically be bound only at that site on the substrate where the complementary oligonucleotide has been synthesized. A crosslinking step would fix the reagent to the substrate. See, e.g., Dattagupta et al. (1985) U.S. Pat. No. 4,542,102 and (1987) U.S. Pat. No. 4,713,326; and Chatterjee, M. et al. (1990) *J. Am. Chem. Soc.* 112:6397–6399, which are hereby incorporated herein by reference. This allows a high density positionally specific collection of specific recognition reagents, e.g., monoclonal antibodies, to be immobilized to a solid substrate using an automated system.

The regions which define particular reagents will usually be generated by selective protecting groups which may be activated or deactivated. Typically the protecting group will be bound to a monomer subunit or spatial region, and can be spatially affected by an activator, such as electromagnetic radiation. Examples of protective groups with utility herein include nitroveratryl oxycarbonyl (NVOC), nitrobenzyl oxycarbony (NBOC), dimethyl dimethoxy benzyloxy carbonyl, 5-bromo-7-nitroindolinyl, O-hydroxy-α-methyl cinnamoyl, and 2-oxymethylene anthraquinone. Examples of activators include ion beams, electric fields, magnetic fields, electron beams, x-ray, and other forms of electromagnetic radiation.

C. Binary Masking

In fact, the means for producing a substrate useful for these techniques are explained in U.S. Ser. No. 07/492,462 (U.S. Pat. No. 5,143,854), which is hereby incorporated herein by reference. However, there are various particular ways to optimize the synthetic processes. Many of these methods are described in U.S. Ser. No. 07/624,120 (U.S. Pat. No. 5,498,678).

Briefly, the binary synthesis strategy refers to an ordered strategy for parallel synthesis of diverse polymer sequences by sequential addition of reagents which may be represented by a reactant matrix, and a switch matrix, the product of which is a product matrix. A reactant matrix is a 1×n matrix of the building blocks to be added. The switch matrix is all or a subset of the binary numbers from 1 to n arranged in columns. In preferred embodiments, a binary strategy is one in which at least two successive steps illuminate half of a region of interest on the substrate. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme, but will still be considered to be a binary masking scheme within the definition herein. A binary "masking" strategy is a binary synthesis which uses light to remove protective groups from materials for addition of other materials such as nucleotides or amino acids.

In particular, this procedure provides a simplified and highly efficient method for saturating all possible sequences of a defined length polymer. This masking strategy is also particularly useful in producing all possible oligonucleotide sequence probes of a given length.

D. Applications

The technology provided by the present invention has very broad applications. Although described specifically for polynucleotide sequences, similar sequencing, fingerprinting, mapping, and screening procedures can be applied to polypeptide, carbohydrate, or other polymers. In particular, the present invention may be used to completely sequence a given target sequence to subunit resolution. This may be for de novo sequencing, or may be used in conjunction with a second sequencing procedure to provide independent verification. See, e.g., (1988) Science 242:1245. For example, a large polynucleotide sequence defined by either the Maxam and Gilbert technique or by the Sanger technique may be verified by using the present invention.

In addition, by selection of appropriate probes, a polynucleotide sequence can be fingerprinted. Fingerprinting is a less detailed sequence analysis which usually involves the characterization of a sequence by a combination of defined features. Sequence fingerprinting is particularly useful because the repertoire of possible features which can be tested is virtually infinite. Moreover, the stringency of matching is also variable depending upon the application. A Southern Blot analysis may be characterized as a means of simple fingerprint analysis. Fingerprinting analysis may be performed to the resolution of specific nucleotides, or may be used to determine homologies, most commonly for large segments. In particular, an array of oligonucleotide probes of virtually any workable size may be positionally localized on a matrix and used to probe a sequence for either absolute complementary matching, or homology to the desired level of stringency using selected hybridization conditions.

In addition, the present invention provides means for mapping analysis of a target sequence or sequences. Mapping will usually involve the sequential ordering of a plurality of various sequences, or may involve the localization of a particular sequence within a plurality of sequences. This may be achieved by immobilizing particular large segments onto the matrix and probing with a shorter sequence to determine which of the large sequences contain that smaller sequence. Alternatively, relatively shorter probes of known or random sequence may be immobilized to the matrix and a map of various different target sequences may be determined from overlaps. Principles of such an approach are described in some detail by Evans et al. (1989) "Physical Mapping of Complex Genomes by Cosmid Multiplex Analysis," Proc. Natl. Acad. Sci. USA 86:5030–5034; Michiels et al. (1987) "Molecular Approaches to Genome Analysis: A Strategy for the Construction of Ordered Overlap Clone Libraries," CABIOS 3:203–210; Olsen et al. (1986) "Random-Clone Strategy for Genomic Restriction Mapping in Yeast," Proc. Natl. Acad. Sci. USA 83:7826–7830; Craig, et al. (1990) "Ordering of Cosmid Clones Covering the Herpes Simplex Virus Type I (HSV-I) Genome: A Test Case for Fingerprinting by Hybridization," Nuc. Acids Res. 18:2653–2660; and Coulson, et al. (1986) "Toward a Physical Map of the Genome of the Nematode Caenorhabditis elegans," Proc. Natl. Acad. Sci. USA 83:7821–7825; each of which is hereby incorporated herein by reference.

Fingerprinting analysis also provides a means of identification. In addition to its value in apprehension of criminals from whom a biological sample, e.g., blood, has been collected, fingerprinting can ensure personal identification for other reasons. For example, it may be useful for identification of bodies in tragedies such as fire, flood, and vehicle crashes. In other cases the identification may be useful in identification of persons suffering from amnesia, or of missing persons. Other forensics applications include establishing the identity of a person, e.g., military identification "dog tags", or may be used in identifying the source of particular biological samples. Fingerprinting technology is described, e.g., in Carrano, et al. (1989) "A High-Resolution, Fluorescence-Based, Semi-automated method for DNA Fingerprinting," Genomics 4: 129–136, which is hereby incorporated herein by reference.

The fingerprinting analysis may be used to perform various types of genetic screening. For example, a single substrate may be generated with a plurality of screening probes, allowing for the simultaneous genetic screening for a large number of genetic markers. Thus, prenatal or diagnostic screening can be simplified, economized, and made more generally accessible.

In addition to the sequencing, fingerprinting, and mapping applications, the present invention also provides means for determining specificity of interaction with particular sequences. Many of these applications were described in U.S. Ser. No. 07/362,901, U.S. Ser. No. 07/492,462 (U.S. Pat. No. 5,143,854), U.S. Ser. No. 07/435,316, and U.S. Ser. No. 07/612,671.

E. Detection Methods and Apparatus

An appropriate detection method applicable to the selected labeling method can be selected. Suitable labels include radionucleotides, enzymes, substrates, cofactors, inhibitors, magnetic particles, heavy metal atoms, and particularly fluorescers, chemiluminescers, and spectroscopic labels. Patents teaching the use of such labels include U.S. Pat. Nos. 3,817,837; 3,850,752; 3,939,350; 3,996,345; 4,277,437; 4,275,149; and 4,366,241.

With an appropriate label selected, the detection system best adapted for high resolution and high sensitivity detection may be selected. As indicated above, an optically detectable system, e.g., fluorescence or chemiluminescence would be preferred. Other detection systems may be adapted to the purpose, e.g., electron microscopy, scanning electron microscopy (SEM), scanning tunneling electron microscopy (STEM), infrared microscopy, atomic force microscopy (AFM), electrical condutance, and image plate transfer.

With a detection method selected, an apparatus for scanning the substrate will be designed. Apparatus, as described in U.S. Ser. No. 07/362,901; or U.S. Ser. No. 07/492,462 (U.S. Pat. No. 5,143,854); or U.S. Ser. No. 07/624,120 (U.S. Pat. No. 5,498,678), are particularly appropriate. Design modifications may also be incorporated therein.

F. Data Analysis

Data is analyzed by processes similar to those described below in the section describing theoretical analysis. More efficient algorithms will be mathematically devised, and will usually be designed to be performed on a computer. Various computer programs which may more quickly or efficiently make measurement samples and distinguish signal from noise will also be devised. See, particularly, U.S. Ser. No. 07/624,120 (U.S. Pat. No. 5,498,678).

The initial data resulting from the detection system is an array of data indicative of fluorescent intensity versus location on the substrate. The data are typically taken over regions substantially smaller than the area in which synthesis of a given polymer has taken place. Merely by way of example, if polymers were synthesized in squares on the substrate having dimensions of 500 microns by 500 microns, the data may be taken over regions having dimensions of 5 microns by 5 microns. In most preferred embodiments, the regions over which florescence data are taken across the substrate are less than about ½ the area of the regions in which individual polymers are synthesized, preferably less than $\frac{1}{10}$ the area in which a single polymer is synthesized, and most preferably less than $\frac{1}{100}$ the area in which a single polymer is synthesized. Hence, within any area in which a given polymer has been synthesized, a large number of fluorescence data points are collected.

A plot of number of pixels versus intensity for a scan should bear a rough resemblance to a bell curve, but spurious data are observed, particularly at higher intensities. Since it is desirable to use an average of fluorescent intensity over a given synthesis region in determining relative binding affinity, these spurious data will tend to undesirably skew the data. Accordingly, in one embodiment of the invention the data are corrected for removal of these spurious data points, and an average of the data points is thereafter utilized in determining relative binding efficiency. In general the data are fitted to a base curve and statistical measures are used to remove spurious data.

In an additional analytical tool, various degeneracy reducing analogues may be incorporated in the hybridization probes. Various aspects of this strategy are described, e.g., in Macevicz, S. (1990) PCT publication number WO 90/04652, which is hereby incorporated herein by reference.

ii. THEORETICAL ANALYSIS

The principle of the denovo hybridization sequencing procedure may be based, in part, upon the ability to determine overlaps of short segments. The VLSIPS technology provides the ability to generate reagents which will saturate the possible short subsequence recognition possibilities. The principle is most easily illustrated by using a binary sequence, such as a sequence of zeros and ones. Once having illustrated the application to a binary alphabet, the principle may easily be understood to encompass three letter, four letter, five or more letter, even 20 letter alphabets. A theoretical treatment of analysis of subsequence information to reconstruction of a target sequence is provided, e.e., in Lysov, Yu., et al. (1988) *Doklady Akademi. Nauk. SSR* 303:1508–1511; Khrapko K., et al. (1989) *FEBS Letters* 256:118–122; Pevzner, P. (1989) *J. of Biomolecular Structure and Dynamics* 7:63–69; and Drmanac, R. et al. (1989) *Genomics* 4:114–128; each of which is hereby incorporated herein by reference.

The reagents for recognizing the subsequences will usually be specific for recognizing a particular polymer subsequence anywhere within a target polymer. It is preferable that conditions may be devised which allow absolute discrimination between high fidelity matching and very low levels of mismatching. The reagent interaction will preferably exhibit no sensitivity to flanking sequences, to the subsequence position within the target, or to any other remote structure within the sequence. For polynucleotide sequencing, the specific reagents can be oligonucleotide probes; for polypeptides and carbohydrates, antibodies will be useful reagents. Antibody reagents should also be useful for other types of polymers.

A. Simple n-mer Structure: Theory

1. Simple two letter alphabet: example

A simple example is presented below of how a sequence of ten digits comprising zeros and ones would be sequenceable using short segments of five digits. For example, consider the sample ten digit sequence:

1010011100.

A VLSIPS™ substrate could be constructed, as discussed elsewhere, which would have reagents attached in a defined matrix pattern which specifically recognize each of the possible five digit sequences of ones and zeros. The number of possible five digit subsequences is $2^5=32$. The number of possible different sequences 10 digits long is $2^{10}=1,024$. The five contiguous digit subsequences within a ten digit sequence number six, i.e., positioned at digits 1–5, 2–6, 3–7, 4–8, 5–9, and 6–10. It will be noted that the specific order of the digits in the sequence is important and that the order is directional, e.g., running left to right versus right to left. The first five digit sequence contained in the target sequence is 10100. The second is 01001, the third is 10011, the fourth is 00111, the fifth is 01110, and the sixth is 11100.

The VLSIPS substrate would have a matrix pattern of positionally attached reagents which recognize each of the different 5-mer subsequences. Those reagents which recognize each of the 6 contained 5-mers will bind the target, and a label allows the positional determination of where the sequence specific interaction has occurred. By correlation of the position in the matrix pattern, the corresponding bound subsequences can be determined.

In the above-mentioned sequence, six different 5-mer sequences would be determined to be present. They would be:

```
          10100
           01001
            10011
             00111
              01110
               11100
```

Any sequence which contains the first five digit sequence, 10100, already narrows the number of possible sequences (e.g., from 1024 possible sequences) which contain it to less than about 192 possible sequences.

This is derived from the observation that with the subsequence 10100 at the far left of the sequence, in positions 1–5, there are only 32 possible sequences. Likewise, for that particular subsequence in positions 2–6, 3–7, 4–8, 5–9, and 6–10. So, to sum up all of the sequences that could contain 10100, there are 32 for each position and 6 positions for a total of about 192 possible sequences. However, some of these 10 digit sequences will have been counted twice. Thus, by virtue of containing the 10100 subsequence, the number of possible 10-mer sequences has been decreased from 1024 sequences to less than about 192 sequences.

In this example, not only do we know that the sequence contains 10100, but we also know that it contains the second five character sequence, 01001. By virtue of knowing that the sequence contains 10100, we can look specifically to determine whether the sequence contains a subsequence of five characters which contains the four leftmost digits plus a next digit to the left. For example, we would look for a sequence of X1010, but we find that there is none. Thus, we know that the 10100 must be at the left end of the 10-mer. We would also look to see whether the sequence contains the rightmost four digits plus a next digit to the right, e.g., 0100X. We find that the sequence also contains the sequence 01001, and that X is a 1. Thus, we know at least that our target sequence has an overlap of 0100 and has the left terminal sequence 101001.

Applying the same procedure to the second 5-mer, we also know that the sequence must include a sequence of five digits having the sequence 1001 Y where Y must be either 0 or 1. We look through the fragments and we see that we have a 10011 sequence within our target, thus Y is also 1. Thus, we would know that our sequence has a sequence of the first seven being 1010011.

Moving to the next 5-mer, we know that there must be a sequence of 0011Z, where Z must be either 0 or 1. We look at the fragments produced above and see that the target sequence contains a 00111 subsequence and Z is 1. Thus, we know the sequence must start with 10100111.

The next 5-mer must be of the sequence 0111W where W must be 0 or 1. Again, looking up at the fragments produced, we see that the target sequence contains a 01110 subsequence, and W is a 0. Thus, our sequence to this point is 101001110. We know that the last 5-mer must be either 11100 or 11101. Looking above, we see that it is 11100 and that must be the last of our sequence. Thus, we have determined that our sequence must have been 1010011100.

However, it will be recognized from the example above with the sequences provided therein, that the sequence analysis can start with any known positive probe subsequence. The determination may be performed by moving linearly along the sequence checking the known sequence with a limited number of next positions. Given this possibility, the sequence may be determined, besides by scanning all possible oligonucleotide probe positions, by specifically looking only where the next possible positions would be. This may increase the complexity of the scanning but may provide a longer time span dedicated towards scanning and detecting specific positions of interest relative to other sequence possibilities. Thus, the scanning apparatus could be set up to work its way along a sequence from a given contained oligonucleotide to only look at those positions on the substrate which are expected to have a positive signal.

It is seen that given a sequence, it can be de-constructed into n-mers to produce a set of internal contiguous subsequences. From any given target sequence, we would be able to determine what fragments would result. The hybridization sequence method depends, in part, upon being able to work in the reverse, from a set of fragments of known sequences to the full sequence. In simple cases, one is able to start at a single position and work in either or both directions towards the ends of the sequence as illustrated in the example.

The number of possible sequences of a given length increases very quickly with the length of that sequence. Thus, a 10-mer of zeros and ones has 1024 possibilities, a 12-mer has 4096. A 20-mer has over a million possibilities, and a 30-mer has over a billion. However, a given 30-mer has, at most, 26 different internal 5-mer sequences. Thus, a 30 character target sequence having over a million possible sequences can be substantially defined by only 26 different 5-mers. It will be recognized that the probe oligonucleotides will preferably, but need not necessarily, be of identical length, and that the probe sequences need not necessarily be contiguous in that the overlapping subsequences need not differ by only a single subunit. Moreover, each position of the matrix pattern need not be homogeneous, but may actually contain a plurality of probes of known sequence. In addition, although all of the possible subsequence specifications would be preferred, a less than full set of sequences specifications could be used. In particular, although a substantial fraction will preferably be at least about 70%, it may be less than that. About 20% would be preferred, more preferably at least about 30% would be desired. Higher percentages would be especially preferred.

2. Example of four letter alphabet

A four letter alphabet may be conceptualized in at least two different ways from the two letter alphabet. One way is to consider the four possible values at each position and to analogize in a similar fashion to the binary example each of the overlaps. A second way is to group the binary digits into groups.

Using the first means, the overlap comparisons are performed with a four letter alphabet rather than a two letter alphabet. Then, in contrast to the binary system with 10 positions where $2^{10}=1024$ possible sequences, in a 4-character alphabet with 10 positions, there will actually be $4^{10}=1,048,576$ possible sequences. Thus, the complexity of a four character sequence has a much larger number of possible sequences compared to a two character sequence. Note, however, that there are still only 6 different internal 5-mers. For simplicity, we shall examine a 5 character string with 3 character subsequences. Instead of only 1 and 0, the characters may be designated, e.g., A, C, G, and T. Let us take the sequence GGCTA. The 3-mer subsequences are:

```
GGC
GCT
CTA
```

Given these subsequences, there is one sequence, or at most only a few sequences which would produce that combination of subsequences, i.e., GGCTA.

Alternatively, with a four character universe, the binary system can be looked at in pairs of digits. The pairs would be 00, 01, 10, and 11. In this manner, the earlier used sequence 1010011100 is looked at as 10,10,01,11,00. Then the first character of two digits is selected from the possible universe of the four representations 00, 01, 10, and 11. Then a probe would be in an even number of digits, e.g., not five digits, but, three pairs of digits or six digits. A similar comparison is performed and the possible overlaps determined. The 3-pair subsequences are:

```
10,10,01
10,01,11
01,11,00
```
and the overlap reconstruction produces 10,10,01,11,00.

and the overlap reconstruction produces 10,10,01,11,00.

The latter of the two conceptual views of the 4 letter alphabet provides a representation which is similar to what would be provided in a digital computer. The applicability to a four nucleotide alphabet is easily seen by assigning, e.g., 00 to A, 01 to C, 10 to G, and 11 to T. And, in fact, if such a correspondence is used, both examples for the 4 character sequences can be seen to represent the same target sequence. The applicability of the hybridization method and its analysis for determining the ultimate sequence is easily seen if A is the representation of adenine, C is the representation of cytosine, G is the representation of guanine, and T is the representation of thymine or uracil.

3. Generalization to m-letter Alphabet

This reconstruction process may be applied to polymers of virtually any number of possible characters in the alphabet, and for virtually any length sequence to be sequenced, though limitations, as discussed below, will limit its efficiency at various extremes of length. It will be recognized that the theory can be applied to a large diversity of systems where sequence is important.

For example, the method could be applied to sequencing of a polypeptide. A polypeptide can have any of twenty natural amino acid possibilities at each position. A twenty letter alphabet is amenable to sequencing by this method so long as reagents exist for recognizing shorter subsequences therein. A preferred reagent for achieving that goal would be a set of monoclonal antibodies each of which recognizes a specific three contiguous amino acid subsequence. A complete set of antibodies which recognize all possible subsequences of a given length, e.g., 3 amino acids, and preferably with a uniform affinity, would be $20^3$=8000 reagents.

It will also be recognized that each target sequence which is recognized by the specific reagents need not have homogeneous termini. Thus, fragments of the entire target sequence will also be useful for hybridizing appropriate subsequences. It is, however, preferable that there not be a significant amount of labeled homogeneous contaminating extraneous sequences. This constraint does usually require the purification of the target molecule to be sequenced, but a specific label technique would dispense with a purification requirement if the unlabeled extraneous sequences do not interfere with the labeled sequences.

In addition, conformational effects of target polypeptide folding may, in certain embodiments, be negligible if the polypeptide is fragmented into sufficiently small peptides, or if the interaction is performed under conditions where conformation, but not specific interaction, is disrupted.

B. Complications

Two obvious complications exist with the method of sequence analysis by hybridization. The first results from a probe of inappropriate length while the second relates to internally repeated sequences.

The first obvious complication is a problem which arises from an inappropriate length of recognition sequence, which causes problems with the specificity of recognition. For example, if the recognized sequence is too short, every sequence which is utilized will be recognized by every probe sequence. This occurs, e.g., in a binary system where the probes are each of sequences which occur relatively frequently, e.g., a two character probe for the binary system. Each possible two character probe would be expected to appear ¼ of the time in every single two character position. Thus, the above sequence example would be recognized by each of the 00, 10, 01, and 11. Thus, the sequence information is virtually lost because the resolution is too low and each recognition reagent specifically binds at multiple sites on the target sequence.

The number of different probes which bind to a target depends on the relationship between the probe length and the target length. At the extreme of short probe length, the just mentioned problem exists of excessive redundancy and lack of resolution. The lack of stability in recognition will also be a problem with extremely short probes. At the extreme of long probe length, each entire probe sequence is on a different position of a substrate. However, a problem arises from the number of possible sequences, which goes up dramatically with the length of the sequence. Also, the specificity of recognition begins to decrease as the contribution to binding by any particular subunit may become sufficiently low that the system fails to distinguish the fidelity of recognition. Mismatched hybridization may be a problem with the polynucleotide sequencing applications, though the fingerprinting and mapping applications may not be so strict in their fidelity requirements. As indicated above, a thirty position binary sequence has over a million possible sequences, a number which starts to become unreasonably large in its required number of different sequences, even though the target length is still very short. Preparing a substrate with all sequence possibilities for a long target may be extremely difficult due to the many different oligomers which must be synthesized.

The above example illustrates how a long target sequence may be reconstructed with a reasonably small number of shorter subsequences. Since the present day resolution of the regions of the substrate having defined oligomer probes attached to the substrate approaches about 10 microns by 10 microns for resolvable regions, about $10^6$, or 1 million, positions can be placed on a one centimeter square substrate. However, high resolution systems may have particular disadvantages which may be outweighed using the lower density substrate matrix pattern. For this reason, a sufficiently large number of probe sequences can be utilized so that any given target sequence may be determined by hybridization to a relatively small number of probes.

A second complication relates to convergence of sequences to a single subsequence. This will occur when a particular subsequence is repeated in the target sequence. This problem can be addressed in at least two different ways. The first, and simpler way, is to separate the repeat sequences onto two different targets. Thus, each single target will not have the repeated sequence and can be analyzed to its end. This solution, however, complicates the analysis by requiring that some means for cutting at a site between the repeats can be located. Typically a careful sequencer would want to have two intermediate cut points so that the intermediate region can also be sequenced in both directions across each of the cut points. This problem is inherent in the hybridization method for sequencing but can be minimized by using a longer known probe sequence so that the frequency of probe repeats is decreased.

Knowing the sequence of flanking sequences of the repeat will simplify the use of polymerase chain reaction (PCR) or a similar technique to further definitively determine the sequence between sequence repeats. Probes can be made to hybridize to those known sequences adjacent the repeat sequences, thereby producing new target sequences for analysis. See, e.g., Innis et al. (eds.) (1990) *PCR Protocols: A Guide to Methods and Applications*, Academic Press; and methods for synthesis of oligonucleotide probes, see, e.g., Gait (1984) *Oligonucleotide Synthesis: A Practical Approach*, IRL Press, Oxford.

Other means for dealing with convergence problems include using particular longer probes, and using degeneracy reducing analogues, see, e.g., Macevicz, S. (1990) PCT publication number WO 90/04652, which is hereby incorporated herein by reference. By use of stretches of the degeneracy reducing analogues with other probes in particular combinations, the number of probes necessary to fully saturate the possible oligomer probes is decreased. For example, with a stretch of 12-mers having the central 4-mer of degenerate nucleotides, in combination with all of the possible 8-mers, the collection numbers twice the number of possible 8-mers, e.g. 65,536+65,536=131,072, but the population provides screening equivalent to all possible 12-mers.

By way of further explanation, all possible oligonucleotide 8-mers may be depicted in the fashion:

N1-N2-N3-N4-N5-N6-N7-N8, in which there are $4^8$=65,536 possible 8-mers. As described in U.S. Ser. No. 07/624,120 (U.S. Pat. No. 5,498,678), producing all possible 8-mers requires 4×8=32 chemical binary synthesis steps to produce the entire matrix pattern of 65,536 8-mer possibilities. By incorporating degeneracy reducing nucleotides, D's, which hybridize nonselectively to any corresponding complementary nucleotide, new oligonucleotides 12-mers can be made in the fashion:

N1-N2-N3-N4-D-D-D-D-N5-N6-N7-N8, in which there are again, as above, only $4^8$=65,536 possible "12-mers", which in reality only have 8 different nucleotides. However, it can be seen that each possible 12-mer probe could be represented by a group of the two 8-mer types. Moreover, repeats of less than 12 nucleotides would not converge, or cause repeat problems in the analysis. Thus, instead of requiring a collection of probes corresponding to all 12-mers, or $4^{12}$=16,777,216 different 12-mers, the same information can be derived by making 2 sets of "8-mers" consisting of the typical 8-mer collection of $4^8$=65,536 and the "12-mer" set with the degeneracy reducing analogues, also requiring making $4^8$=65,536. The combination of the two sets, requires making 65,536+65,536=131,072 different molecules, but giving the information of 16,777,216 molecules. Thus, incorporating the degeneracy reducing analogue decreases the number of molecules necessary to get 12-mer resolution by a factor of about 128-fold.

C. Non-polynucleotide Embodiments

The above example is directed towards a polynucleotide embodiment. This application is relatively easily achieved because the specific reagents will typically be complementary oligonucleotides, although in certain embodiments other specific reagents may be desired. For example, there may be circumstances where other than complementary base pairing will be utilized. The polynucleotide targets, will usually be single strand, but may be double or triple stranded in various applications. However, a triple stranded specific interaction might be sometimes desired, or a protein or other specific binding molecule may be utilized. For example, various promoter or DNA sequence specific binding proteins might be used, including, e.g., restriction enzyme binding domains, other binding domains, and antibodies. Thus, specific recognition reagents besides oligonucleotides may be utilized.

For other polymer targets, the specific reagents will often be polypeptides. These polypeptides may be protein binding domains from enzymes or other proteins which display specificity for binding. Usually an antibody molecule may be used, and monoclonal antibodies may be particularly desired. Classical methods may be applied for preparing antibodies, see, e.g., Harlow and Lane (1988) *Antibodies: A Laboratory Manual* Cold Spring Harbor Press, N.Y.; and Goding (1986) *Monoclonal Antibodies: Principles and Practice* (2d Ed.) Academic Press, San Diego. Other suitable techniques for in vitro exposure of lymphocytes to the antigens or selection of libraries of antibody binding sites are described, e.g., in Huse et al. (1989) *Science* 246:1275–1281; and Ward et al. 91989) *Nature* 341:544–546, each of which is hereby incorporated herein by reference. Unusual antibody production methods are also described, e.g., in Hendricks et al. (1989) *BioTechnology* 7:1271–1274; and Hiatt et al. (1989) *Nature* 342:76–78, each of which is hereby incorporated herein by reference. Other molecules which may exhibit specific binding interaction may be useful for attachment to a VLSIPS substrate by various methods, including the caged biotin methods, see, e.g., U.S. Ser. No. 07/435,316, and U.S. Ser. No. 07/612,671.

The antibody specific reagents should be particularly useful for the polypeptide, carbohydrate, and synthetic polymer applications. Individual specific reagents might be generated by an automated process to generate the number of reagents necessary to advantageously use the high density positional matrix pattern. In an alternative approach, a plurality of hybridoma cells may be screened for their ability to bind to a VLSIPS matrix possessing the desired sequences whose binding specificity is desired. Each cell might be individually grown up and its binding specificity determined by VLSIPS apparatus and technology. An alternative strategy would be to expose the same VLSIPS matrix to a polyclonal serum of high titer. By a successively large volume of serum and different animals, each region of the VLSIPS substrate would have attached to it a substantial number of antibody molecules with specificity of binding. The substrate, with non-covalently bound antibodies could be derivatized and the antibodies transferred to an adjacent second substrate in the matrix pattern in which the antibody molecules had attached to the first matrix. If the sensitivity of detection of binding interaction is sufficiently high, such a low efficiency transfer of antibody molecules may produce a sufficiently high signal to be useful for many purposes, including the sequencing applications.

In another embodiment, capillary forces may be used to transfer the selected reagents to a new matrix, to which the reagents would be positionally attached in the pattern of the recognized sequences. Or, the reagents could be transversely electrophoresed, magnetically transferred, or otherwise transported to a new substrate in their retained positional pattern.

iii. POLYNUCLEOTIDE SEQUENCING

The making of a substrate having a positionally defined matrix pattern of all possible oligonucleotides of a given length involves a conceptually simple method of synthesizing each and every different possible oligonucleotide, and affixing them to a definable position. Oligonucleotide synthesis is presently mechanized and enabled by current technology, see, e.g., U.S. Ser. No. 07/362,901; U.S. Ser. No. 07/492,462 (U.S. Pat. No. 5,143,854); and instruments supplied by Applied Biosystems, Foster City, Calif.

A. Preparation of Substrate Matrix

The production of the collection of specific oligonucleotides used in polynucleotide sequencing may be produced in at least two different ways. Present technology certainly allows production of ten nucleotide oligomers on a solid phase or other synthesizing system. See, e.g., instrumentation provided by Applied Biosystems, Foster City, Calif. Although a single oligonucleotide can be relatively easily made, a large collection of them would typically require a fairly large amount of time and investment. For example, there are $4^{10}=1,048,576$ possible ten nucleotide oligomers. Present technology allows making each and every one of them in a separate purified form though such might be costly and laborious.

Once the desired repertoire of possible oligomer sequences of a given length have been synthesized, this collection of reagents may be individually positionally attached to a substrate, thereby allowing a batchwise hybridization step. Present technology also would allow the possibility of attaching each and every one of these 10-mers to a separate specific position on a solid matrix. This attachment could be automated in any of a number of ways, particularly through the use of a caged biotin type linking. This would produce a matrix having each of different possible 10-mers.

A batchwise hybridization is much preferred because of its reproducibility and simplicity. An automated process of attaching various reagents to positionally defined sites on a substrate is provided in U.S. Ser. No. 07/492,462 (U.S. Pat. No. 5,143,854); U.S. Ser. No. 07/624,120 (U.S. Pat. No. 5,498,678); and U.S. Ser. No. 07/612,671; each of which is hereby incorporated herein by reference.

Instead of separate synthesis of each oligonucleotide, these oligonucleotides are conveniently synthesized in parallel by sequential synthetic processes on a defined matrix pattern as provided in U.S. Ser. No. 07/492,462 (U.S. Pat. No. 5,143,854); and U.S. Ser. No. 07/624,120 (U.S. Pat. No. 5,498,678), which are incorporated herein by reference. Here, the oligonucleotides are synthesized stepwise on a substrate at positionally separate and defined positions. Use of photosensitive blocking reagents allows for defined sequences of synthetic steps over the surface of a matrix pattern. By use of the binary masking strategy, the surface of the substrate can be positioned to generate a desired pattern of regions, each having a defined sequence oligonucleotide synthesized and immobilized thereto.

Although the prior art technology can be used to generate the desired repertoire of oligonucleotide probes, an efficient and cost effective means would be to use the VLSIPS technology described in U.S. Ser. No. 07/492,462 (U.S. Pat. No. 5,143,854) and U.S. Ser. No. 07/624,120 (U.S. Pat. No. 5,498,678). In this embodiment, the photosensitive reagents involved in the production of such a matrix are described below.

The regions for synthesis may be very small, usually less than about 100 $\mu$m×100 $\mu$m, more usually less than about 50 $\mu$m×50 $\mu$m. The photolithography technology allows synthetic regions of less than about 10 $\mu$m×10 $\mu$m, about 3 $\mu$m×3 $\mu$m, or less. The detection also may detect such sized regions, though larger areas are more easily and reliably measured.

At a size of about 30 microns by 30 microns, one million regions would take about 11 centimeters square or a single wafer of about 4 centimeters by 4 centimeters. Thus the present technology provides for making a single matrix of that size having all one million plus possible oligonucleotides. Region size is sufficiently small to correspond to densities of at least about 5 regions/cm$^2$, 20 regions/cm$^2$, 50 regions/cm$^2$, 100 regions/cm$^2$, and greater, including 300 regions/cm$^2$, 1000 regions/cm$^2$, 3K regions/cm$^2$, 10K regions/cm$^2$, 30K regions/cm$^2$, 100K regions/cm$^2$, 300K regions/cm$^2$ or more, even in excess of one million regions/cm$^2$.

Although the pattern of the regions which contain specific sequences is theoretically not important, for practical reasons certain patterns will be preferred in synthesizing the oligonucleotides. The application of binary masking algorithms for generating the pattern of known oligonucleotide probes is described in related U.S. Ser. No.07/624,120 (U.S. Pat. No. 5,498,678), which was filed simultaneously with this application. By use of these binary masks, a highly efficient means is provided for producing the substrate with the desired matrix pattern of different sequences. Although the binary masking strategy allows for the synthesis of all lengths of polymers, the strategy may be easily modified to provide only polymers of a given length. This is achieved by omitting steps where a subunit is not attached.

The strategy for generating a specific pattern may take any of a number of different approaches. These approaches are well described in related application U.S. Ser. No. 07/624,120 (U.S. Pat. No. 5,498,678), and include a number of binary masking approaches which will not be exhaustively discussed herein. However, the binary masking and binary synthesis approaches provide a maximum of diversity with a minimum number of actual synthetic steps.

The length of oligonucleotides used in sequencing applications will be selected on criteria determined to some extent by the practical limits discussed above. For example, if probes are made as oligonucleotides, there will be 65,536 possible eight nucleotide sequences. If a nine subunit oligonucleotide is selected, there are 262,144 possible permeations of sequences. If a ten-mer oligonucleotide is selected, there are 1,048,576 possible permeations of sequences. As the number gets larger, the required number of positionally defined subunits necessary to saturate the possibilities also increases. With respect to hybridization conditions, the length of the matching necessary to confer stability of the conditions selected can be compensated for. See, e.g., Kanehisa, M. (I984) *Nuc. Acids Res.* 12:203–213, which is hereby incorporated herein by reference.

Although not described in detail here, but below for oligonucleotide probes, the VLSIPS technology would typically use a photosensitive protective group on an oligonucleotide. In particular, the photoprotective group on the nucleotide molecules may be selected from a wide variety of positive light reactive groups preferably including nitro aromatic compounds such as o-nitro-benzyl derivatives or benzylsulfonyl. See, e.g., Gait (1984) *Oligonucleotide Synthesis: A Practical Approach,* IRL Press, Oxford, which is hereby incorporated herein by reference. In a preferred embodiment, 6-nitro-veratryl oxycarbony (NVOC), 2-nitrobenzyl oxycarbonyl (NBOC), MeNVOC, MeNPOC, or α,α-dimethyl-dimethoxybenzyl oxycarbonyl (DEZ) is used. Photoremovable protective groups are described in, e.g., Patchornik (1970) *J. Amer. Chem. Soc.* 92:6333–6335; and Amit et al. (1974) *J. Organic Chem.* 39:192–196, and U.S. Ser. No. 08/444,598; each of which is hereby incorporated herein by reference. A photosensitive blocked nucleotide may be attached to specific locations of unblocked prior cycles of attachments on the substrate and can be successively built up to the correct length oligonucleotide probe.

It should be noted that multiple substrates may be simultaneously exposed to a single target sequence where each substrate is a duplicate of one another or where, in combination, multiple substrates together provide the complete or desired subset of possible subsequences. This provides the opportunity to overcome a limitation of the density of positions on a single substrate by using multiple substrates. In the extreme case, each probe might be attached to a single bead or substrate and the beads sorted by whether there is a binding interaction. Those beads which do bind might be encoded to indicate the subsequence specificity of reagents attached thereto.

Then, the target may be bound to the whole collection of beads and those beads that have appropriate specific reagents on them will bind to the target. Then a sorting system may be utilized to sort those beads that actually bind the target from those that do not. This may be accomplished by presently available cell sorting devices or a similar apparatus. After the relatively small number of beads which have bound the target have been collected, the encoding scheme may be read off to determine the specificity of the reagent on the bead. An encoding system may include a magnetic system, a shape encoding system, a color encoding system, or a combination of any of these, or any other encoding system. Once again, with the collection of specific interactions that have occurred, the binding may be analyzed for sequence information, fingerprint information, or mapping information.

The parameters of polynucleotide sizes of both the probes and target sequences are determined by the applications and other circumstances. The length of the oligonucleotide probes used will depend in part upon the limitations of the VLSIPS technology to provide the number of desired probes. For example, in an absolute sequencing application, it is often useful to have virtually all of the possible oligonucleotides of a given length. As indicated above, there are 65,536 8-mers, 262,144 9-mers, 1,048,576 10-mers, 4,194,304 11-mers, etc. As the length of the oligomer increases the number of different probes which must be synthesized also increases at a rate of a factor of 4 for every additional nucleotide. Eventually the size of the matrix and the limitations in the resolution of regions in the matrix will reach the point where an increase in number of probes becomes disadvantageous. However, this sequencing procedure requires that the system be able to distinguish, by appropriate selection of hybridization and washing conditions, between binding of absolute fidelity and binding of complementary sequences containing mismatches. On the other hand, if the fidelity is unnecessary, this discrimination is also unnecessary and a significantly longer probe may be used. Significantly longer probes would typically be useful in fingerprinting or mapping applications.

The length of the probe is selected for a length that will allow the probe to bind with specificity to possible targets. The hybridization conditions are also very important in that they will determine how closely the homology of complementary binding will be detected. In fact, a single target may be evaluated at a number of different conditions to determine its spectrum of specificity for binding particular probes. This may find use in a number of other applications besides the polynucleotide sequencing fingerprinting or mapping. For example, it will be desired to determine the spectrum of binding affinities and specificities of cell surface antigens with binding by particular antibodies immobilized on the substrate surface, particularly under different interaction conditions. In a related fashion, different regions with reagents having differing affinities or levels of specificity may allow such a spectrum to be defined using a single incubation, where various regions, at a given hybridization condition, show the binding affinity. For example, fingerprint probes of various lengths, or with specific defined non-matches may be used. Unnatural nucleotides or nucleotides exhibiting modified specificity of complementary binding are described in greater detail in Macevicz (1990) PCT pub. No. WO 90/04652; and see the section on modified nucleotides in the Sigma Chemical Company catalogue.

B. Labeling Target Nucleotide

The label used to detect the target sequences will be determined, in part, by the detection methods being applied. Thus, the labeling method and label used are selected in combination with the actual detecting systems being used.

Once a particular label has been selected, appropriate labeling protocols will be applied, as described below for specific embodiments. Standard labeling protocols for nucleic acids are described, e.g., in Sambrook et al.; Kambara, H. et al. (1988) *BioTechnology* 6:816–821; Smith, L. et al. (1985) *Nuc. Acids Res.* 13:2399–2412; for polypeptides, see, e.g., Allen G. (1989) *Sequencing of Proteins and Peptides,* Elsevier, N.Y., especially chapter 5, and Greenstein and Winitz(1961) *Chemistry of the Amino Acids,* Wiley and Sons, New York. Carbohydrate labeling is described, e.g., in Chaplin and Kennedy (1986) *Carbohydrate Analysis: A Practical Approach,* IRL Press, Oxford. Labeling of other polymers will be performed by methods applicable to them as recognized by a person having ordinary skill in manipulating the corresponding polymer.

In some embodiments, the target need not actually be labeled if a means for detecting where interaction takes place is available. As described below, for a nucleic acid embodiment, such may be provided by an intercalating dye which intercalates only into double stranded segments, e.g., where interaction occurs. See, e.g., Sheldon et al. U.S. Pat. No. 4,582,789.

In many uses, the target sequence will be absolutely homogeneous, both with respect to the total sequence and with respect to the ends of each molecule. Homogeneity with respect to sequence is important to avoid ambiguity. It is preferable that the target sequences of interest not be contaminated with a significant amount of labeled contaminating sequences. The extent of allowable contamination will depend on the sensitivity of the detection system and the inherent signal to noise of the system. Homogeneous contamination sequences will be particularly disruptive of the sequencing procedure.

However, although the target polynucleotide must have a unique sequence, the target molecules need not have identical ends. In fact, the homogeneous target molecule preparation may be randomly sheared to increase the numerical number of molecules. Since the total information content remains the same, the shearing results only in a higher number of distinct sequences which may be labeled and bind to the probe. This fragmentation may give a vastly superior signal relative to a preparation of the target molecules having homogeneous ends. The signal for the hybridization is likely to be dependent on the numerical frequency of the target-probe interactions. If a sequence is individually found on a larger number of separate molecules a better signal will result. In fact, shearing a homogeneous preparation of the target may often be preferred before the labeling procedure is performed, thereby producing a large number of labeling groups associated with each subsequence.

C. Hybridization Conditions

The hybridization conditions between probe and target should be selected such that the specific recognition interaction, i.e., hybridization, of the two molecules is both sufficiently specific and sufficiently stable. See, e.g., Hames and Higgins (1985) *Nucleic Acid Hybridisation: A Practical Approach,* IRL Press, Oxford. These conditions will be dependent both on the specific sequence and often on the guanine and cytosine (GC) content of the complementary hybrid strands. The conditions may often be selected to be universally equally stable independent of the specific sequences involved. This typically will make use of a reagent such as an arylammonium buffer. See, Wood et al. (1985) "Base Composition-independent Hybridization in Tetramethylammonium Chloride: A Method for Oligonucleotide Screening of Highly Complex Gene Libraries," *Proc. Natl. Acad. Sci. USA,* 82:1585–1588; and Krupov et al. (1989) "An Oligonucleotide Hybridization Approach to DNA Sequencing," *FEBS Letters,* 256:118–122; each of which is hereby incorporated herein by reference. An arylammonium buffer tends to minimize differences in hybridization rate and stability due to GC content. By virtue of the fact that sequences then hybridize with approximately equal affinity and stability, there is relatively little bias in strength or kinetics of binding for particular sequences. Temperature and salt conditions along with other buffer parameters should be selected such that the kinetics of renaturation should be essentially independent of the specific target subsequence or oligonucleotide probe involved. In order to ensure this, the hybridization reactions will usually be performed in a single incubation of all the substrate matrices together exposed to the identical same target probe solution under the same conditions.

Alternatively, various substrates may be individually treated differently. Different substrates may be produced, each having reagents which bind to target subsequences with substantially identical stabilities and kinetics of hybridization. For example, all of the high GC content probes could be synthesized on a single substrate which is treated accordingly. In this embodiment, the arylammonium buffers could be unnecessary. Each substrate is then treated in a manner such that the collection of substrates show essentially uniform binding and the hybridization data of target binding to the individual substrate matrix is combined with the data from other substrates to derive the necessary subsequence binding information. The hybridization conditions will usually be selected to be sufficiently specific such that the fidelity of base matching will be properly discriminated. Of course, control hybridizations should be included to determine the stringency and kinetics of hybridization.

D. Detection: VLSIPS™ Technology Scanning

The next step of the sequencing process by hybridization involves labeling of target polynucleotide molecules. A quickly and easily detectable signal is preferred. The VLSIPS apparatus is designed to easily detect a fluorescent label, so fluorescent tagging of the target sequence is preferred. Other suitable labels include heavy metal labels, magnetic probes, chromogenic labels (e.g., phosphorescent labels, dyes, and fluorophores) spectroscopic labels, enzyme linked labels, radioactive labels, and labeled binding proteins. Additional labels are described in U.S. Pat. No. 4,366,241, which is incorporated herein by reference.

The detection methods used to determine where hybridization has taken place will typically depend upon the label selected above. Thus, for a fluorescent label a fluorescent detection step will typically be used. U.S. Ser. No. 07/492,462 (U.S. Pat. No. 5,143,854) and U.S. Ser. No. 07/624,120 (U.S. Pat. No. 5,498,678) describe apparatus and mechanisms for scanning a substrate matrix using fluorescence detection, but a similar apparatus is adaptable for other optically detectable labels.

The detection method provides a positional localization of the region where hybridization has taken place. However, the position is correlated with the specific sequence of the probe since the probe has specifically been attached or synthesized at a defined substrate matrix position. Having collected all of the data indicating the subsequences present in the target sequence, this data may be aligned by overlap to reconstruct the entire sequence of the target, as illustrated above.

It is also possible to dispense with actual labeling if some means for detecting the positions of interaction between the sequence specific reagent and the target molecule are available. This may take the form of an additional reagent which can indicate the sites either of interaction, or the sites of lack of interaction, e.g., a negative label. For the nucleic acid embodiments, locations of double strand interaction may be detected by the incorporation of intercalating dyes, or other reagents such as antibody or other reagents that recognize helix formation, see, e.g., Sheldon, et al. (1986) U.S. Pat. No. 4,582,789, which is hereby incorporated herein by reference.

E. Analysis

Although the reconstruction can be performed manually as illustrated above, a computer program will typically be used to perform the overlap analysis. A program may be written and run on any of a large number of different computer hardware systems. The variety of operating systems and languages useable will be recognized by a computer software engineer. Various different languages may be used, e.g., BASIC; C; PASCAL; etc.

F. Substrate Reuse

Finally, after a particular sequence has been hybridized and the pattern of hybridization analyzed, the matrix substrate should be reusable and readily prepared for exposure to a second or subsequent target polynucleotides. In order to do so, the hybrid duplexes are disrupted and the matrix treated in a way which removes all traces of the original target. The matrix may be treated with various detergents or solvents to which the substrate, the oligonucleotide probes, and the linkages to the substrate are inert. This treatment may include an elevated temperature treatment, treatment with organic or inorganic solvents, modifications in pH, and other means for disrupting specific interaction. Thereafter, a second target may actually be applied to the recycled matrix and analyzed as before.

G. Non-Polynucleotide Aspects

Although the sequencing, fingerprinting, and mapping functions will make use of the natural sequence recognition property of complementary nucleotide sequences, the non-polynucleotide sequences typically require other sequence recognition reagents. These reagents will take the form, typically, of proteins exhibiting binding specificity, e.g., enzyme binding sites or antibody binding sites.

Enzyme binding sites may be derived from promoter proteins, restriction enzymes, and the like. See, e.g., Stryer, L. (1988) *Biochemistry,* W. H.Freeman, Palo Alto. Antibodies will typically be produced using standard procedures, see, e.g., Harlow and Lane (1988) *Antibodies: A Laboratory*

*Manual,* Cold Spring Harbor Press, New York; and Goding (1986) *Monoclonal Antibodies: Principles and Practice,* (2d Ed.) Academic Press, San Diego.

Typically, an antigen, or collection of antigens are presented to an immune system. This may take the form of synthesized short polymers produced by the VLSIPS technology, or by the other synthetic means, or from isolation of natural products. For example, antigen for the polypeptides may be made by the VLSIPS technology, by standard peptide synthesis, by isolation of natural proteins with or without degradation to shorter segments, or by expression of a collection of short nucleic acids of random or defined sequences. See, e.g., Tuerk and Gold (1990) *Science* 249:505–510, for generation of a collection of randomly mutagenized oligonucleotides useful for expression.

The antigen or collection is presented to an appropriate immune system, e.g., to a whole animal as in a standard immunization protocol, or to a collection of immune cells or equivalent. In particular, see Ward et al. (1989) *Nature* 341:544–546; and Huse et al. (1989) *Science* 246:1275–1281, each of which is hereby incorporated herein by reference.

A large diversity of antibodies will be generated, some of which have specificities for the desired sequences. Antibodies may be purified having the desired sequence specificities by isolating the cells producing them. For example, a VLSIPS substrate with the desired antigens synthesized thereon may be used to isolate cells with cell surface reagents which recognize the antigens. The VLSIPS substrate may be used as an affinity reagent to select and recover the appropriate cells. Antibodies from those cells may be attached to a substrate using the caged biotin methodology, or by attaching a targeting molecule, e.g., an oligonucleotide. Alternatively, the supernatants from antibody producing cells can be easily assayed using a VLSIPS substrate to identify the cells producing the appropriate antibodies.

Although cells may be isolated, specific antibody molecules which perform the sequence recognition will also be sufficient. Preferably populations of antibody with a known specificity can be isolated. Supernatants from a large population of producing cells may be passed over a VLSIPS substrate to bind to the desired antigens attached to the substrate. When a sufficient density of antibody molecules are attached, they may be removed by an automated process, preferably as antibody populations exhibiting specificity of binding.

In one particular embodiment, a VLSIPS substrate, e.g., with a large plurality of fingerprint antigens attached thereto, is used to isolate antibodies from a supernatant of a population of cells producing antibodies to the antigens. Using the substrate as an affinity reagent, the antibodies will attach to the appropriate positionally defined antigens. The antibodies may be carefully removed therefrom, preferably by an automated system which retains their homogeneous specificities. The isolated antibodies can be attached to a new substrate in a positionally defined matrix pattern.

In a further embodiment, these spatially separated antibodies may be isolated using a specific targeting method for isolation. In this embodiment, a linker molecule which attaches to a particular portion of the antibody, preferably away from the binding site, can be attached to the antibodies. Various reagents will be used, including staphylococcus protein A or antibodies which bind to domains remote from the binding site. Alternatively, the antibodies in the population, before affinity purification, may be derivatized with an appropriate reagent compatible with new VLSIPS synthesis. A preferred reagent is a nucleotide which can serve as a linker to synthetic VLSIPS steps for synthesizing a specific sequence thereon. Then, by successive VLSIPS cycles, each of the antibodies attached to the defined antigen regions can have a defined oligonucleotide synthesized thereon and corresponding in area to the region of the substrate having each antigen attached. These defined oligonucleotides will be useful as targeting reagents to attach those antibodies possessing the same target sequence specificity at defined positions on a new substrate, by virtue of having bound to the antigen region, to a new VLSIPS substrate having the complementary target oligonucleotides positionally located on it. In this fashion, a VLSIPS substrate having the desired antigens attached thereto can be used to generate a second VLSIPS substrate with positionally defined reagents which recognize those antigens.

The selected antigens will typically be selected to be those which define particular functionalities or properties, so as to be useful for fingerprinting and other uses. They will also be useful for mapping and sequencing embodiments.

iv. FINGERPRINTING

A. General

Many of the procedures and techniques used in the polynucleotide sequencing section are also appropriate for fingerprinting applications. See, e.g., Poustka, et al. (1986) *Cold Spring Harbor Symposia on Quant. Biol.,* vol. LI, 131–139, Cold Spring Harbor Press, New York; which is hereby incorporated herein by reference. The fingerprinting method provided herein is based, in part, upon the ability to positionally localize a large number of different specific probes onto a single substrate. This high density matrix pattern provides the ability to screen for, or detect, a very large number of different sequences simultaneously. In fact, depending upon the hybridization conditions, fingerprinting to the resolution of virtually absolute matching of sequence is possible thereby approaching an absolute sequencing embodiment. And the sequencing embodiment is very useful in identifying the probes useful in further fingerprinting uses. For example, characteristic features of genetic sequences will be identified as being diagnostic of the entire sequence. However, in most embodiments, longer probe and target will be used, and for which slight mismatching may not need to be resolved.

B. Preparation of Substrate Matrix

A collection of specific probes may be produced by either of the methods described above in the section on sequencing. Specific oligonucleotide probes of desired lengths may be individually synthesized on a standard oligonucleotide synthesizer. The length of these probes is limited only by the ability of the synthesizer to continue to accurately synthesize a molecule. Oligonucleotides or sequence fragments may also be isolated from natural sources. Biological amplification methods may be coupled with synthetic synthesizing procedures such as, e.g., polymerase chain reaction.

In one embodiment, the individually isolated probes may be attached to the matrix at defined positions. These probe reagents may be attached by an automated process making use of the caged biotin methodology described in U.S. Ser. No. 07/612,671, or using photochemical reagents, see, e.g., Dattagupta et al. (1985) U.S. Pat. No. 4,542,102 and (1987) U.S. Pat. No. 4,713,326. Each individually purified reagent can be attached individually at specific locations on a substrate.

In another embodiment, the VLSIPS synthesizing technique may be used to synthesize the desired probes at specific positions on a substrate. The probes may be synthesized by successively adding appropriate monomer subunits, e.g., nucleotides, to generate the desired sequences.

In another embodiment, a relatively short specific oligonucleotide is used which serves as a targeting reagent for positionally directing the sequence recognition reagent. For example, the sequence specific reagents having a separate additional sequence recognition segment (usually of a different polymer from the target sequence) can be directed to target oligonucleotides attached to the substrate. By use of non-natural targeting reagents, e.g., unusual nucleotide analogues which pair with other unnatural nucleotide analogues and which do not interfere with natural nucleotide interactions, the natural and non-natural portions can coexist on the same molecule without interfering with their individual functionalities. This can combine both a synthetic and biological production system analogous to the technique for targeting monoclonal antibodies to locations on a VLSIPS substrate at defined positions. Unnatural optical isomers of nucleotides may be useful unnatural reagents subject to similar chemistry, but incapable of interfering with the natural biological polymers. See also, U.S. Ser. No. 07/626,730, which is hereby incorporated herein by reference.

After the separate substrate attached reagents are attached to the targeting segment, the two are crosslinked, thereby permanently attaching them to the substrate. Suitable crosslinking reagents are known, see, e.g., Dattagupta et al. (1985) U.S. Pat. No. 4,542,102 and (1987) "Coupling of nucleic acids to solid support by photochemical methods," U.S. Pat. No. 4,713,326, each of which is hereby incorporated herein by reference. Similar linkages for attachment of proteins to a solid substrate are provided, e.g., in Merrifield (1986) *Science* 232:341–347, which is hereby incorporated herein by reference.

C. Labeling Target Nucleotides

The labeling procedures used in the sequencing embodiments will also be applicable in the fingerprinting embodiments. However, since the fingerprinting embodiments often will involve relatively large target molecules and relatively short oligonucleotide probes, the amount of signal necessary to incorporate into the target sequence may be less critical than in the sequencing applications. For example, a relatively long target with a relatively small number of labels per molecule may be easily amplified or detected because of the relatively large target molecule size.

In various embodiments, it may be desired to cleave the target into smaller segments as in the sequencing embodiments. The labeling procedures and cleavage techniques described in the sequencing embodiments would usually also be applicable here.

D. Hybridization Conditions

The hybridization conditions used in fingerprinting embodiments will typically be less critical than for the sequencing embodiments. The reason is that the amount of mismatching which may be useful in providing the fingerprinting information would typically be far greater than that necessary in sequencing uses. For example, Southern hybridizations do not typically distinguish between slightly mismatched sequences. Under these circumstances, important and valuable information may be arrived at with less stringent hybridization conditions while providing valuable fingerprinting information. However, since the entire substrate is typically exposed to the target molecule at one time, the binding affinity of the probes should usually be of approximately comparable levels. For this reason, if oligonucleotide probes are being used, their lengths should be approximately comparable and will be selected to hybridize under conditions which are common for most of the probes on the substrate. Much as in a Southern hybridization, the target and oligonucleotide probes are of lengths typically greater than about 25 nucleotides. Under appropriate hybridization conditions, e.g., typically higher salt and lower temperature, the probes will hybridize irrespective of imperfect complementarity. In fact, with probes of greater than, e.g., about fifty nucleotides, the difference in stability of different sized probes will be relatively minor.

Typically the fingerprinting is merely for probing similarity or homology. Thus, the stringency of hybridization can usually be decreased to fairly low levels. See, e.g., Wetmur and Davidson (1968) "Kinetics of Renaturation of DNA," *J. Mol. Biol.,* 31:349–370; and Kanehisa, M. (1984) *Nuc. Acids Res.,* 12:203–213.

E. Detection: VLSIPS™ Technology Scanning

Detection methods will be selected which are appropriate for the selected label. The scanning device need not necessarily be digitized or placed into a specific digital database, though such would most likely be done. For example, the analysis in fingerprinting could be photographic. Where a standardized fingerprint substrate matrix is used, the pattern of hybridizations may be spatially unique and may be compared photographically. In this manner, each sample may have a characteristic pattern of interactions and the likelihood of identical patterns will preferably be such low frequency that the fingerprint pattern indeed becomes a characteristic pattern virtually as unique as an individual's fingertip fingerprint. With a standardized substrate, every individual could be, in theory, uniquely identifiable on the basis of the pattern of hybridizing to the substrate.

Of course, the VLSIPS™ Technology scanning apparatus may also be useful to generate a digitized version of the fingerprint pattern. In this way, the identification pattern can be provided in a linear string of digits. This sequence could also be used for a standardized identification system providing significant useful medical transferability of specific data. In one embodiment, the probes used are selected to be of sufficiently high resolution to measure the antigens of the major histo compatibility complex. It might even be possible to provide transplantation matching data in a linear stream of data. The fingerprinting data may provide a condensed version, or summary, of the linear genetic data, or any other information data base.

F. Analysis

The analysis of the fingerprint will often be much simpler than a total sequence determination. However, there may be particular types of analysis which will be substantially simplified by a selected group of probes. For example, probes which exhibit particular populational heterogeneity may be selected. In this way, analysis may be simplified and practical utility enhanced merely by careful selection of the specific probes and a careful matrix layout of those probes.

G. Substrate Reuse

As with the sequencing application, the fingerprinting usages may also take advantage of the reusability of the substrate. In this way, the interactions can be disrupted, the substrate treated, and the renewed substrate is equivalent to an unused substrate.

H. Non-polynucleotide Aspects

Besides polynucleotide applications, the fingerprinting analysis may be applied to other polymers, especially polypeptides, carbohydrates, and other polymers, both organic and inorganic. Besides using the fingerprinting method for analyzing a particular polymer, the fingerprinting method may be used to characterize various samples. For example, a cell or population of cells may be tested for their expression of specific antigens or their mRNA sequence content. For example, a T-cell may be classified by virtue of its combination of expressed surface antigens. With specific reagents which interact with these antigens, a cell or a population of cells or a lysed cell may be exposed to a VLSIPS substrate. The biological sample may be classified or characterized by analyzing the pattern of specific interaction. This may be applicable to a cell or tissue type, to the messenger RNA population expressed by a cell to the genetic content of a cell, or to virtually any sample which can be classified and/or identified by its combination of specific molecular properties.

The ability to generate a high density means for screening the presence or absence of specific interactions allows for the possibility of screening for, if not saturating, all of a very large number of possible interactions. This is very powerful in providing the means for testing the combinations of molecular properties which can define a class of samples. For example, a species of organism may be characterized by its DNA sequences, e.g., a genetic fingerprint. By using a fingerprinting method, it may be determined that all members of that species are sufficiently similar in specific sequences that they can be easily identified as being within a particular group. Thus, newly defined classes may be resolved by their similarity in fingerprint patterns. Alternatively, a non-member of that group will fail to share those many identifying characteristics. However, since the technology allows testing of a very large number of specific interactions, it also provides the ability to more finely distinguish between closely related different cells or samples. This will have important applications in diagnosing viral, bacterial, and other pathological on nonpathological infections.

In particular, cell classification may be defined by any of a number of different properties. For example, a cell class may be defined by its DNA sequences contained therein. This allows species identification for parasitic or other infections. For example, the human cell is presumably genetically distinguishable from a monkey cell, but different human cells will share many genetic markers. At higher resolution, each individual human genome will exhibit unique sequences that can define it as a single individual.

Likewise, a developmental stage of a cell type may be definable by its pattern of expression of messenger RNA. For example, in particular stages of cells, high levels of ribosomal RNA are found whereas relatively low levels of other types of messenger RNAs may be found. The high resolution distinguishability provided by this fingerprinting method allows the distinction between cells which have relatively minor differences in its expressed mRNA population. Where a pattern is shown to be characteristic of a stage, a stage may be defined by that particular pattern of messenger RNA expression.

In a similar manner, the antigenic determinants found on a protein may very well define the cell class. For example, immunological T-cells are distinguishable from B-cells because, in part, the cell surface antigens on the cell types are distinguishable. Different T-cell subclasses can be also distinguished from one another by whether they contain particular T-cell antigens. The present invention provides the possibility for high resolution testing of many different interactions simultaneously, and the definition of new cell types will be possible.

The high resolution VLSIPS™ substrate may also be used as a very powerful diagnostic tool to test the combination of presence, of a plurality of different assays from a biological sample. For example, a cancerous condition may be indicated by a combination of various different properties found in the blood. For example, a cancerous condition may be indicated by a combination of expression of various soluble antigens found in the blood along with a high number of various cellular antigens found on lymphocytes and/or particular cell degradation products. With a substrate as provided herein, a large number of different features can be simultaneously performed on a biological sample. In fact, the high resolution of the test will allow more complete characterization of parameters which define particular diseases. Thus, the power of diagnostic tests may be limited by the extent of statistical correlation with a particular condition rather than with the number of antigens or interactions which are tested. The present invention provides the means to generate this large universe of possible reagents and the ability to actually accumulate that correlative data.

In another embodiment, a substrate as provided herein may be used for genetic screening. This would allow for simultaneous screening of thousands of genetic markers. As the density of the matrix is increased, many more molecules can be simultaneously tested. Genetic screening then becomes a simpler method as the present invention provides the ability to screen for thousands, tens of thousands, and hundreds of thousands, even millions of different possible genetic features. However, the number of high correlation genetic markers for conditions numbers only in the hundreds. Again, the possibility for screening a large number of sequences provides the opportunity for generating the data which can provide correlation between sequences and specific conditions or susceptibility. The present invention provides the means to generate extremely valuable correlations useful for the genetic detection of the causative mutation leading to medical conditions. In still another embodiment, the present invention would be applicable to distinguishing two individuals having identical genetic compositions. The antibody population within an individual is dependent both on genetic and historical factors. Each individual experiences a unique exposure to various infectious agents, and the combined antibody expression is partly determined thereby. Thus, individuals may also be fingerprinted by their immunological content, either of actively expressed antibodies, or their immunological memory. Similar sorts of immunological and environmental histories may be useful for fingerprinting, perhaps in combination with other screening properties. In particular, the present invention may be useful for screening allergic reactions or susceptibilities, and a simple IgE specificity test may be useful in determining a spectrum of allergies.

With the definition of new classes of cells, a cell sorter will be used to purify them. Moreover, new markers for defining that class of cells will be identified. For example, where the class is defined by its RNA content, cells may be screened by antisense probes which detect the presence or absence of specific sequences therein. Alternatively, cell lysates may provide information useful in correlating intracellular properties with extracellular markers which indicate functional differences. Using standard cell sorter technology with a fluorescence or labeled antisense probe which recognizes the internal presence of the specific sequences of interest, the cell sorter will be able to isolate a relatively homogeneous population of cells possessing the particular marker. Using successive probes the sorting process should be able to select for cells having a combination of a large number of different markers.

In a non-polynucleotide embodiment, cells may be defined by the presence of other markers. The markers may be carbohydrates, proteins, or other molecules. Thus, a substrate having particular specific reagents, e.g., antibodies, attached to it should be able to identify cells having particular patterns of marker expression. Of course, combinations of these made be utilized and a cell class may be defined by a combination of its expressed mRNA, its carbohydrate expression, its antigens, and other properties. This fingerprinting should be useful in determining the physiological state of a cell or population of cells.

Having defined a cell type whose function or properties are defined by the reagents attachable to a VLSIPS substrate, such as cellular antigens, these structural manifestations of function may be used to sort cells to generate a relatively homogeneous population of that class of cells. Standard cell sorter technology may be applied to purify such a population, see, e.g., Dangl, J. and Herzenberg (1982) "Selection of hybridomas and hybridoma variants using the fluorescence activated cell sorter," *J. Immunological Methods* 52:1–14; and Becton Dickinson, Fluorescence Activated Cell Sorter Division, San Jose, Calif., and Coulter Diagnostics, Hialeah, Fla.

With the fingerprinting method an identification means arises from mosaicism problems in an organism. A mosaic organism is one whose genetic content in different cells is significantly different. Various clonal populations should have similar genetic fingerprints, though different clonal populations may have different genetic contents. See, for example, Suzuki et al. *An Introduction to Genetic Analysis* (4th Ed.), Freeman and Co., New York, which is hereby incorporated herein by reference. However, this problem should be a relatively rare problem and could be more carefully evaluated with greater experience using the fingerprinting methods.

The invention will also find use in detecting changes, both genetic and antigenic, e.g., in a rapidly "evolving" protozoa infection, or similarly changing organism.

v. MAPPING

A. General

The use of the present invention for mapping parallels its use for fingerprinting and sequencing. Where a polymer is a linear molecule, the mapping provides the ability to locate particular segments along the length of the polymer. Branched polymers can be treated as a series of individual linear polymers. The mapping provides the ability to locate, in a relative sense, the order of various subsequences. This may be achieved using at least two different approaches.

The first approach is to take the large sequence and fragment it at specific points. The fragments are then ordered and attached to a solid substrate. For example, the clones resulting from a chromosome walking process may be individually attached to the substrate by methods, e.g., caged biotin techniques, indicated earlier. Segments of unknown map position will be exposed to the substrate and will hybridize to the segment which contains that particular sequence. This procedure allows the rapid determination of a number of different labeled segments, each mapping requiring only a single hybridization step once the substrate is generated. The substrate may be regenerated by removal of the interaction, and the next mapping segment applied.

In an alternative method, a plurality of subsequences can be attached to a substrate. Various short probes may be applied to determine which segments may contain particular overlaps. The theoretical basis and a description of this mapping procedure is contained in, e.g., Evans et al. 1989 "Physical Mapping of Complex Genomes by Cosmid Multiplex Analysis," *Proc. Natl. Acad. Sci. USA* 86:5030–5034, and other references cited above in the Section labeled "Overall Description." Using this approach, the details of the mapping embodiment are very similar to those used in the fingerprinting embodiment.

B. Preparation of Substrate Matrix

The substrate may be generated in either of the methods generally applicable in the sequencing and fingerprinting embodiments. The substrate may be made either synthetically, or by attaching otherwise purified probes or sequences to the matrix. The probes or sequences may be derived either from synthetic or biological means. As indicated above, the solid phase substrate synthetic methods may be utilized to generate a matrix with positionally defined sequences. In the mapping embodiment, the importance of saturation of all possible subsequences of a preselected length is far less important than in the sequencing embodiment, but the length of the probes used may be desired to be much longer. The processes for making a substrate which has longer oligonucleotide probes should not be significantly different from those described for the sequencing embodiments, but the optimization parameters may be modified to comply with the mapping needs.

C. Labeling

The labeling methods will be similar to those applicable in sequencing and fingerprinting embodiments. Again, it may be desirable to fragment the target sequences.

D. Hybridization/Specific Interaction

The specificity of interaction between the targets and probe would typically be closer to those used for fingerprinting embodiments, where homology is more important th an absolute distinguishability of high fidelity complementary hybridization. Usually, the hybridization conditions will be such that merely homologous segments will interact and provide a positive signal. Much like the fingerprinting embodiment, it may be useful to measure the extent of homology by successive incubations at higher stringency conditions. Or, a plurality of different probes, each having various levels of homology may be used. In either way, the spectrum of homologies can be measured.

Where non-nucleic acid hybridization is involved, the specific interactions may also be compared in a fingerprint-like manner. The specific reagents may have less specificity, e.g., monoclonal antibodies which recognize a broader spectrum of sequences may be utilized relative to a sequencing embodiment. Again, the specificity of interaction may be measured under various conditions of increasing stringency to determine the spectrum of matching across the specific probes selected, or a number of different stringency reagents may be included to indicate the binding affinity.

E. Detection

The detection methods used in the mapping procedure will be virtually identical to those used in the fingerprinting embodiment. The detection methods will be selected in combination with the labeling methods.

F. Analysis

The analysis of the data in a mapping embodiment will typically be somewhat different from that in fingerprinting. The fingerprinting embodiment will test for the presence or absence of specific or homologous segments. However, in the mapping embodiment, the existence of an interaction is coupled with some indication of the location of the interaction. The interaction is mapped in some manner to the physical polymer sequence. Some means for determining the relative positions of different probes is performed. This may be achieved by synthesis of the substrate in pattern, or may result from analysis of sequences after they have been attached to the substrate.

For example, the probes may be randomly positioned at various locations on the substrate. However, the relative positions of the various reagents in the original polymer may be determined by using short fragments, e.g., individually, as target molecules which determine the proximity of different probes. By an automated system of testing each different short fragment of the original polymer, coupled with proper analysis, it will be possible to determine which probes are adjacent one another on the original target sequence and correlate that with positions on the matrix. In this way, the matrix is useful for determining the relative locations of various new segments in the original target molecule. This sort of analysis is described in Evans, and the related references described above.

G. Substrate Reuse

The substrate should be reusable in the manner described in the fingerprinting section. The substrate is renewed by removal of the specific interactions and is washed and prepared for successive cycles of exposure to new target sequences.

H. Non-polynucleotide Aspects

The mapping procedure may be used on other molecules than polynucleotides. Although hybridization is one type of specific interaction which is clearly useful for use in this mapping embodiment, antibody reagents may also be very useful. In the same way that polypeptide sequencing or other polymers may be sequenced by the reagents and techniques described in the sequencing section and fingerprinting section, the mapping embodiment may also be used similarly.

In another form of mapping, as described above in the fingerprinting section, the developmental map of a cell or biological system may be measured using fingerprinting type technology. Thus, the mapping may be along a temporal dimension rather than along a polymer dimension. The mapping or fingerprinting embodiments may also be used in determining the genetic rearrangements which may be genetically important, as in lymphocyte and B-cell development. In another example, various rearrangements or chromosomal dislocations may be tested by either the fingerprinting or mapping methods. These techniques are similar in many respects and the fingerprinting and mapping embodiments may overlap in many respects.

vi. ADDITIONAL SCREENING AND APPLICATIONS

A. Specific Interactions

As originally indicated in the parent filing of VLSIPS™, the production of a high density plurality of spatially segregated polymers provides the ability to generate a very large universe or repertoire of individually and distinct sequence possibilities. As indicated above, particular oligonucleotides may be synthesized in automated fashion at specific locations on a matrix. In fact, these oligonucleotides may be used to direct other molecules to specific locations by linking specific oligonucleotides to other reagents which are in batch exposed to the matrix and hybridized in a complementary fashion to only those locations where the complementary oligonucleotide has been synthesized on the matrix. This allows for spatially attaching a plurality of different reagents onto the matrix instead of individually attaching each separate reagent at each specific location. Although the caged biotin method allows automated attachment, the speed of the caged biotin attachment process is relatively slow and requires a separate reaction for each reagent being attached. By use of the oligonucleotide method, the specificity of position can be done in an automated and parallel fashion. As each reagent is produced, instead of directly attaching each reagent at each desired position, the reagent may be attached to a specific desired complementary oligonucleotide which will ultimately be specifically directed toward locations on the matrix having a complementary oligonucleotide attached thereat.

In addition, the technology allows screening for specificity of interaction with particular reagents. For example, the oligonucleotide sequence specificity of binding of a potential reagent may be tested by presenting to the reagent all of the possible subsequences available for binding. Although secondary or higher order sequence specific features might not be easily screenable using this technology, it does provide a convenient, simple, quick, and thorough screen of interactions between a reagent and its target recognition sequences. See, e.g., Pfeifer et al. (1989) *Science* 246:810–812.

For example, the interaction of a promoter protein with its target binding sequence may be tested for many different, or all, possible binding sequences. By testing the strength of interactions under various different conditions, the interaction of the promoter protein with each of the different potential binding sites may be analyzed. The spectrum of strength of interactions with each different potential binding site may provide significant insight into the types of features which are important in determining specificity.

An additional example of a sequence specific interaction between reagents is the testing of binding of a double stranded nucleic acid structure with a single stranded oligonucleotide. Often, a triple stranded structure is produced which has significant aspects of sequence specificity. Testing of such interactions with either sequences comprising only natural nucleotides, or perhaps the testing of nucleotide analogs may be very important in screening for particularly useful diagnostic or therapeutic reagents. See, e.g., Häner and Dervan (1990) *Biochemistry* 29:9761–6765, and references therein.

B. Sequence Comparisons

Once a gene is sequenced, the present invention provides a means to compare alleles or related sequences to locate and identify differences from the control sequence. This would be extremely useful in further analysis of genetic variability at a specific gene locus.

C. Categorizations

As indicated above in the fingerprinting and mapping embodiments, the present invention is also useful in defining specific stages in the temporal sequence of cells, e.g., development, and the resulting tissues within an organism. For example, the developmental stage of a cell, or population of cells, can be dependent upon the expression of particular messenger RNAs or cellular antigens. The screening procedures provided allow for high resolution definition of new classes of cells. In addition, the temporal development of particular cells will be characterized by the presence or expression of various mRNAs. Means to simultaneously screen a plurality or very large number of different sequences are provided. The combination of different markers made available dramatically increases the ability to distinguish fairly closely related cell types. Other markers may be combined with markers and methods made available herein to define new classifications of biological samples, e.g., based upon new combinations of markers.

The presence or absence of particular marker sequences will be used to define temporal developmental stages. Once the stages are defined, fairly simple methods can be applied to actually purify those particular cells. For example, antisense probes or recognition reagents may be used with a cell sorter to select those cells containing or expressing the critical markers. Alternatively, the expression of those sequences may result in specific antigens which may also be used in defining cell classes and sorting those cells away from others. In this way, for example, it should be possible to select a class of omnipotent immune system cells which are able to completely regenerate a human immune system. Based upon the cellular classes defined by the parameters made available by this technology, purified classes of cells having identifiable differences, structural or functional, are made available.

In an alternative embodiment, a plurality of antigens or specific binding proteins attached to the substrate may be used to define particular cell types. For example, subclasses of T-cells are defined, in part, by the combination of expressed cell surface antigens. The present invention allows for the simultaneous screening of a large plurality of different antigens together. Thus, higher resolution classification of different T-cell subclasses becomes possible and, with the definitions and functional differences which correlate with those antigenic or other parameters, the ability to purify those cell types becomes available. This is applicable not only to T-cells, but also to lymphocyte cells, or even to freely circulating cells. Many of the cells for which this would be most useful will be immobile cells found in particular tissues or organs. Tumor cells will be diagnosed or detected using these fingerprinting techniques. Coupled with a temporal change in structure, developmental classes may also be selected and defined using these technologies. The present invention also provides the ability not only to define new classes of cells based upon functional or structural differences, but it also provides the ability to select or purify populations of cells which share these particular properties. Standard cell sorting procedures using antibody markers may be used to detect extracellular features. Intracellular features would also be detectable by introducing the label reagents into the cell. In particular, antisense DNA or RNA molecules may be introduced into a cell to detect RNA sequences therein. See, e.g., Weintraub (1990) *Scientific American* 262:40–46.

D. Statistical Correlations

In an additional embodiment, the present invention also allows for the high resolution correlation of medical conditions with various different markers. For example, the present available technology, when applied to amniocentesis or other genetic screening methods, typically screen for tens of different markers at most. The present invention allows simultaneous screening for tens, hundreds, thousands, tens of thousands, hundreds of thousands, and even millions of different genetic sequences. Thus, applying the fingerprinting methods of the present invention to a sufficiently large population allows detailed statistical analysis to be made, thereby correlating particular medical conditions with particular markers, typically antigenic or genetic. Tumor specific antigens will be identified using the present invention.

Various medical conditions may be correlated against an enormous data base of the sequences within an individual. Genetic propensities and correlations then become available and high resolution genetic predictability and correlation become much more easily performed. With the enormous data base, the reliability of the predictions is also better tested. Particular markers which are partially diagnostic of particular medical conditions or medical susceptibilities will be identified and provide direction in further studies and more careful analysis of the markers involved. Of course, as indicated above in the sequencing embodiment, the present invention will find much use in intense sequencing projects. For example, sequencing of the entire human genome in the human genome project will be greatly simplified and enabled by the present invention.

vi. FORMATION OF SUBSTRATE

The substrate is provided with a pattern of specific reagents which are positionally localized on the surface of the substrate. This matrix of positions is defined by the automated system which produces the substrate. The instrument will typically be one similar to that described in U.S. Ser. No. 07/492,462 (U.S. Pat. No. 5,143,854), and U.S. Ser. No. 07/624,120 (U.S. Pat. No. 5,498,678). The instrumentation described therein is directly applicable to the applications used here. In particular, the apparatus comprises a substrate, typically a silicon containing substrate, on which positions on the surface may be defined by a coordinate system of positions. These positions can be individually addressed or detected by the VLSIPS™ technology apparatus.

Typically, the VLSIPS apparatus uses optical methods used in semiconductor fabrication applications. In this way, masks may be used to photo-activate positions for attachment or synthesis of specific sequences on the substrate. These manipulations may be automated by the types of apparatus described in U.S. Ser. No. 07/462,492 and U.S. Ser. No. 07/624,120 (U.S. Pat. No. 5,498,678).

Selectively removable protecting groups allow creation of well defined areas of substrate surface having differing reactivities. Preferably, the protecting groups are selectively removed from the surface by applying a specific activator, such as electromagnetic radiation of a specific wavelength and intensity. More preferably, the specific activator exposes selected areas of surface to remove the protecting groups in the exposed areas.

Protecting groups of the present invention are used in conjunction with solid phase oligomer syntheses, such as peptide syntheses using natural or unnatural amino acids, nucleotide syntheses using deoxyribonucleic and ribonucleic acids, oligosaccharide syntheses, and the like. In addition to protecting the substrate surface from unwanted reaction, the protecting groups block a reactive end of the monomer to prevent self-polymerization. For instance, attachment of a protecting group to the amino terminus of an activated amino acid, such as the N-hydroxysuccinimide-activated ester of the amino acid prevents the amino terminus of one monomer from reacting with the activated ester portion of another during peptide synthesis.

Alternatively, the protecting group may be attached to the carboxyl group of an amino acid to prevent reaction at this site. Most protecting groups can be attached to either the amino or the carboxyl group of an amino acid, and the nature of the chemical synthesis will dictate which reactive group will require a protecting group. Analogously, attachment of a protecting group to the 5'-hydroxyl group of a nucleoside during synthesis using for example, phosphate-triester coupling chemistry, prevents the 5'-hydroxyl of one nucleoside from reacting with the 3'-activated phosphate-triester of another.

Regardless of the specific use, protecting groups are employed to protect a moiety on a molecule from reacting with another reagent. Protecting groups of the present invention have the following characteristics: they prevent selected reagents from modifying the group to which they are attached; they are stable (that is, they remain attached) to the synthesis reaction conditions; they are removable under conditions that do not adversely affect the remaining structure; and once removed, do not react appreciably with the surface or surface-bound oligomer. The selection of a suitable protecting group will depend, of course, on the chemical nature of the monomer unit and oligomer, as well as the specific reagents they are to protect against.

In a preferred embodiment, the protecting groups will be photoactivatable. The properties and uses of photoreactive protecting compounds have been reviewed. See, McCray et al., *Ann. Rev. of Biophys, and Biophys. Chem.* (1989) 18:239–270, which is incorporated herein by reference. Preferably, the photosensitive protecting groups will be removable by radiation in the ultraviolet (UV) or visible portion of the electromagnetic spectrum. More preferably, the protecting groups will be removable by radiation in the near UV or visible portion of the spectrum. In some embodiments, however, activation may be performed by other methods such as localized heating, electron beam lithography, laser pumping, oxidation or reduction with microelectrodes, and the like. Sulfonyl compounds are suitable reactive groups for electron beam lithography. Oxidative or reductive removal is accomplished by exposure of the protecting group to an electric current source, preferably using microelectrodes directed to the predefined regions of the surface which are desired for activation. A more detailed description of these protective groups is provided in U.S. Ser. No. 07/624,120 (U.S. Pat. No. 5,498,678), which is hereby incorporated herein by reference.

The density of reagents attached to a silicon substrate may be varied by standard procedures. The surface area for attachment of reagents may be increased by modifying the silicon surface. For example, a matte surface may be machined or etched on the substrate to provide more sites for attachment of the particular reagents. Another way to increase the density of reagent binding sites is to increase the derivitization density of the silicon. Standard procedures for achieving this are described, below.

One method to control the derivatization density is to highly derivative the substrate with photochemical groups at high density. The substrate is then photolyzed for various predetermined times, which photoactivate the groups at a measurable rate, and react them with a capping reagent. By this method, the density of linker groups may be modulated by using a desired time and intensity of photoactivation.

In many applications, the number of different sequences which may be provided may be limited by the density and the size of the substrate on which the matrix pattern is generated. In situations where the density is insufficiently high to allow the screening of the desired number of sequences, multiple substrates may be used to increase the number of sequences tested. Thus, the number of sequences tested may be increased by using a plurality of different substrates. Because the VLSIPS apparatus is almost fully automated, increasing the number of substrates does not lead to a significant increase in the number of manipulations which must be performed by humans. This again leads to greater reproducibility and speed in the handling of these multiple substrates.

A. Instrumentation

The concept of using VLSIPS™ technology generally allows a pattern or a matrix of reagents to be generated. The procedure for making the pattern is performed by any of a number of different methods. An apparatus and instrumentation useful for generating a high density VLSIPS substrate is described in detail in U.S. Ser. No. 07/492,462 (U.S. Pat. No. 5,143,854) and U.S. Ser. No. 07/624,120 (U.S. Pat. No. 5,498,678).

B. Binary Masking

The details of the binary masking are described in an accompanying application filed simultaneously with this, U.S. Ser. No. 07/624,120 (U.S. Pat. No. 5,498,678) whose specification is incorporated herein by reference.

For example, the binary masking technique allows for producing a plurality of sequences based on the selection of either of two possibilities at any particular location. By a series of binary masking steps, the binary decision may be the determination, on a particular synthetic cycle, whether or not to add any particular one of the possible subunits. By treating various regions of the matrix pattern in parallel, the binary masking strategy provides the ability to carry out spatially addressable parallel synthesis.

C. Synthetic Methods

The synthetic methods in making a substrate are described in the parent application, U.S. Ser. No. 07/492,462 (U.S. Pat. No. 5,143,854). The construction of the matrix pattern on the substrate will typically be generated by the use of photosensitive reagents. By use of photo-lithographic optical methods, particular segments of the substrate can be irradiated with light to activate or deactivate blocking agents, e.g., to protect or deprotect particular chemical groups. By an appropriate sequence of photo-exposure steps at appropriate times with appropriate masks and with appropriate reagents, the substrates can have known polymers synthesized at positionally defined regions on the substrate. Methods for synthesizing various substrates are described in U.S. Ser. No. 07/492,462 (U.S. Pat. No. 5,143,854) and U.S. Ser. No. 07/624,120 (Pat. No. 5,498,678). By a sequential series of these photo-exposure and reaction manipulations, a defined matrix pattern of known sequences may be generated, and is typically referred to as a VLSIPS™ technology substrate.

A matrix pattern of new reagents may be targeted to each specific oligonucleotide position by attaching a complementary oligonucleotide to which the substrate bound form is complementary. For instance, a number of regions may have homogeneous oligonucleotides synthesized at various locations. Oligonucleotide sequences complementary to each of these can be individually generated and linked to a particular specific reagents. Often these specific reagents will be antibodies. As each of these is specific for finding its complementary oligonucleotide, each of the specific reagents will bind through the oligonucleotide to the appropriate matrix position. A single step having a combination of different specific reagents being attached specifically to a particular oligonucleotide will thereby bind to its complement at the defined matrix position. The oligonucleotides will typically then be covalently attached, using, e.g., an acridine dye, for photocrosslinking. Psoralen is a commonly used acridine dye for photocrosslinking purposes, see, e.g., Song et al. (1979) *Photochem. Photobiol.* 29:1177–1197; Cimino et al. (1985) *Ann. Rev. Biochem.* 54:1151–1193; Parsons (1980) *Photochem. Photobiol.* 32:813–821; and Dattagupta et al. (1985) U.S. Pat. No. 4,542,102, and (1987) U.S. Pat. No. 4,713,326; each of which is hereby incorporated herein by reference. This method allows a single attachment manipulation to attach all of the specific reagents to the matrix at defined positions and results in the specific reagents being homogeneously located at defined positions. In many embodiments, the specific reagents will be antibodies.

In an alternative embodiment, antibody molecules may be used to specifically direct binding to defined positions on a substrate. The VLSIPS technology may be used to generate specific epitopes at each position on the substrate. Antibody molecules having specificity of interaction may be used to attach oligonucleotides, thereby avoiding the interference of internal polynucleotide sequences from binding to the substrate complementary oligonucleotides. In fact, the specificity of interaction for positional targeting may be achieved by use of nucleotide analogues which do not interact with the natural nucleotides. For example, other synthetic nucleotides have been made which undergo base pairing, thereby providing the specificity of targeting, but the synthetic nucleotides also do not interact with the natural biological nucleotides. Thus, synthetic oligonucleotides would be useful for attachment to biological nucleotides and specific targeting. Moreover, the VLSIPS synthetic processes would be useful in generating the VLSIPS substrate, and standard oligonucleotide synthesis could be applied, with minor modifications, to produce the complementary sequences which would be attached to other specific reagents.

D. Surface Immobilization

1. Caged biotin

An alternative method of attaching reagents in a positionally defined matrix pattern is to use a caged biotin system. See U.S. Ser. No. 07/612,671, which is hereby incorporated herein by reference, for additional details on the chemistry and application of caged biotin embodiments. In short, the caged biotin has a photosensitive blocking moiety which prevents the combination of avidin to biotin. At positions where the photo-lithographic process has removed the blocking group, high affinity biotin sites are generated. Thus, by a sequential series of photolithographic deblocking steps interspersed with exposure of those regions to appropriate biotin containing reagents, only those locations where the deblocking takes place will form an avidin-biotin interaction. Because the avidin-biotin binding is very tight, this will usually be virtually irreversible binding.

2. Crosslinked interactions

The surface immobilization may also take place by photo crosslinking of defined oligonucleotides linked to specific reagents. After hybridization of the complementary oligonucleotides, the oligonucleotides may be crosslinked by a reagent by psoralen or another similar type of acridine dye. Other useful cross linking reagents are described in Dattagupta et al. (1985) U.S. Pat. No. 4,542,102, and (1987) U.S. Pat. No. 4,713,326.

In another embodiment, colony or phage plaque transfer of biological polymers may be transferred directly onto a silicon substrate. For example, a colony plate may be transferred onto a substrate having a generic oligonucleotide sequence which hybridizes to another generic complementary sequence contained on all of the vectors into which inserts are cloned. This will specifically only bind those molecules which are actually contained in the vectors containing the desired complementary sequence. This immobilization allows for producing a matrix onto which a sequence specific reagent can bind, or for other purposes. In a further embodiment, a plurality of different vectors each having a specific oligonucleotide attached to the vector may be specifically attached to particular regions on a matrix having a complementary oligonucleotide attached thereto.

viii. HYBRIDIZATION/SPECIFIC INTERACTION

A. General

As discussed previously in the VLSIPS™ technology parent applications, the VLSIPS™ technology substrates may be used for screening for specific interactions with sequence specific targets or probes.

In addition, the availability of substrates having the entire repertoire of possible sequences of a defined length opens up the possibility of sequencing by hybridization. This sequence may be de novo determination of an unknown sequence, particularly of nucleic acid, verification of a sequence determined by another method, or an investigation of changes in a previously sequenced gene, locating and identifying specific changes. For example, often Maxam and Gilbert sequencing techniques are applied to sequences which have been determined by Sanger and Coulson. Each of those sequencing technologies have problems with resolving particular types of sequences. Sequencing by hybridization may serve as a third and independent method for verifying other sequencing techniques. See, e.g., (1988) *Science* 242:1245.

In addition, the ability to provide a large repertoire of particular sequences allows use of short subsequences and hybridization as a means to fingerprint a sample. This may be used in a nucleic acid, as well as other polymer embodiments. For example, fingerprinting to a high degree of specificity of sequence matching may be used for identifying highly similar samples, e.g., those exhibiting high homology to the selected probes. This may provide a means for determining classifications of particular sequences. This should allow determination of whether particular genomes of bacteria, phage, or even higher cells might be related to one another.

In addition, fingerprinting may be used to identify an individual source of biological sample. See, e.g., Lander, E. (1989) *Nature,* 339:501–505, and references therein. For example, a DNA fingerprint may be used to determine whether a genetic sample arose from another individual. This would be particularly useful in various sorts of forensic tests to determine, e.g., paternity or sources of blood samples. Significant detail on the particulars of genetic fingerprinting for identification purposes are described in, e.g., Morris et al. (1989) "Biostatistical evolution of evidence from continuous allele frequency distribution DNA probes in reference to disputed paternity of identity," *J. Forensic Science* 34:1311–1317; and Neufeld et al. (1990) *Scientific American* 262:46–53; each of which is hereby incorporated herein by reference.

In another embodiment, a fingerprinting-like procedure may be used for classifying cell types by analyzing a pattern of specific nucleic acids present in the cell. A series of antibodies may be used to identify cell markers, e.g., proteins, usually on the cell surface, but intracellular markers may also be used. Antigens which are extracellularly expressed are preferred so cell lysis is unnecessary in the screening, but intracellular markers may also be useful. The markers will usually be proteins, but may be nucleic acids, lipids, metabolites, carbohydrates, or other cellular components. See, e.g., Winkelgren, I. (1990) *Science News* 136:234–237, which indicates extracellular DNA may be common, and suggesting that such might be characteristic of cell types, stage, or physiology. This may also be useful in defining the temporal stage of development of cells, e.g., stem cells or other cells which undergo temporal changes in development. For example, the stage of a cell, or group of cells, may be tested or defined by isolating a sample of mRNA from the population and testing to see what sequences are present in messenger populations. Direct samples, or amplified samples, may be used. Where particular mRNA or other nucleic acid sequences may be characteristic of or shown to be characteristic of particular developmental stages, physiological states, or other conditions, this fingerprinting method may define them. Similar sorts of fingerprinting may be used for determining T-cell classes or perhaps even to generate classification schemes for such proteins as major histocompatibility complex antigens. Thus, the ability to make these substrates allows both the generation of reagents which will be used for defining subclasses or classes of cells or other biological materials, but also provides the mechanisms for selecting those cells which may be found in defined population groups.

In addition to cell classification defined by such a combination of properties, typically expression of extracellular antigens, the present invention also provides the means for isolating homogeneous population of cells. Once the antigenic determinants which define a cell class have been identified, these antigens may be used in a sequential selection process to isolate only those cells which exhibit the combination of defining structural properties.

The present invention may also be used for mapping sequences within a larger segment. This may be performed by at least two methods, particularly in reference to nucleic acids. Often, enormous segments of DNA are subcloned into a large plurality of subsequences. Ordering these subsequences may be important in determining the overlaps of sequences upon nucleotide determinations. Mapping may be performed by immobilizing particularly large segments onto a matrix using the VLSIPS™ technology. Alternatively, sequences may be ordered by virtue of subsequences shared by overlapping segments. See, e.g., Craig et al. (1990) *Nuc. Acids Res.* 18:2653–2660; Michiels et al. (1987) *CABIOS* 3:203–210; and Olson et al. (1986) *Proc. Natl. Acad. Sci. USA* 83:7826–7830.

B. Important Parameters

The extent of specific interaction between reagents immobilized to the VLSIPS™ technology substrate and another sequence specific reagent may be modified by the conditions of the interaction. Sequencing embodiments typically require high fidelity hybridization and the ability to discriminate perfect matching from imperfect matching. Fingerprinting and mapping embodiments may be performed using less stringent conditions, depending upon the circumstances.

For example, the specificity of antibody/antigen interaction may depend upon such parameters as pH, salt concentration, ionic composition, solvent composition, detergent composition and concentration, and chaotropic agent concentration. See, e.g., Harlow and Lane (1988) *Antibodies: A Laboratory Manual,* Cold Spring Harbor Press, New York. By careful control of these parameters, the affinity of binding may be mapped across different sequences.

In a nucleic acid hybridization embodiment, the specificity and kinetics of hybridization have been described in detail by, e.g., Wetmur and Davidson (1968) *J. Mol. Biol.,* 31:349–370, Britten and Kohne (1968) *Science* 161:529–530, and Kanehisa, (1984) *Nuc. Acids Res.* 12:203–213, each of which is hereby incorporated herein by reference. Parameters which are well known to affect specificity and kinetics of reaction include salt conditions, ionic composition of the solvent, hybridization temperature, length of oligonucleotide matching sequences, guanine and cytosine (GC) content, presence of hybridization accelerators, pH, specific bases found in the matching sequences, solvent conditions, and addition of organic solvents.

In particular, the salt conditions required for driving highly mismatched sequences to completion typically include a high salt concentration. The typical salt used is sodium chloride (NaCl), however, other ionic salts may be utilized, e.g., KCl. Depending on the desired stringency hybridization, the salt concentration will often be less than about 3 molar, more often less than 2.5 molar, usually less than about 2 molar, and more usually less than about 1.5 molar. For applications directed towards higher stringency matching, the salt concentrations would typically be lower. Ordinary high stringency conditions will utilize salt concentration of less than about 1 molar, more often less than about 750 millimolar, usually less than about 500 millimolar, and may be as low as about 250 or 150 millimolar.

The kinetics of hybridization and the stringency of hybridization both depend upon the temperature at which the hybridization is performed and the temperature at which the washing steps are performed. Temperatures at which steps for low stringency hybridization are desired would typically be lower temperatures, e.g., ordinarily at least about 15° C., more ordinarily at least about 20° C., usually at least about 25° C., and more usually at least about 30° C. For those applications requiring high stringency hybridization, or fidelity of hybridization and sequence matching, temperatures at which hybridization and washing steps are performed would typically be high. For example, temperatures in excess of about 35 ° C. would often be used, more often in excess of about 40° C., usually at least about 45° C., and occasionally even temperatures as high as about 50° C. or 60° C. or more. Of course, the hybridization of oligonucleotides may be disrupted by even higher temperatures. Thus, for stripping of targets from substrates, as discussed below, temperatures as high as 80° C., or even higher may be used.

The base composition of the specific oligonucleotides involved in hybridization affects the temperature of melting, and the stability of hybridization as discussed in the above references. However, the bias of GC rich sequences to hybridize faster and retain stability at higher temperatures can be compensated for by the inclusion in the hybridization incubation or wash steps of various buffers. Sample buffers which accomplish this result include the triethly-and trimethyl ammonium buffers. See, e.g., Wood et al. (1987) *Proc. Natl. Acad. Sci. USA,* 82:1585–1588, and Khrapko, K. et al. (1989) *FEBS Letters* 256:118–122.

The rate of hybridization can also be affected by the inclusion of particular hybridization accelerators. These hybridization accelerators include the volume exclusion agents characterized by dextran sulfate, or polyethylene glycol (PEG). Dextran sulfate is typically included at a concentration of between 1% and 40% by weight. The actual concentration selected depends upon the application, but typically a faster hybridization is desired in which the concentration is optimized for the system in question. Dextran sulfate is often included at a concentration of between 0.5% and 2% by weight or dextran sulfate at a concentration between about 0.5% and 5%. Alternatively, proteins which accelerate hybridization may be added, e.g., the recA protein found in *E. coli* or other homologous proteins.

With respect to those embodiments where specific reagents are not oligonucleotides, the conditions of specific interaction would depend on the affinity of binding between the specific reagent and its target. Typically parameters which would be of particular importance would be pH, salt concentration anion and cation compositions, buffer concentration, organic solvent inclusion, detergent concentration, and inclusion of such reagents such as chaotropic agents. In particular, the affinity of binding may be tested over a variety of conditions by multiple washes and repeat scans or by using reagents with differences in binding affinity to determine which reagents bind or do not bind under the selected binding and washing conditions. The spectrum of binding affinities may provide an additional dimension of information which may be very useful in identification purposes and mapping.

Of course, the specific hybridization conditions will be selected to correspond to a discriminatory condition which provides a positive signal where desired but fails to show a positive signal at affinities where interaction is not desired. This may be determined by a number of titration steps or with a number of controls which will be run during the hybridization and/or washing steps to determine at what point the hybridization conditions have reached the stage of desired specificity.

ix. DETECTION METHODS

Methods for detection depend upon the label selected. The criteria for selecting an appropriate label are discussed below, however, a fluorescent label is preferred because of its extreme sensitivity and simplicity. Standard labeling procedures are used to determine the positions where interactions between a sequence and a reagent take place. For example, if a target sequence is labeled and exposed to a matrix of different probes, only those locations where probes do interact with the target will exhibit any signal. Alternatively, other methods may be used to scan the matrix to determine where interaction takes place. Of course, the spectrum of interactions may be determined in a temporal manner by repeated scans of interactions which occur at each of a multiplicity of conditions. However, instead of testing each individual interaction separately, a multiplicity of sequence interactions may be simultaneously determined on a matrix.

A. Labeling Techniques

The target polynucleotide may be labeled by any of a number of convenient detectable markers. A fluorescent label is preferred because it provides a very strong signal with low background. It is also optically detectable at high resolution and sensitivity through a quick scanning procedure. Other potential labeling moieties include, radioisotopes, chemiluminescent compounds, labeled binding proteins, heavy metal atoms, spectroscopic markers, magnetic labels, and linked enzymes. Another method for labeling may bypass any label of the target sequence. The target may be exposed to the probes, and a double strand hybrid is formed at those positions only. Addition of a double strand specific reagent will detect where hybridization takes place. An intercalative dye such as ethidium bromide may be used as long as the probes themselves do not fold back on themselves to a significant extent forming hairpin loops. See, e.g., Sheldon et al. (1986) U.S. Pat. No. 4,582,789. However, the length of the hairpin loops in short oligonucleotide probes would typically be insufficient to form a stable duplex.

In another embodiment, different targets may be simultaneously sequenced where each target has a different label. For instance, one target could have a green fluorescent label and a second target could have a red fluorescent label. The scanning step will distinguish sites of binding of the red label from those binding the green fluorescent label. Each sequence can be analyzed independently from one another.

Suitable chromogens will include molecules and compounds which absorb light in a distinctive range of wavelengths so that a color may be observed, or emit light when irradiated with radiation of a particular wave length or wave length range, e.g., fluorescers. Biliproteins, e.g., phycoerythrin, may also serve as labels.

A wide variety of suitable dyes are available, being primarily chosen to provide an intense color with minimal absorption by their surroundings. Illustrative dye types include quinoline dyes, triarylmethane dyes, acridine dyes, alizarine dyes, phthaleins, insect dyes, azo dyes, anthraquinoid dyes, cyanine dyes, phenazathionium dyes, and phenazoxonium dyes.

A wide variety of fluorescers may be employed either by themselves or in conjunction with quencher molecules. Fluorescers of interest fall into a variety of categories having certain primary functionalities. These primary functionalities include 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidzaolylphenylarnine, 2-oxo-3-chromen, indole, xanthen, 7-hydroxycoumarin, phenoxazine, salicylate, strophanthidin, porphyrins, triarylmethanes and flavin. Individual fluorescent compounds which have functionalities for linking or which can be modified to incorporate such functionalities include, e.g., dansyl chloride; fluoresceins such as 3,6-dihydroxy-9-phenylxanthhydrol; rhodamineisothiocyanate; N-phenyl 1-amino-8-sulfonatonaphthalene; N-phenyl 2-amino-6-sulfonatonaphthalene; 4-acetamido-4-isothiocyanato-stilbene-2,2'-disulfonic acid; pyrene-3-sulfonic acid; 2-toluidinonaphthalene-6-sulfonate; N-phenyl, N-methyl 2-aminoaphthalene-6-sulfonate; ethidium bromide; stebrine; auromine-0,2-(9'-anthroyl)palmitate; dansyl phosphatidylethanolamine; N,N'-dioctadecyl oxacarbocyanine; N,N'-dihexyl oxacarbocyanine; merocyanine, 4-(3'pyrenyl) butyrate; d-3-aminodesoxy-equilenin; 12-(9'-anthroyl) stearate; 2-methylanthracene; 9-vinylanthracene; 2,2'-(vinylene-p-phenylene)bisbenzoxazole; p-bis[2-(4-methyl-5-phenyl-oxazolyl)]benzene; 6-dimethylamino-1,2-benzophenazin; retinol; bis(3'-aminopyridinium) 1,10-decandiyl diiodide; sulfonaphthylhydrazone of hellibrienin; chlorotetracycline; N-(7-dimethylamino-4-methyl-2-oxo-3-chromenyl)maleimide; N-[p-(2-benzimidazolyl)-phenyl] maleimide; N-(4-fluoranthyl)maleimide; bis(homovanillic acid); resazarin; 4-chloro-7-nitro-2,1,3-benzooxadiazole; merocyanine 540; resorufin; rose bengal; and 2,4-diphenyl-3(2H)-furanone.

Desirably, fluorescers should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye may differ from the unbound dye. Therefore, when referring to the various wavelength ranges and characteristics of the dyes, it is intended to indicate the dyes as employed and not the dye which is unconjugated and characterized in an arbitrary solvent.

Fluorescers are generally preferred because by irradiating a fluorescer with light, one can obtain a plurality of emissions. Thus, a single label can provide for a plurality of measurable events.

Detectable signal may also be provided by chemiluminescent and bioluminescent sources. Chemiluminescent sources include a compound which becomes electronically excited by a chemical reaction and may then emit light which serves as the detectible signal or donates energy to a fluorescent acceptor. A diverse number of families of compounds have been found to provide chemiluminescence under a variety of conditions. One family of compounds is 2,3-dihydro-1,4-phthalazinedione. The most popular compound is luminol, which is the 5-amino compound. Other members of the family include the 5-amino-6,7,8-trimethoxy- and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Cherniluminescent analogs include para-dimethylamino and -methoxy substituents. Chemiluminescence may also be obtained with oxalates, usually oxalyl active esters, e.g., p-nitrophenyl and a peroxide, e.g., hydrogen peroxide, under basic conditions. Alternatively, luciferins may be used in conjunction with luciferase or lucigenins to provide biolu minescence.

Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

B. Scanning System

With the automated detection apparatus, the correlation of specific positional labeling is converted to the presence on the target of sequences for which the reagents have specificity of interaction. Thus, the positional information is directly converted to a database indicating what sequence interactions have occurred. For example, in a nucleic acid hybridization application, the sequences which have interacted between the substrate matrix and the target molecule can be directly listed from the positional information. The detection system used is described in U.S. Ser. No. 07/649,642; and U.S. Ser. No. 07/624,120 (U.S. Pat. No. 5,498,678). Although the detection described therein is a fluorescence detector, the detector may be replaced by a spectroscopic or other detector. The scanning system may make use of a moving detector relative to a fixed substrate, a fixed detector with a moving substrate, or a combination. Alternatively, mirrors or other apparatus can be used to transfer the signal directly to the detector. See, e.g, U.S. Ser. No. 07/624,120 (U.S. Pat. No. 5,498,678), which is hereby incorporated herein by reference.

The detection method will typically also incorporate some signal processing to determine whether the signal at a particular matrix position is a true positive or may be a spurious signal. For example, a signal from a region which has actual positive signal may tend to spread over and provide a positive signal in an adjacent region which actually should not have one. This may occur, e.g., where the scanning system is not properly discriminating with sufficiently high resolution in its pixel density to separate the two regions. Thus, the signal over the spatial region may be evaluated pixel by pixel to determine the locations and the actual extent of positive signal. A true positive signal should, in theory, show a uniform signal at each pixel location. Thus, processing by plotting number of pixels with actual signal intensity should have a clearly uniform signal intensity. Regions where the signal intensities show a fairly wide dispersion, may be particularly suspect and the scanning system may be programmed to more carefully scan those positions.

In another embodiment, as the sequence of a target is determined at a particular location, the overlap for the sequence would necessarily have a known sequence. Thus, the system can compare the possibilities for the next adjacent position and look at these in comparison with each other. Typically, only one of the possible adjacent sequences should give a positive signal and the system might be programmed to compare each of these possibilities and select that one which gives a strong positive. In this way, the system can also simultaneously provide some means of measuring the reliability of the determination by indicating what the average signal to background ratio actually is.

More sophisticated signal processing techniques can be applied to the initial determination of whether a positive signal exists or not. See, e.g., U.S. Ser. No. 07/624,120 (U.S. Pat. No. 5,498,678).

From a listing of those sequences which interact, data analysis may be performed on a series of sequences. For example, in a nucleic acid sequence application, each of the sequences may be analyzed for their overlap regions and the original target sequence may be reconstructed from the collection of specific subsequences obtained therein. Other sorts of analyses for different applications may also be performed, and because the scanning system directly interfaces with a computer the information need not be transferred manually. This provides for the ability to handle large amounts of data with very little human intervention. This, of course, provides significant advantages over manual manipulations. Increased throughput and reproducibility is thereby provided by the automation of a vast majority of steps in any of these applications.

xi. DATA ANALYSIS

A. General

Data analysis will typically involve aligning the proper sequences with their overlaps to determine the target sequence. Although the target "sequence" may not specifically correspond to any specific molecule, especially where the target sequence is broken and fragmented in the sequencing process, the sequence corresponds to a contiguous sequence of the subfragments.

The data analysis can be performed by a computer using an appropriate program. See, e.g., Drmanac, R. et al. (1989) *Genomics* 4:114–128; and a commercially available analysis program available from the Genetic Engineering Center, P.O. Box 794, 11000 Belgrade, Yugoslavia. Although the specific manipulations necessary to reassemble the target sequence from fragments may take many forms, one embodiment uses a sorting program to sort all of the subsequences using a defined hierarchy. The hierarchy need not necessarily correspond to any physical hierarchy, but provides a means to determine, in order, which subfragments have actually been found in the target sequence. In this manner, overlaps can be checked and found directly rather than having to search throughout the entire set after each selection process. For example, where the oligonucleotide probes are 10-mers, the first 9 positions can be sorted. A particular subsequence can be selected as in the examples, to determine where the process starts. As analogous to the theoretical example provided above, the sorting procedure provides the ability to immediately find the position of the subsequence which contains the first 9 positions and can compare whether there exists more than 1 subsequence during the first 9 positions. In fact, the computer can easily generate all of the possible target sequences which contain given combination of subsequences. Typically there will be only one, but in various situations, there will be more.

Figure 4:
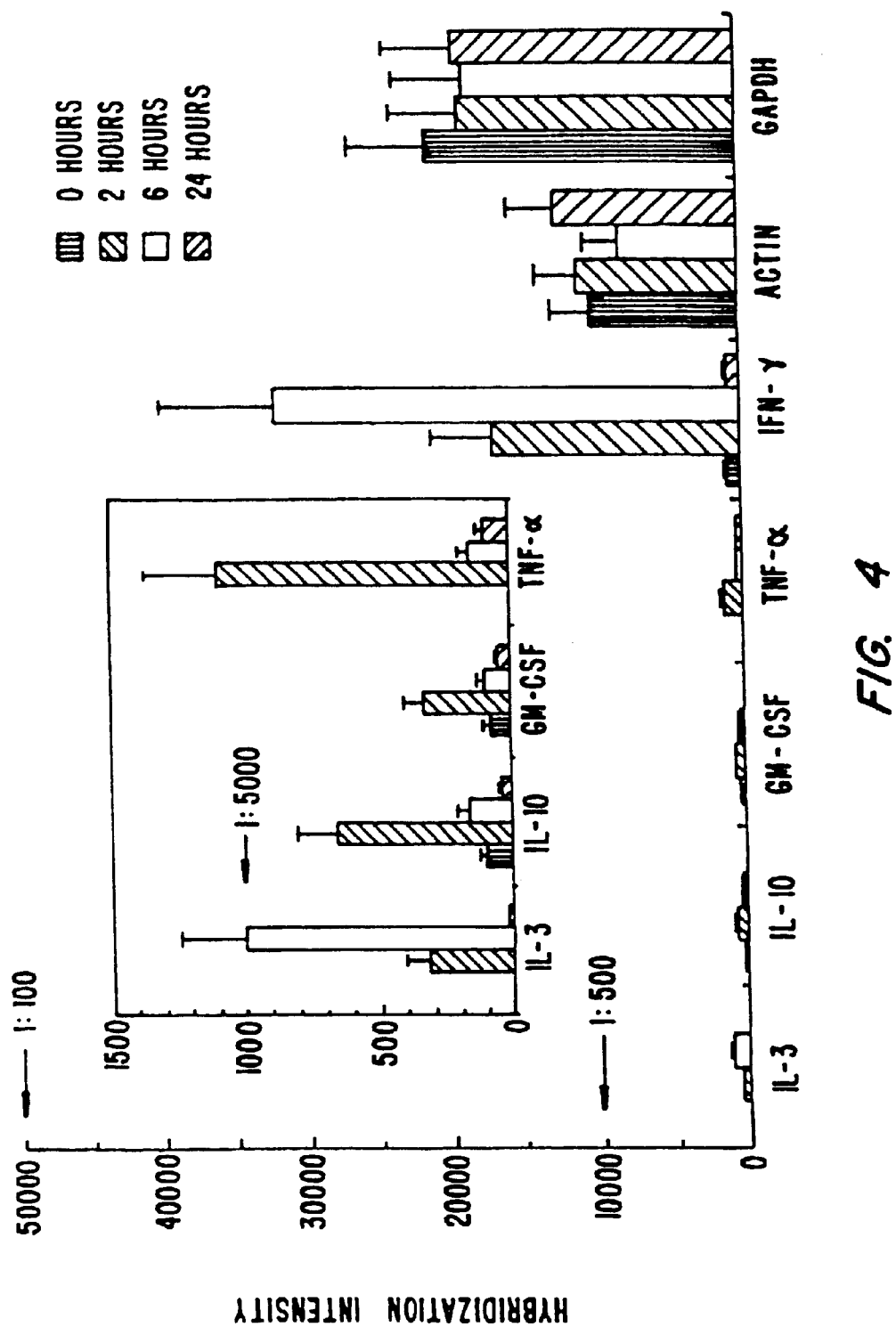
FIG. 4 shows cytokine mRNA levels in the murine 2D6 T helper cell line at different times following stimulation with PMA and a calcium ionophore. Poly (A)$^+$ RNA was extracted at 0, 2, 6, and 24 hours following stimulation and converted to double stranded cDNA containing an RNA polymerase promoter. The cDNA pool was then transcribed in the presence of biotin labeled ribonucleotide triphosphates, fragmented, and hybridized to the oligonucleotide probe arrays for 2 and 22 hours. The fluorescence intensities were converted to RNA frequencies by comparison with the signals obtained for a bacterial RNA (biotin synthetase) spiked into the samples at known amounts prior to hybridization. A signal of 50,000 corresponds to a frequency of approximately 1:100,000 to a frequency of 1:5,000, and a signal of 100 to a frequency of 1:50,000. RNAs for IL-2, IL-4, IL-6, and IL-12p40 were not detected above the level of approximately 1:200,000 in these experiments. The error bars reflect the estimated uncertainty (25 percent) in the level for a given RNA relative to the level for the same RNA at a different time point. The relative uncertainty estimate was based on the results of repeated spiking experiments, and on repeated measurements of IL-10, β-actin and GAPDH RNAs in preparations from both T10 and 2D6 cells (unstimulated). The uncertainty in the absolute frequencies includes message-to-message differences in the hybridization efficiency as well as differences in the mRNA isolation, cDNA synthesis, and RNA synthesis and labeling steps. The uncertainty in the absolute frequencies is estimated to be a factor of three.

An exemplary flow chart for a sequencing program is provided in FIG. 4. In general terms, the program provides for automated scanning of the substrate to determine the positions of probe and target interaction. Simple processing of the intensity of the signal may be incorporated to filter out clearly spurious signals. The positions with positive interaction are correlated with the sequence specificity of specific matrix positions, to generate the set of matching subsequences. This information is further correlated with other target sequence information, e.g., restriction fragment analysis. The sequences are then aligned using overlap data, thereby leading to possible corresponding target sequences which will, optimally, correspond to a single target sequence.

B. Hardware

A variety of computer systems may be used to run a sequencing program. The program may be written to provide both the detecting and scanning steps together and will typically be dedicated to a particular scanning apparatus. However, the components and functional steps may be separated and the scanning system may provide an output, e.g., through tape or an electronic connection into a separate computer which separately runs the sequencing analysis program. The computer may be any of a number of machines provided by standard computer manufacturers, e.g., IBM compatible machines, Apple™ machines, VAX machines, and others, which may often use a UNIX™ operating system. Of course, the hardware used to run the analysis program will typically determine what programming language would be used.

C. Software

Software would be easily developed by a person of ordinary skill in the programming art, following the flow chart provided, or based upon the input provided and the desired result.

Of course, an exemplary embodiment is a polynucleotide sequence system. However, the theoretical and mathematical manipulations necessary for data analysis of other linear molecules, such as polypeptides, carbohydrates, and various other polymers are conceptually similar. Simple branching polymers will usually also be sequencable using similar technology. However, where there is branching, it may be desired that additional recognition reagents be used to determine the nature and location of branches. This can easily be provided by use of appropriate specific reagents which would be generated by methods similar to those used to produce specific reagents for linear polymers.

xii. SUBSTRATE REUSE

Where a substrate is made with specific reagents that are relatively insensitive to the handling and processing steps involved in a single cycle of use, the substrate may often be reused. The target molecules are usually stripped off of the solid phase specific recognition molecules. Of course, it is preferred that the manipulations and conditions be selected as to be mild and to not affect the substrate. For example, if a substrate is acid labile, a neutral pH would be preferred in all handling steps. Similar sensitivities would be carefully respected where recycling is desired.

A. Removal of Label

Typically for a recycling, the previously attached specific interaction would be disrupted and removed. This will typically involve exposing the substrate to conditions under which the interaction between probe and target is disrupted. Alternatively, it may be exposed to conditions where the target is destroyed. For example, where the probes are oligonucleotides and the target is a polynucleotide, a heating and low salt wash will often be sufficient to disrupt the interactions. Additional reagents may be added such as detergents, and organic or inorganic solvents which disrupt the interaction between the specific reagents and target. In an embodiment where the specific reagents are antibodies, the substrate may be exposed to a gentle detergent which will denature the specific binding between the antibody and its target. The conditions are selected to avoid severe disruption or destruction of the structure of the antibody and to maintain the specificity of the antibody binding site. Conditions with specific pH, detergent concentration, salt concentration, ionic concentration, and other parameters may be selected which disrupt the specific interactions.

B. Storage and Preservation

As indicated above, the matrix will typically be maintained under conditions where the matrix itself and the linkages and specific reagents are preserved. Various specific preservatives may be added which prevent degradation. For example, if the reagents are acid or base labile, a neutral pH buffer will typically be added. It is also desired to avoid destruction of the matrix by growth of organisms which may destroy organic reagents attached thereto. For this reason, a preservative such as cyanide or azide may be added. However, the chemical preservative should also be selected to preserve the chemical nature of the linkages and other components of the substrate. Typically, a detergent may also be included.

C. Processes to Avoid Degradation of Oligomers

In particular, a substrate comprising a large number of oligomers will be treated in a fashion which is known to maintain the quality and integrity of oligonucleotides. These include storing the substrate in a carefully controlled environment under conditions of lower temperature, cation depletion (EDTA and EGTA), sterile conditions, and inert argon or nitrogen atmosphere.

xiii. INTEGRATED SEQUENCING STRATEGY

A. Initial Mapping Strategy

As indicated above, although the VLSIPS™ technology may be applied to sequencing embodiments, it is often useful to integrate other concepts to simplify the sequencing. For example, nucleic acids may be easily sequenced by careful selection of the vectors and hosts used for amplifying and generating the specific target sequences. For example, it may be desired to use specific vectors which have been designed to interact most efficiently with the VLSIPS substrate. This is also important in fingerprinting and mapping strategies. For example, vectors may be carefully selected having particular complementary sequences which are designed to attach to a genetic or specific oligomer on the substrate. This is also applicable to situations where it is desired to target particular sequences to specific locations on the matrix.

In one embodiment, unnatural oligomers may be used to target natural probes to specific locations on the VLSIPS substrate. In addition, particular probes may be generated for the mapping embodiment which are designed to have specific combinations of characteristics. For example, the construction of a mapping substrate may depend upon use of another automated apparatus which takes clones isolated from a chromosome walk and attaches them individually or in bulk to the VLSIPS substrate.

In another embodiment, a variety of specific vectors having known and particular "targeting" sequences adjacent to the cloning sites may be individually used to clone a selected probe, and the isolated probe will then be targetable to a site on the VLSIPS substrate with a sequence complementary to the "target" sequence.

B. Selection of Smaller Clones

In the fingerprinting and mapping embodiments, the selection of probes may be very important. Significant mathematical analysis may be applied to determine which specific sequences should be used as those probes. Of course, for fingerprinting use, these sequences would be most desired that show significant heterogeneity across the human population. Selection of the specific sequences which would most favorably be utilized will tend to be single copy sequences within the genome.

Various hybridization selection procedures may be applied to select sequences which tend not to be repeated within a genome, and thus would tend to be conserved across individuals. For example, hybridization selections may be made for non-repetitive and single copy sequences. See, e.g., Britten and Kohne (1968) "Repeated Sequences in DNA," *Science* 161:529–540. On the other hand, it may be desired under certain circumstances to use repeated sequences. For example, where a fingerprint may be used to identify or distinguish different species, or where repetitive sequences may be diagnostic of specific species, repetitive sequences may be desired for inclusion in the fingerprinting probes. In either case, the sequencing capability will greatly assist in the selection of appropriate sequences to be used as probes.

Also as indicated above, various means for constructing an appropriate substrate may involve either mechanical or automated procedures. The standard VLSIPS automated procedure involves synthesizing oligonucleotides or short polymers directly on the substrate. In various other embodiments, it is possible to attach separately synthesized reagents onto the matrix in an ordered array. Other circumstances may lend themselves to transfer a pattern from a petri plate onto a solid substrate. Also, there are methods for site specifically directing collections of reagents to specific locations using unnatural nucleotides or equivalent sorts of targeting molecules.

While a brute force manual transfer process may be utilized sequentially for attaching various samples to successive positions, instrumentation for automating such procedures may also be devised. The automated system for performing such would preferably be relatively easily designed and conceptually easily understood.

xiv. COMMERCIAL APPLICATIONS

A. Sequencing

As indicated above, sequencing may be performed either de novo or as a verification of another sequencing method (sequence checking). The present hybridization technology provides the ability to sequence nucleic acids and polynucleotides de novo, or as a means to verify either the Maxam and Gilbert chemical sequencing technique or Sanger and Coulson dideoxy—sequencing techniques. The hybridization method is useful to verify sequencing determined by any other sequencing technique and to closely compare two similar sequences, e.g., to identify and locate sequence differences.

Besides polynucleotide sequencing, the present invention also provides means for sequencing other polymers. This includes polypeptides, carbohydrates, synthetic organic polymers, and other polymers. Again, the sequencing may be either verification or de novo.

Of course, sequencing can be very important in many different sorts of environments. For example, it will be useful in determining the genetic sequence of particular markers in various individuals. In addition, polymers may be used as markers or for information containing molecules to encode information. For example, a short polynucleotide sequence may be included in large bulk production samples indicating the manufacturer, date, and location of manufacture of a product. For example, various drugs may be encoded with this information with a small number of molecules in a batch. For example, a pill may have somewhere from 10 to 100 to 1,000 or more very short and small molecules encoding this information. When necessary, this information may be decoded from a sample of the material using a polymerase chain reaction (PCR) or other amplification method. This encoding system may be used to provide the origin of large bulky samples without significantly affecting the properties of those samples. For example, chemical samples may also be encoded by this method thereby providing means for identifying the source and manufacturing details of lots. The origin of bulk hydrocarbon samples may be encoded. Production lots of organic compounds such as benzene or plastics may be encoded with a short molecule polymer. Food stuffs may also be encoded using similar marking molecules. Even toxic waste samples can be encoded determining the source or origin. In this way, proper disposal can be traced or more easily enforced.

Similar sorts of encoding may be provided by fingerprinting-type analysis. Whether the resolution is absolute or less so, the concept of coding information on molecules such as nucleic acids, which can be amplified and later decoded, may be a very useful and important application.

This technology also provides the ability to include markers for origins of biological materials. For example, a patented animal line may be transformed with a particular unnatural sequence which can be traced back to its origin. With a selection of multiple markers, the likelihood could be negligible that a combination of markers would have independently arisen from a source other than the patented or specifically protected source. This technique may provide a means for tracing the actual origin of particular biological materials. Bacteria, plants, and animals will be subject to marking by such encoding sequences.

B. Fingerprinting

As indicated above, fingerprinting technology may also be used for data encryption. Moreover, fingerprinting allows for significant identification of particular individuals. Where the fingerprinting technology is standardized, and used for identification of large numbers of people, related equipment and peripheral processing will be developed to accompany the underlying technology. For example, specific equipment may be developed for automatically taking a biological sample and generating or amplifying the information molecules within the sample to be used in fingerprinting analysis. Moreover, the fingerprinting substrate may be mass produced using particular types of automatic equipment. Synthetic equipment may produce the entire matrix simultaneously by stepwise synthetic methods as provided by the VLSIPS™ technology. The attachment of specific probes onto a substrate may also be automated, e.g., making use of the caged biotin technology. See, e.g., U.S. Ser. No. 07/612, 671. As indicated above, there are automated methods for actually generating the matrix and substrate with distinct sequence reagents positionally located at each of the matrix positions. Where such reagents are, e.g., unnatural amino acids, a targeting function may be utilized which does not interfere with a natural nucleotide functionality.

In addition, peripheral processing may be important and may be dedicated to this specific application. Thus, automated equipment for producing the substrates may be designed, or particular systems which take in a biological sample and output either a computer readout or an encoded instrument, e.g., a card or document which indicates the information and can provide that information to others. An identification having a short magnetic strip with a few million bits may be used to provide individual identification and important medical information useful in a medical emergency.

In fact, data banks may be set up to correlate all of this information of fingerprinting with medical information. This may allow for the determination of correlations between various medical problems and specific DNA sequences. By collating large populations of medical records with genetic information, genetic propensities and genetic susceptibilities to particular medical conditions may be developed. Moreover, with standardization of substrates, the micro encoding data may be also standardized to reproduce the information from a centralized data bank or on an encoding device carried on an individual person. On the other hand, if the fingerprinting procedure is sufficiently quick and routine, every hospital may routinely perform a fingerprinting operation and from that determine many important medical parameters for an individual.

In particular industries, the VLSIPS sequencing, fingerprinting, or mapping technology will be particularly appropriate. As mentioned above, agricultural livestock suppliers may be able to encode and determine whether their particular strains are being used by others. By incorporating particular markers into their genetic stocks, the markers will indicate origin of genetic material. This is applicable to seed producers, livestock producers, and other suppliers of medical or agricultural biological materials.

This may also be useful in identifying individual animals or plants. For example, these markers may be useful in determining whether certain fish return to their original breeding grounds, whether sea turtles always return to their original birthplaces, or to determine the migration patterns and viability of populations of particular endangered species. It would also provide means for tracking the sources of particular animal products. For example, it might be useful for determining the origins of controlled animal substances such as elephant ivory or particular bird populations whose importation or exportation is controlled.

As indicated above, polymers may be used to encode important information on source and batch and supplier. This is described in greater detail, e.g., "Applications of PCR to industrial problems," (1990) in *Chemical and Engineering News* 68:145, which is hereby incorporated herein by reference. In fact, the synthetic method can be applied to the storage of enormous amounts of information. Small substrates may encode enormous amounts of information, and its recovery will make use of the inherent replication capacity. For example, on regions of 10 $\mu$m×10 $\mu$m, 1 cm$^2$ has 10$^6$ regions. In theory, the entire human genome could be attached in 1000 nucleotide segments on a 3 cm$^2$ surface. Genomes of endangered species may be stored on these substrates.

Fingerprinting may also be used for genetic tracing or for identifying individuals for forensic science purposes. See, e.g., Morris, J. et al. (1989) "Biostatistical Evaluation of Evidence From Continuous Allele Frequency Distribution DNA Probes in Reference to Disputed Paternity and Identity," J. *Forensic Science* 34:1311–1317, and references provided therein; each of which is hereby incorporated herein by reference.

In addition, the high resolution fingerprinting allows the distinguishability to high resolution of particular samples. As indicated above, new cell classifications may be defined based on combinations of a large number of properties. Similar applications will be found in distinguishing different species of animals or plants. In fact, microbial identification may become dependent on characterization of the genetic content. Tumors or other cells exhibiting abnormal physiology will be detectable by use of the present invention. Also, knowing the genetic fingerprint of a microorganism may provide very useful information on how to treat an infection by such organism.

Modifications of the fingerprint embodiments may be used to diagnose the condition of the organism. For example, a blood sample is presently used for diagnosing any of a number of different physiological conditions. A multi-dimensional fingerprinting method made available by the present invention could become a routine means for diagnosing an enormous number of physiological features simultaneously. This may revolutionize the practice of medicine in providing information on an enormous number of parameters together at one time. In another way, the genetic predisposition may also revolutionize the practice of medicine providing a physician with the ability to predict the likelihood of particular medical conditions arising at any particular moment. It also provides the ability to apply preventive medicine.

The present invention might also find application in use for screening new drugs and new reagents which may be very important in medical diagnosis or other applications. For example, a description of generating a population of monoclonal antibodies with defined specificities may be very useful for producing various drugs or diagnostic reagents.

Also available are kits with the reagents useful for performing sequencing, fingerprinting, and mapping procedures. The kits will have various compartments with the desired necessary reagents, e.g., substrate, labeling reagents for target samples, buffers, and other useful accompanying products.

C. Mapping

The present invention also provides the means for mapping sequences within enormous stretches of sequence. For example, nucleotide sequences may be mapped within enormous chromosome size sequence maps. For example, it would be possible to map a chromosomal location within the chromosome which contains hundreds of millions of nucleotide base pairs. In addition, the mapping and fingerprinting embodiments allow for testing of chromosomal translocations, one of the standard problems for which amniocentesis is performed.

Thus, the present invention provides a powerful tool and the means for performing sequencing, fingerprinting, and mapping functions on polymers. Although most easily and directly applicable to polynucleotides, polypeptides, carbohydrates, and other sorts of molecules can be advantageously utilized using the present technology.

XII. Additional Particular Implementations

This section describes additional particular implmentations of the above-described methodologies. A reagent-dispensing device may be useful in practicing the method. The device generally includes a reagent dispenser having an elongate open capillary channel adapted to hold a quantity of the reagent solution as will be described below. The capillary channel is formed by a pair of spaced-apart, coextensive, elongate members which are tapered toward one another and converge at a tip or tip region at the lower end of the channel. More generally, the open channel is formed by at least two elongate, spaced-apart members adapted to hold a quantity of reagent solutions and having a tip region at which aqueous solution in the channel forms a meniscus, such as the concave meniscus The advantages of the open channel construction of the dispenser are discussed below.

The dispenser device also includes structure for moving the dispenser rapidly toward and away from a support surface, for effecting deposition of a known amount of solution in the dispenser on a support. This structure includes a solenoid which is activatable to draw a solenoid piston rapidly downwardly, then release the piston, e.g., under spring bias, to a normal, raised position, as shown. The dispenser is carried by a piston. The just-described moving structure is also referred to herein as dispensing means for moving the dispenser into engagement with a solid support, for dispensing a known volume of fluid on the support.

The dispensing device just described is carried on an arm that may be moved either linearly or in an x-y plane to position the dispenser at a selected deposition position, as will be described. The support is a polymer, glass, or other solid-material support having a surface.

In one general embodiment, the surface is a relatively hydrophilic, i.e., wettable surface, such as a surface having native, bound or covalently attached charged groups. On such surface described below is a glass surface having an absorbed layer of a polycationic polymer, such as poly-1-lysine.

In another embodiment, the surface has or is formed to have a relatively hydrophobic character, i.e., one that causes aqueous medium deposited on the surface to bead. A variety of known hydrophobic polymers, such as polystyrene, polypropylene, or polyethylene have desired hydrophobic properties, as do glass and a variety of lubricant or other hydrophobic films that may be applied to the support surface.

Initially, the dispenser is loaded with a selected analyte-specific reagent solution, such as by dipping the dispenser tip, after washing, into a solution of the reagent, and allowing filling by capillary flow into the dispenser channel. The dispenser is now moved to a selected position with respect to a support surface, placing the dispenser tip directly above the support-surface position at which the reagent is to be deposited. This movement takes place with the dispenser tip in its raised position where the tip is typically at least several 1–5 mm above the surface of the substrate.

With the dispenser so positioned, the solenoid is now activated to cause the dispenser tip to move rapidly toward and away from the substrate surface, making momentary contact with the surface in effect, tapping the tip of the dispenser against the support surface. The tapping movement of the tip against the surface acts to break the liquid meniscus in the tip channel, bringing the liquid in the tip into contact with the support surface. This, in turn, produces a flowing of the liquid into the capillary space between the tip and the surface, acting to draw liquid out of the dispenser channel.

The fluid from the tip flows onto the support surface, which in this case is a hydrophobic surface. The figure illustrates that liquid continues to flow from the dispenser onto the support surface until it forms a liquid bead. At a given bead size, i. e., volume, the tendency of liquid to flow onto the surface will be balanced by the hydrophobic surface interaction of the bead with the support surface, which acts to limit the total bead area on the surface, and by the surface tension of the droplet, which tends toward a given bead curvature. At this point, a given bead volume will have formed, and continued contact of the dispenser tip with the bead, as the dispenser tip is being withdrawn, will have little or no effect on bead volume.

For liquid-dispensing on a more hydrophilic surface, the liquid will have less of a tendency to bead, and the dispensed volume will be more sensitive to the total dwell time of the dispenser tip in the immediate vicinity of the support surface The desired deposition volume, i.e., bead volume, formed by this method is preferably in the range 2 pl (picoliters) to 2 nl (nanoliters), although volumes as high as 100 nl or more may be dispensed. It will be appreciated that the selected dispensed volume will depend on (i) the "footprint" of the dispenser tip, i.e., the size of the area spanned by the tip, (ii) the hydrophobicity of the support surface, and (iii) the time of contact with and rate of withdrawal of the tip from the support surface. In addition, bead size may be reduced by increasing the viscosity of the medium, effectively reducing the flow time of liquid from the dispenser onto the support surface. The drop size may be further constrained by depositing the drop in a hydrophobic region surrounded by a hydrophobic grid pattern on the support surface.

In a typical embodiment, the dispenser tip is tapped rapidly against the support surface, with a total residence time in contact with the support of less than about 1 msec, and a rate of upward travel from the surface of about 10 cm/sec.

Assuming that the bead that forms on contact with the surface is a hemispherical bead, with a diameter approximately equal to the width of the dispenser tip the volume of the bead formed in relation to dispenser tip width is given in the Table below. As seen, the volume of the bead ranges between 2 pl to 2 nl as the width size is increased from about 20 to 200 $\mu$m.

TABLE

| d | Volume (Ul) |
|---|---|
| 20 $\mu$m | 2 × 10 − 1 |
| 50 $\mu$m | 3.1 × 104 |
| 100 $\mu$m | 2.5 × 10 − 1 |
| 200 $\mu$m | 2 |

At a given tip size, bead volume can be reduced in a controlled fashion by increasing surface hydrophobicity, reducing time of contact of the tip with the surface, increasing rate of movement of the tip away from the surface, and/or increasing the viscosity of the medium. Once these parameters are fixed, a selected deposition volume in the desired pl to nl range can be achieved in a repeatable fashion.

After depositing a bead at one selected location on a support, the tip is typically moved to a corresponding position on a second support, a droplet is deposited at that position, and this process is repeated until a liquid droplet of the reagent has been deposited at a selected position on each of a plurality of supports.

The tip is then washed to remove the reagent liquid, filled with another reagent liquid and this reagent is now deposited at each another array position on each of the supports. In one embodiment, the tip is washed and refilled by the steps of (i) dipping the capillary channel of the device in a wash solution, (ii) removing wash solution drawn into the capillary channel, and (iii) dipping the capillary channel into the new reagent solution.

From the foregoing, it will be appreciated that the tweezers-like, open-capillary dispenser tip provides the advantages that (i) the open channel of the tip facilitates rapid, efficient washing and drying before reloading the tip with a new reagent, (ii) passive capillary action can load the sample directly from a standard microwell plate while retaining sufficient sample in the open capillary reservoir for the printing of numerous arrays, (iii) open capillaries are less prone to clogging than closed capillaries, and (iv) open capillaries do not require a perfectly faced bottom surface for fluid delivery.

The array is formed of a plurality of analyte-specific reagent regions where each region may include a different analyte-specific reagent. As indicated above, the diameter of each region is preferably between about 20–200 $\mu$m. The spacing between each region and its closest (non-diagonal) neighbor, measured from center-to-center, is preferably in the range of about 20–400 $\mu$m. Thus, for example, an array having a center-to-center spacing of about 250 $\mu$m contains about 40 regions/cm or 1,600 regions/cm$^2$. After formation of the array, the support is treated to evaporate the liquid of the droplet forming each region, to leave a desired array of dried, relatively flat regions. This drying may be done by heating or under vacuum.

In some cases, it is desired to first rehydrate the droplets containing the analyte reagents to allow for more time for adsorption to the solid support. It is also possible to spot out the analyte reagents in a humid environment so that droplets do not dry until the arraying operation is complete.

In another aspect, the invention includes an automated apparatus for forming an array of analyte-assay regions on a solid support, where each region in the array has a known amount of a selected, analytespecific reagent. A dispenser device in the apparatus has the basic construction described above and includes a dispenser having an open-capillary channel terminating at a tip.

The dispenser is mounted in the device for movement toward and away from a dispensing position at which the tip of the dispenser taps a support surface, to dispense a selected volume of reagent solution, as described above. This movement is effected by a solenoid as described above. The solenoid is under the control of a control unit whose operation will be described below. The solenoid is also referred to herein as dispensing means for moving the device into tapping engagement with a support, when the device is positioned at a defined array position with respect to that support.

The dispenser device is carried on an arm which is threadedly mounted on a worm screw driven (rotated) in a desired direction by a stepper motor also under the control of unit. At its left end in the figure screw is carried in a sleeve for rotation about the screw axis. At its other end, the screw is mounted to the drive shaft of the stepper motor, which in turn is carried on a sleeve. The dispenser device, worm screw, the two sleeves mounting the worm screw, and the stepper motor used in moving the device in the "x" (horizontal) direction is referred to here collectively as a displacement assembly.

The displacement assembly is constructed to produce precise, micro-range movement in the direction of the screw, i.e., along an x axis in the figure. In one mode, the assembly functions to move the dispenser in x-axis increments having a selected distance in the range 5–25 $\mu$m. In another mode, the dispenser unit may be moved in precise x-axis increments of several microns or more, for positioning the dispenser at associated positions on adjacent supports, as will be described below.

The displacement assembly, in turn, is mounted for movement in the "y" (vertical) axis of the figure, for positioning the dispenser at a selected y axis position. The structure mounting the assembly includes a fixed rod 88 mounted rigidly between a pair of frame bars and a worm screw mounted for rotation between a pair of frame bars. The worm screw is driven (rotated) by a stepper motor which operates under the control of unit. The motor is mounted on a bar.

The structure just described, including the worm screw and motor is constructed to produce precise, micro-range movement in the direction of the screw, i.e., along an y axis in the figure. As above, the structure functions in one mode to move the dispenser in y-axis increments having a selected distance in the range 5–250 $\mu$m, and in a second mode, to move the dispenser in precise y-axis increments of several microns ($\mu$m) or more, for positioning the dispenser at associated positions on adjacent supports.

The displacement assembly and structure for moving this assembly in the y axis are referred to herein collectively as positioning means for positioning the dispensing device at a selected array position with respect to a support.

A holder in the apparatus functions to hold a plurality of supports, such as supports on which the microarrays of regent regions are to be formed by the apparatus. The holder provides a number of recessed slots which receive the supports, and position them at precise selected positions with respect to the frame bars on which the dispenser moving means is mounted.

As noted above, the control unit in the device functions to actuate the two stepper motors and dispenser solenoid in a sequence designed for automated operation of the apparatus in forming a selected microarray of reagent regions on each of a plurality of supports.

The control unit is constructed, according to conventional microprocessor control principles, to provide appropriate signals to each of the solenoid and each of the stepper motors, in a given timed sequence and for appropriate signalling time. The construction of the unit, and the settings that are selected by the user to achieve a desired array patterns will be understood from the following description of a typical apparatus operation.

Initially, one or more supports are placed in one or more slots in the holder. The dispenser is then moved to a position directly above a well (not shown) containing a solution of the first reagent to be dispensed on the support(s). The dispenser solenoid is actuated now to lower the dispenser tip into this well, causing the capillary channel in the dispenser to fill. Motors are now actuated to position the dispenser at a selected array position at the first of the supports. Solenoid actuation of the dispenser is then effective to dispense a selected-volume droplet of that reagent at this location. As noted above, this operation is effective to dispense a selected volume preferably between 2 pl and 2 nl of the reagent solution.

The dispenser is now moved to the corresponding position at an adjacent support and a similar volume of the solution is dispensed at this position. The process is repeated until the reagent has been dispensed at this preselected corresponding position on each of the supports.

Where it is desired to dispense a single reagent at more than two array positions on a support, the dispenser may be moved to different array positions at each support, before moving the dispenser to a new support, or solution can be dispensed at individual positions on each support, at one selected position, then the cycle repeated for each new array position.

To dispense the next reagent, the dispenser is positioned over a wash solution (not shown), and the dispenser tip is dipped in and out of this solution until the reagent solution has been substantially washed from the tip. Solution can be removed from the tip, after each dipping, by vacuum, compressed air spray, sponge, or the like.

The dispenser tip is now dipped in a second reagent well, and the filled tip is moved to a second selected array position in the first support. The process of dispensing reagent at each of tho corresponding second-array positions is then carried as above. This process is repeated until an entire microarray of reagent solutions on each of the supports has been formed.

A. Microarray Substrate

This section describes embodiments of a substrate having a microarray of biological polymers carried on the substrate surface. Subsection A describes a multi cell substrate, each cell of which contains a microarray, and preferably an identical microarray, of distinct biopolymers, such as distinct polynucleotides, formed on a porous surface. Subsection B describes a microarray of distinct polynucleotides bound on a glass slide coated with a polycationic polymer.

1. Multi-Cell Substrate

The substrate in one embodiment has an 8×12 rectangular array of cells formed on the substrate surface. Each cell in turn supports a microarray of distinct biopolymers, such as polypeptides or polynucleotides at known, addressable regions of the microarray. The 96-cell array shown in has typically array dimensions between about 12 and 244 mm in width and 8 and 400 im in length, with the cells in the array having width and length dimension of 1/12 and 1/8 the array width and length dimensions, respectively, i.e., between about 1 and 20 in width and 1 and 50 mm in length. The substrate includes a water-impermeable backing, such as a glass slide or rigid polymer sheet. Formed on the surface of the backing is a water-permeable film. The film is formed of a porous membrane material, such as nitrocellulose membrane, or a porous web material, such as a nylon, polypropylene, or PVDF porous polymer material. The thickness of the film is preferably between about 10 and 1000 μm. The film may be applied to the backing by spraying or coating uncured material on the backing, or by applying a preformed membrane to the backing. The backing and film may be obtained as a preformed unit from commercial source, e.g., a plastic-backed nitrocellulose film available from Schleicher and Schuell Corporation.

The film-covered surface in the substrate is partitioned into a desired array of cells by water-impermeable grid lines which have infiltrated the film down to the level of the backing, and extend above the surface of the film as shown, typically a distance of 100 to 2000 μm above the film surface.

The grid lines are formed on the substrate by laying down an uncured or otherwise flowable resin or elastomer solution in an array grid, allowing the material to infiltrate the porous film down to the backing, then curing or otherwise hardening the grid lines to form the cell-array substrate.

One preferred material for the grid is a flowable silicone available from Loctite Corporation. The barrier material can be extruded through a narrow syringe e.g., 22 gauge) using air pressure or mechanical pressure. The syringe is moved relative to the solid support to print the barrier elements as a grid pattern. The extruded bead of silicone wicks into the pores of the solid support and cures to form a shallow waterproof barrier separating the regions of the solid support.

In alternative embodiments, the barrier element can be a wax-based material or a thermoset material such as epoxy. The barrier material can also be a UV-curing polymer which is exposed to UV light after being printed onto the solid support. The barrier material may also be applied to the solid support using printing techniques such as silk-screen printing. The barrier material may also be a heat-seal stamping of the porous solid support which seals its pores and forms a water-impervious barrier element. The barrier material may also be a shallow grid which is laminated or otherwise adhered to the solid support.

In addition to plastic-backed nitrocellulose, the solid support can be virtually any porous membrane with or without a non-porous backing. Such membranes are readily available from numerous vendors and are made from nylon, PVDF, polysulfone and the like. In an alternative embodiment, the barrier element may also be used to adhere the porous membrane to a non-porous backing in addition to functioning as a barrier to prevent cross contamination of the assay reagents.

In an alternative embodiment, the solid support can be of a non-porous material. The barrier can be printed either before or after the microarray of biomolecules is printed on the solid support.

As can be appreciated, the cells formed by the grid lines and the underlying backing are water-impermeable, having side barriers projecting above the porous film in the calls. Thus, defined-volume samples can be placed in each well without risk of cross-contamination with sample material in adjacent cells.

As noted above, each well contains a microarray of distinct biopolymers. In one general embodiment, the microarrays in the well are identical arrays of distinct biopolymers, e.g., different sequence polynucleotides. Such arrays can be formed in accordance with the methods described in Section II, by depositing a first selected polynucleotide at the same selected microarray position in each of the cells, then depositing a second polynucleotide at a different microarray position in each well, and so on until a complete, identical microarray is formed in each cell.

In a preferred embodiment, each microarray contains about $10^3$ distinct polynucleotide or polypeptide biopolymers per surface area of less than about 1 $cm^2$. Also in a preferred embodiment, the biopolymers in each microarray region are present in a defined amount between about 0.1 femtomoles and 100 nanomoles.

Also in a preferred embodiments, the biopolymers are polynucleotides having lengths of at least about 50 bp, i.e., substantially longer than oligonucleotides which can be formed in high-density arrays by schemes involving parallel, step-wise polymer synthesis on the array surface.

In the case of a polynucleotide array, in an assay procedure, a small volume of the labeled DNA probe mixture in a standard hybridization solution is loaded onto each cell. The solution will spread to cover the entire microarray and stop at the barrier elements. The solid support is then incubated in a humid chamber at the appropriate temperature as required by the assay.

Each assay may be conducted in an "open-face" format where no further sealing step is required, since the hybridization solution will be kept properly hydrated by the water vapor in the humid chamber. At the conclusion of the incubation step, the entire solid support containing the numerous microarrays is rinsed quickly enough to dilute the assay reagents so that no significant cross contamination occurs. The entire solid support is then reacted with detection reagents if needed and analyzed using standard calorimetric, radioactive or fluorescent detection means. All processing and detection steps are performed simultaneously to all of the microarrays on the solid support ensuring uniform assay conditions for all of the microarrays on the solid support.

2. Glass-Slide Polynucleotide Array

The substrate includes a glass substrate having formed on its surface, a coating of a polycationic polymer, preferably a cationic polypeptide, such as polylysine or polyarginine. Formed on the polycationic coating is a microarray of distinct polynucleotides, each localized at known selected array regions, such as regions.

The slide is coated by placing a uniform-thickness film of a polycationic polymer, e.g., poly-1-lysine, on the surface of a slide and drying the film to form a dried coating. The amount of polycationic polymer added is sufficient to form at least a monolayer of polymers on the glass surface. The polymer film is bound to surface via electrostatic binding between negative silyl-OH groups on the surface and charged amine groups in the polymers. Poly-1-lysine coated glass slides may be obtained commercially, e.g., from Sigma Chemical Co. (St. Louis, Mo.).

To form the microarray, defined volumes of distinct polynucleotides are deposited on the polymercoated slide. According to an important feature of the substrate, the deposited polynucleotides remain bound to the coated slide surface non-covalently when an aqueous DNA sample is applied to the substrate under conditions which allow hybridization of reporter-labeled polynucleotides in the sample to complementary-sequence (single-stranded) polynucleotides in the substrate array.

To illustrate this feature, a substrate of the type just described, but having an array of same-sequence polynucleotides, was mixed with fluorescent-labeled complementary DNA under hybridization conditions. After washing to remove non-hybridized material, the substrate was examined by low-power fluorescence microscopy. The array can be visualized by the relatively uniform labeling pattern of the array regions.

In a preferred embodiment, each microarray contains at least 10³ distinct polynucleotide or polypeptide biopolymers per surface area of less than about 1 cm². In one embodiment, the microarray contains 400 regions in an area of about 16 mm², or 2.5×10³ regions/cm². Also in a preferred embodiment, the polynucleotides in the each microarray region are present in a defined amount between about 0.1 femtomoles and 100 nanomoles in the case of polynucleotides. Also in a preferred embodiments, the polynucleotides have lengths of at least about 50 bp, i.e., substantially longer than oligonucleotides which can be formed in high-density arrays by various in situ synthesis schemes.

B. Utility

Microarrays of immobilized nucleic acid sequences prepared in accordance with the invention can be used for large scale hybridization assays in numerous genetic applications, including genetic and physical napping of genomes, monitoring of gene expression, DNA sequencing, genetic diagnosis, genotyping of organisms, and distribution of DNA reagents to researchers.

For gene mapping, a gene or a cloned DNA fragment is hybridized to an ordered array of DNA fragments, and the identity of the DNA elements applied to the array is unambiguously established by the pixel or pattern of pixels of the array that are detected. One application of such arrays for creating a genetic map is described by Nelson, et al. (1993). In constructing physical maps of the genome, arrays of immobilized cloned DNA fragments are hybridized with other cloned DNA fragments to establish whether the cloned fragments in the probe mixture overlap and are therefore contiguous to the immobilized clones on the array. For example, Lahrach, et al., describe such a process.

The arrays of immobilized DNA fragments may also be used for genetic diagnostics. To illustrate, an array containing multiple forms of a mutated gene or genes can be probed with a labeled mixture of a patient's DNA which will preferentially interact with only one of the immobilized versions of the gene.

The detection of this interaction can lead to a medical diagnosis. Arrays of immobilized DNA fragments can also be used in DNA probe diagnostics. For example, the identity of a pathogenic microorganism can be established unambiguously by hybridizing a sample of the unknown pathogen's DNA to an array containing many types of known pathogenic DNA. A similar technique can also be used for unambiguous genotyping of any organism. Other molecules of genetic interest, such as cDNA's and RNA's can be immobilized on the array or alternately used as the labeled probe mixture that is applied to the array.

In one application, an array of cDNA clones representing genes is hybridized with total cDNA from an organism to monitor gene expression for research or diagnostic purposes. Labeling total cDNA from a normal cell with one color fluorophore and total cDNA from a diseased cell with another color fluorophore and simultaneously hybridizing the two cDNA samples to the same array of cDNA clones allows for differential gene expression to be measured as the ratio of the two fluorophore intensities. This two-color experiment can be used to monitor gene expression in different tissue types, disease states, response to drugs, or response to environmental factors.

By way of example and without implying a limitation of scope, such a procedure could be used to simultaneously screen many patients against all known mutations in a disease gene. This invention could be used in the form of, for example, 96 identical 0.9 cm×2.2 cm microarrays fabricated on a single 12 cm×18 cm sheet of plastic-backed nitrocellulose where each microarray could contain, for example, 100 DNA fragments representing all known mutations of a given gene. The region of interest from each of the DNA samples from 96 patients could be amplified, labeled, and hybridized to the 96 individual arrays with each assay performed in 100 microliters of hybridization solution. The approximately 1" thick silicone rubber barrier elements between individual arrays prevent cross contamination of the patient samples by sealing the pores of the nitrocellulose and by acting as a physical barrier between each microarray. The solid support containing all 96 microarrays assayed with the 96 patient samples is incubated, rinsed, detected and analyzed as a single sheet of material using standard radioactive, fluorescent, or calorimetric detection means (Maniatas, et al., 1989). Previously, such a procedure would involve the handling, processing and tracking of 96 separate membranes in 96 separate sealed chambers. By processing all 96 arrays as a single sheet of material, significant time and cost savings are possible.

The assay format can be reversed where the patient or organism's DNA is immobilized as the array elements and each array is hybridized with a different mutated allele or genetic marker. The gridded solid support can also be used for parallel non-DNA ELISA assays. Furthermore, the invention allows for the use of all standard detection methods without the need to remove the shallow barrier elements to carry out the detection step.

In addition to the genetic applications listed above, arrays of whole cells, peptides, enzymes, antibodies, antigens, receptors, ligands, phospholipids, polymers, drug cogener preparations or chemical substances can be fabricated by the means described in this invention for large scale screening assays in medical diagnostics, drug discovery, molecular biology, immunology and toxicology.

The multi-cell substrate aspect of the invention allows for the rapid and convenient screening of many DNA probes against many ordered arrays of DNA fragments. This eliminates the need to handle and detect many individual arrays for performing mass screenings for genetic research and diagnostic applications. Numerous microarrays can be fabricated on the same solid support and each microarray reacted with a different DNA probe while the solid support is processed as a single sheet of material.

EXAMPLES

The following examples are offered to illustrate, but not to limit the present invention.

Example 1

First Generation Oligonucleotide Arrays Designed to Measure mRNA Levels for a Small Number of Murine Cytokines A. Preparation of Labeled RNA 1. From Each of the Preselected Genes Fourteen genes (IL-2, IL-3, Il-4, IL-6, Il-10, IL-12p40, GM-CSF, IFN-γ, TNF-α, CTLA8, β-actin, GAPDH, IL-11 receptor, and Bio B) were each cloned into the p Bluescript II KS (+) phagemid (Stratagene, La Jolla, Calif., USA). The orientation of the insert was such that T3 RNA polymerase gave sense transcripts and T7 polymerase gave antisense RNA.

Labeled ribonucleotides in an in vitro transcription (IVT) reaction. Either biotin- or fluorescein-labeled UTP and CTP (1:3 labeled to unlabeled) plus unlabeled ATP and GTP were used for the reaction with 2500 units of T7 RNA polymerase (Epicentre Technologies, Madison, Wis., USA). In vitro transcription was done with cut templates in a manner like that described by Melton et al., *Nucleic Acids Research,* 12: 7035–7056 (1984). A typical in vitro transcription reaction used 5 µg DNA template, a buffer such as that included in Ambion's Maxiscript in vitro Transcription Kit (Ambion Inc., Huston, Tex., USA) and GTP (3 mM), ATP (1.5 mM), and CTP and fluoresceinated UTP (3 mM total, UTP: Fl-UTP 3:1) or UTP and fluoresceinated CTP (2 mM total, CTP: Fl-CTP, 3:1). Reactions done in the Ambion buffer had 20 mM DTT and RNase inhibitor. The reaction was run from 1.5 to about 8 hours.

Following the reaction, unincorporated nucleotide triphosphates were removed using a size-selective membrane (microcon-100) or Pharmacia microspin S-200 column. The total molar concentration of RNA was based on a measurement of the absorbance at 260 nm. Following quantitation of RNA amounts, RNA was fragmented randomly to an average length of approximately 50–100 bases by heating at 94° C. in 40 mM Tris-acetate pH 8.1, 100 mM potassium acetate, 30 mM magnesium acetate for 30–40 minutes. Fragmentation reduces possible interference from RNA secondary structure, and minimizes the effects of multiple interactions with closely spaced probe molecules.

2. From cDNA Libraries

Labeled RNA was produced from one of two murine cell lines; T10, a B cell plasmacytoma which was known not to express the genes (except IL-10, actin and GAPDH) used as target genes in this study, and 2D6, an IL-12 growth dependent T cell line ($Th_1$ subtype) that is known to express most of the genes used as target genes in this study. Thus, RNA derived from the T10 cell line provided a good total RNA baseline mixture suitable for spiking with known quantities of RNA from the particular target genes. In contrast, mRNA derived from the 2D6 cell line provided a good positive control providing typical endogenously transcribed amounts of the RNA from the target genes.

a) The T10 Murine B Cell Line

The T10 cell line (B cells) was derived from the IL-6 dependent murine plasmacytoma line T1165 (Nordan et al. (1986) *Science* 233: 566–569) by selection in the presence of IL-11. To prepare the directional cDNA library, total cellular RNA was isolated from T10 cells using RNAStat60 (Tel-Test B), and poly $(A)^+$ RNA was selected using the PolyAtract kit (Promega, Madison, Wis., USA). First and second strand cDNA was synthesized according to Toole et al., (1984) *Nature,* 312: 342–347, except that 5-methyldeoxycytidine 5'-triphosphate (Pharmacia LKB, Piscataway, N.J., USA) was substituted for DCTP in both reactions.

To determine cDNA frequencies T10 libraries were plated, and DNA was transfered to nitrocellulose filters and probed with $^{32}$P-labeled β-actin, GAPDH and IL-10 probes. Actin was represented at a frequency of 1:3000, GAPDH at 1;1000, and IL-10 at 1:35,000. Labeled sense and antisense T10 RNA samples were synthesized from NotI and SfiI cut CDNA libraries in in vitro transcription reactions as described above.

b) The 2D6 Murine Helper T Cells Line.

The 2D6 cell line is a murine IL-12 dependent T cell line developed by Fujiwara et al. Cells were cultured in RPMI 1640 medium with 10% heat inactivated fetal calf serum (JRH Biosciences), 0.05 mM P-mercaptoethanol and recombinant murine IL-12 (100 units/mL, Genetics Institute, Cambridge, Mass., USA). For cytokine induction, cells were preincubated overnight in IL-12 free medium and then resuspended ($10^6$ cells/ml). After incubation for 0, 2, 6 and 24 hours in media containing 5 nM calcium ionophore A23187 (Sigma Chemical Co., St. Louis Mo., USA) and 100 nM 4-phorbol-12-myristate 13-acetate (Sigma), cells were collected by centrifugation and washed once with phosphate buffered saline prior to isolation of RNA.

Labeled 2D6 mRNA was produced by directionally cloning the 2D6 cDNA with αZipLox, NotI-SalI arms available from GibcoBRL in a manner similar to T10. The linearized pZ11 library was transcribed with T7 to generate sense RNA as described above.

c) RNA Preparation.

For material made directly from cellular RNA, cytoplasmic RNA was extracted from cells by the method of Favaloro et al., (1980) *Meth. Enzym.,* 65: 718–749, and poly $(A)^+$ RNA was isolated with an oligo dT selection step (PolyAtract, Promega, ). RNA was amplified using a modification of the procedure described by Eberwine et al. (1992) *Proc. Natl. Acad. Sci. USA,* 89: 3010–3014 (see also Van Gelder et al. (1990) *Science* 87: 1663–1667). One microgram of poly $(A)^+$ RNA was converted into double-stranded cDNA using a cDNA synthesis kit (Life Technologies) with an oligo dT prime incorporating a T7 RNA polymerase promoter site. After second strand synthesis, the reaction mixture was extracted with phenol/chloroform and the double-stranded DNA isolated using a membrane filtration step (Mircocon-100, Amicon, Inc. Beverly, Mass., USA). Labeled cRNA was made directly from the cDNA pool with an IVT step as described above. The total molar concentration of labeled CRNA was determined from the absorbance at 260 and assuming an average RNA size of 1000 ribonucleotides. RNA concentration was calculated using the conventional conversion that 1 OD is equivalent to 40 µg of RNA, and that 1 µg of cellular mRNA consists of 3 pmoles of RNA molecules.

Cellular mRNA was also labeled directly without any intermediate cDNA or RNA synthesis steps. Poly $(A)^+$ RNA was fragmented as described above, and the 5' ends of the fragments were kinased and then incubated ovenight with a biotinylated oligoribonucleotide (5'-biotin-AAAAAA-3') in the presence of T4 RNA ligase (Epicentre Technologies). Alternatively, mRNA was labeled directly by UV-induced crosslinking to a psoralen derivative linked to biotin (Schleicher & Schuell).

B. High Density Array Preparation

A high density array of 20 mer oligonucleotide probes was produced using VLSIPS technology. The high density array included the oligonucleotide probes as listed in Table 2. A central mismatch control probe was provided for each gene-specific probe resulting in a high density array containing over 16,000 different oligonucleotide probes.

TABLE 2

High density array design. For every probe there was also a mismatch control having a central 1 base mismatch.

| Probe Type | Target Nucleic Acid | Number of Probes |
| --- | --- | --- |
| Test Probes: | IL-2 | 691 |
| | IL-3 | 751 |
| | IL-4 | 361 |
| | IL-6 | 691 |

TABLE 2-continued

High density array design. For every probe there was also a mismatch control having a central 1 base mismatch.

| Probe Type | Target Nucleic Acid | Number of Probes |
|---|---|---|
| | IL-10 | 481 |
| | IL-12p40 | 911 |
| | GM-CSF | 661 |
| | IFN-γ | 991 |
| | TNF-α | 641 |
| | mCTLA8 | 391 |
| | IL-11 receptor | 158 |
| House Keeping Genes: | GAPDH | 388 |
| | β-actin | 669 |
| Bacterial gene (sample preparation/amplification control) | Bio B | 286 |

The high density array was synthesized on a planar glass slide.

C. Array Hybridization and Scanning

The RNA transcribed from cDNA was hybridized to the high density oligonucleotide probe array(s) at low stringency and then washed under more stringent conditions. The hybridization solutions contained 0.9 M NaCl, 60 mM $NaH_2PO_4$, 6 mM EDTA and 0.005% Triton X-100, adjusted to pH 7.6 (referred to as 6×SSPE-T). In addition, the solutions contained 0.5 mg/ml unlabeled, degraded herring sperm DNA (Sigma Chemical Co., St. Louis, Mo., USA). Prior to hybridization, RNA samples were heated in the hybridization solution to 9° C. for 10 minutes, placed on ice for 5 minutes, and allowed to equilibrate at room temperature before being placed in the hybridization flow cell, Following hybridization, the solution was removed, the arrays were washed with 6×SSPE-T at 22° C. for 7 minutes, and then washed with 0.5×SSPE-T at 40° C. for 15 minutes. When biotin-labeled RNA was used, the hybridized RNA was stained with a streptavidin-phycoerythrin conjugate (Molecular Probes, Inc., Eugene, Oreg., USA) prior to reading. Hybridized arrays were stained with 2 µg/ml streptavidinphycoerythrin in 6×SSPE-T at 40° C. for 5 minutes.

The arrays were read using scanning confocal microscope (Molecular Dynamics, Sunnyvale, Calif., USA) modified for the purpose. The scanner uses an argon ion laser as the excitation source, and the emission was detected with a photomultiplier tube through either a 530 nm bandpass filter (fluorescein) or a 560 nm longpass filter (phycoerythrin).

Nucleic acids of either sense or antisense orientations were used in hybridization experiments. Arrays with for either orientation (reverse complements of each other) were made using the same set of photolithographic masks by reversing the order of the photochemical steps and incorporating the complementary nucleotide.

D. Quantitative Analysis of Hybridization Patterns and Intensities

The quantitative analysis of the hybridization results involved counting the instances in which the perfect match probe (PM) was brighter than the corresponding mismatch probe (MM), averaging the differences (PM minus MM) for each probe family (i.e., probe collection for each gene), and comparing the values to those obtained in a side-by-side experiment on an identically synthesized array with an unspiked sample (if applicable). The advantage of the difference method is that signals from random cross hybridization contribute equally, on average, to the PM and MM probes while specific hybridization contributes more to the PM probes. By averaging the pairwise differences, the real signals add constructively while the contributions from cross hybridization tend to cancel.

The magnitude of the changes in the average of the difference (PM–MM) values was interpreted by comparison with the results of spiking experiments as well as the signal observed for the internal standard bacterial RNA spiked into each sample at a known amount. Analysis was performed using algorithms and software described herein.

E. Optimization of Probe Selection

In order to optimize probe selection for each of the target genes, the high density array of oligonucleotide probes was hybridized with the mixture of labeled RNAs transcribed from each of the target genes. Fluorescence intensity at each location on the high density array was determined by scanning the high density array with a laser illuminated scanning confocal fluorescence microscope connected to a data acquisition system.

Probes were then selected for further data analysis in a two-step procedure. First, in order to be counted, the difference in intensity between a probe and its corresponding mismatch probe had to exceed a threshold limit (50 counts, or about half background, in this case). This eliminated from consideration probes that did not hybridize well and probes for which the mismatch control hybridizes at an intensity comparable to the perfect match.

The high density array was hybridized to a labeled RNA sample which, in principle, contains none of the sequences on the high density array. In this case, the oligonucleotide probes were chosen to be complementary to the sense RNA. Thus, an anti-sense RNA population should have been incapable of hybridizing to any of the probes on the array. Where either a probe or its mismatch showed a signal above a threshold value (100 counts above background) it was not included in subsequent analysis.

Then, the signal for a particular gene was counted as the average difference (perfect match—mismatch control) for the selected probes for each gene.

F. Results: The High Density Arrays Provide Specific and Sensitive Detection of Target Nucleic Acids.

As explained above, the initial arrays contained more than 16,000 probes that were complementary to 12 murine mRNAs—9 cytokines, 1 cytokine receptor, 2 constitutively expressed genes (5-actin and glyceraldehyde 3-phosphate dehydrogenase)—1 rat cytokine and 1 bacterial gene (E. coli biotin synthetase, bioB) which serves as a quantitation reference. The initial experiments with these relatively simple arrays were designed to determine whether short in situ synthesized oligonucleotides can be made to hybridize with sufficient sensitivity and specificity to quantitatively detect RNAs in a complex cellular RNA population. These arrays were intentionally highly redundant, containing hundreds of oligonucleotide probes per RNA, many more than necessary for the determination of expression levels. This was done to investigate the hybridization behavior of a large number of probes and develop general sequence rules for a priori selection of minimal probe sets for arrays covering substantially larger numbers of genes.

The oligonucleotide arrays contained collections of pairs of probes for each of the RNAs being monitored. Each probe pair consisted of a 20-mer that was perfectly complementary (referred to as a perfect match, or PM probe) to a subsequence of a particular message, and a companion that was identical except for a single base difference in a central position. The mismatch (MM) probe of each pair served as an internal control for hybridization specificity. The analysis of PM/MM pairs allowed low intensity hybridization patterns from rare RNAs to be sensitively and accurately recognized in the presence of crosshybridization signals.

For array hybridization experiments, labeled RNA target samples were prepared from individual clones, cloned cDNA libraries, or directly from cellular mRNA as described above. Target RNA for array hybridization was prepared by incorporating fluorescently labeled ribonucleotides in an in vitro transcription (IVT) reaction and then randomly fragmenting the RNA to an average size of 30–100 bases. Samples were hybridized to arrays in a self-contained flow cell (volume ~200 $\mu$L) for times ranging from 30 minutes to 22 hours. Fluorescence imaging of the arrays was accomplished with a scanning confocal microscope (Molecular Dynamics). The entire array was read at a resolution of 11.25 $\mu$m (~80-fold oversampling in each of the 100×100 $\mu$m synthesis regions) in less than 15 minutes, yielding a rapid and quantitative measure of each of the individual hybridization reactions.

1. Specificity of Hybridization

In order to evaluate the specificity of hybridization, the high density array described above was hybridized with 50 pM of the RNA sense strand of IL-2, IL-3, IL-4, IL-6, Actin, GAPDH and Bio B or IL-10, IL-12p40, GM-CSF, IFN-$\gamma$, TNF-$\alpha$, mCTLA8 and Bio B. The hybridized array showed strong specific signals for each of the test target nucleic acids with minimal cross hybridization.

2. Detection of Gene Expression Levels in a Complex Target Sample

To determine how well individual RNA targets could be detected in the presence of total mammalian cell message populations, spiking experiments were carried out. Known amounts of individual RNA targets were spiked into labeled RNA derived from a representative cDNA library made from the murine B cell line T10. The T10 cell line was chosen because of the cytokines being monitored, only IL-10 is expressed at a detectable level.

Because simply spiking the RNA mixture with the selected target genes and then immediately hybridizing might provide an artificially elevated reading relative to the rest of the mixture, the spiked sample was treated to a series of procedures to mitigate differences between the library RNA and the added RNA. Thus the "spike" was added to the sample which was then heated to 37° C. and annealed. The sample was then frozen, thawed, boiled for 5 minutes, cooled on ice and allowed to return to room temperature before performing the hybridization.

Figure 2A:
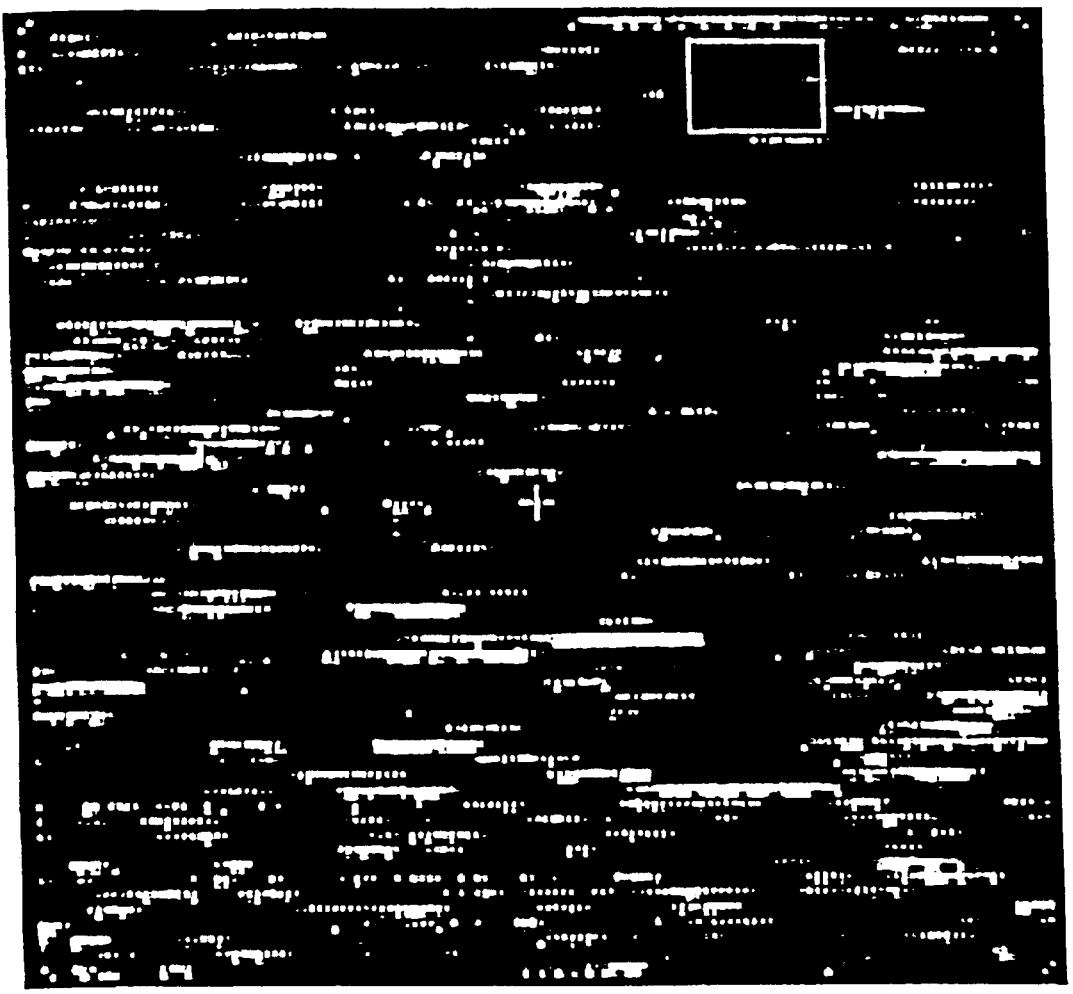
FIG. 2A shows a fluorescent image of a high density array containing over 16,000 different oligonucleotide probes. The image was obtained following hybridization (15 hours at 40° C.) of biotin-labeled randomly fragmented sense RNA transcribed from the murine B cell (T10) cDNA library, and spiked at the level of 1:3,000 (50 pM equivalent to about 100 copies per cell) with 13 specific RNA targets. The brightness at any location is indicative of the amount of labeled RNA hybridized to the particular oligonucleotide probe.
Figure 2C:
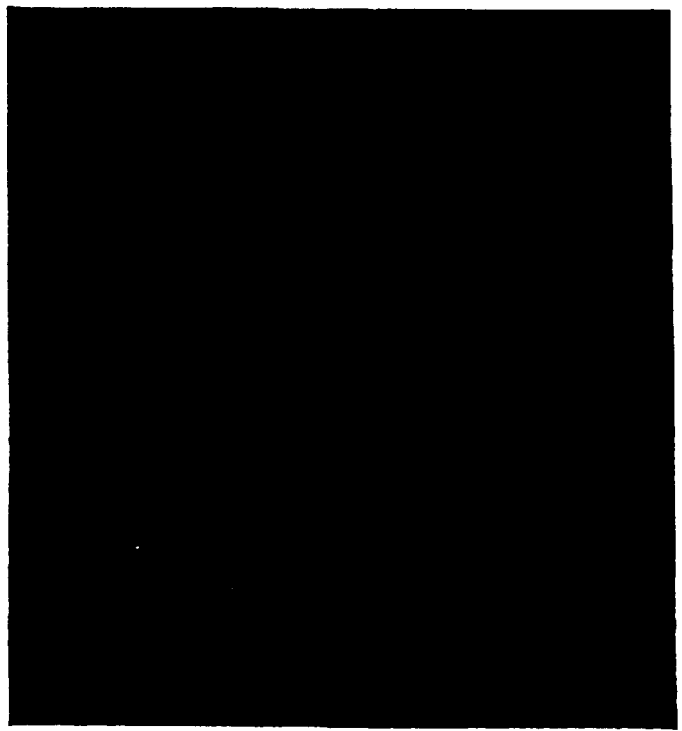
FIG. 2C shows shown the same region of the array following hybridization with an unspiked T10 RNA samples (T10 cells do not express IL-2 and IL-3). The variation in the signal intensity was highly reproducible and reflected the sequence dependence of the hybridization efficiencies. The central cross and the four corners of the array contain a control sequence that is complementary to a biotin-labeled oligonucleotide that was added to the hybridization solution at a constant concentration (50 pM). The sharpness of the images near the boundaries of the features was limited by the resolution of the reading device (11.25 $\mu$m) and not by the spatial resolution of the array synthesis. The pixels in the border regions of each synthesis feature were systematically ignored in the quantitative analysis of the images.
Figure 2B:
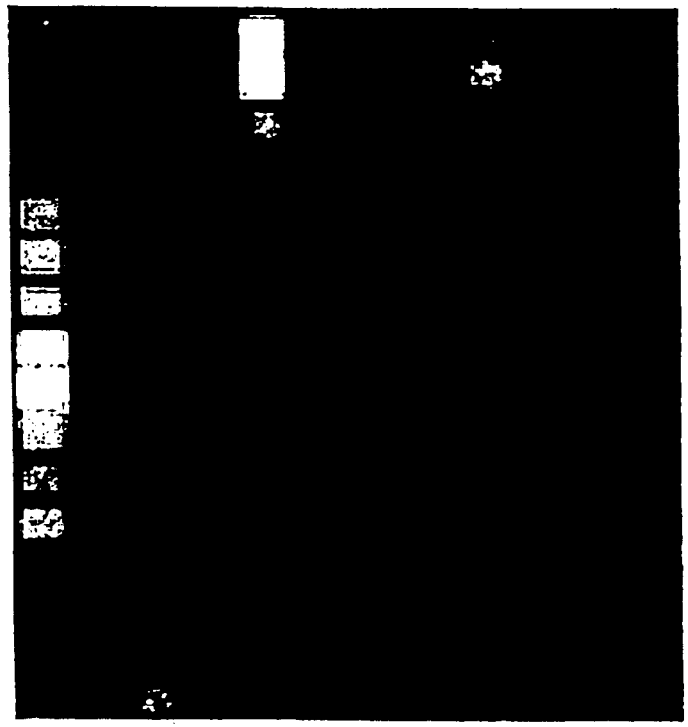
FIG. 2B shows a small portion of the array (the boxed region of FIG. 2A) containing probes for IL-2 and IL-3 RNAS. For comparison.

FIG. 2A shows the results of an experiment in which 13 target RNAS were spiked into the total RNA pool at a level of 1:3000 (equivalent to a few hundred copies per cell). RNA frequencies are given as the molar amount of an individual RNA per mole of total RNA. FIG. 2B shows a small portion of the array (the boxed region of 2A) containing probes specific for interleukin-2 and interleukin-3 (IL-2 and IL-3,) RNA, and FIG. 2C shows the same region in the absence of the spiked targets. The hybridization signals are specific as indicated by the comparison between the spiked and unspiked images, and perfect match (PM) hybridizations are well discriminated from missmatches (MM) as shown by the pattern of alternating brighter rows (corresponding to PM probes) and darker rows (corresponding to MM probes). The observed variation among the different perfect match hybridization signals was highly reproducible and reflects the sequence dependence of the hybridizations. In a few instances, the perfect match (PM) probe was not significantly brighter than its mismatch (MM) partner because of cross-hybridization with other members of the complex RNA population. Because the patterns are highly reproducible and because detection does not depend on only a single probe per RNA, infrequent cross hybridization of this type did not preclude sensitive and accurate detection of even low level RNAS.

Similarly, infrequent poor hybridization due to, for example, RNA or probe secondary structure, the presence of polymorphism or database sequence errors does not preclude detection. An analysis of the observed patterns of hybridization and cross hybridization led to the formulation of general rules for the selection of oligonucleotide probes with the best sensitivity and specificity described herein.

3. Relationship Between Target Concentration and Hybridization Signal

Figure 3:
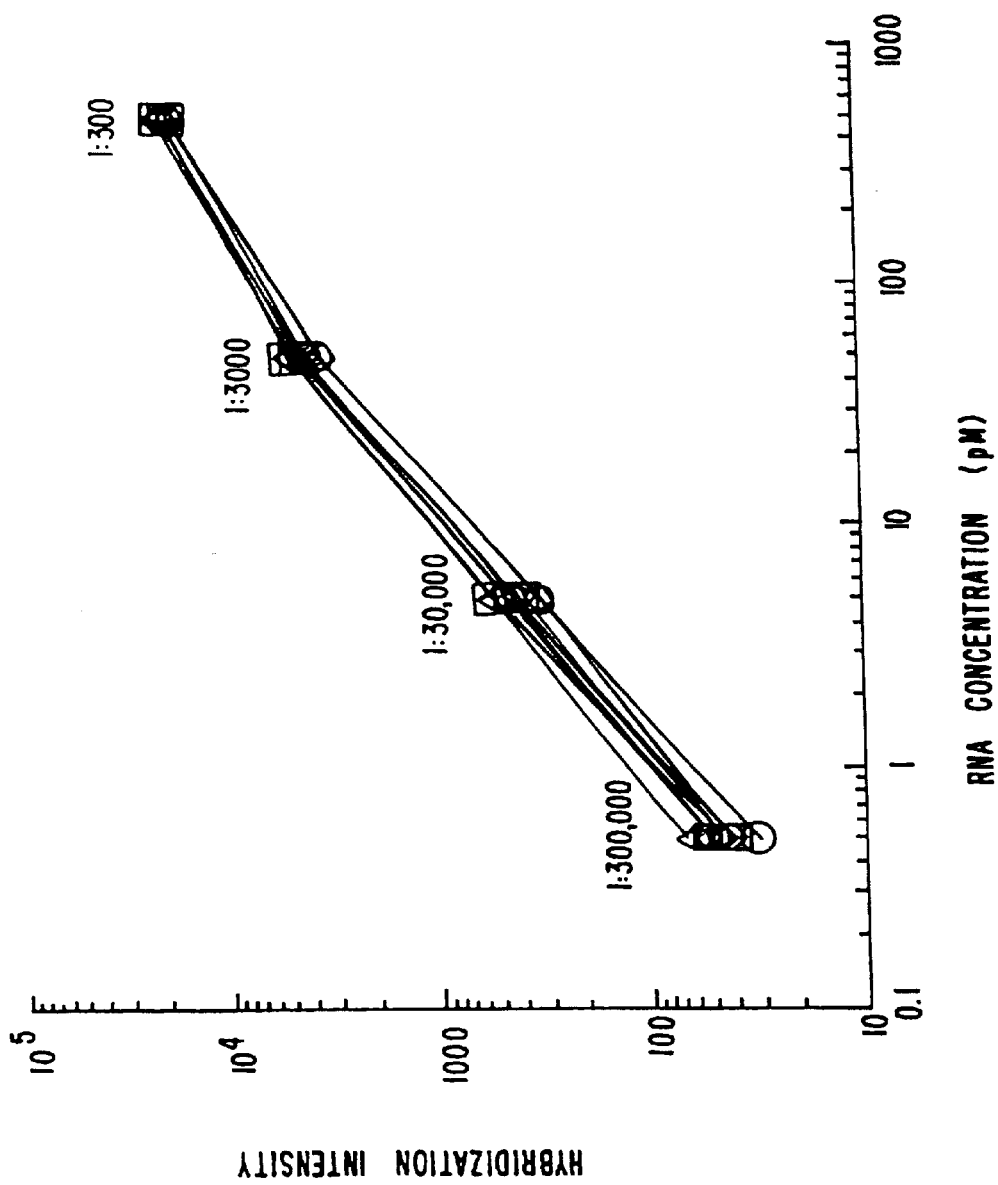
FIG. 3 provides a log/log plot of the hybridization intensity (average of the PM-MM intensity differences for each gene) versus concentration for 11 different RNA targets. The hybridization signals were quantitatively related to target concentration. The experiments were performed as described in the Examples herein and in FIG. 2. The ten 10 cytokine RNAs (plus bioB) were spiked into labeled T10 RNA at levels ranging from 1:300,000 to 1:3,000. The signals continued to increase with increased concentration up to frequencies of 1:300, but the response became sublinear at the high levels due to saturation of the probe sites, The linear range can be extended to higher concentrations by using shorter hybridization times. RNAs from genes expressed in T10 cells (IL-10, β-actin and GAPDH) were also detected at levels consistent with results obtained by probing cDNA libraries.

A second set of spiking experiments was carried out to determine the range of concentrations over which hybridization signals could be used for direct quantitation of RNA levels. FIG. 3 shows the results of experiments in which the ten cytokine RNAs were spiked together into 0.05 mg/ml of labeled RNA from the B cell (T10) cDNA library at levels ranging from 1:300 to 1:300,000. A frequency of 1:300,000 is that of an mRNA present at less than a few copies per cell. In 10 $\mu$g of total RNA and a volume of 200 $\mu$l, a frequency of 1:300,000 corresponds to a concentration of approximately 0.5 picomolar and 0.1 femtomole (~6×10$^7$ molecules or about 30 picograms)of specific RNA.

Hybridizations were carried out in parallel at 40° C. for 15 to 16 hours. The presence of each of the 10 cytokine RNAs was reproducibly detected above the background even at the lowest frequencies. Furthermore, the hybridization intensity was linearly related to RNA target concentration between 1:300,000 and 1:3000 (FIG. 3). Between 1:3000 and 1:300, the signals increased by a factor of 4–5 rather than 10 because the probe sites were beginning to saturate at the higher concentrations in the course of a 15 hour hybridization. The linear response range can be extended to higher concentrations by reducing the hybridization time. Short and long hybridizations can be combined to quantitatively cover more than a 10$^4$-fold range in RNA concentration.

Blind spiking experiments were performed to test the ability to simultaneously detect and quantitate multiple related RNAs present at a wide range of concentrations in a complex RNA population. A set of four samples was prepared that contained 0.05 mg/ml of sense RNA transcribed from the murine B cell CDNA library, plus combinations of the 10 cytokine RNAs each at a different concentration. Individual cytokine RNAs were spiked at one of the following levels: 0, 1:300,000, 1:30,000, 1:3000, or 1:300. The four samples plus an unspiked reference were hybridized to separate arrays for 15 hours at 40° C. The presence or absence of an RNA target was determined by the pattern of hybridization and how it differed from that of the unspiked reference, and the concentrations were detected by the intensities. The concentrations of each of the ten cytokines in the four blind samples were correctly determined, with no false positives or false negatives.

One case is especially noteworthy: IL-10 is expressed in the mouse B cells used to make the CDNA library, and was known to be present in the library at a frequency of 1:60,000 to 1:30,000. In one of the unknowns, an additional amount of IL-10 RNA (corresponding to a frequency of 1:300,000) was spiked into the sample. The amount of the spiked IL-10 RNA was correctly determined, even though it represented an increase of only 10–20% above the intrinsic level. These results indicate that subtle changes in expression are sensitively determined by performing side-by-side experiments with identically prepared samples on identically synthesized arrays.

Example 2

T Cell Induction Experiments Measuring Cytokine mRNAs as a Function of Time Following Stimulation The high density arrays of this invention were next used to monitor cytokine mRNA levels in murine T cells at different times following a biochemical stimulus. Cells from the murine T helper cell line (2D6) were treated with the phorbol ester 4-phorbol-12-myristate 13-acetate (PMA) and a calcium ionophore. Poly $(A)^+$ mRNA was then isolated at 0, 2, 6 and 24 hours after stimulation. Isolated mRNA (approximately 1 $\mu$g) was converted to labeled antisense RNA using a procedure that combines a double-stranded cDNA synthesis step with a subsequent in vitro transcription reaction. This RNA synthesis and labeling procedure amplifies the entire mRNA population by 20 to 50-fold in an apparently unbiased and reproducible fashion (Table 2).

The labeled antisense T-cell RNA from the four time points was then hybridized to DNA probe arrays for 2 and 22 hours. A large increase in the $\gamma$-interferon mRNA level was observed, along with significant changes in four other cytokine mRNAs (IL-3, IL-10, GM-CSF and TNF$\alpha$). As shown in FIG. 4, the cytokine messages were not induced with identical inetics. Changes in cytokine mRNA levels of less than 1:130,000 were unambiguously detected along with the very large changes observed for $\gamma$-interferon.

These results highlight the value of the large experimental dynamic range inherent in the method. The quantitative assessment of RNA levels from the hybridization results is direct, with no additional control hybridizations, sample manipulation, amplification, cloning or sequencing. The method is also efficient. Using current protocols, instrumentation and analysis software, a single user with a single scanner can read and analyze as many as 30 arrays in a day.

Example 3

Higher-Density Arrays Containing 65,000 Probes for Over 100 Murine Genes

Figure 5:
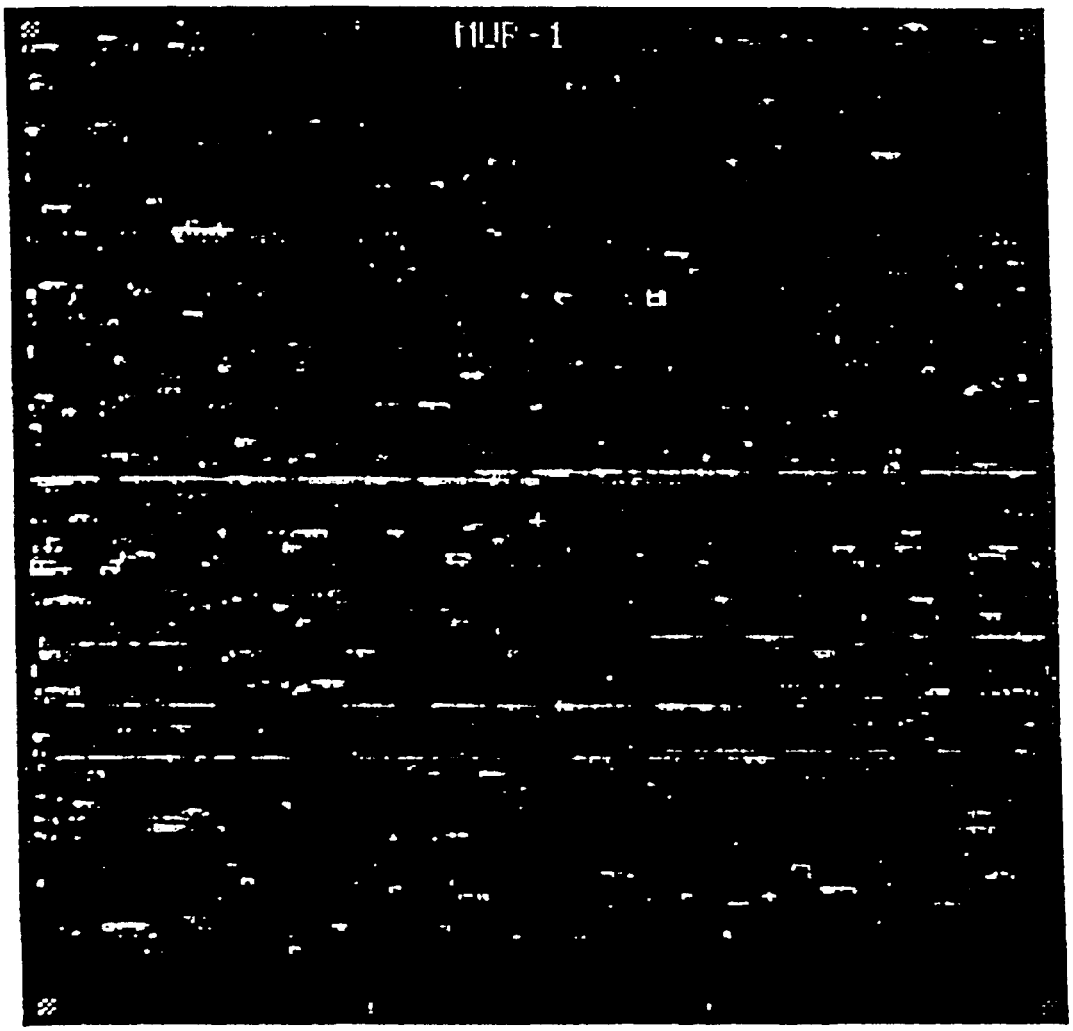
FIG. 5 shows a fluorescence image of an array containing over 63,000 different oligonucleotide probes for 118 genes. The image was obtained following overnight hybridization of a labeled murine B cell RNA sample. Each square synthesis region is 50×50 μm and contains 107 to 108 copies of a specific oligonucleotide. The array was scanned at a resolution of 7.5 μm in approximately 15 minutes. The bright rows indicate RNAs present at high levels. Lower level RNAs were unambiguously detected based on quantitative evaluation of the hybridization patterns. A total of 21 murine RNAs were detected at levels ranging from approximately 1:300,000 to 1:100. The cross in the center, the checkerboard in the corners, and the MUR-1 region at the top contain probes complementary to a labeled control oligonucleotide that was added to all samples.

FIG. 5 shows an array that contains over 65,000 different oligonucleotide probes (50 $\mu$m feature size) following hybridization with an entire murine B cell RNA population. Arrays of this complexity were read at a resolution of 7.5 lim in less than fifteen minutes. The array contains probes for 118 genes including 12 murine genes represented on the simpler array described above, 35 U.S.C. §102 ( ) additional murine genes, three bacterial genes and one phage gene. There are approximately 300 probe pairs per gene, with the probes chosen using the selection rules described herein. The probes were chosen from the 600 bases of sequence at the 3' end of the translated region of each gene. A total of 21 murine RNAs were unambiguously detected in the B cell RNA population, at levels ranging from approximately 1:300,000 to 1:100.

Labeled RNA samples from the T cell induction experiments (FIG. 4) were hybridized to these more complex 118-gene arrays, and similar results were obtained for the set of genes in common to both chip types. Expression changes were unambiguously observed for more than 20 other genes in addition to those shown in FIG. 4.

To determine whether much smaller sets of probes per gene are sufficient for reliable detection of RNAs, hybridization results from the 118 gene chip were analyzed using ten different subsets of 20 probe pairs per gene. That is to say, the data were analyzed as if the arrays contained only 20 probe pairs per gene. The ten subsets of 20 pairs were chosen from the approximately 300 probe pairs per gene on the arrays. The initial probe selection was made utilizing the probe selection and pruning algorithms described above. The ten subjects of 20 pairs were then randomly chosen from those probes that survived selection and pruning. Labeled RNAs were spiked into the murine B cell RNA population at levels of 1:25,000, 1:50,000 and 1:100,000. Changes in hybridization signals for the spiked RNAs were consistently detected at all three levels with the smaller probe sets. As expected, the hybridization intensities do not cluster as tightly as when averaging over larger numbers of probes. This analysis indicates that sets of 20 probe pairs per gene are sufficient for the measurement of expression changes at low levels, but that improvements in probe selection and experimental procedures will are preferred to routinely detect RNAs at the very lowest levels with such small probe sets. Such improvements include, but are not limited to higher stringency hybridizations coupled with use of slightly longer oligonucleotide probes (e.g., 25 mer probes)) are in progress.

Example 4

Scale Up to Thousands of Genes

A set of four high density arrays each containing 25-mer oligonucleotide probes approximately 1650 different human genes provided probes to a total of 6620 genes. There were about 20 probes for each gene. The feature size on arrays was 50 microns. This high density array was successfully hybridized to a cDNA library using essentially the protocols described above. Similar sets of high density arrays containing oligonucleotide probes to every known expressed sequence tag (EST) are in preparation.

Example 5

Direct Scale-up for the Simultaneous Monitoring of Tens of Thousands of RNAs In addition to being sensitive, specific and quantitative, the approach described here is intrinsically parallel and readily scalable to the monitoring of very large numbers of mRNAs. The number of RNAs monitored can be increased greatly by decreasing the number of probes per RNA and increasing the number of probes per array. For example, using the above-described technology, arrays containing as many as 400,000 probes in an area of 1.6 cm$^2$ (20×20 $\mu$m synthesis features) are currently synthesized and read. Using 20 probe pairs per gene allows 10,000 genes to be monitored on a single array while maintaining the important advantages of probe redundancy. A set of four such arrays could cover the more than 40,000 human genes for which there are expressed sequence tags (ESTS) in the public data bases, and new ESTs can be incorporated as they become available. Because of the combinatorial nature of the chemical synthesis, arrays of this complexity are made in the same amount of time with the same number of steps as the simpler ones used here. The use of even fewer probes per gene and arrays of higher density makes possible the simultaneous monitoring of all sequenced human genes on a single, or small number of small chips.

The quantitative monitoring of expression levels for large numbers of genes will prove valuable in elucidating gene function, exploring the causes and mechanisms of disease, and for the discovery of potential therapeutic and diagnostic targets. As the body of genomic information grows, highly parallel methods of the type described here provide an efficient and direct way to use sequence information to help elucidate the underlying physiology of the cell.

Example 6

Probe Selection Using a Neural Net

A neural net can be trained to predict the hybridization and cross hybridization intensities of a probe based on the sequence of bases in the probe, or on other probe properties. The neural net can then be used to pick an arbitrary number of the "best" probes. When a neural net was trained to do this it produced a moderate (0.7) correlation between predicted intensity and measured intensity, with a better model for cross hybridization than hybridization.

A. Input/Output Mapping

The neural net was trained to identify the hybridization properties of 20-mer probes. The 20-mer probes were mapped to an eighty bit long input vector, with the first four bits representing the base in the first position of the probe, the next four bits representing the base in the second position, etc. Thus, the four bases were encoded as follows:

A: 1000
C: 0100
G: 0010
T: 0001

The neural network produced two outputs; hybridization intensity, and crosshybridization intensity. The output was scaled linearly so that 95% of the outputs from the actual experiments fell in the range 0. to 1.

B. Neural Net Architecture

The neural net was a backpropagation network with 80 input neurons, one hidden layer of 20 neurons, and an output layer of two neurons. A sigmoid transfer function was used: $(s(x)=1/(1+\exp(-1*x)))$ that scales the input values from 0 to 1 in a non-linear (sigmoid) manner.

C. Neural Net Training

The network was trained using the default parameters from Neural Works Professional 2.5 for a backprop network. (Neural Works Professional is a product of NeuralWare, Pittsburgh, Pa., USA). The training set consisted of approximately 8000 examples of probes, and the associated hybridization and crosshybridization intensities.

D. Neural Net Weights

Neural net weights are provided in two matrices; an 81×20 matrix (Table 3) (weights_1) and a 2×20 matrix Table 4 (weights_2).

TABLE 3

Neural net weights (81 × 20 matrix) (weights_1).

| | | | | | |
|---|---|---|---|---|---|
| −0.0316746 | −0.0263491 | 0.15907079 | −0.0353881 | −0.0529314 | 0.09014647 |
| 0.19370709 | −0.0515666 | 0.06444275 | −0.0480836 | 0.29237783 | 0.034054 |
| 0.02240546 | 0.08460676 | 0.14313674 | 0.06798329 | 0.06746746 | 0.033717 |
| 0.16692482 | −0.0913482 | 0.05571244 | 0.22345543 | 0.04707823 | 0.0035547 |
| 0.02129388 | 0.12105247 | 0.1405973 | −0.0066357 | −0.0760119 | 0.11165894 |
| 0.03684745 | −0.0714359 | 0.02903421 | 0.09420238 | 0.12839544 | 0.08542864 |
| 0.0603615 | 0.04986877 | 0.02134438 | 0.0852259 | 0.13453935 | 0.03089394 |
| 0.11111762 | 0.12571541 | 0.09278143 | 0.11373715 | 0.03250757 | 0.0460193 |
| 0.1354388 | 0.1131407 | 0.06123798 | 0.14818664 | 0.07090721 | 0.05089445 |
| 0.0635492 | −0.0227965 | 0.1081195 | 0.13419148 | 0.08916269 | 0.010634 |
| 0.18790121 | 0.09624594 | −0.0865264 | −0.0126238 | 0.11497019 | −0.0057307 |
| 0.02378313 | 0.10295142 | 0.05553147 | −0.0193289 | −0.0627925 | −0.024633 |
| −0.0403537 | 0.23566079 | 0.10335726 | 0.07325625 | 0.11329328 | 0.2555581 |
| −0.0694051 | −0.0637478 | 0.2687766= | | | |
| −0.0731941 | 0.08858298 | 0.39719725 | −0.0709359 | 0.14039235 | 0.23244983 |
| 0.06500423 | 0.11003297 | 0.0403917 | 0.02953459 | 0.26901209 | 0.0605089 |
| 0.03036973 | 0.06836637 | 0.02345118 | 0.0206452 | −0.0079707 | 0.20967795 |
| 0.17097448 | −0.007098 | −0.0348659 | 0.09989586 | 0.07417496 | 0.1236805 |
| 0.05442215 | 0.23686385 | 0.01979881 | −9.80E−06 | −0.0549301 | 0.08891765 |
| 0.08683836 | 0.14047802 | 0.00982503 | 0.11756061 | 0.09054346 | 0.028868 |
| 0.08829379 | 0.17381326 | 0.12465772 | 0.13134554 | 0.09500015 | 0.04572553 |
| 0.0749867 | 0.08564588 | 0.05334799 | 0.14341639 | 0.11468539 | 0.14277624 |
| 0.05022619 | 0.14544216 | 0.03519877 | 0.12799838 | 0.01427337 | 0.16172577 |
| 0.08078995 | −0.0022168 | 0.05439407 | −0.0789278 | 0.07312368 | 0.11417327 |
| 0.03405219 | 0.06140256 | 0.01802093 | 0.0954654 | 0.00130152 | 0.035995 |
| 0.11517255 | 0.17431773 | 0.09664405 | 0.01782892 | 0.03840308 | 0.05180788 |
| 0.14236264 | 0.17182963 | 0.02306779 | −0.0489743 | −0.0006051 | 0.19077648 |
| −0.0866363 | 0.11008894 | 0.40543473= | | | |
| −0.6163019 | 0.06256609 | 0.16058824 | 0.14149499 | 0.15698175 | 0.1197781 |
| 0.38030735 | 0.28241798 | 0.2882407 | −0.2227429 | 0.34799534 | 0.38490915 |
| 0.23144296 | −0.3207987 | 0.56366867 | 0.35976714 | 0.20325874 | 0.343972 |
| 0.46158856 | 0.20649959 | 0.35099933 | −0.5071837 | 0.56459975 | 0.21605791 |
| 0.45084599 | −0.5829023 | 0.51297456 | 0.33494622 | 0.43086055 | 0.5538613 |
| 0.55080342 | 0.30968052 | 0.54485208 | −0.7155912 | 0.30799151 | 0.29871368 |
| 0.36848074 | −0.5196409 | 0.33829662 | 0.21612473 | 0.41646513 | 0.5573701 |
| 0.47133151 | 0.30909833 | 0.37790757 | −0.464661 | 0.50172138 | 0.21158406 |
| 0.46017882 | −0.5331213 | 0.60684419 | 0.47586009 | 0.28597337 | 0.3345993 |
| 0.33042327 | 0.4072904 | 0.24270254 | −0.3750777 | 0.14083703 | 0.30998308 |
| 0.19591335 | −0.4028497 | 0.30585453 | 0.35896543 | 0.24851802 | 0.2937264 |
| 0.19672842 | 0.16133355 | 0.21780767 | −0.2419563 | 0.17847325 | 0.07593013 |
| 0.1710967 | −0.2728708 | 0.1234024 | 0.06987085 | 0.1741322 | 0.05922241 |
| 0.03326527 | 0.22045346 | 0.98782647= | | | |
| −0.0752053 | −0.0571054 | −0.1834571 | 0.14263187 | −0.0715346 | −0.0524248 |
| −0.0838031 | 0.01667063 | −0.0945634 | −0.1137057 | −0.1040308 | 0.04263301 |
| −0.2039919 | −0.0532526 | −0.0828366 | 0.1373803 | −0.0562212 | −0.2127942 |
| −0.0482095 | 0.04316666 | −0.1732933 | 0.0550463 | −0.0526818 | 0.06739104 |
| −0.0065265 | −0.2011867 | −0.0434558 | −0.0369132 | −0.0196296 | −0.1314755 |
| 0.09420983 | −0.0010159 | −0.1768979 | −0.2365085 | −0.0150508 | 0.14120786 |
| 0.00565713 | −0.1990354 | 0.11568499 | −0.0690084 | −0.1509431 | −0.0575663 |
| 0.11275655 | 0.01772332 | −0.0016695 | −0.249011 | 0.09066539 | 0.05357879 |
| −0.0850152 | −0.1931012 | 0.08498721 | 0.03673514 | −0.1446398 | −0.199778 |
| 0.1065109 | 0.07205399 | −0.1304159 | −0.1723315 | 0.09151162 | 0.05596334 |

TABLE 3-continued

| Neural net weights (81 × 20 matrix) (weights_1). | | | | | |
|---|---|---|---|---|---|
| −0.0922655 | −0.1478272 | 0.08858409 | 0.14206541 | −0.0314846 | −0.1985286 |
| 0.19862956 | −0.0502828 | −0.11447 | −0.1440073 | 0.01366408 | 0.11101657 |
| −0.0721622 | −0.1506944 | 0.14910588 | 0.03297219 | −0.0266356 | −0.2501774 |
| 0.20344114 | −0.061502 | −0.1647823= | | | |
| 0.02848385 | 0.00254791 | −0.0646306 | 0.02634032 | −0.0654473 | 0.04731949 |
| −0.0742345 | −0.0545447 | −0.1119258 | 0.10765317 | −0.0606677 | 0.05693235 |
| −0.0747124 | 0.13325705 | −0.0508435 | −0.1761459 | −0.0883804 | −0.0777852 |
| −0.1090026 | −0.0988943 | −0.0445145 | 0.03802977 | −0.0484086 | −0.0337959 |
| 0.07326921 | 0.02654305 | −0.1239398 | 0.03043288 | 0.09781751 | 0.02590732 |
| −0.0586419 | −0.08015 | −0.0073617 | −0.1682889 | 0.00400978 | 0.01282504 |
| 0.05150735 | −0.1449667 | 0.06144469 | 0.1005446 | 0.22570252 | 0.3763289 |
| −0.0001517 | −0.0521925 | 0.21106339 | −0.4393073 | 0.0053312 | 0.13283829 |
| 0.12470152 | −0.3589714 | −0.0061972 | 0.07370338 | 0.25447422 | 0.3289591 |
| −0.049451 | 0.05717351 | 0.14784867 | −0.3082401 | 0.01207511 | 0.1141143 |
| 0.18880892 | −0.3259364 | 0.04754021 | −0.0576587 | 0.02376083 | 0.2828108 |
| 0.0234996 | −0.1177034 | 0.02549919 | −0.1671077 | 0.00582423 | 0.0715723 |
| 0.16712189 | −0.0122822 | −0.109654 | −0.0327367 | 0.01481733 | 0.0636454 |
| −0.0487184 | 0.01467591 | −0.0759871= | | | |
| 0.146753 | −0.0931665 | −0.1475015 | 0.07284982 | −0.0609536 | −0.0945313 |
| −0.0739603 | 0.17018235 | −0.0636651 | 0.04693379 | −0.2586751 | 0.15550844 |
| −0.1548294 | −0.0908961 | −0.0415557 | 0.04915113 | −0.0436857 | −0.031472 |
| −0.1728483 | 0.12621336 | −0.1321529 | −0.1091831 | −0.0989133 | 0.0294641 |
| −0.0950026 | −0.1562225 | −0.0917397 | 0.18711324 | 0.04599057 | 0.2039073 |
| 0.07691807 | 0.13016214 | 0.10801306 | −0.3151104 | 0.0105284 | 0.10938062 |
| −0.035349 | −0.302975 | 0.03706082 | 0.12322487 | 0.07198878 | 0.2535323 |
| 0.04664604 | 0.08887579 | −0.0210248 | −0.1427284 | 0.09078772 | 0.08646259 |
| 0.00194441 | −0.1631221 | 0.11259725 | −0.0984519 | −0.0939511 | −0.218395 |
| 0.13777457 | 0.00339417 | −0.2007502 | −0.0703103 | 0.1548807 | 0.13540466 |
| −0.0514387 | −0.0722146 | 0.07706029 | 0.04593663 | −0.2334163 | −0.0250262 |
| 0.0994828 | −0.035077 | −0.106266 | −0.059766 | 0.13616422 | 0.22308858 |
| −0.1571046 | −0.1713289 | 0.14155054 | 0.00283311 | 0.01067419 | 0.360891 |
| 0.13411179 | −0.0159559 | −0.1296399= | | | |
| −0.0304715 | −0.0845574 | 0.17682472 | −0.0552084 | 0.07044557 | 0.1482136 |
| 0.13328855 | −0.1492282 | 0.11350834 | −0.1121938 | 0.02089526 | 0.00104415 |
| 0.0217719 | −0.3102229 | 0.18922243 | −0.0940011 | 0.08787836 | 0.1835242 |
| 0.04117605 | 0.03997391 | 0.06022124 | −0.1808036 | 0.04742034 | 0.0744867 |
| 0.08965616 | −0.1572192 | 0.00942572 | 0.07957069 | 0.12980177 | 0.2440033 |
| 0.08670026 | 0.03785197 | 0.21052985 | −0.3564453 | 0.01492627 | 0.04286519 |
| 0.00865917 | −0.2995701 | −0.083597 1 | 0.14536868 | 0.08446889 | 0.1689682 |
| −0.1322389 | 0.21433547 | 0.08046963 | −0.1548838 | −0.021533 | 0.0558197 |
| 0.1623435 | −0.3362183 | −0.1335399 | 0.10284293 | 0.16658102 | 0.3004514 |
| −0.0887844 | 0.07691832 | 0.11459036 | −0.056257 | 0.01970494 | 0.08940192 |
| 0.08622501 | −0.2421202 | 0.00845924 | −0.0151014 | 0.19088623 | 0.1967196 |
| −0.0290916 | −0.0839412 | 0.10590381 | −0.1593935 | −0.0399097 | −0.0861852 |
| 0.17453311 | −0.1529943 | 0.02726452 | 0.06178628 | 0.06624542 | 0.01004315 |
| −0.158326 | −0.0149114 | −0.1479269= | | | |
| 0.11429903 | −0.0432327 | 0.14520219 | 0.51860482 | 0.19151463 | 0.1127352 |
| 0.33529782 | 0.24581231 | 0.07311282 | −0.2268714 | 0.31717882 | 0.35736522 |
| 0.09062219 | −0.2974442 | 0.46336258 | 0.17145836 | 0.32802406 | 0.3898261 |
| 0.49959001 | 0.22195752 | 0.32254469 | 1.4994924 | 0.75497276 | 0.35112098 |
| 0.52447188 | −0.5555881 | 0.68481833 | 0.20251468 | 0.39860719 | 0.7198414 |
| 0.78773916 | 0.45518181 | 0.71273196 | −0.7655811 | 0.7155844 | 0.39701831 |
| 0.47296903 | −0.672706 | 0.69020337 | 0.37193877 | 0.47959387 | 0.9032337 |
| 0.80210346 | 0.40167103 | 0.50383294 | −0.6195157 | 0.80366057 | 0.3984458 |
| 0.45408139 | −0.7316507 | 0.48975253 | 0.47984859 | 0.33738744 | 0.5510914 |
| 0.56882453 | 0.29653791 | 0.4472059 | −0.5177853 | 0.36228263 | 0.40129057 |
| 0.4490836 | −0.4754149 | 0.46366793 | 0.31378582 | 0.48470935 | 0.2453159 |
| 0.39600489 | 0.24787127 | 0.20359448 | −0.203447 | 0.25734761 | 0.17168433 |
| 0.35209069 | −0.203685 | 0.25115264 | 0.21313109 | 0.12461348 | 0.10632347 |
| 0.13266218 | 0.20236486 | 1.1073833= | | | |
| −0.0112394 | 0.01601524 | 0.11363719 | −0.1440069 | 0.05522444 | 0.0711868 |
| 0.09505147 | −0.0220034 | 0.0714381 | −0.1994763 | 0.12304886 | 0.1611445 |
| 0.16811867 | −0.4498019 | 0.10313182 | −0.0149997 | 0.47659364 | 0.4639786 |
| −0.0380792 | −0.0468904 | 0.37975076 | −0.7120748 | −0.1078557 | 0.10635795 |
| 0.42699403 | −0.6348544 | 0.00025528 | 0.06202703 | 0.57867163 | 0.6733171 |
| −0.0381787 | 0.09532065 | 0.50065184 | −0.7413587 | −0.0193744 | −0.1180785 |
| 0.74187845 | −0.8996705 | 0.03180836 | 0.04010354 | 0.32366729 | 0.6429569 |
| 0.02410492 | −0.0632124 | 0.73732454 | −0.8188882 | 0.04538922 | 0.1471086 |
| 0.7597335 | −0.6287012 | 0.03615654 | −0.1248241 | 0.56647652 | 0.6294683 |
| 0.15992545 | −0.1780757 | 0.3820785 | −0.5642462 | −0.0609947 | −0.0350918 |
| 0.25537059 | −0.4526066 | −0.0761788 | −0.0242514 | 0.35473567 | 0.3512402 |
| −0.1888455 | 0.1974159 | 0.01620384 | −0.1306533 | −0.1468564 | 0.25235301 |
| 0.08058657 | −0.0768841 | −0.316401 | 0.09779498 | 0.08537519 | 0.0738487 |
| −0.2839164 | 0.12684187 | −0.2450078= | | | |
| −0.1147067 | −0.0084124 | −0.5239977 | −0.5021591 | 0.02636886 | 0.1470097 |
| −0.5139894 | −0.6221746 | −0.3979228 | 0.30136263 | −0.742976 | −0.4011821 |
| 0.19038832 | 0.55414283 | −1.1652025 | −0.3686967 | −0.4750175 | 0.54713631 |

TABLE 3-continued

Neural net weights (81 × 20 matrix) (weights_1).

| | | | | | |
|---|---|---|---|---|---|
| −0.9312411 | −0.410718 | −0.1498093 | 0.55332947 | −1.0870041 | −0.4378341 |
| −0.5433689 | 0.92539561 | −0.9013531 | −0.6145319 | −0.5512772 | 1.0310978 |
| −0.9422795 | −0.6914638 | −0.7839714 | 1.4393494 | −0.7092296 | −0.894987 |
| −0.6896155 | 1.1251011 | −0.8161536 | −0.8204682 | −0.8957642 | 1.3315079 |
| −1.0231192 | −0.5556009 | −0.7499282 | 1.281976 | −0.9347371 | −0.6562014 |
| −0.6568274 | 1.1967098 | −1.150661 | −0.5503616 | −0.6640182 | 0.84698498 |
| −0.7811472 | −0.5740913 | −0.4527726 | 0.64911795 | −0.6970047 | −0.5759697 |
| −0.4704399 | 0.51728982 | −0.545236 | −0.8311051 | −0.4240301 | 0.37167478 |
| −0.7735854 | −0.3031097 | −0.4083092 | −0.0152683 | −0.2330878 | −0.5839304 |
| −0.1544528 | 0.2042688 | −0.8989772 | −0.3088974 | −0.2014994 | 0.11505035 |
| −0.4815812 | −0.5319371 | −1.3798244= | | | |
| 0.07143499 | −0.1589592 | 0.04816094 | −0.0301291 | 0.15144217 | 0.3037405 |
| 0.1549352 | −0.0608833 | 0.21059546 | −0.4705076 | 0.16360784 | 0.0684895 |
| 0.44703272 | −0.6194252 | 0.19459446 | −0.0523894 | 0.31194624 | 0.8030509 |
| 0.2595928 | −0.119705 | 0.4913742 | −0.8455008 | 0.15694356 | 0.0023983 |
| 0.53066176 | −0.9705743 | 0.1324198 | 0.08982921 | 0.43900672 | 0.8588745 |
| 0.1702383 | 0.02221953 | 0.44412452 | −0.7700244 | 0.10496679 | 0.14137991 |
| 0.5403164 | −0.5077381 | 0.00849557 | 0.1611405 | 0.31764683 | 0.5240273 |
| −0.092208 | 0.21902563 | 0.25788471 | −0.3861519 | −0.2022993 | 0.13711917 |
| 0.22238699 | −0.156256 | −0.2092034 | 0.16458821 | 0.20111787 | 0.1418906 |
| −0.180493 | 0.17164391 | 0.15690604 | −0.0254563 | −0.1990184 | 0.10211211 |
| 0.17421109 | −0.0730809 | −0.3717274 | 0.1436436 | −0.0215865 | −0.2363243 |
| −0.1982318 | 0.06996673 | 0.19735655 | 0.05625506 | −0.241524 | 0.12768924 |
| 0.05979542 | −0.0623277 | −0.2521037 | 0.0944353 | −0.0492548 | 0.05238663 |
| −0.1978694 | 0.05119598 | −0.2067173= | | | |
| 0.06230025 | −0.0752745 | 0.32974288 | 0.00985043 | 0.07881941 | 0.0835249 |
| 0.1073643 | −0.090154 | −0.0938452 | 0.00704324 | 0.2569764 | 0.08700065 |
| −0.0272076 | −0.1014201 | 0.19723812 | −0.0935401 | 0.0913924 | −0.0728388 |
| 0.33091745 | −0.0610701 | 0.01335303 | 0.02156818 | 0.21619918 | 0.0909865 |
| 0.01069087 | 0.02569587 | 0.11676744 | −0.0213131 | 0.1322203 | 0.11848255 |
| 0.11231339 | −0.0392407 | 0.06117272 | −0.0234323 | 0.14693312 | 0.13509636 |
| −0.0213237 | −0.0261696 | 0.09474246 | −0.0100756 | 0.10580003 | 0.0147534 |
| 0.12980145 | −0.038394 | 0.08167668 | −0.0105376 | 0.02142166 | 0.0161705 |
| 0.15833771 | 0.01835199 | 0.04420554 | 0.02605363 | 0.27427858 | 0.05774866 |
| −0.0696303 | 0.03802699 | 0.0806741 | 0.03993953 | −0.0121658 | 0.07568218 |
| 0.05538817 | 0.01067943 | 0.04131892 | −0.0267609 | 0.14418064 | 0.0897231 |
| −0.0677462 | −0.0772208 | 0.16641215 | 0.09142463 | 0.02115551 | 0.0876383 |
| 0.14652038 | 0.06084725 | −0.1150111 | −0.0687876 | 0.10878915 | 0.32776353 |
| −0.1929855 | 0.00694158 | 0.26604816= | | | |
| −0.0786668 | 0.05454836 | −0.0834711 | 0.07707115 | 0.05665099 | 0.0285798 |
| −0.0029815 | −0.0837616 | 0.02468397 | 0.03531792 | −0.1437671 | 0.10122854 |
| −0.1259448 | −0.0845026 | 0.10171869 | −0.0541042 | 0.05257236 | 0.04065102 |
| −0.1091328 | 0.0090488 | 0.06142418 | −0.167912 | −0.098868 | 0.02574896 |
| 0.00333312 | −0.2912204 | 0.02039073 | −0.052828 | −0.0439769 | −0.0458286 |
| 0.14768517 | 0.02989549 | 0.09454407 | −0.1860176 | −0.0505908 | 0.088718 |
| 0.0611263 | −0.1895157 | 0.08583955 | 0.09382812 | −0.0001466 | −0.4065202 |
| 0.09951859 | 0.14843601 | 0.12351749 | −0.1327625 | 0.10949049 | 0.07129322 |
| 0.05554885 | −0.3743193 | −0.0205463 | 0.12675567 | 0.0775801 | −0.1869074 |
| 0.01806534 | 0.09599103 | −0.0570596 | −0.1523381 | 0.08384241 | 0.00704122 |
| 0.10942505 | −0.0473638 | 0.01151769 | 0.09737793 | 0.07082167 | 0.2184597 |
| −0.0365961 | −0.0962418 | 0.01007566 | −0.0049753 | 0.01404589 | 0.0406134 |
| 0.01934035 | −0.0073082 | −0.0489736 | 0.10457312 | −0.0520154 | −0.0454775 |
| −0.0525739 | 0.06086259 | −0.1788069= | | | |
| 0.19904579 | −0.2001437 | 0.04977471 | 0.26628217 | 0.19910193 | 0.15184447 |
| 0.01703933 | 0.06875326 | 0.09066898 | −0.2003548 | 0.26507998 | 0.0629725 |
| 0.39202845 | −0.6033413 | 0.57940209 | −0.0460919 | 0.53419203 | 0.7680888 |
| 0.65535748 | 0.32430753 | 0.64831889 | −1.0950515 | 0.80829531 | 0.05049393 |
| 0.95144385 | −1.2075449 | 0.94851351 | −0.0852669 | 0.94320357 | 1.680338 |
| 0.99852085 | 0.48870567 | 1.7470727 | −1.7586045 | 0.56886804 | 0.66196042 |
| 1.2572207 | −1.5854638 | 0.89351815 | 0.39586932 | 1.586942 | −1.6365775 |
| 0.73526824 | 0.31977594 | 1.2270083 | −1.2818555 | 0.71813524 | 0.37488377 |
| 0.95438999 | −1.2543333 | 0.55854511 | 0.1672449 | 0.56084049 | 0.7980669 |
| 0.45917389 | 0.27823627 | 0.26928344 | −0.9804664 | 0.62299174 | 0.53984308 |
| 0.33946255 | −0.5412283 | 0.1085042 | 0.44658452 | 0.39120093 | 0.5676367 |
| 0.19083619 | 0.37056214 | 0.24114503 | −0.3020035 | 0.39015424 | 0.09788869 |
| 0.30190364 | −0.3655235 | 0.33355939 | 0.44246852 | 0.17172456 | 0.3479928 |
| 0.18584418 | 0.34009755 | 4.5490937= | | | |
| 0.13698889 | −0.0798945 | 0.3366704 | 0.17313539 | 0.01228174 | 0.2679709 |
| 0.31540671 | 0.08274947 | 0.11212139 | −0.428847 | 0.57447821 | 0.0305296 |
| 0.00119518 | −0.1978176 | 0.59532708 | −0.0309942 | −0.0107875 | −0.7312108 |
| 0.74023747 | 0.38564634 | 0.03748908 | −0.6475483 | 0.87958473 | 0.05327692 |
| 0.06987014 | −0.5168169 | 1.0081589 | −0.0517421 | 0.08651814 | 0.761238 |
| 0.7840901 | 0.4372991 | 0.13783893 | −0.8574924 | 0.90612286 | 0.06334394 |
| 0.05702339 | −0.5161278 | 0.66693234 | −0.0496743 | 0.07691617 | 0.5775976 |
| 0.70519674 | 0.15731441 | 0.08724558 | −0.7325026 | 0.65517086 | 0.29064488 |
| 0.11747536 | −0.612968 | 0.98160452 | 0.02407174 | 0.02613025 | 0.677594 |
| 0.81293154 | 0.18651071 | 0.03182137 | −0.7051651 | 0.89682412 | 0.181806 |

TABLE 3-continued

| Neural net weights (81 × 20 matrix) (weights_1). | | | | | |
|---|---|---|---|---|---|
| 0.24770954 | −0.4320194 | 0.72470272 | 0.12951751 | 0.14626819 | 0.3964331 |
| 0.54755467 | 0.08819038 | 0.22105552 | −0.3489864 | 0.4620938 | 0.06516677 |
| 0.03049339 | −0.1913544 | 0.4782092 | −0.098419 | −0.0160188 | 0.07177288 |
| 0.1008145 | 0.01412579 | 0.42727205= | | | |
| −0.0048454 | 0.1204864 | 0.15507312 | 0.25648347 | 0.03982652 | 0.14641231 |
| −0.0273505 | 0.10494121 | 0.1988914 | 0.09454013 | −0.0560908 | 0.07466536 |
| 0.1325469 | 0.15324508 | −0.01398 | 0.08281901 | 0.07990969 | 0.36858437 |
| −0.0007111 | 0.13285491 | −0.1658676 | 0.25348473 | 0.08835109 | 0.16466415 |
| −0.118853 | 0.26435438 | −0.0775707 | 0.09143513 | −0.1019902 | 0.29236633 |
| 0.07947435 | 0.07329605 | −0.0903666 | 0.10754076 | 0.04456592 | 0.18368921 |
| −0.162177 | 0.18712705 | 0.03216886 | 0.04698242 | −0.0385783 | 0.2276271 |
| 0.04106503 | 0.08498254 | −0.0325038 | 0.29328787 | 0.01249749 | 0.10016124 |
| −0.0012895 | 0.2371086 | 0.14713244 | −0.053306 | −0.0808243 | 0.28909287 |
| 0.13412228 | 0.10756335 | −0.0486093 | 0.05799349 | 0.21323961 | 0.0118695 |
| −0.142963 | 0.09792294 | 0.06907349 | 0.05942665 | −0.143813 | 0.21673524 |
| 0.19903891 | 0.02989559 | 0.15750381 | −0.0373194 | 0.12471988 | 0.10462648 |
| −0.0027455 | 0.16604523 | 0.06245366 | −0.0775013 | −0.0160873 | 0.21550164 |
| 0.25000233 | 0.05931267 | 0.22881882= | | | |
| 0.04679342 | 0.10158926 | −0.122116 | 0.23491009 | −0.0625733 | 0.19985424 |
| −0.1704439 | 0.302394 | −0.0671487 | 0.33251444 | −0.0581705 | 0.21095584 |
| −0.215752 | 0.32740423 | −0.1597161 | 0.18950906 | −0.1232446 | 0.27883759 |
| −0.0430407 | 0.04886867 | −0.0914212 | 0.28192514 | 0.05275658 | 0.21014904 |
| −0.1322077 | 0.2981362 | 0.1254565 | 0.15627012 | 0.04116358 | 0.08507752 |
| 0.10109599 | 0.23081669 | −0.1617257 | 0.29508773 | −0.0405337 | −0.0497829 |
| −0.0808031 | 0.15750171 | 0.08072432 | 0.12990661 | −0.1935954 | 0.29120663 |
| 0.13912162 | 0.04256131 | −0.1625126 | 0.25232118 | 0.04736055 | 0.0530935 |
| −0.2270383 | 0.22945035 | 0.18167619 | 0.00080986 | −0.1253632 | 0.15695702 |
| 0.01596376 | 0.03504543 | 0.00964208 | 0.11757879 | −0.0230768 | 0.04350457 |
| −0.1284984 | 0.24145114 | 0.20540115 | 0.07580803 | −0.0932236 | 0.14288881 |
| 0.00538179 | 0.05302088 | −0.1001294 | 0.27505419 | 0.22654785 | 0.02395938 |
| −0.0861699 | 0.05814215 | 0.21307872 | 0.01372274 | 0.04515802 | 0.0269269 |
| 0.20031671 | 0.23140682 | 0.16010799= | | | |
| 0.37838998 | 0.00934576 | −0.139213 | 0.29823828 | 0.40640026 | 0.067578 |
| −0.038453 | 0.24550894 | 0.30729383 | −0.2807365 | −0.0689575 | 0.26537073 |
| 0.58336282 | −0.2145292 | −0.2378269 | 0.25939462 | 0.64761585 | 0.3581158 |
| 0.07741276 | 0.45081589 | 0.65251595 | −0.4543131 | −0.0671543 | 0.48592216 |
| 0.85640681 | −0.6068144 | −0.1187844 | 0.35959438 | 0.71842372 | 0.7140775 |
| −0.0642752 | 0.37914035 | 0.71409059 | −0.7180941 | 0.21169594 | 0.27888221 |
| 0.79736245 | −0.7102081 | 0.14268413 | 0.41374633 | 0.75569016 | 0.7394939 |
| 0.02592243 | 0.37013471 | 0.82774776 | −0.8136597 | 0.24068722 | 0.45081198 |
| 0.88004726 | −0.6990998 | 0.23456772 | 0.24596012 | 0.67229778 | 0.8148533 |
| 0.30492786 | 0.39735735 | 0.55497372 | −0.6593497 | 0.20656242 | 0.3752968 |
| 0.54989374 | −0.5660355 | 0.1205707 | 0.22377795 | 0.46045718 | 0.519361 |
| 0.17151839 | 0.39539635 | 0.50465524 | −0.3791285 | 0.07184427 | 0.36315975 |
| 0.51068121 | −0.3502096 | −0.2094818 | 0.31471297 | 0.18174268 | 0.1241962 |
| −0.1255455 | 0.35898197 | 0.79502285= | | | |
| 0.02952595 | −0.0751979 | −0.2556099 | −0.3040917 | −0.0942183 | −0.0541431 |
| −0.6262965 | −0.1423945 | −0.0537339 | 0.11189342 | −0.3791296 | −0.3382006 |
| 0.02978903 | 0.20563391 | −0.5457558 | −0.3666513 | −0.1922515 | 0.29512301 |
| −0.7473708 | −0.0415357 | 0.18283925 | 0.28153449 | −0.7847292 | −0.2313099 |
| 0.00290797 | 0.6284017 | −0.6397845 | −0.5606785 | −0.1479581 | 0.57049137 |
| −1.0829539 | −0.1822221 | −0.1832336 | 0.49371469 | −0.6362705 | −0.2790937 |
| 0.06966544 | 0.75524592 | −0.9053063 | −0.5826979 | −0.114608 | 0.90401584 |
| −0.8823278 | −0.3404879 | −0.0334436 | 0.50130409 | −0.57275 | −0.3842527 |
| 0.0915129 | 0.44590429 | −0.7808504 | −0.4399623 | −0.1189605 | 0.59226018 |
| −0.499517 | −0.4873153 | −0.2889721 | 0.47303999 | −0.4015501 | −0.2875251 |
| −0.1106236 | 0.27437851 | −0.6061368 | −0.4166524 | −0.0637606 | 0.33875695 |
| −0.6255118 | −0.1046614 | −0.2710638 | 0.26425925 | −0.4123208 | −0.2157291 |
| −0.1468192 | −0.1719856 | −0.4140109 | −0.1058299 | 0.02873472 | 0.1210428 |
| −0.213571 | −0.1335077 | −0.7155944= | | | |
| 0.06424081 | −0.0978306 | −0.1169782 | 0.13909493 | −0.0838893 | −0.1300299 |
| −0.1032737 | 0.11563963 | −0.0709175 | −0.028875 | −0.1718288 | −0.026291 |
| 0.05533361 | −0.033985 | −0.049436 | 0.11520655 | −0.0279296 | −0.01.70352 |
| 0.05850215 | 0.03830531 | −0.0893732 | −0.0066427 | 0.06969514 | 0.13403182 |
| −0.012636 | −0.1925185 | 0.13028348 | −0.0045112 | 0.05226076 | 0.2759708 |
| −0.0395793 | 0.03069885 | 0.07913893 | −0.1470363 | 0.09080192 | 0.19741131 |
| −0.0917266 | −0.2185763 | 0.04743406 | −0.0364127 | 0.00991712 | 0.2093729 |
| 0.23327024 | −0.0898143 | −0.0578982 | −0.2096201 | 0.09257686 | 0.00566842 |
| 0.10926479 | −0.1167006 | 0.18223672 | 0.09710353 | 0.03838636 | 0.2026017 |
| 0.12219627 | 0.05705986 | 1.0505442 | −0.1334345 | −0.0204458 | 0.01167099 |
| −0.1091286 | −0.075133 | 0.02949276 | −0.0217044 | −0.0782921 | −0.1160332 |
| −0.0210903 | 0.11607172 | −0.0943146 | −0.1014408 | 0.02903902 | 0.02963065 |
| −0.1233738 | −0.0760847 | 0.00098273 | 0.07522969 | 0.05794976 | 0.1959872 |
| 0.06584878 | −0.0323083 | −0.0581293= | | | |

TABLE 4

| Second neural net weighting matrix (2 × 21) (weights_2). | | | | | |
|---|---|---|---|---|---|
| −0.5675537 | −0.6119734 | 0.20069507 | 0.26132998 | −0.5071653 | 0.2793434 |
| −0.5328685 | 0.31165671 | −0.9999997 | −0.4128213 | −1.0000007 | −0.6456627 |
| −0.209518 | 1.6362301 | −1.9999975 | −0.2563241 | 0.04389827 | 1.7597554 |
| 2.0453076 | 0.08412334 | −0.1645829= | | | |
| 0.55343837 | 0.68506879 | −1.1869608 | 0.39551663 | 0.38050765 | 0.40832204 |
| 0.12712023 | −1.7462951 | 0.0818732 | 6.111361 | 0.62210494 | 0.42921746 |
| 0.19891988 | −4.0000067 | −0.5605077 | 1.3601962 | 1.7318885 | −1.0558798 |
| 3.1242371 | 0.22860088 | 1.6726165= | | | |

E. Code for Running the Net

Code for running the neural net is provided below in Table 5 (neural_n.c) and

TABLE 5

Code for running the neural net (neural_n.c).

```
#define local far
#include <windows.h>
#include <alioc.h>
#include "utils.h"
#include <string.h>
#include <ctype.h>
#include <stdio.h>
#include <math.h>
#include <mem.h>
#include "tdes_util.h'
#include "tchipwin.h"
#include "lin_alg.h"
void reportProblem( char local * message, short errorClass);
char iniFileName[] = "designer.ini";
static void sigmoid( vector local * transformMe ){
    short i;
    for( i = 0; i < transformMe->size; i++)
        transformMe->values[i] = 1/1 + exp(-1 * transformMe->values[i]));
}
static short getNumCols(char far * buffer){
    short count = 1;
    for( ;*buffer != 0; buffer++)
        if( *buffer == '\t') count++;
    return count;
}
static short getNumRows(char far * buffer){
    char far * last, far * current;
    short count = -1;
    current = buffer;
    do{
        count++;
        last = current;
        current = strchr( last+1, 0);
    }while( current > last+1 );
    return count;
}
static void readMatrix( matrix local * theMat, char far * buffer ){
    short i,j;
    char far * temp;
    temp = buffer;
    for( i = 0; i < theMat->numRows; i++){
        for(j = 0; j < theMat->numCols; j++){
            while( isspace( *temp) || (*temp == 0 && *(temp-1) != 0)) = temp++;
            sscanf( temp, "%f", &theMat->values[i][j]);
            while( !isspace( *temp) && *temp != 0) temp++;
        }
    }
}
#define MaxNumLines (20)
#define MaxLineSize (1024)
short readNeuralNetWeights(matrix local *weights1, matrix local *weights2
){
    char far * buffer;
    int copiedLength;
    short numCols, numRows;
    buffer = farcalloc( MaxNumLines * MaxLineSize, sizeof( char));
```

TABLE 5-continued

Code for running the neural net (neural_n.c).

```
        if (buffer == NULL ){ errorHwnd( "failed to allocate file reading = buffer"); return
FALSE;}
        copiedLength = GetPrivateProfileString("weights_1", NULL, "†0[0]†0", buffer,
MaxNumLines * MaxLineSize, iniFileName);
        if( copiedLength <10 || copiedLength >= (MaxNumLines * MaxLineSize =
-10)){
                errorHwnd("failed to read .ini file"); return FALSE;
        }
        numCols = getNumCols( buffer );
        numRows = getNumRows( buffer );
        if( !allocateMatrix( weights1, numRows, numCols )) return FALSE;
        readMatrix( weights1, buffer);
        copiedLength = GetPrivateProfileString("weights_2", NULL, "†0†0", buffer,
MaxNumLines * MaxLineSize, iniFileName);
        if( copiedLength <10 || copiedLength >= (MaxNumLmes * MaxLineSize
-10)){
                errorHwnd("failed to read .ini file"),
                farfree(buffer);
                return FALSE;
        }
        numCols = getNumCols( buffer );
        numRows = getNumRows( buffer );
        if( !allocateMatrix( weights2, numRows, numCols )){ farfree( buffer ); return FALSE; }
        readMatrix( weights2, buffer);
        farfree(buffer);
    return TRUE;
}
short runForward( vector local *input, vector Iocai *output,
                                matrix local *weights1, matrix local *weights2){
        vector hiddenLayer;
        if( !allocateVector( &hiddenLayer, (short)(weights1->numRows +1))) return FALSE;
        if( ! vectorTimesMatrix( input, &hiddenLayer, weights1 )) {
           freeVector( &hiddenLayer); return FALSE;
        }
        sigmoid( &hiddenLayer);
        hiddenLayer.values[hiddenLayer.size -1] = 1;
        if( !vectorTimesMatrix( &hiddenLayer, output, weights2 )){
           freeVector( &hiddenLayer); return FALSE;
        }
freeVector( &hiddenLayer);
        sigmoid( output);
        return TRUE;
}
static vector inputVector= {NULL, 0}, outputVector = {NULL, 0}; static matrix firstWeights =
{NULL, 0, 0}, secondWeights = {NULL, 0, 0};
static short beenHereDoneThis = FALSE;
static short makeSureNetIsSetUp( void ){
        if( beenHereDoneThis ) return TRUE;
        if( !readNeuralNetWeights( &firstWeights, &secondWeights )) return = FALSE;
        if( !allocateVector( &inputVector, firstWeights.numCols )) return = FALSE;
        if( !allocateVector( &outputVector, secondWeights.numRows )) return = FALSE;
        beenHereDoneThis = TRUE;
        return TRUE;
}
void removeNetFromMemory( void ) {
        freeVector( &inputVector); freeVector( &outputVector );
        freeMatrix( &firstWeights); freeMatrix( &secondWeights );
    beenThereDoneThis = FALSE;
}
short nnEstimateHybAndXHyb( float local * hyb, float local * xHyb, char = local * probe){
        short probeLength, i;
        if( !makeSureNetIsSetUp()) return FALSE;
        probeLength = (short)(strlen( probe ));
        if( probeLength *4 + 1) != inputVector.size ){
//      reportProblem("Neural net not set up to deal with probes of this = length", 0);
                if( #robeLength *4 + 1) > inputVector.size ){
//              reportProblem( "probe being trimmed to do annlysis", 1);
                        probeLength = (short)(inputVector.size/4);
                }
        }
        memset( inputVector.values, 0, inputVector.size * sizeof( float));
        inputVector.values[inputVector.size-1] = 1;
        for( i = 0; i < probeLength; i++)
                inputVector.values[i * 4 + lookupIndex( tolower(probe[i] ))]= 1;
        runForward( &inputVector, &outputVector, &firstWeights, &secondWeights);
        *hyb = outputVector.values[0];
        *xHyb = outputVector.values[1];
```

TABLE 5-continued

Code for running the neural net (neural_n.c).

```
        return TRUE;
}
```

TABLE 6

Code for running the neural net (lin_alg.c).

```
lin_alg.c
#include "utils.h"
#include "lin_alg.h"
#include <alloc.h>
short allocateMatrix( matrix local * theMat, short rows, short colulmns){
        short i;
        theMat->values = calloc( rows, sizeof ( float local * ));
        if( theMat->values == NULL ){ errorHwnd( "failed to allocate = matrix"); return
FALSE;}
        for(i = 0; i < rows;i++){
                theMat->values[i] = calloc( columns, sizeof (float) );
                if( theMat->values[i] = NULL ){
                        errorHwnd ("failed to allocate matrix");
                        for( --4; i >= 0; i--)
                                free( theMat->values[i]);
                        return FALSE;
                }
        }
        theMat->numRows = rows; theMat->numCols = columns;
        return TRUE;
} short allocateVector( vector local * theVec, short columns) {
        theVec->values = calloc( columns, sizeof ( float));
  if( theVec->values = NULL) { errorHwnd( "faile to allocate = vector"); return FALSE;}
        theVec->size = columns;
        return TRUE;
}
void freeVector( vector local * theVec ){
        free( theVec->values);
  theVec->values = NULL;
  theVec->size = 0;
}
void freeMatrix( matrix local * theMat) {
        short i;
        for( i = 0; i <theMat->numRows; i++)
    free( theMat->values[i]);
        free( theMat->values );
 theMat->values = NULL;
 theMat->numRows = theMat->numCols = 0;
}
float vDot( float local * input1, float local * input2, short size ){
        float returnValue = 0;
        short i;
        for(i = 0; i < size;i++)
                returnVaiue += input1[i] * input2[i];
        return returnValue;
}
short vectorTimesMatrix( vector local *input, vector local *output,
                                matrix local *mat ){
        short i;
        if( (input->size != mat->numCols) || (output->size < mat->numRows) ){
                errorHwnd( "illegal multiply");
                return FALSE;
        }
        for( i = 0; i < mat->numRows; i++)
                output->values[i] = vDot->input->values, mat->values[i], input->size =
);
        return TRUE;
}
```

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method for comparing and identifying differences if any in nucleic acid sequences in two or more collections of labeled nucleic acids, the method comprising:

providing a plurality of probes bound to a solid surface, at least some of said plurality comprising a nucleic acid complementary to a nucleic acid sequence in said collections to be compared;

contacting the probes with
- a first collection of labeled nucleic acids having a first label, and
- at least a second collection of labeled nucleic acids having a
- second label;

wherein said first and second labels are distinguishable from each other and wherein said labeled nucleic acids in said first and second collections bind to said probes; and detecting the binding for each of the first and at least second labeled nucleic acids to the probes;

thereby comparing and identifying differences if any in said nucleic acid sequences in said two or more collections.

2. The method as recited in claim 1 wherein the labeled nucleic acids are from two cell types and are labeled with labels of first and second fluorescent reporters.

3. The method as recited in claim 2 wherein said first and second fluorescent reporters are different colors of flurescent reporters.

4. The method as recited in claim 3 wherein said colors are red and green.

5. The method as recited in claim 1 wherein said probes are provided by synthesis of RNA or DNA on the solid surface.

6. The method of claim 1 wherein the nucleic acids are DNA.

7. The method of claim 1 wherein the nucleic acids are cDNA.

8. The method of claim 1 wherein the first and second labeled nucleic acids comprise human DNA.

9. The method of claim 1 wherein the nucleic acids are greater than about 25 nucleotides in complexity.

10. The method of claim 1 wherein the solid surface is glass.

11. The method of claim 1 wherein the first and second labels are fluorescent labels.

12. The method of claim 1 wherein the first labeled nucleic acids comprise mRNA or cDNA from a test cell and the second labeled nucleic acids comprise mRNA or cDNA from a reference cell.

13. The method of claim 1 wherein the first labeled nucleic acids are from a test genome and the second labeled nucleic acids are from a normal reference genome.

14. The method of claim 1 wherein the first labeled nucleic acids are from a tumor.

15. The method according to claim 1 wherein the plurality of probes includes more than 100 probes per square centimeter bound to said solid surface.

16. The method according to claim 1 wherein the plurality of probes includes more than 1000 probes per square centimeter bound to said solid surface.

17. The method according to claim 1 wherein the plurality of probes includes more than 10,000 probes per square centimeter bound to said solid surface.

* * * * *